US009422285B2

(12) United States Patent
Vakalopoulos et al.

(10) Patent No.: US 9,422,285 B2
(45) Date of Patent: Aug. 23, 2016

(54) SUBSTITUTED PYRAZOLO[1,5-A]-PYRIDINE-3-CARBOXAMIDES AND USE THEREOF

(71) Applicant: Bayer Pharma Aktiengesellschaft, Berlin (DE)

(72) Inventors: Alexandros Vakalopoulos, Hilden (DE); Markus Follmann, Cologne (DE); Philipp Buchgraber, Berlin (DE); Alexey Gromov, Erkrath (DE); Ingo Hartung, Berlin (DE); Niels Lindner, Wuppertal (DE); Frank Wunder, Wuppertal (DE); Johannes-Peter Stasch, Munich (DE); Tobias Marquardt, Wuppertal (DE); Gorden Redlich, Bochum (DE); Lisa Dietz, Wuppertal (DE); Volkhart Min-Jian Li, Velbert (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/909,881

(22) PCT Filed: Aug. 5, 2014

(86) PCT No.: PCT/EP2014/066780
§ 371 (c)(1),
(2) Date: Feb. 3, 2016

(87) PCT Pub. No.: WO2015/018814
PCT Pub. Date: Feb. 12, 2015

(65) Prior Publication Data
US 2016/0185775 A1 Jun. 30, 2016

(51) Int. Cl.
| | |
|---|---|
| *C07D 471/04* | (2006.01) |
| *A61K 31/437* | (2006.01) |
| *A61K 45/06* | (2006.01) |
| *A61K 31/4545* | (2006.01) |
| *C07D 519/00* | (2006.01) |
| *A61K 31/4709* | (2006.01) |
| *A61K 31/55* | (2006.01) |
| *A61K 31/5377* | (2006.01) |
| *A61K 31/444* | (2006.01) |
| *A61K 31/4375* | (2006.01) |
| *A61K 31/541* | (2006.01) |
| *A61K 31/496* | (2006.01) |
| *A61K 31/4985* | (2006.01) |

(52) U.S. Cl.
CPC ............ *C07D 471/04* (2013.01); *A61K 31/437* (2013.01); *A61K 31/4375* (2013.01); *A61K 31/444* (2013.01); *A61K 31/4545* (2013.01); *A61K 31/4709* (2013.01); *A61K 31/496* (2013.01); *A61K 31/4985* (2013.01); *A61K 31/5377* (2013.01); *A61K 31/541* (2013.01); *A61K 31/55* (2013.01); *A61K 45/06* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 5,698,704 A | 12/1997 | Jackson | |
| 6,180,656 B1 | 1/2001 | Fuerstner et al. | |
| 8,129,423 B2 | 3/2012 | Ackermann et al. | |
| 9,126,998 B2 * | 9/2015 | Vakalopoulos | C07D 471/04 |
| 2016/0010143 A1 | 1/2016 | Burkhardt et al. | |

FOREIGN PATENT DOCUMENTS

| | | |
|---|---|---|
| WO | WO 98/16223 A1 | 4/1998 |
| WO | WO 2008/061626 A1 | 5/2008 |
| WO | WO 2010/117787 A2 | 10/2010 |
| WO | WO 2010/123792 A1 | 10/2010 |
| WO | WO 2012/072512 A1 | 6/2012 |

OTHER PUBLICATIONS

International Search Report (PCT/ISA/210) issued on Oct. 21, 2014, by the European Patent Office as the International Searching Authority for International Application No. PCT/EP2014/066780.
Written Opinion (PCT/ISA/237) issued on Oct. 21, 2014, by the European Patent Office as the International Searching Authority for International Application No. PCT/EP2014/066780.
Kojima et al., "Phosphodiesterase inhibitors. Part 6: Design, synthesis, and structure-activity relationships of PDE4-inhibitory pyrazolo[1,5-α]pyridines with anti-inflammatory activity", Bioorganic & Medicinal Chemistry Letters, Aug. 2013, pp. 5311-5316, vol. 23.
Bai et al., "Lewis Acid Catalyzed Intramolecular [4+2] and [3+2] Cross-Cycloaddition of Alkynylcyclopropane Ketones with Carbonyl Compounds and Imines", Angew. Chem. Int. Ed., 2012, pp. 4112-4116, vol. 51.
Chen et al., "Radical Formation in the Oxidation of 2,2'-Azo-2-methyl-6-heptene by Thianthrene Cation Radical", J. Org. Chem., 1996, pp. 4716-4719, vol. 61, No. 14.
Deng et al., "Studies on Phosphoroheterocycle Chemistry II: A Simple and New Route to 1,3,2-Diazaphospholidine-4-thione 2-sulfide Derivatives", Synthesis, 2001, pp. 2445-2449, No. 16.
Fernandez et al., "Design, synthesis and structure-activity-relationship of 1,5-tetrahydronaphthyridines as CETP inhibitors", Bioorganic & Medicinal Chemistry Letters, 2012, pp. 3056-3062, vol. 22.
Freifelder et al., "Synthesis of Primary 1,2-Diamines by Hydrogenation of α-Aminonitriles", J. Am. Chem. Soc., 1960, pp. 696-698, vol. 82.

(Continued)

*Primary Examiner* — Yevegeny Valenrod
(74) *Attorney, Agent, or Firm* — Buchanan Ingersoll & Rooney PC

(57) ABSTRACT

The present application relates to novel pyrazolo[1,5-a]pyridine-3-carboxamides, to processes for preparation thereof, to the use thereof, alone or in combinations, for treatment and/or prophylaxis of diseases, and to the use thereof for production of medicaments for treatment and/or prophylaxis of diseases, especially for treatment and/or prophylaxis of cardiovascular disorders.

13 Claims, No Drawings

(56) References Cited

OTHER PUBLICATIONS

Hamill et al., "Improved Patch-Clamp Techniques for High-Resolution Current Recording from Cells and Cell-Free Membrane Patches", Pfluegers Arch European Journal of Physiology, 1981, pp. 85-100.

Himmel, "Suitability of commonly used excipients for electrophysiological in-vitro safety pharmacology assessment of effects on hERG potassium current and on rabbit Purkinje fiber action potential", Journal of Pharmacological and Toxicological Methods, 2007, pp. 145-158, vol. 56.

Hiroi et al., "A Novel Method for Direct Construction of Indole Skeletons by Intramolecular Carbopalladation of Allenes Followed by Nucleophilic Substitution", Synlett, 2001, pp. 263-265, No. 2.

Hjørringgaard et al., "An Automatic Solid-Phase Synthesis of Peptaibols", J. Org. Chem., 2009, pp. 1329-1332, vol. 74.

Hoenicka et al., "Purified soluble guanylyl cyclase expressed in a baculovirus/Sf9 system: stimulation by YC-1, nitric oxide, and carbon monoxide", J Mol Med, 1999, pp. 14-23.

Hossain et al., "Synthesis of Vicinal Diamino-Endo, Cis-Norbornene Derivatives", Synthetic Communications, 2012, pp. 1200-1210.

Klapper et al., "Poly(methylenamin)—Synthese eines Polymers mit der höchstmöglichen Zahl an Aminogruppen an einer polymeren Hauptkette", Angew. Chem., 2003, pp. 4835-4838.

Mülsch et al., "Effect of YC-1, an NO-independent, superoxide-sensitive stimulator of soluble guanylyl cyclase, on smooth muscle responsiveness to nitrovasodilators", British Journal of Pharmacology, 1997, pp. 681-689, vol. 120.

Ogrel et al., "Synthesis of $^{15}$N-Labelled D-Isovaline and á-Aminoisobutyric Acid", Eur. J. Org. Chem., 2000, pp. 857-859.

Pettibone et al., "A Structurally Novel Stimulator of Guanylate Cyclase With Long-Lasting Hypotensive Activity in the Dog", European Journal of Pharmacology, 1985, pp. 307-312, vol. 116.

Rubottom et al., "Preparation of Methyl Ketones by the Sequential Treatment of Carboxylic Acids with Methyllithium and Chlorotrimethylsilane", J. Org. Chem., 1983, pp. 1550-1552, vol. 48, No. 9.

Scheel et al., "Introduction of a Modular Automated Voltage-Clamp Platform and Its Correlation with Manual Human Ether-a-go-go Related Gene Voltage-Clamp Data", Assay and Drug Development Technologies, Dec. 2011, pp. 600-608, vol. 9, No. 6.

Scholz et al., "cis-1,2-Cyclobutandiamine durch photosensibilisierte Cycloaddition von 1,3-Diacetyl-4-imidazolin-2-onen an Olefine", Liebigs Ann. Chem., 1981, pp. 248-255.

Stasch et al., "Cardiovascular actions of a novel NO-independent guanylyl cyclase stimulator, BAY 41-8543: in vivo studies", British Journal of Pharmacology, 2002, pp. 344-355, vol. 135, No. 2.

Von Der Saal et al., "Synthese und H-NMR-Spektren diastereomerenreiner 1,2-Cyclopropandiamine und 1,2-Cyclopropandiamrmonium-dibromide", Liebigs Ann. Chem., 1994, pp. 569-579 (English Abstract).

Wu et al., "YC-1, a Novel Activator of Platelet Guanylate Cyclase", Blood, Dec. 1994, pp. 4226-4233, vol. 84, No. 12.

Wube et al., "Design, synthesis and antimycobacterial activities of 1-methyl-2-alkenyl-4(1H)-quinolones", Bioorganic & Medicinal Chemistry, 2011, pp. 567-579, vol. 19.

Wunder et al., "A cell-based cGMP assay useful for ultra-high-throughput screening and identification of modulators of the nitric oxide/cGMP pathway", Analytical Biochemistry, 2005, pp. 104-112, vol. 339.

Yu et al., "Vasorelaxant effect of isoliquiritigenin, a novel soluble guanylate cyclase activator, in rat aorta", British Journal of Pharmacology, 1995, pp. 1587-1594, vol. 114.

Zhou et al., "Properties of HERG Channels Stably Expressed in HEK 293 Cells Studied at Physiological Temperature", Biophysical Journal, Jan. 1996, pp. 230-241, vol. 74.

Ko et al., "Universal Peptidomimetics", J. Am. Chem. Soc., 2011, pp. 462-477, vol. 133.

McConathy et al., "Radiolabeled Amino Acids for Tumor Imaging with PET: Radiosynthesis and Biological Evaluation of 2-Amino-3-[$^{18}$F]fluoro-2-methylpropanoic Acid and 3-[$^{18}$F]Fluoro-2-methyl-2-methylamino)propanoic Acid", J. Med. Chem., 2002, pp. 2240-2249, vol. 45, No. 11.

Mikami et al., "Applications of the Tandem [2,3]-Wittig-Oxy-Cope Rearrangement to Syntheses of exo-Brevicomin and Oxocrinol. The Scope and Limitation of the Sigmatropic Sequences as a Synthetic Method for Σε-Unsaturated Ketones", Chemistry Letters, 1982, pp. 1349-1352.

Witte et al., "Experimental heart failure in rats: effects on cardiovascular circadian rhythms and on myocardial β-adrenergic signaling," Cardiovascular Research, 2000, 47:350-358.

Van Den Buuse, "Circadian Rhythms of Blood Pressure, Heart Rate, and Locomotor Activity in Spontaneously Hypertensive Rats as Measured with Radio-Telemetry," Physiology & Behavior, 1994, 55:(4) 783-787.

Bergman et al., "Organic Fluorine Compounds. Part XXVII.* Fluorinated α-Aminoisobutyric Acids", J. Am. Chem. Soc., 1963, pp. 3462-3463.

Glass et al., "Stimulation of Human Platelet Guanylate Cyclase by Fatty Acids", The Journal of Biological Chemistry, Feb. 1977, pp. 1279-1285, vol. 252, No. 4.

* cited by examiner

SUBSTITUTED PYRAZOLO[1,5-A]-PYRIDINE-3-CARBOXAMIDES AND USE THEREOF

This application is a U.S. National Stage Application filed under 35 U.S.C. §371 of International Application No. PCT/EP2014/066780, filed Aug. 5, 2014, the contents of which are hereby incorporated herein by reference for all purposes, which claims priority under 35 U.S.C. §119 to European Patent Application Nos. 13179782.1, filed Aug. 8, 2013, and Ser. No. 14/166,893.9, filed May 2, 2014, The present application relates to novel substituted pyrazolo[1,5-a]pyridine-3-carboxamides, to processes for preparation thereof, to the use thereof, alone or in combinations, for treatment and/or prophylaxis of diseases, and to the use thereof for production of medicaments for treatment and/or prophylaxis of diseases, especially for treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory centre. This is of central importance for the activation mechanism. NO is able to bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

Through the formation of cGMP and the resulting regulation of phosphodiesterases, ion channels and protein kinases, guanylate cyclase plays a crucial role in different physiological processes, more particularly in the relaxation and proliferation of smooth muscle cells, in platelet aggregation and platelet adhesion, and in neuronal signal transmission, and also in the event of disorders based on disruption of the abovementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Therapeutic stimulation of soluble guanylate cyclase has to date been accomplished using exclusively compounds such as organic nitrates, the effect of which is based on NO. The latter is formed by bioconversion and activates soluble guanylate cyclase by attack at the central iron atom of haem. In addition to the side effects, the development of tolerance is one of the crucial disadvantages of this mode of treatment.

In the last few years, there have been descriptions of some compounds which stimulate soluble guanylate cyclase directly, i.e. without prior release of NO, for example 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

WO 2012/072512-A1 and WO 2010/117787, among other documents, disclose various pyrazolo[1,5-a]pyridine derivatives which can be used for treatment of disorders.

It was an object of the present invention to provide novel substances which act as stimulators of soluble guanylate cyclase and are suitable as such for treatment and/or prophylaxis of diseases.

The present invention provides compounds of the general formula (I)

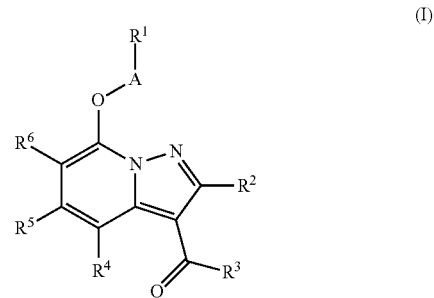

in which

A is $CH_2$, $CD_2$ or $CH(CH_3)$, $R^1$ is $(C_4-C_6)$-alkyl, $(C_3-C_7)$-cycloalkyl, pyridyl or phenyl,
  where $(C_4-C_6)$-alkyl may be substituted up to six times by fluorine,
  where $(C_3-C_7)$-cycloalkyl may be substituted by 1 to 4 substituents each independently selected from fluorine, trifluoromethyl and $(C_1-C_4)$-alkyl,
  where pyridyl is substituted by 1 or 2 substituents each selected independently from the group of halogen, cyano and $(C_1-C_4)$-alkyl,
  and
  where phenyl may be substituted by 1 to 4 substituents each independently selected from the group of halogen, cyano, monofluoromethyl, difluoromethyl, trifluoromethyl, $(C_1-C_4)$-alkyl, $(C_2-C_3)$-alkynyl, $(C_1-C_4)$-alkoxy, $(C_3-C_5)$-cycloalkyl, difluoromethoxy and trifluoromethoxy, or may be substituted on two adjacent carbon atoms in the phenyl by a difluoromethylenedioxy bridge, $R^2$ is hydrogen, $(C_1-C_4)$-alkyl, $(C_1-C_4)$-alkoxymethyl, cyclopropyl, monofluoromethyl, difluoromethyl or trifluoromethyl, $R^3$ is a group of the formula

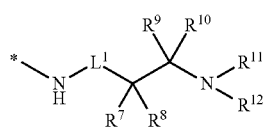

or

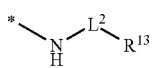

or

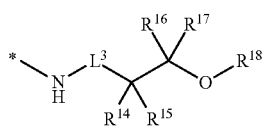

or

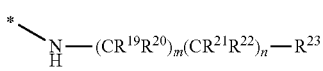

where
* is the attachment site to the carbonyl group,
$L^1$ is a bond, methanediyl or 1,2-ethanediyl,
in which methanediyl and 1,2-ethanediyl may be substituted by 1 or 2 substituents each independently selected from the group of fluorine, trifluoromethyl, $(C_1-C_4)$-alkyl, $(C_3-C_5)$-cycloalkyl, hydroxyl and $(C_1-C_4)$-alkoxy,
$L^2$ is a bond or $(C_1-C_4)$-alkanediyl,
in which $(C_1-C_4)$-alkanediyl may be substituted by 1 to 3 substituents each independently selected from the group of fluorine, trifluoromethyl, $(C_1-C_4)$-alkyl, $(C_3-C_5)$-cycloalkyl, hydroxyl and $(C_1-C_4)$-alkoxy,
$L^3$ is a bond, methanediyl or 1,2-ethanediyl,
in which methanediyl or 1,2-ethanediyl may be substituted by 1 or 2 substituents each independently selected from the group of fluorine, trifluoromethyl, $(C_1-C_4)$-alkyl, $(C_3-C_7)$-cycloalkyl, hydroxyl and $(C_1-C_4)$-alkoxy,
$R^7$ is hydrogen, $(C_1-C_6)$-alkyl, $(C_2-C_6)$-alkenyl, $(C_2-C_6)$-alkynyl, $(C_3-C_7)$-cycloalkyl, 5- or 6-membered heteroaryl or phenyl,
in which $(C_1-C_6)$-alkyl may be substituted by 1 to 3 substituents each independently selected from the group of fluorine, trifluoromethyl, difluoromethoxy, trifluoromethoxy, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy,
in which phenyl, phenoxy and benzyloxy may be substituted by 1 to 3 halogen substituents,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy,
and
in which phenyl and 5- or 6-membered heteroaryl may be substituted by 1 to 3 substituents each independently selected from the group of halogen, cyano, nitro, trifluoromethyl, $(C_1-C_4)$-alkyl, $(C_1-C_4)$-alkoxy, difluoromethoxy, trifluoromethoxy and $(C_1-C_4)$-alkylsulphonyl,
$R^8$ is hydrogen or $(C_1-C_6)$-alkyl,
or
$R^7$ and $R^8$ together with the carbon atom to which they are bonded form a 3- to 7-membered carbocycle or a 4- to 7-membered heterocycle, in which the 3- to 7-membered carbocycle and the 4- to 7-membered heterocycle may in turn be substituted by 1 or 2 substituents each independently selected from the group of fluorine and $(C_1-C_4)$-alkyl,
$R^9$ is hydrogen, $(C_1-C_6)$-alkyl, $(C_3-C_7)$-cycloalkyl, $(C_2-C_6)$-alkenyl, $(C_2-C_6)$-alkynyl, 5- or 6-membered heteroaryl or phenyl,
in which $(C_1-C_6)$-alkyl may be substituted by 1 to 3 substituents each independently selected from the group of fluorine, difluoromethyl, trifluoromethyl, difluoromethoxy, trifluoromethoxy, hydroxyl, $(C_1-C_4)$-alkoxy, benzyloxy, phenoxy and phenyl,
in which benzyloxy, phenoxy and phenyl may be substituted by 1 to 3 halogen substituents,
in which $(C_3-C_7)$-cycloalkyl may be substituted by 1 or 2 fluorine or $(C_1-C_4)$-alkyl substituents,
and
in which phenyl and 5- or 6-membered heteroaryl may be substituted by 1 to 3 substituents each independently selected from the group of halogen, cyano, trifluoromethyl, $(C_1-C_4)$-alkyl, $(C_1-C_4)$-alkoxy and $(C_1-C_4)$-alkylsulphonyl,
$R^{10}$ is hydrogen or $(C_1-C_6)$-alkyl,
or
$R^9$ and $R^{10}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^7$ and $R^9$ together with the carbon atoms to which they are bonded form a 3- to 7-membered carbocycle or a 4- to 7-membered heterocycle,
with the proviso that not more than one of the $R^7$ and $R^8$, $R^9$ and $R^{10}$, and $R^7$ and $R^9$ radical pairs at the same time forms a carbo- or heterocycle,
with the proviso that the $R^7$ and $R^9$ radicals are not at the same time both phenyl or 5- or 6-membered heteroaryl,
$R^{11}$ is hydrogen or $(C_1-C_4)$-alkyl,
in which $(C_1-C_4)$-alkyl may be substituted by 1 to 3 substituents each independently selected from the group of fluorine, trifluoromethyl, hydroxyl and $(C_1-C_4)$-alkoxy,
$R^{12}$ is hydrogen, $(C_1-C_6)$-alkyl, $(C_3-C_7)$-cycloalkyl, phenyl or benzyl,
in which $(C_1-C_6)$-alkyl may be substituted by 1 to 3 substituents each independently selected from the group of fluorine, trifluoromethyl, hydroxyl, $(C_1-C_4)$-alkoxy and phenoxy,
and
in which phenyl and benzyl may be substituted by 1 to 3 substituents each independently selected from the group of halogen and trifluoromethyl,
or
$R^{11}$ and $R^{12}$ together with the nitrogen atom to which they are bonded form a 4- to 7-membered azaheterocycle,
$R^{13}$ is 5- to 9-membered azaheterocyclyl bonded via a ring carbon atom,
in which 5- to 9-membered azaheterocyclyl may be substituted by 1 to 5 substituents each independently selected from the group of fluorine, trifluoromethyl, $(C_1-C_4)$-alkyl, $(C_3-C_7)$-cycloalkyl and benzyl,
and
in which 5- to 9-membered azaheterocyclyl may be fused to a phenyl ring which may in turn be substituted by 1 or 2 substituents selected from halogen, $(C_1-C_4)$-alkyl and trifluoromethyl, $R^{14}$ is hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, —(C=O)NR$^{24}$R$^{25}$, 5- or 6-membered heteroaryl or phenyl, in which $(C_1-C_6)$-alkyl may be substituted by 1 to 3 substituents each independently selected from the group of fluorine, trifluoromethyl, difluoromethoxy, trifluoromethoxy, hydroxyl, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy,
in which phenyl, phenoxy and benzyloxy may in turn be substituted by 1 to 3 halogen substituents,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy,
in which $R^{24}$ is hydrogen, $(C_1-C_4)$-alkyl, $(C_3-C_7)$-cycloalkyl, aryl or naphthyl,
in which $R^{25}$ is hydrogen or methyl,
and
in which phenyl and 5- or 6-membered heteroaryl may be substituted by 1 to 3 substituents each independently selected from the group of halogen, cyano, trifluoromethyl, $(C_1-C_4)$-alkyl, $(C_1-C_4)$-alkoxy and $(C_1-C_4)$-alkylsulphonyl, $R^{15}$ is hydrogen or $(C_1-C_6)$-alkyl,
in which $(C_1-C_4)$-alkyl may be substituted by hydroxyl,
or
$R^{14}$ and $R^{15}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl, $R^{16}$ is hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, 5- or 6-membered heteroaryl or phenyl,
in which $(C_1-C_6)$-alkyl may be substituted by 1 to 3 substituents each independently selected from the group of fluorine, trifluoromethyl, difluoromethoxy, trifluoromethoxy, hydroxyl, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy,
in which phenyl, phenoxy and benzyloxy may in turn be substituted by 1 to 3 halogen substituents,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy,
and
in which phenyl and 5- or 6-membered heteroaryl may be substituted by 1 to 3 substituents each independently selected from the group of halogen, cyano, trifluoromethyl, $(C_1-C_4)$-alkyl, $(C_1-C_4)$-alkoxy and $(C_1-C_4)$-alkylsulphonyl, $R^{17}$ is hydrogen or $(C_1-C_6)$-alkyl,
in which $(C_1-C_4)$-alkyl may be substituted by hydroxyl,
or
$R^{16}$ and $R^{17}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
with the proviso that the $R^{14}$ and $R^{16}$ radicals are not at the same time both phenyl or 5- or 6-membered heteroaryl,
or
$R^{14}$ and $R^{16}$ together with the carbon atoms to which they are bonded form a 3- to 7-membered carbocycle or a 4- to 7-membered heterocycle,
with the proviso that not more than one of the $R^{14}$ and $R^{15}$, $R^{16}$ and $R^{17}$, and $R^{14}$ and $R^{16}$ radical pairs at the same time forms a carbo- or heterocycle, $R^{18}$ is hydrogen or $(C_1-C_4)$-alkyl,
in which $(C_1-C_4)$-alkyl may be substituted by 1 to 5 fluorine substituents, m is 0, 1 or 2,
n is 0 or 1, $R^{19}$ is hydrogen, cyano or $(C_1-C_4)$-alkyl,
in which $(C_1-C_4)$-alkyl may be substituted by 1 to 5 fluorine substituents, $R^{20}$ is hydrogen or $(C_1-C_4)$-alkyl,
in which $(C_1-C_4)$-alkyl may be substituted by 1 to 5 fluorine substituents, $R^{21}$ is hydrogen or $(C_1-C_4)$-alkyl,
in which $(C_1-C_4)$-alkyl may be substituted by 1 to 5 fluorine substituents, $R^{22}$ is hydrogen or $(C_1-C_4)$-alkyl,
in which $(C_1-C_4)$-alkyl may be substituted by 1 to 3 fluorine substituents,
or
$R^{19}$ and $R^{20}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^{21}$ and $R^{22}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^{19}$ and $R^{21}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
with the proviso that not more than one of the $R^{19}$ and $R^{20}$, $R^{21}$ and $R^{22}$, and $R^{19}$ and $R^{21}$ radical pairs at the same time forms a carbo- or heterocycle, $R^{23}$ is $(C_1-C_6)$-alkyl, 5- to 9-membered heterocyclyl bonded via a ring carbon atom, 5- to 9-membered carbocyclyl, phenyl, indanyl or 5- to 10-membered heteroaryl,
where $(C_1-C_6)$-alkyl may be substituted by 1 to 3 substituents independently selected from the group of fluorine, trifluoromethyl and cyano,
where phenyl may be substituted by 1 to 3 substituents each independently selected from the group of halogen, cyano, trifluoromethyl, difluoromethyl, $(C_1-C_6)$-alkyl, $(C_1-C_4)$-alkylcarbonyl, $(C_1-C_4)$-alkoxycarbonyl, hydroxycarbonyl, —(C=O)NR$^{26}$R$^{27}$, $(C_1-C_4)$- alkylsulphonyl, $(C_3-C_6)$-cycloalkylsulphonyl, $(C_1-C_4)$-alkylthio, $(C_1-C_4)$-alkoxy, trifluoromethoxy, difluoromethoxy, phenoxy, hydroxyl, 5- to 10-membered heteroaryl and $(C_3-C_7)$-cycloalkyl, in which $(C_1-C_6)$-alkyl may be substituted by 1 or 2 substituents each independently selected from the group of fluorine, trifluoromethoxy, $(C_1-C_4)$-alkylcarbonyl, $-(C=O)NR^{26}R^{27}$, $(C_1-C_4)$-alkoxy, $(C_3-C_6)$-cycloalkyl, morpholinyl, piperidinyl, pyrrolidinyl, piperazinyl, phenyl, hydroxyl and amino, in which phenyl may be substituted by 1 to 3 halogen substituents, in which amino may be substituted by 1 or 2 substituents each independently selected from $(C_1-C_6)$-alkyl, $(C_1-C_4)$-alkylcarbonyl, $(C_3-C_6)$-cycloalkylsulphonyl, $(C_1-C_4)$-alkylsulphonyl and methoxy-$(C_1-C_4)$-alkyl, in which $(C_3-C_6)$-cycloalkyl may be substituted by amino or hydroxyl, and in which $R^{26}$ and $R^{27}$ are each independently hydrogen, $(C_1-C_4)$-alkyl or $(C_3-C_7)$-cycloalkyl, where indanyl may be substituted by 1 or 2 substituents each independently selected from the group of fluorine, trifluoromethyl and hydroxyl, where 5- to 10-membered heteroaryl may be substituted by 1 to 3 substituents each independently selected from the group of fluorine, chlorine, cyano, $(C_1-C_6)$-alkyl, trifluoromethyl, $(C_1-C_4)$-alkoxy, amino, $(C_1-C_4)$-alkoxycarbonyl, hydroxycarbonyl, $-(C=O)NR^{25}R^{26}$, phenyl, pyridyl, pyrimidyl, 1,3-thiazol-5-yl and $(C_3-C_7)$-cycloalkyl, in which $(C_1-C_6)$-alkyl may be substituted by 1 to 3 substituents each independently selected from the group of halogen, cyano, hydroxyl, amino, trifluoromethyl, difluoromethyl, $(C_1-C_4)$-alkylsulphonyl, $(C_1-C_4)$-alkylcarbonyl, $(C_1-C_4)$-alkoxycarbonyl, hydroxycarbonyl, $(C_1-C_4)$-alkylthio, $(C_1-C_4)$-alkoxy, trifluoromethoxy, difluoromethoxy, phenoxy, phenyl, pyridyl, pyrimidyl, 5-membered heteroaryl, tetrahydrothiophenyl-1,1-dioxide, $(C_3-C_7)$-cycloalkyl, morpholinyl, piperidinyl, pyrrolidinyl, 2-oxopyrrolidin-1-yl, piperazinyl, tetrahydrothiophenyl-1,1-dioxide, thiomorpholinyl-1,1-dioxide and azetidine, in which 5-membered heteroaryl may be substituted by 1 to 3 substituents each independently selected from the group of halogen, $(C_1-C_4)$-alkyl and $(C_1-C_4)$-alkoxy, in which piperidinyl may be substituted by 1 to 4 fluorine substituents, in which phenyl may be substituted by 1 to 3 substituents each independently selected from the group of halogen, $(C_1-C_4)$-alkyl and $(C_1-C_4)$-alkoxy, in which azetidine may be substituted by hydroxyl, in which piperazinyl may be substituted by 1 to 3 substituents each independently selected from the group of $(C_1-C_4)$-alkyl, $(C_3-C_7)$-cycloalkyl and trifluoromethyl, and in which $R^{26}$ and $R^{27}$ are each independently hydrogen, $(C_1-C_4)$-alkyl or $(C_3-C_7)$-cycloalkyl, where 5- to 9-membered heterocyclyl bonded via a ring carbon atom may be substituted by 1 or 2 substituents each independently selected from the group of oxo, fluorine, hydroxyl and $(C_1-C_4)$-alkyl, and where 5- to 9-membered carbocyclyl may be substituted by 1 or 2 substituents each independently selected from the group of trifluoromethyl, fluorine, hydroxyl, hydroxycarbonyl, $(C_1-C_4)$-alkoxycarbonyl and $(C_1-C_4)$-alkyl, $R^4$ is hydrogen, $R^5$ is hydrogen, halogen, cyano, difluoromethyl, trifluoromethyl, $(C_1-C_4)$-alkyl, $(C_3-C_7)$-cycloalkyl, $(C_2-C_4)$-alkynyl, $(C_1-C_4)$-alkylamino, difluoromethoxy, trifluoromethoxy, $(C_1-C_4)$-alkoxy, amino, 4- to 7-membered heterocyclyl or 5- or 6-membered heteroaryl, $R^6$ is hydrogen, cyano or halogen, and the N-oxides, salts, solvates, salts of the N-oxides and solvates of the N-oxides or salts thereof.

The present invention provides compounds of the general formula (I)

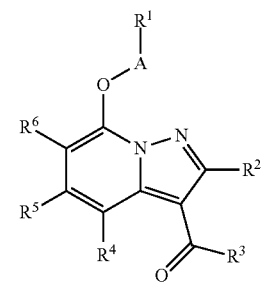

in which

A is $CH_2$, $CD_2$ or $CH(CH_3)$, $R^1$ is $(C_4-C_6)$-alkyl, $(C_3-C_7)$-cycloalkyl, pyridyl or phenyl, where $(C_4-C_6)$-alkyl may be substituted up to six times by fluorine, where $(C_3-C_7)$-cycloalkyl may be substituted by 1 to 4 substituents each independently selected from fluorine, trifluoromethyl and $(C_1-C_4)$-alkyl, where pyridyl is substituted by 1 or 2 substituents each selected independently from the group of halogen, cyano and $(C_1-C_4)$-alkyl, and where phenyl may be substituted by 1 to 4 substituents each independently selected from the group of halogen, cyano, monofluoromethyl, difluoromethyl, trifluoromethyl, $(C_1-C_4)$-alkyl, $(C_2-C_3)$-alkynyl, $(C_1-C_4)$-alkoxy, $(C_3-C_5)$-cycloalkyl, difluoromethoxy and trifluoromethoxy, or may be substituted on two adjacent carbon atoms in the phenyl by a difluoromethylenedioxy bridge, $R^2$ is hydrogen, $(C_1-C_4)$-alkyl, $(C_1-C_4)$-alkoxymethyl, cyclopropyl, cyclobutyl, monofluoromethyl, difluoromethyl or trifluoromethyl, $R^3$ is a group of the formula

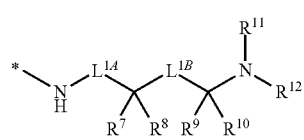

or

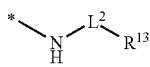

or

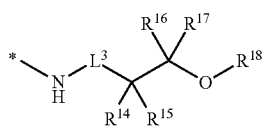

or

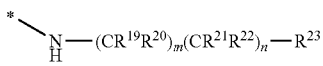

where

* is the attachment site to the carbonyl group,
$L^{1A}$ is a bond, methanediyl, 1,2-ethanediyl or 1,3-propanediyl,
  in which methanediyl, 1,2-ethanediyl or 1,3-propanediyl may be substituted by 1 or 2 substituents each independently selected from the group of fluorine, trifluoromethyl, $(C_1-C_4)$-alkyl, $(C_3-C_5)$-cycloalkyl, hydroxyl and $(C_1-C_4)$-alkoxy,
$L^{1B}$ is a bond, methanediyl or 1,2-ethanediyl,
$L^2$ is a bond or $(C_1-C_4)$-alkanediyl,
  in which $(C_1-C_4)$-alkanediyl may be substituted by 1 to 3 substituents each independently selected from the group of fluorine, trifluoromethyl, $(C_1-C_4)$-alkyl, $(C_3-C_5)$-cycloalkyl, hydroxyl and $(C_1-C_4)$-alkoxy,
$L^3$ is a bond, methanediyl or 1,2-ethanediyl,
  in which methanediyl or 1,2-ethanediyl may be substituted by 1 or 2 substituents each independently selected from the group of fluorine, trifluoromethyl, hydroxyl, $(C_1-C_4)$-alkyl, $(C_3-C_7)$-cycloalkyl, hydroxyl and $(C_1-C_4)$-alkoxy,
$R^7$ is hydrogen, $(C_1-C_6)$-alkyl, $(C_3-C_7)$-cycloalkyl, $(C_2-C_6)$-alkenyl, $(C_2-C_6)$-alkynyl, cyano, 5- to 10-membered heteroaryl or phenyl,
  in which $(C_1-C_6)$-alkyl may be substituted by 1 or 2 substituents each independently selected from the group of difluoromethoxy, trifluoromethoxy, hydroxyl, $(C_1-C_4)$-alkoxy, $(C_1-C_4)$-alkoxycarbonyl, $(C_1-C_4)$-alkylsulphonyl, $(C_1-C_4)$-alkylthio, benzyloxy, phenoxy, 5- or 6-membered heteroaryl and phenyl, and may be substituted up to six times by fluorine,
    in which benzyloxy, phenoxy, 5- or 6-membered heteroaryl and phenyl may be substituted by 1 to 3 substituents each independently selected from the group of halogen and $(C_1-C_4)$-alkoxy,
  in which $(C_3-C_7)$-cycloalkyl may be substituted by 1 or 2 fluorine, trifluoromethyl, $(C_1-C_4)$-alkyl or $(C_1-C_4)$-alkoxy substituents,
  in which phenyl and 5- to 10-membered heteroaryl may be substituted by 1 to 4 substituents each independently selected from the group of halogen, cyano, nitro, trifluoromethyl, $(C_1-C_4)$-alkyl, $(C_2-C_4)$-alkenyl, $(C_1-C_4)$-alkoxy, difluoromethoxy, trifluoromethoxy, $(C_1-C_4)$-alkoxycarbonyl and $(C_1-C_4)$-alkylsulphonyl,
    in which $(C_1-C_4)$-alkoxy may be substituted by hydroxyl,
  and
  in which phenyl may be substituted on two adjacent carbon atoms in the phenyl by a methylenedioxy bridge or ethylenedioxy bridge,
  or
  may be fluorine when $L^{1A}$ is not a bond,
$R^8$ is hydrogen or $(C_1-C_6)$-alkyl,
  or
  may be fluorine when $L^{1A}$ is not a bond,
or
$R^7$ and $R^8$ together with the carbon atom to which they are bonded form a 3- to 7-membered carbocycle or a 4- to 7-membered heterocycle,
  in which the 3- to 7-membered carbocycle and the 4- to 7-membered heterocycle may in turn be substituted by 1 or 2 substituents each independently selected from the group of fluorine and $(C_1-C_4)$-alkyl,
$R^9$ is hydrogen, $(C_1-C_6)$-alkyl, $(C_3-C_7)$-cycloalkyl, $(C_2-C_6)$-alkenyl, $(C_2-C_6)$-alkynyl, cyano, 5- to 10-membered heteroaryl or phenyl,
  in which $(C_1-C_6)$-alkyl may be substituted by 1 or 2 substituents each independently selected from the group of difluoromethoxy, trifluoromethoxy, hydroxyl, $(C_1-C_4)$-alkoxy, $(C_1-C_4)$-alkoxycarbonyl, $(C_1-C_4)$-alkylsulphonyl, hydroxyl, $(C_1-C_4)$-alkylthio, benzyloxy, phenoxy, 5- or 6-membered heteroaryl and phenyl, and may be substituted up to six times by fluorine,
    in which benzyloxy, phenoxy, 5- or 6-membered heteroaryl and phenyl may be substituted by 1 to 3 substituents each independently selected from the group of halogen and $(C_1-C_4)$-alkoxy,
  in which $(C_3-C_7)$-cycloalkyl may be substituted by 1 or 2 fluorine, trifluoromethyl, $(C_1-C_4)$-alkyl or $(C_1-C_4)$-alkoxy substituents,
  in which phenyl and 5- to 10-membered heteroaryl may be substituted by 1 to 4 substituents each independently selected from the group of halogen, cyano, nitro, trifluoromethyl, $(C_1-C_4)$-alkyl, $(C_2-C_4)$-alkenyl, $(C_1-C_4)$-alkoxy, difluoromethoxy, trifluoromethoxy, $(C_1-C_4)$-alkoxycarbonyl and $(C_1-C_4)$-alkylsulphonyl,
    in which $(C_1-C_4)$-alkoxy may be substituted by hydroxyl,
  and
  in which phenyl may be substituted on two adjacent carbon atoms in the phenyl by a methylenedioxy bridge or ethylenedioxy bridge,
$R^{10}$ is hydrogen or $(C_1-C_6)$-alkyl,
or
$R^9$ and $R^{10}$ together with the carbon atom to which they are bonded form a 3- to 7-membered carbocycle or a 4- to 7-membered heterocycle,
  in which the 3- to 7-membered carbocycle and the 4- to 7-membered heterocycle may in turn be substituted by 1 or 2 substituents each independently selected from the group of fluorine and $(C_1-C_4)$-alkyl,
or
$R^7$ and $R^9$ together with the carbon atoms to which they are bonded form a 3- to 7-membered carbocycle or a 4- to 7-membered heterocycle,
  in which the 3- to 7-membered carbocycle and the 4- to 7-membered heterocycle may be substituted by 1 or 2 $(C_1-C_4)$-alkyl substituents,
  and in which the 3- to 7-membered carbocycle and the 4- to 7-membered heterocycle may be fused to a phenyl ring or a pyridyl ring, which may in turn be substituted by 1 or 2 substituents selected from halogen, $(C_1-C_4)$-alkyl and trifluoromethyl, with the proviso that not more than one of the $R^7$ and $R^8$, $R^9$ and $R^{10}$, and $R^7$ and $R^9$ radical pairs at the same time forms a carbo- or heterocycle, with the proviso that the $R^7$ and $R^9$ radicals are not at the same time both phenyl or 5- or 6-membered heteroaryl, $R^{11}$ is hydrogen or $(C_1-C_4)$-alkyl,
   in which $(C_1-C_4)$-alkyl may be substituted by 1 or 2 substituents each independently selected from the group of hydroxyl and $(C_1-C_4)$-alkoxy, and may be substituted up to six times by fluorine, $R^{12}$ is hydrogen, $(C_1-C_6)$-alkyl, $(C_1-C_4)$-alkylcarbonyl, $(C_1-C_4)$-alkoxycarbonyl, $(C_3-C_7)$-cycloalkyl, phenyl or benzyl,
   in which $(C_1-C_6)$-alkyl may be substituted by 1 to 3 substituents each independently selected from the group of fluorine, trifluoromethyl, hydroxyl, $(C_1-C_4)$-alkoxy and phenoxy,
   and
   in which phenyl and benzyl may be substituted by 1 to 3 substituents each independently selected from the group of halogen and trifluoromethyl,
or
$R^{11}$ and $R^{12}$ together with the nitrogen atom to which they are bonded form a 4- to 7-membered azaheterocycle,
   in which the 4- to 7-membered azaheterocycle may be substituted by $(C_1-C_4)$-alkyl, $R^{13}$ is 5- to 10-membered azaheterocyclyl bonded via a ring carbon atom,
   in which 5- to 10-membered azaheterocyclyl bonded via a ring carbon atom may be substituted by 1 to 2 trifluoromethyl, $(C_3-C_7)$-cycloalkyl, oxo and benzyl substituents, and up to four times by $(C_1-C_4)$-alkyl and up to twice by fluorine,
   in which 5- to 10-membered azaheterocyclyl may be fused to a phenyl ring or a pyridyl ring, which may in turn be substituted by 1 or 2 substituents selected from halogen, $(C_1-C_4)$-alkyl, $(C_1-C_4)$-alkoxy and trifluoromethyl,
or
   may be amino when $L^2$ is a bond,
   in which amino may be substituted by $(C_1-C_{10})$-alkyl, $(C_1-C_4)$-alkylcarbonyl, $(C_3-C_6)$-carbocyclyl, 4- to 7-membered heterocyclyl, phenyl or 5- or 6-membered heteroaryl,
      in which $(C_1-C_4)$-alkylcarbonyl may be substituted by monoalkylamino or dialkylamino,
      in which $(C_3-C_6)$-carbocyclyl and 4- to 7-membered heterocyclyl may be substituted by hydroxyl,
      and
      in which phenyl and 5- or 6-membered heteroaryl may be substituted by 1 to 3 substituents each independently selected from the group of halogen, $(C_1-C_4)$-alkyl and trifluoromethyl, $R^{14}$ is hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, —(C=O)NR$^{24}$R$^{25}$, 5- or 6-membered heteroaryl or phenyl,
   in which $(C_1-C_6)$-alkyl may be substituted by 1 or 2 substituents each independently selected from the group of difluoromethoxy, trifluoromethoxy, hydroxyl, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy, and may be substituted up to six times by fluorine,
   in which phenyl, phenoxy and benzyloxy may in turn be substituted by 1 to 3 halogen substituents,
   in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy,
   in which $R^{24}$ is hydrogen, $(C_1-C_4)$-alkyl, $(C_3-C_7)$-cycloalkyl, aryl or naphthyl,
   in which $R^{25}$ is hydrogen or methyl,
   and
   in which phenyl and 5- or 6-membered heteroaryl may be substituted by 1 to 3 substituents each independently selected from the group of halogen, cyano, trifluoromethyl, $(C_1-C_4)$-alkyl, $(C_1-C_4)$-alkoxy and $(C_1-C_4)$-alkylsulphonyl, $R^{15}$ is hydrogen or $(C_1-C_6)$-alkyl,
   in which $(C_1-C_4)$-alkyl may be substituted by hydroxyl,
or
$R^{14}$ and $R^{15}$ together with the carbon atom to which they are bonded form a 3- to 7-membered carbocycle or a 4- to 7-membered heterocycle,
   in which the 3- to 7-membered carbocycle and the 4- to 7-membered heterocycle may in turn be substituted by 1 or 2 substituents each independently selected from the group of fluorine and $(C_1-C_4)$-alkyl, $R^{16}$ is hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, 5- or 6-membered heteroaryl or phenyl,
   in which $(C_1-C_6)$-alkyl may be substituted by 1 or 2 substituents each independently selected from the group of fluorine, trifluoromethyl, difluoromethoxy, trifluoromethoxy, hydroxyl, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy, and may be substituted up to six times by fluorine,
   in which phenyl, phenoxy and benzyloxy may in turn be substituted by 1 to 3 halogen substituents,
   in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy,
   and
   in which phenyl and 5- or 6-membered heteroaryl may be substituted by 1 to 3 substituents each independently selected from the group of halogen, cyano, trifluoromethyl, $(C_1-C_4)$-alkyl, $(C_1-C_4)$-alkoxy and $(C_1-C_4)$-alkylsulphonyl, $R^{17}$ is hydrogen or $(C_1-C_6)$-alkyl,
   in which $(C_1-C_4)$-alkyl may be substituted by hydroxyl,
or
$R^{16}$ and $R^{17}$ together with the carbon atom to which they are bonded form a 3- to 7-membered carbocycle or a 4- to 7-membered heterocycle,
   in which the 3- to 7-membered carbocycle and the 4- to 7-membered heterocycle may in turn be substituted by 1 or 2 substituents each independently selected from the group of fluorine and $(C_1-C_4)$-alkyl, with the proviso that the $R^{14}$ and $R^{16}$ radicals are not at the same time both phenyl or 5- or 6-membered heteroaryl,
or
$R^{14}$ and $R^{16}$ together with the carbon atoms to which they are bonded form a 3- to 7-membered carbocycle or a 4- to 7-membered heterocycle, with the proviso that not more than one of the $R^{14}$ and $R^{15}$, $R^{16}$ and $R^{17}$, and $R^{14}$ and $R^{16}$ radical pairs at the same time forms a carbo- or heterocycle, $R^{18}$ is hydrogen or $(C_1-C_4)$-alkyl,
  in which $(C_1-C_4)$-alkyl may be substituted by 1 to 5 fluorine substituents, m is 0, 1 or 2, n is 0 or 1, $R^{19}$ is hydrogen, cyano or $(C_1-C_6)$-alkyl,
  in which $(C_1-C_6)$-alkyl may be substituted by 1 to 5 fluorine substituents, $R^{20}$ is hydrogen or $(C_1-C_4)$-alkyl,
  in which $(C_1-C_4)$-alkyl may be substituted by 1 to 5 fluorine substituents, $R^{21}$ is hydrogen or $(C_1-C_6)$-alkyl,
  in which $(C_1-C_6)$-alkyl may be substituted by 1 to 5 fluorine substituents, $R^{22}$ is hydrogen or $(C_1-C_4)$-alkyl,
  in which $(C_1-C_4)$-alkyl may be substituted by 1 to 5 fluorine substituents, or $R^{19}$ and $R^{20}$ together with the carbon atom to which they are bonded form a 3- to 7-membered carbocycle or a 4- to 7-membered heterocycle,
  in which the 3- to 7-membered carbocycle and the 4- to 7-membered heterocycle may in turn be substituted by 1 or 2 substituents each independently selected from the group of fluorine and $(C_1-C_4)$-alkyl, or $R^{21}$ and $R^{22}$ together with the carbon atom to which they are bonded form a 3- to 7-membered carbocycle or a 4- to 7-membered heterocycle,
  in which the 3- to 7-membered carbocycle and the 4- to 7-membered heterocycle may in turn be substituted by 1 or 2 substituents each independently selected from the group of fluorine and $(C_1-C_4)$-alkyl, or $R^{19}$ and $R^{21}$ together with the carbon atom to which they are bonded form a 3- to 7-membered carbocycle or a 4- to 7-membered heterocycle,
  in which the 3- to 7-membered carbocycle and the 4- to 7-membered heterocycle may in turn be substituted by 1 or 2 substituents each independently selected from the group of fluorine and $(C_1-C_4)$-alkyl, with the proviso that not more than one of the $R^{19}$ and $R^{20}$, $R^{21}$ and $R^{22}$, and $R^{19}$ and $R^{21}$ radical pairs at the same time forms a carbo- or heterocycle, $R^{23}$ is $(C_1-C_6)$-alkyl, $(C_1-C_6)$-alkoxy, $(C_1-C_4)$-alkoxycarbonyl, hydroxycarbonyl, aminocarbonyl, aminosulphonyl, 5- to 10-membered heterocyclyl bonded via a ring carbon atom, 5- to 10-membered carbocyclyl, phenyl or 5- to 10-membered heteroaryl,
  in which $(C_1-C_6)$-alkyl may be substituted by cyano, and up to six times by fluorine,
  in which $(C_1-C_6)$-alkoxy may be substituted by hydroxyl, amino, monoalkylamino, dialkylamino, cyclopropyl, phenyl or $(C_2-C_4)$-alkenyl,
  in which aminocarbonyl may be substituted by $(C_1-C_6)$-alkyl or $(C_3-C_6)$-cycloalkyl,
  in which aminosulphonyl may be substituted by $(C_1-C_6)$-alkyl or $(C_3-C_6)$-cycloalkyl,
  in which phenyl may be substituted by 1 to 3 substituents each independently selected from the group of halogen, cyano, trifluoromethyl, difluoromethyl, $(C_1-C_6)$-alkyl, $(C_1-C_4)$-alkylcarbonyl, $(C_1-C_4)$-alkoxycarbonyl, hydroxycarbonyl, —(C=O)NR$^{26}$R$^{27}$, $(C_1-C_4)$-alkylsulphonyl, $(C_3-C_6)$-cycloalkylsulphonyl, $(C_1-C_4)$-alkylthio, $(C_1-C_4)$-alkoxy, trifluoromethoxy, difluoromethoxy, phenoxy, hydroxyl, 5- to 10-membered heteroaryl, 4- to 7-membered heterocyclyl and $(C_3-C_7)$-cycloalkyl,
  in which $(C_1-C_6)$-alkyl may be substituted by 1 or 2 substituents each independently selected from the group of fluorine, trifluoromethoxy, $(C_1-C_4)$-alkylcarbonyl, —(C=O)NR$^{26}$R$^{27}$, $(C_1-C_4)$-alkoxy, $(C_3-C_6)$-cycloalkyl, morpholinyl, piperidinyl, pyrrolidinyl, piperazinyl, phenyl, hydroxyl and amino,
    in which phenyl may be substituted by 1 to 3 halogen substituents,
    in which amino may be substituted by 1 or 2 substituents each independently selected from $(C_1-C_6)$-alkyl, $(C_1-C_4)$-alkylcarbonyl, $(C_3-C_6)$-cycloalkylsulphonyl, $(C_1-C_4)$-alkylsulphonyl and methoxy-$(C_1-C_4)$-alkyl,
    in which $(C_3-C_6)$-cycloalkyl may be substituted by amino or hydroxyl,
    and in which
    $R^{26}$ and $R^{27}$ are each independently hydrogen, $(C_1-C_4)$-alkyl or $(C_3-C_7)$-cycloalkyl,
  in which 5- to 10-membered heteroaryl may be substituted by 1 to 3 substituents each independently selected from the group of fluorine, chlorine, cyano, $(C_1-C_6)$-alkyl, trifluoromethyl, $(C_1-C_4)$-alkoxy, amino, $(C_1-C_4)$-alkoxycarbonyl, hydroxycarbonyl, —(C=O)NR$^{25}$R$^{26}$, phenyl, pyridyl, pyrimidyl, 1,3-thiazol-5-yl and $(C_3-C_7)$-cycloalkyl,
    in which $(C_1-C_6)$-alkyl may be substituted by 1 to 3 substituents each independently selected from the group of halogen, cyano, hydroxyl, amino, trifluoromethyl, difluoromethyl, $(C_1-C_4)$-alkylsulphonyl, $(C_1-C_4)$-alkylcarbonyl, $(C_1-C_4)$-alkoxycarbonyl, hydroxycarbonyl, $(C_1-C_4)$-alkylthio, $(C_1-C_4)$-alkoxy, trifluoromethoxy, difluoromethoxy, phenoxy, phenyl, pyridyl, pyrimidyl, 5-membered heteroaryl, tetrahydrothiophenyl-1,1-dioxide, $(C_3-C_7)$-cycloalkyl, morpholinyl, piperidinyl, pyrrolidinyl, 2-oxopyrrolidin-1-yl, piperazinyl, tetrahydrothiophenyl-1,1-dioxide, thiomorpholinyl-1,1-dioxide and azetidine,
    in which 5-membered heteroaryl may be substituted by 1 to 3 substituents each independently selected from the group of halogen, $(C_1-C_4)$-alkyl and $(C_1-C_4)$-alkoxy,
    in which piperidinyl may be substituted by 1 to 4 fluorine substituents,
    in which phenyl may be substituted by 1 to 3 substituents each independently selected from the group of halogen, $(C_1-C_4)$-alkyl and $(C_1-C_4)$-alkoxy,
    in which azetidine may be substituted by hydroxyl,
    in which piperazinyl may be substituted by 1 to 3 substituents each independently selected from the group of $(C_1-C_4)$-alkyl, $(C_3-C_7)$-cycloalkyl and trifluoromethyl,
    and in which
    $R^{26}$ and $R^{27}$ are each independently hydrogen, $(C_1-C_4)$-alkyl or $(C_3-C_7)$-cycloalkyl,
  in which 5- to 10-membered heterocyclyl bonded via a ring carbon atom may be substituted by 1 to 3 substituents each independently selected from the group of oxo, fluorine, trifluoromethyl, hydroxyl and $(C_1-C_4)$-alkyl,
  in which 5- to 10-membered heterocyclyl bonded via a ring carbon atom may be fused to a phenyl ring or a pyridyl ring, which may in turn be substituted by 1 to 3 substituents selected from the group of halogen, $(C_1-C_4)$-alkyl and trifluoromethyl, and in which 5- to 10-membered carbocyclyl may be substituted by 1 to 3 substituents each independently selected from the group of trifluoromethyl, fluorine, cyano, hydroxyl, hydroxycarbonyl, $(C_1-C_4)$-alkoxycarbonyl, amino and $(C_1-C_4)$-alkyl, in which $(C_1-C_4)$-alkyl may be substituted by hydroxyl or hydroxycarbonyl, in which 5- to 10-membered carbocyclyl may be fused to a phenyl ring or a pyridyl ring, which may in turn be substituted by 1 to 3 substituents selected from the group of halogen, $(C_1-C_4)$-alkyl, $(C_1-C_4)$-alkoxy and trifluoromethyl, $R^4$ is hydrogen, $R^5$ is hydrogen, halogen, cyano, difluoromethyl, trifluoromethyl, $(C_1-C_4)$-alkyl, $(C_3-C_7)$-cycloalkyl, $(C_2-C_4)$-alkynyl, $(C_1-C_4)$-alkylamino, difluoromethoxy, trifluoromethoxy, $(C_1-C_4)$-alkoxy, amino, 4- to 7-membered heterocyclyl or 5- or 6-membered heteroaryl, $R^6$ is hydrogen, cyano or halogen, and the N-oxides, salts, solvates, salts of the N-oxides and solvates of the N-oxides or salts thereof.

The present invention provides compounds of the general formula (I)

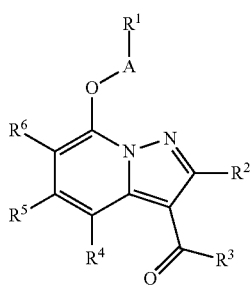

(I)

in which

A is $CH_2$, $CD_2$ or $CH(CH_3)$, $R^1$ is $(C_4-C_6)$-alkyl, $(C_3-C_7)$-cycloalkyl, pyridyl or phenyl, where $(C_4-C_6)$-alkyl may be substituted up to six times by fluorine, where $(C_3-C_7)$-cycloalkyl may be substituted by 1 to 4 substituents each independently selected from fluorine, trifluoromethyl and $(C_1-C_4)$-alkyl, where pyridyl is substituted by 1 or 2 substituents each selected independently from the group of halogen, cyano and $(C_1-C_4)$-alkyl, and where phenyl may be substituted by 1 to 4 substituents each independently selected from the group of halogen, cyano, monofluoromethyl, difluoromethyl, trifluoromethyl, $(C_1-C_4)$-alkyl, $(C_2-C_3)$-alkynyl, $(C_1-C_4)$-alkoxy, $(C_3-C_5)$-cycloalkyl, difluoromethoxy and trifluoromethoxy, or may be substituted on two adjacent carbon atoms in the phenyl by a difluoromethylenedioxy bridge, $R^2$ is hydrogen, $(C_1-C_4)$-alkyl, $(C_1-C_4)$-alkoxymethyl, cyclopropyl, cyclobutyl, monofluoromethyl, difluoromethyl or trifluoromethyl, $R^3$ is a group of the formula

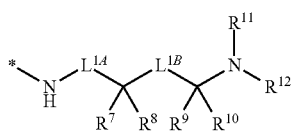

or

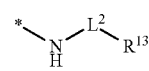

or

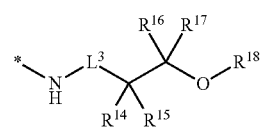

or

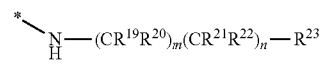

where

* is the attachment site to the carbonyl group, $L^{1A}$ is a bond, methanediyl, 1,2-ethanediyl or 1,3-propanediyl, in which methanediyl, 1,2-ethanediyl or 1,3-propanediyl may be substituted by 1 or 2 substituents each independently selected from the group of fluorine, trifluoromethyl, $(C_1-C_4)$-alkyl, $(C_3-C_5)$-cycloalkyl, hydroxyl and $(C_1-C_4)$-alkoxy, $L^{1B}$ is a bond, methanediyl or 1,2-ethanediyl, $L^2$ is a bond or $(C_1-C_4)$-alkanediyl, in which $(C_1-C_4)$-alkanediyl may be substituted by 1 to 3 substituents each independently selected from the group of fluorine, trifluoromethyl, $(C_1-C_4)$-alkyl, $(C_3-C_5)$-cycloalkyl, hydroxyl and $(C_1-C_4)$-alkoxy, $L^3$ is a bond, methanediyl or 1,2-ethanediyl, in which methanediyl or 1,2-ethanediyl may be substituted by 1 or 2 substituents each independently selected from the group of fluorine, trifluoromethyl, $(C_1-C_4)$-alkyl, $(C_3-C_7)$-cycloalkyl, hydroxyl and $(C_1-C_4)$-alkoxy, $R^7$ is hydrogen, $(C_1-C_6)$-alkyl, $(C_3-C_7)$-cycloalkyl, $(C_2-C_6)$-alkenyl, $(C_2-C_6)$-alkynyl, cyano, 5- to 10-membered heteroaryl or phenyl, in which $(C_1-C_6)$-alkyl may be substituted by 1 or 2 substituents each independently selected from the group of difluoromethoxy, trifluoromethoxy, hydroxyl, $(C_1-C_4)$-alkoxy, $(C_1-C_4)$-alkoxycarbonyl, $(C_1-C_4)$-alkylsulphonyl, $(C_1-C_4)$-alkylthio, benzyloxy, phenoxy, 5- or 6-membered heteroaryl and phenyl, and may be substituted up to six times by fluorine, in which benzyloxy, phenoxy, 5- or 6-membered heteroaryl and phenyl may be substituted by 1 to 3 substituents each independently selected from the group of halogen and $(C_1-C_4)$-alkoxy, in which $(C_3-C_7)$-cycloalkyl may be substituted by 1 or 2 fluorine, trifluoromethyl, $(C_1-C_4)$-alkyl or $(C_1-C_4)$-alkoxy substituents, in which phenyl and 5- to 10-membered heteroaryl may be substituted by 1 to 4 substituents each independently selected from the group of halogen, cyano, nitro, trifluoromethyl, difluoromethyl, $(C_1-C_4)$-alkyl, $(C_2-C_4)$-alkenyl, $(C_1-C_4)$-alkoxy, difluoromethoxy, trifluoromethoxy, $(C_1-C_4)$-alkoxycarbonyl and $(C_1-C_4)$-alkylsulphonyl,
  in which $(C_1-C_4)$-alkoxy may be substituted by hydroxyl,
  in which $(C_1-C_4)$-alkyl may be substituted by amino or hydroxyl,
  and
  in which phenyl may be substituted on two adjacent carbon atoms in the phenyl by a methylenedioxy bridge or ethylenedioxy bridge,
or
  may be fluorine when $L^{1.4}$ is not a bond,
$R^8$ is hydrogen or $(C_1-C_6)$-alkyl,
or
  may be fluorine when $L^{1.4}$ is not a bond,
or
$R^7$ and $R^8$ together with the carbon atom to which they are bonded form a 3- to 7-membered carbocycle or a 4- to 7-membered heterocycle,
  in which the 3- to 7-membered carbocycle and the 4- to 7-membered heterocycle may in turn be substituted by 1 or 2 substituents each independently selected from the group of fluorine and $(C_1-C_4)$-alkyl,
$R^9$ is hydrogen, $(C_1-C_6)$-alkyl, $(C_3-C_7)$-cycloalkyl, $(C_2-C_6)$-alkenyl, $(C_2-C_6)$-alkynyl, cyano, 5- to 10-membered heteroaryl or phenyl,
  in which $(C_1-C_6)$-alkyl may be substituted by 1 or 2 substituents each independently selected from the group of difluoromethoxy, trifluoromethoxy, hydroxyl, $(C_1-C_4)$-alkoxy, $(C_1-C_4)$-alkoxycarbonyl, $(C_1-C_4)$-alkylsulphonyl, $(C_1-C_4)$-alkylthio, benzyloxy, phenoxy, 5- or 6-membered heteroaryl and phenyl, and may be substituted up to six times by fluorine,
    in which benzyloxy, phenoxy, 5- or 6-membered heteroaryl and phenyl may be substituted by 1 to 3 substituents each independently selected from the group of halogen and $(C_1-C_4)$-alkoxy,
  in which $(C_3-C_7)$-cycloalkyl may be substituted by 1 or 2 fluorine, trifluoromethyl, $(C_1-C_4)$-alkyl or $(C_1-C_4)$-alkoxy substituents,
  in which phenyl and 5- to 10-membered heteroaryl may be substituted by 1 to 4 substituents each independently selected from the group of halogen, cyano, nitro, trifluoromethyl, $(C_1-C_4)$-alkyl, $(C_2-C_4)$-alkenyl, $(C_1-C_4)$-alkoxy, difluoromethoxy, trifluoromethoxy, $(C_1-C_4$-alkoxycarbonyl and $(C_1-C_4)$-alkylsulphonyl,
    in which $(C_1-C_4)$-alkoxy may be substituted by hydroxyl,
    and
    in which phenyl may be substituted on two adjacent carbon atoms in the phenyl by a methylenedioxy bridge or ethylenedioxy bridge,
$R^{10}$ is hydrogen or $(C_1-C_6)$-alkyl,
or
$R^9$ and $R^{10}$ together with the carbon atom to which they are bonded form a 3- to 7-membered carbocycle or a 4- to 7-membered heterocycle,
  in which the 3- to 7-membered carbocycle and the 4- to 7-membered heterocycle may in turn be substituted by 1 or 2 substituents each independently selected from the group of fluorine and $(C_1-C_4)$-alkyl,
or
$R^7$ and $R^9$ together with the carbon atoms to which they are bonded form a 3- to 7-membered carbocycle or a 4- to 7-membered heterocycle,
  in which the 3- to 7-membered carbocycle and the 4- to 7-membered heterocycle may be substituted by 1 or 2 $(C_1-C_4)$-alkyl substituents,
  and
  in which the 3- to 7-membered carbocycle and the 4- to 7-membered heterocycle may be fused to a phenyl ring or a pyridyl ring, which may in turn be substituted by 1 or 2 substituents selected from halogen, $(C_1-C_4)$-alkyl and trifluoromethyl,
with the proviso that not more than one of the $R^7$ and $R^8$, $R^9$ and $R^{10}$, and $R^7$ and $R^9$ radical pairs at the same time forms a carbo- or heterocycle,
with the proviso that the $R^7$ and $R^9$ radicals are not at the same time both phenyl or 5- or 6-membered heteroaryl,
$R^{11}$ is hydrogen or $(C_1-C_4)$-alkyl,
  in which $(C_1-C_4)$-alkyl may be substituted by 1 or 2 substituents each independently selected from the group of hydroxyl and $(C_1-C_4)$-alkoxy, and may be substituted up to six times by fluorine,
$R^{12}$ is hydrogen, $(C_1-C_6)$-alkyl, $(C_1-C_4)$-alkylcarbonyl, $(C_1-C_4)$-alkoxycarbonyl, $(C_3-C_7)$-cycloalkyl, phenyl or benzyl,
  in which $(C_1-C_6)$-alkyl may be substituted by 1 to 3 substituents each independently selected from the group of fluorine, trifluoromethyl, hydroxyl, $(C_1-C_4)$-alkoxy and phenoxy,
  and
  in which phenyl and benzyl may be substituted by 1 to 3 substituents each independently selected from the group of halogen and trifluoromethyl,
or
$R^{11}$ and $R^{12}$ together with the nitrogen atom to which they are bonded form a 4- to 7-membered azaheterocycle,
  in which the 4- to 7-membered azaheterocycle may be substituted by $(C_1-C_4)$-alkyl,
$R^{13}$ is 5- to 10-membered azaheterocyclyl bonded via a ring carbon atom or 5- or 6-membered heterocyclyl bonded via a ring nitrogen atom,
  in which 5- to 10-membered azaheterocyclyl bonded via a ring carbon atom may be substituted by 1 to 2 trifluoromethyl, $(C_3-C_7)$-cycloalkyl, oxo and benzyl substituents, and up to four times by $(C_1-C_4)$-alkyl and up to twice by fluorine,
  in which 5- to 10-membered azaheterocyclyl may be fused to a phenyl ring or a pyridyl ring, which may in turn be substituted by 1 or 2 substituents selected from halogen, $(C_1-C_4)$-alkyl, $(C_1-C_4)$-alkoxy and trifluoromethyl,
  in which 5- or 6-membered heterocyclyl bonded via a ring nitrogen atom may be substituted by $(C_1-C_4)$-alkyl or $(C_1-C_4)$-cycloalkyl,
    in which $(C_1-C_4)$-alkyl may be substituted by difluoromethyl or trifluoromethyl,
or
  may be amino when $L^2$ is a bond,
    in which amino may be substituted by $(C_1-C_{10})$-alkyl, $(C_1-C_4)$-alkylcarbonyl, $(C_3-C_6)$-carbocyclyl, 4- to 7-membered heterocyclyl, phenyl or 5- or 6-membered heteroaryl,
      in which $(C_1-C_4)$-alkylcarbonyl may be substituted by monoalkylamino, dialkylamino or 5- or 6-membered heterocyclyl bonded via a ring nitrogen atom, in which 5- or 6-membered heterocyclyl bonded via a ring nitrogen atom may be substituted by oxo,
in which $(C_3-C_6)$-carbocyclyl and 4- to 7-membered heterocyclyl may be substituted by hydroxyl, and
in which phenyl and 5- or 6-membered heteroaryl may be substituted by 1 to 3 substituents each independently selected from the group of halogen, $(C_1-C_4)$-alkyl and trifluoromethyl, $R^{14}$ is hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, —(C═O)NR$^{24}$R$^{25}$, 5- or 6-membered heteroaryl or phenyl,
in which $(C_1-C_6)$-alkyl may be substituted by 1 or 2 substituents each independently selected from the group of difluoromethoxy, trifluoromethoxy, hydroxyl, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy, and may be substituted up to six times by fluorine,
in which phenyl, phenoxy and benzyloxy may in turn be substituted by 1 to 3 halogen substituents,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy,
in which $R^{24}$ is hydrogen, $(C_1-C_4)$-alkyl, $(C_3-C_7)$-cycloalkyl, aryl or naphthyl,
in which $R^{25}$ is hydrogen or methyl, and
in which phenyl and 5- or 6-membered heteroaryl may be substituted by 1 to 3 substituents each independently selected from the group of halogen, cyano, trifluoromethyl, difluoromethyl, $(C_1-C_4)$-alkyl, $(C_1-C_4)$-alkoxy and $(C_1-C_4)$-alkylsulphonyl,
in which $(C_1-C_4)$-alkyl may be substituted by amino or hydroxyl, $R^{15}$ is hydrogen or $(C_1-C_6)$-alkyl,
in which $(C_1-C_4)$-alkyl may be substituted by hydroxyl, or $R^{14}$ and $R^{15}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl, $R^{16}$ is hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, 5- or 6-membered heteroaryl or phenyl,
in which $(C_1-C_6)$-alkyl may be substituted by 1 or 2 substituents each independently selected from the group of fluorine, trifluoromethyl, difluoromethoxy, trifluoromethoxy, hydroxyl, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy, and may be substituted up to six times by fluorine,
in which phenyl, phenoxy and benzyloxy may in turn be substituted by 1 to 3 halogen substituents,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy, and
in which phenyl and 5- or 6-membered heteroaryl may be substituted by 1 to 3 substituents each independently selected from the group of halogen, cyano, trifluoromethyl, $(C_1-C_4)$-alkyl, $(C_1-C_4)$-alkoxy and $(C_1-C_4)$-alkylsulphonyl, $R^{17}$ is hydrogen or $(C_1-C_6)$-alkyl,
in which $(C_1-C_4)$-alkyl may be substituted by hydroxyl, or $R^{16}$ and $R^{17}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
with the proviso that the $R^{14}$ and $R^{16}$ radicals are not at the same time both phenyl or 5- or 6-membered heteroaryl, or $R^{14}$ and $R^{16}$ together with the carbon atoms to which they are bonded form a 3- to 7-membered carbocycle or a 4- to 7-membered heterocycle,
with the proviso that not more than one of the $R^{14}$ and $R^{15}$, $R^{16}$ and $R^{17}$, and $R^{14}$ and $R^{16}$ radical pairs at the same time forms a carbo- or heterocycle, $R^{18}$ is hydrogen or $(C_1-C_4)$-alkyl,
in which $(C_1-C_4)$-alkyl may be substituted by 1 to 5 fluorine substituents, m is 0, 1 or 2,
n is 0 or 1, $R^{19}$ is hydrogen, cyano or $(C_1-C_6)$-alkyl,
in which $(C_1-C_6)$-alkyl may be substituted by 1 to 5 fluorine substituents, $R^{20}$ is hydrogen or $(C_1-C_4)$-alkyl,
in which $(C_1-C_4)$-alkyl may be substituted by 1 to 5 fluorine substituents, $R^{21}$ is hydrogen or $(C_1-C_6)$-alkyl,
in which $(C_1-C_6)$-alkyl may be substituted by 1 to 5 fluorine substituents, $R^{22}$ is hydrogen or $(C_1-C_4)$-alkyl,
in which $(C_1-C_4)$-alkyl may be substituted by 1 to 5 fluorine substituents,
or $R^{19}$ and $R^{20}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or $R^{21}$ and $R^{22}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or $R^{19}$ and $R^{21}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
with the proviso that not more than one of the $R^{19}$ and $R^{20}$, $R^{21}$ and $R^{22}$, and $R^{19}$ and $R^{21}$ radical pairs at the same time forms a carbo- or heterocycle, $R^{23}$ is $(C_1-C_6)$-alkyl, $(C_1-C_6)$-alkoxy, $(C_1-C_4)$-alkoxycarbonyl, hydroxycarbonyl, aminocarbonyl, aminosulphonyl, 5- to 10-membered heterocyclyl bonded via a ring carbon atom, 5- to 10-membered carbocyclyl, phenyl or 5- to 10-membered heteroaryl,
  in which $(C_1-C_6)$-alkyl may be substituted by cyano, and up to six times by fluorine,
  in which $(C_1-C_6)$-alkoxy may be substituted by hydroxyl, amino, monoalkylamino, dialkylamino, cyclopropyl, phenyl or $(C_2-C_4)$-alkenyl,
  in which aminocarbonyl may be substituted by $(C_1-C_6)$-alkyl or $(C_3-C_6)$-cycloalkyl,
  in which aminosulphonyl may be substituted by $(C_1-C_6)$-alkyl or $(C_3-C_6)$-cycloalkyl,
  in which phenyl may be substituted by 1 to 3 substituents each independently selected from the group of halogen, cyano, trifluoromethyl, difluoromethyl, $(C_1-C_6)$-alkyl, $(C_1-C_4)$-alkylcarbonyl, $(C_1-C_4)$-alkoxycarbonyl, hydroxycarbonyl, —(C=O)NR$^{26}$R$^{27}$, $(C_1-C_4)$-alkylsulphonyl, $(C_3-C_6)$-cycloalkylsulphonyl, $(C_1-C_4)$-alkylthio, $(C_1-C_4)$-alkoxy, trifluoromethoxy, difluoromethoxy, phenoxy, hydroxyl, 5- to 10-membered heteroaryl, 4- to 7-membered heterocyclyl and $(C_3-C_7)$-cycloalkyl,
    in which $(C_1-C_6)$-alkyl may be substituted by 1 or 2 substituents each independently selected from the group of fluorine, trifluoromethoxy, $(C_1-C_4)$-alkylcarbonyl, —(C=O)NR$^{26}$R$^{27}$, $(C_1-C_4)$-alkoxy, $(C_3-C_6)$-cycloalkyl, morpholinyl, piperidinyl, pyrrolidinyl, piperazinyl, phenyl, hydroxyl and amino,
      in which phenyl may be substituted by 1 to 3 halogen substituents,
      in which amino may be substituted by 1 or 2 substituents each independently selected from $(C_1-C_6)$-alkyl, $(C_1-C_4)$-alkylcarbonyl, $(C_3-C_6)$-cycloalkylsulphonyl, $(C_1-C_4)$-alkylsulphonyl and methoxy-$(C_1-C_4)$-alkyl,
      in which $(C_3-C_6)$-cycloalkyl may be substituted by amino or hydroxyl,
      and in which
      R$^{26}$ and R$^{27}$ are each independently hydrogen, $(C_1-C_4)$-alkyl or $(C_3-C_7)$-cycloalkyl,
  in which 5- to 10-membered heteroaryl may be substituted by 1 to 3 substituents each independently selected from the group of fluorine, chlorine, cyano, $(C_1-C_6)$-alkyl, trifluoromethyl, $(C_1-C_4)$-alkoxy, amino, $(C_1-C_4)$-alkoxycarbonyl, hydroxycarbonyl, —(C=O)NR$^{25}$R$^{26}$, phenyl, pyridyl, pyrimidyl, 1,3-thiazol-5-yl and $(C_3-C_7)$-cycloalkyl,
    in which $(C_1-C_6)$-alkyl may be substituted by 1 to 3 substituents each independently selected from the group of halogen, cyano, hydroxyl, amino, trifluoromethyl, difluoromethyl, $(C_1-C_4)$-alkylsulphonyl, $(C_1-C_4)$-alkylcarbonyl, $(C_1-C_4)$-alkoxycarbonyl, hydroxycarbonyl, $(C_1-C_4)$-alkylthio, $(C_1-C_4)$-alkoxy, trifluoromethoxy, difluoromethoxy, phenoxy, phenyl, pyridyl, pyrimidyl, 5-membered heteroaryl, tetrahydrothiophenyl-1,1-dioxide, $(C_3-C_7)$-cycloalkyl, morpholinyl, piperidinyl, pyrrolidinyl, 2-oxopyrrolidin-1-yl, piperazinyl, tetrahydrothiophenyl-1,1-dioxide, thiomorpholinyl-1,1-dioxide and azetidine,
    in which 5-membered heteroaryl may be substituted by 1 to 3 substituents each independently selected from the group of halogen, $(C_1-C_4)$-alkyl and $(C_1-C_4)$-alkoxy,
    in which piperidinyl may be substituted by 1 to 4 fluorine substituents,
    in which phenyl may be substituted by 1 to 3 substituents each independently selected from the group of halogen, $(C_1-C_4)$-alkyl and $(C_1-C_4)$-alkoxy,
    in which azetidine may be substituted by hydroxyl,
    in which piperazinyl may be substituted by 1 to 3 substituents each independently selected from the group of $(C_1-C_4)$-alkyl, $(C_3-C_7)$-cycloalkyl and trifluoromethyl,
    and in which
    R$^{26}$ and R$^{27}$ are each independently hydrogen, $(C_1-C_4)$-alkyl or $(C_3-C_7)$-cycloalkyl,
  in which 5- to 10-membered heterocyclyl bonded via a ring carbon atom may be substituted by 1 to 3 substituents each independently selected from the group of oxo, fluorine, trifluoromethyl, hydroxyl and $(C_1-C_4)$-alkyl,
  in which 5- to 10-membered heterocyclyl bonded via a ring carbon atom may be fused to a phenyl ring or a pyridyl ring, which may in turn be substituted by 1 to 3 substituents selected from the group of halogen, $(C_1-C_4)$-alkyl and trifluoromethyl,
  and
  in which 5- to 10-membered carbocyclyl may be substituted by 1 to 3 substituents each independently selected from the group of trifluoromethyl, fluorine, cyano, hydroxyl, hydroxycarbonyl, $(C_1-C_4)$-alkoxycarbonyl, amino and $(C_1-C_4)$-alkyl,
    in which $(C_1-C_4)$-alkyl may be substituted by hydroxyl or hydroxycarbonyl,
    in which 5- to 10-membered carbocyclyl may be fused to a phenyl ring or a pyridyl ring, which may in turn be substituted by 1 to 3 substituents selected from the group of halogen, $(C_1-C_4)$-alkyl, $(C_1-C_4)$-alkoxy and trifluoromethyl,
$R^4$ is hydrogen,
$R^5$ is hydrogen, halogen, cyano, difluoromethyl, trifluoromethyl, $(C_1-C_4)$-alkyl, $(C_3-C_7)$-cycloalkyl, $(C_2-C_4)$-alkynyl, $(C_1-C_4)$-alkylamino, difluoromethoxy, trifluoromethoxy, $(C_1-C_4)$-alkoxy, amino, 4- to 7-membered heterocyclyl or 5- or 6-membered heteroaryl,
$R^6$ is hydrogen, cyano or halogen,
and the N-oxides, salts, solvates, salts of the N-oxides and solvates of the N-oxides or salts thereof.

Inventive compounds are the compounds of the formula (I) and the salts, solvates and solvates of the salts thereof, the compounds, encompassed by formula (I), of the formulae specified hereinafter and the salts, solvates and solvates of the salts thereof, and the compounds encompassed by formula (I) and specified hereinafter as working examples and the salts, solvates and solvates of the salts thereof, to the extent that the compounds encompassed by formula (I) and specified hereinafter are not already salts, solvates and solvates of the salts.

In the context of the present invention, preferred salts are physiologically acceptable salts of the inventive compounds. Also encompassed are salts which are not themselves suitable for pharmaceutical applications but can be used, for example, for isolation or purification of the inventive compounds.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the inventive compounds which, in the solid or liquid state, form a complex by coordination with solvent molecules. Hydrates are a specific form of solvates in which the coordination is with water. Preferred solvates in the context of the present invention are hydrates.

Depending on their structure, the inventive compounds may exist in different stereoisomeric forms, i.e. in the form of configurational isomers or if appropriate also as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, more particularly HPLC chromatography on an achiral or chiral phase.

If the inventive compounds can occur in tautomeric forms, the present invention encompasses all the tautomeric forms.

The present invention also encompasses all suitable isotopic variants of the inventive compounds. An isotopic variant of an inventive compound is understood here to mean a compound in which at least one atom within the inventive compound has been exchanged for another atom of the same atomic number, but with a different atomic mass from the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of an inventive compound, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the inventive compounds can be prepared by the processes known to those skilled in the art, for example by the methods described below and the procedures described in the working examples, by using corresponding isotopic modifications of the respective reagents and/or starting compounds.

In addition, the present invention also encompasses prodrugs of the inventive compounds. The term "prodrugs" here denotes compounds which may themselves be biologically active or inactive, but are converted (for example by metabolic or hydrolytic means) to inventive compounds during their residence time in the body.

In the context of the present invention, the substituents, unless specified otherwise, are each defined as follows:

Alkyl in the context of the invention is a linear or branched alkyl radical having the particular number of carbon atoms specified. Preferred examples include: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Cycloalkyl or carbocycle or carbocyclyl in the context of the invention is a monocyclic, bicyclic or tricyclic saturated alkyl radical having the particular number of carbon atoms specified. Preferred examples include: cyclopropyl, cyclobutyl, cyclopentyl, cyclohexyl, cycloheptyl and adamantyl.

Alkenyl in the context of the invention is a linear or branched alkenyl radical having 2 to 6 carbon atoms and one or two double bonds. Preference is given to a linear or branched alkenyl radical having 2 to 4 carbon atoms and one double bond. Preferred examples include: vinyl, allyl, isopropenyl and n-but-2-en-1-yl.

Alkynyl in the context of the invention is a linear or branched alkynyl radical having 2 to 6 carbon atoms and one triple bond. Preferred examples include: ethynyl, n-prop-1-yn-1-yl, n-prop-2-yn-1-yl, n-but-2-yn-1-yl and n-but-3-yn-1-yl.

Alkanediyl in the context of the invention is a linear or branched divalent alkyl radical having 1 to 4 carbon atoms. Preferred examples include: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl and butane-2,3-diyl.

Monoalkylamino in the context of the invention is an amino group having a linear or branched alkyl substituent having 1 to 4 carbon atoms. Preferred examples include: methylamino, ethylamino, n-propylamino, isopropylamino and tert-butylamino.

Dialkylamino in the context of the invention is an amino group having two identical or different, linear or branched alkyl substituents each having 1 to 4 carbon atoms. Preferred examples include: N,N-dimethylamino, N,N-diethylamino, N-ethyl-N-methylamino, N-methyl-N-n-propylamino, N-isopropyl-N-n-propylamino and N-tert-butyl-N-methylamino.

Alkoxy in the context of the invention is a linear or branched alkoxy radical having 1 to 4 carbon atoms. Preferred examples include: methoxy, ethoxy, n-propoxy, isopropoxy, 1-methylpropoxy, n-butoxy, isobutoxy and tert-butoxy.

Alkoxycarbonyl in the context of the invention is a linear or branched alkoxy radical having 1 to 4 carbon atoms and a carbonyl group attached to the oxygen atom. Preferred examples include: methoxycarbonyl, ethoxycarbonyl, n-propoxycarbonyl, isopropoxycarbonyl and tert-butoxycarbonyl.

Alkylsulphonyl in the context of the invention is a linear or branched alkyl radical which has 1 to 4 carbon atoms and is bonded via a sulphonyl group. Preferred examples include: methylsulphonyl, ethylsulphonyl, n-propylsulphonyl, isopropylsulphonyl, n-butylsulphonyl and tert-butylsulphonyl.

A 4- to 7-membered or 5- to 10-membered heterocyclyl in the context of the invention is a monocyclic saturated heterocycle which has a total of 4 to 7 ring atoms or 5 to 10 ring atoms, contains one or two ring heteroatoms from the group of N, O, S, SO and/or $SO_2$ and is bonded via a ring carbon atom or, where appropriate, a ring nitrogen atom. Examples include: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to azetidinyl, oxetanyl, pyrrolidinyl, tetrahydrofuranyl, piperidinyl, piperazinyl, tetrahydropyranyl and morpholinyl.

A 4- to 7-membered azaheterocycle in the context of the invention, in $R^{11}$ and $R^{12}$, is a monocyclic saturated heterocycle which has a total of 4 to 7 ring atoms, contains a nitrogen atom and may additionally contain a further ring heteroatom from the group of N, O, S, SO and $SO_2$, and is bonded via a ring nitrogen atom. Examples include: azetidinyl, pyrrolidinyl, pyrazolidinyl, piperidinyl, piperazinyl, morpholinyl, thiomorpholinyl, 1,1-dioxothiomorpholinyl, hexahydroazepinyl and hexahydro-1,4-diazepinyl.

5- to 10-membered azaheterocyclyl in the context of the invention, in $R^{13}$, is a monocyclic or bicyclic, saturated or partly unsaturated heterocycle which has a total of 5 to 10 ring atoms, contains a nitrogen atom and may additionally contain one or two further ring heteroatom(s) from the group of N, O, S, SO and/or $SO_2$, and is bonded via a ring carbon atom. Examples include: pyrrolidinyl, pyrazolidinyl, piperidinyl, piperazinyl, morpholinyl, thiomorpholinyl, 1,1-dioxothiomorpholinyl, hexahydroazepinyl, hexahydro-1,4-diazepinyl, 1,2,3,4-tetrahydroisoquinolinyl, 1,2,3,4-tetrahydroquinolinyl, indolinyl, 8-azabicyclo[3.2.1]octanyl, 9-azabicyclo[3.3.1]nonanyl, 3-azabicyclo[4.1.0]heptanyl and quinuclidinyl.

Heteroaryl in the context of the invention is a mono- or bicyclic aromatic heterocycle (heteroaromatic) which contains up to four identical or different ring heteroatoms from the group of N, O and S and is bonded via a ring carbon atom or, where appropriate, via a ring nitrogen atom. Preferred examples include: furyl, pyrrolyl, thienyl, pyrazolyl, imidazolyl, quinolinyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl and triazinyl.

Halogen in the context of the invention includes fluorine, chlorine, bromine and iodine. Preference is given to chlorine or fluorine.

In the formula of the group that $R^3$ or $R^1$ may represent, the end point of the line marked by the symbol * and # does not represent a carbon atom or a $CH_2$ group but is part of the bond to the respective atom to which $R^3$ or $R^1$ is bonded.

When radicals in the inventive compounds are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

Preference is given in the context of the present invention to compounds of the formula (I) in which A is $CH_2$ or $CD_2$, $R^1$ is $(C_3-C_6)$-cycloalkyl, pyridyl or phenyl,
  where $(C_3-C_6)$-cycloalkyl may be substituted by 1 to 2 substituents each independently selected from the group of fluorine, trifluoromethyl, methyl and ethyl,
  where pyridyl is substituted by 1 or 2 F substituents,
  and
  where phenyl may be substituted by 1 to 4 substituents each independently selected from the group of halogen, cyano, difluoromethyl, trifluoromethyl, $(C_1-C_4)$-alkyl, $(C_1-C_4)$-alkoxy and $(C_3-C_5)$-cycloalkyl, $R^2$ is hydrogen, $(C_1-C_4)$-alkyl, cyclopropyl, difluoromethyl or trifluoromethyl, $R^3$ is a group of the formula

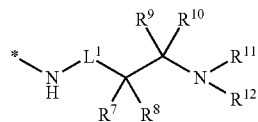

or

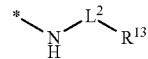

or

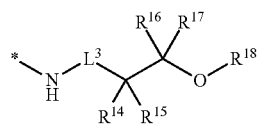

or

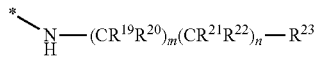

where
* is the attachment site to the carbonyl group,
$L^1$ is a bond, methanediyl or 1,2-ethanediyl,
$L^2$ is a bond, methanediyl or 1,2-ethanediyl,
$L^3$ is a bond, methanediyl or 1,2-ethanediyl,
$R^7$ is hydrogen, $(C_1-C_6)$-alkyl, $(C_3-C_7)$-cycloalkyl, phenyl or 5- or 6-membered heteroaryl,
  in which $(C_1-C_6)$-alkyl may be substituted by 1 to 5 fluorine substituents,
  and
  in which phenyl and 5- or 6-membered heteroaryl may be substituted by 1 to 3 substituents each independently selected from the group of fluorine, chlorine, bromine, cyano, trifluoromethyl, methyl, ethyl, methoxy or ethoxy, $R^8$ is hydrogen or $(C_1\text{-}C_4)$-alkyl, or $R^7$ and $R^8$ together with the carbon atom to which they are bonded form a 3- to 5-membered carbocycle, $R^9$ is hydrogen, $(C_1\text{-}C_6)$-alkyl, $(C_3\text{-}C_5)$-cycloalkyl, 5- or 6-membered heteroaryl or phenyl, in which $(C_1\text{-}C_6)$-alkyl may be substituted by 1 to 5 fluorine substituents, in which $(C_1\text{-}C_6)$-alkyl may be substituted by $(C_1\text{-}C_4)$-alkoxy, benzyloxy or phenoxy, in which benzyloxy and phenoxy may be substituted by 1 to 3 substituents each independently selected from the group of fluorine, chlorine and bromine, in which $(C_3\text{-}C_5)$-cycloalkyl may be substituted by 1 or 2 fluorine or $(C_1\text{-}C_4)$-alkyl substituents, and in which phenyl and 5- or 6-membered heteroaryl may be substituted by 1 to 3 substituents each independently selected from the group of fluorine, chlorine, bromine, cyano, trifluoromethyl, methyl, ethyl, methoxy or ethoxy, $R^{10}$ is hydrogen or $(C_1\text{-}C_4)$-alkyl, or $R^9$ and $R^{10}$ together with the carbon atom to which they are bonded form a 3- to 5-membered carbocycle, or $R^7$ and $R^9$ together with the carbon atom to which they are bonded form a 3- to 6-membered carbocycle or a 4- to 7-membered heterocycle, in which the 3- to 6-membered carbocycle and the 4- to 7-membered heterocycle may be substituted by 1 or 2 fluorine or $(C_1\text{-}C_4)$-alkyl substituents, with the proviso that not more than one of the $R^7$ and $R^8$, $R^9$ and $R^{10}$, and $R^7$ and $R^9$ radical pairs at the same time forms a carbo- or heterocycle, and with the proviso that the $R^7$ and $R^9$ radicals are not at the same time both phenyl or 5- or 6-membered heteroaryl, $R^{11}$ is hydrogen or $(C_1\text{-}C_4)$-alkyl, in which $(C_1\text{-}C_4)$-alkyl may be substituted by 1 to 5 fluorine substituents, $R^{12}$ is hydrogen, $(C_1\text{-}C_6)$-alkyl or $(C_3\text{-}C_7)$-cycloalkyl, in which $(C_1\text{-}C_6)$-alkyl may be substituted by 1 to 5 fluorine substituents, or $R^{11}$ and $R^{12}$ together with the nitrogen atom to which they are bonded form a 4- to 7-membered azaheterocycle, $R^{13}$ is 5- to 9-membered azaheterocyclyl bonded via a ring carbon atom, in which 5- to 9-membered azaheterocyclyl may be substituted by 1 to 5 substituents each independently selected from the group of fluorine, methyl and ethyl, $R^{14}$ is hydrogen, $(C_1\text{-}C_6)$-alkyl, $(C_3\text{-}C_5)$-cycloalkyl, —(C=O)NR$^{24}$R$^{25}$, 5- or 6-membered heteroaryl or phenyl, in which $(C_1\text{-}C_6)$-alkyl may be substituted by 1 to 3 substituents each independently selected from the group of fluorine, trifluoromethyl, difluoromethoxy, trifluoromethoxy, hydroxyl and $(C_1\text{-}C_4)$-alkoxy, in which $R^{24}$ is hydrogen, $(C_1\text{-}C_4)$-alkyl, aryl or naphthyl, in which $R^{25}$ is hydrogen, and in which phenyl and 5- or 6-membered heteroaryl may be substituted by 1 to 3 substituents each independently selected from the group of fluorine, chlorine, bromine, trifluoromethyl, methyl and ethyl, $R^{15}$ is hydrogen or $(C_1\text{-}C_4)$-alkyl, or $R^{14}$ and $R^{15}$ together with the carbon atom to which they are bonded form a 3- to 5-membered carbocycle, $R^{16}$ is hydrogen, $(C_1\text{-}C_6)$-alkyl or $(C_3\text{-}C_5)$-cycloalkyl, in which $(C_1\text{-}C_6)$-alkyl may be substituted by 1 to 5 fluorine substituents, and in which $(C_3\text{-}C_5)$-cycloalkyl may be substituted by 1 or 2 substituents independently of one another selected from the group consisting of fluorine, trifluoromethyl, hydroxyl and $(C_1\text{-}C_4)$-alkyl, $R^{17}$ is hydrogen or $(C_1\text{-}C_4)$-alkyl, or $R^{16}$ and $R^{17}$ together with the carbon atom to which they are bonded form a 3- to 6-membered carbocycle, in which the 3- to 6-membered carbocycle may be substituted by 1 or 2 fluorine or $(C_1\text{-}C_4)$-alkyl substituents, or $R^{14}$ and $R^{16}$ together with the carbon atom to which they are bonded form a 3- to 6-membered carbocycle or a 4- to 7-membered heterocycle, in which the 3- to 6-membered carbocycle and the 4- to 7-membered heterocycle may be substituted by 1 or 2 fluorine or $(C_1\text{-}C_4)$-alkyl substituents, with the proviso that the $R^{14}$ and $R^{16}$ radicals are not at the same time both phenyl, and with the proviso that not more than one of the $R^{14}$ and $R^{15}$, $R^{16}$ and $R^{17}$, and $R^{14}$ and $R^{16}$ radical pairs at the same time forms a carbo- or heterocycle, $R^{18}$ is hydrogen or $(C_1\text{-}C_4)$-alkyl, in which $(C_1\text{-}C_4)$-alkyl may be substituted by 1 to 5 fluorine substituents, m is 0 or 1, n is 0 or 1, $R^{19}$ is hydrogen, cyano or $(C_1\text{-}C_4)$-alkyl, in which $(C_1\text{-}C_4)$-alkyl may be substituted by 1 to 5 fluorine substituents, $R^{20}$ is hydrogen or $(C_1\text{-}C_4)$-alkyl, in which $(C_1\text{-}C_4)$-alkyl may be substituted by 1 to 5 fluorine substituents, $R^{21}$ is hydrogen or $(C_1\text{-}C_4)$-alkyl, in which $(C_1\text{-}C_4)$-alkyl may be substituted by 1 to 5 fluorine substituents, $R^{22}$ is hydrogen or $(C_1\text{-}C_4)$-alkyl, in which $(C_1\text{-}C_4)$-alkyl may be substituted by 1 to 5 fluorine substituents, or $R^{19}$ and $R^{20}$ together with the carbon atom to which they are bonded form a 3- to 5-membered carbocycle, in which the 3- to 5-membered carbocycle may be substituted by 1 or 2 substituents each independently selected from the group of fluorine, methyl and ethyl, or $R^{21}$ and $R^{22}$ together with the carbon atom to which they are bonded form a 3- to 5-membered carbocycle, in which the 3- to 5-membered carbocycle may be substituted by 1 or 2 substituents each independently selected from the group of fluorine, methyl and ethyl, or $R^{19}$ and $R^{21}$ together with the carbon atom to which they are bonded form a 3- to 5-membered carbocycle, in which the 3- to 5-membered carbocycle may be substituted by 1 or 2 substituents each independently selected from the group of fluorine, methyl and ethyl, with the proviso that not more than one of the R¹⁹ and R²⁰, R²¹ and R²², and R¹⁹ and R²¹ radical pairs at the same time forms a carbo- or heterocycle, R²³ is (C₁-C₆)-alkyl, 5- to 9-membered heterocyclyl bonded via a ring carbon atom, 5- to 9-membered carbocyclyl, phenyl, indanyl or 5- to 10-membered heteroaryl, where (C₁-C₆)-alkyl may be substituted by cyano or up to three times by fluorine, where phenyl may be substituted by 1 to 3 substituents each independently selected from the group of halogen, cyano, trifluoromethyl, difluoromethyl, (C₁-C₄)-alkyl, (C₁-C₄)-alkoxy and 5- to 10-membered heteroaryl, in which (C₁-C₄)-alkyl may be substituted by 1 or 2 substituents each independently selected from the group of fluorine, trifluoromethoxy, (C₁-C₄)-alkoxy, (C₃-C₆)-cycloalkyl, hydroxyl and amino, where indanyl may be substituted by 1 or 2 substituents each independently selected from the group of fluorine, trifluoromethyl and hydroxyl, where 5- to 10-membered heteroaryl may be substituted by 1 to 3 substituents each independently selected from the group of fluorine, chlorine, cyano, trifluoromethyl, (C₁-C₄)-alkyl, (C₁-C₄)-alkoxy, amino and hydroxyl, in which (C₁-C₄)-alkyl may be substituted by 1 to 3 substituents each independently selected from the group of halogen, cyano, hydroxyl, amino, trifluoromethyl, difluoromethyl, (C₁-C₄)-alkoxy, trifluoromethoxy, difluoromethoxy and phenyl, in which phenyl may be substituted by 1 to 3 halogen substituents, where 5- to 9-membered heterocyclyl bonded via a ring carbon atom may be substituted by 1 or 2 substituents each independently selected from the group of oxo, fluorine, hydroxyl and (C₁-C₄)-alkyl, and where 5- to 9-membered carbocyclyl may be substituted by 1 or 2 substituents each independently selected from the group of trifluoromethyl, fluorine, hydroxyl, hydroxycarbonyl, (C₁-C₄)-alkoxycarbonyl and (C₁-C₄)-alkyl, R⁴ is hydrogen, R⁵ is hydrogen, fluorine, chlorine, bromine, cyano, difluoromethyl, trifluoromethyl, (C₁-C₄)-alkyl, (C₂-C₄)-alkynyl or (C₃-C₅)-cycloalkyl, R⁶ is hydrogen or fluorine, and the N-oxides, salts, solvates, salts of the N-oxides and solvates of the N-oxides or salts thereof.

Preference is given in the context of the present invention to compounds of the formula (I) in which A is CH₂ or CD₂, R¹ is (C₃-C₆)-cycloalkyl, pyridyl or phenyl, where (C₃-C₆)-cycloalkyl may be substituted by 1 to 2 substituents each independently selected from the group of fluorine, trifluoromethyl, methyl and ethyl, where pyridyl is substituted by 1 or 2 fluorine substituents, and where phenyl may be substituted by 1 to 4 substituents each independently selected from the group of halogen, cyano, difluoromethyl, trifluoromethyl, (C₁-C₄)-alkyl, (C₁-C₄)-alkoxy and (C₃-C₅)-cycloalkyl, R² is hydrogen, (C₁-C₄)-alkyl, cyclopropyl, cyclobutyl, difluoromethyl or trifluoromethyl, R³ is a group of the formula

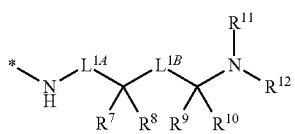

or

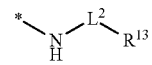

or

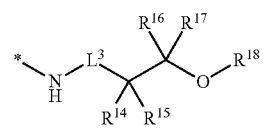

or

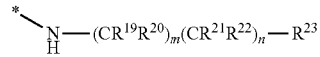

where

* is the attachment site to the carbonyl group,

L¹ᴬ is a bond, methanediyl, 1,2-ethanediyl or 1,3-propanediyl,

L¹ᴮ is a bond, methanediyl or 1,2-ethanediyl,

L² is a bond, methanediyl or 1,2-ethanediyl,

L³ is a bond, methanediyl or 1,2-ethanediyl,

R⁷ is hydrogen, (C₁-C₆)-alkyl, (C₃-C₇)-cycloalkyl, 5- or 6-membered heteroaryl or phenyl, in which (C₁-C₆)-alkyl may be substituted up to five times by fluorine, in which phenyl and 5- or 6-membered heteroaryl may be substituted by 1 to 3 substituents each independently selected from the group of fluorine, chlorine, bromine, cyano, nitro, trifluoromethyl, methyl, ethyl, methoxy, ethoxy, difluoromethoxy, trifluoromethoxy, methoxycarbonyl and ethoxycarbonyl, and in which phenyl may be substituted on two adjacent carbon atoms in the phenyl by a methylenedioxy bridge or ethylenedioxy bridge, or may be fluorine when L¹ᴬ is not a bond, R⁸ is hydrogen or (C₁-C₄)-alkyl, or may be fluorine when L¹ᴬ is not a bond, or R⁷ and R⁸ together with the carbon atom to which they are bonded form a 3- to 7-membered carbocycle, R⁹ is hydrogen, (C₁-C₆)-alkyl, (C₃-C₅)-cycloalkyl, cyano, 5- to 10-membered heteroaryl or phenyl, in which (C₁-C₆)-alkyl may be substituted by (C₁-C₄)-alkoxy, (C₁-C₄)-alkoxycarbonyl, (C₁-C₄)-alkylsulphonyl, (C₁-C₄)-alkylthio, benzyloxy, phenoxy, 5- or 6-membered heteroaryl and phenyl, and may be substituted up to five times by fluorine, in which benzyloxy, phenoxy, 5- or 6-membered heteroaryl and phenyl may be substituted by 1 to 3 substituents each independently selected from the group of fluorine, chlorine, bromine, methoxy and ethoxy,
in which $(C_3-C_5)$-cycloalkyl may be substituted by 1 or 2 fluorine, trifluoromethyl, methyl, ethyl, methoxy or ethoxy substituents,
in which phenyl and 5- to 10-membered heteroaryl may be substituted by 1 to 3 substituents each independently selected from the group of fluorine, chlorine, bromine, cyano, nitro, trifluoromethyl, methyl, ethyl, ethenyl, propenyl, methoxy, ethoxy, difluoromethoxy, trifluoromethoxy, methoxycarbonyl and ethoxycarbonyl,
in which methoxy and ethoxy may be substituted by hydroxyl,
and
in which phenyl may be substituted on two adjacent carbon atoms in the phenyl by a methylenedioxy bridge or ethylenedioxy bridge,
$R^{10}$ is hydrogen or $(C_1-C_4)$-alkyl,
or
$R^9$ and $R^{10}$ together with the carbon atom to which they are bonded form a 3- to 7-membered carbocycle or a 4- to 7-membered heterocycle,
or
$R^7$ and $R^9$ together with the carbon atoms to which they are bonded form a 3- to 7-membered carbocycle or a 4- to 7-membered heterocycle,
in which the 3- to 7-membered carbocycle and the 4- to 7-membered heterocycle may be substituted by 1 or 2 $(C_1-C_4)$-alkyl substituents,
and
in which the 3- to 7-membered carbocycle and the 4- to 7-membered heterocycle may be fused to a phenyl ring or a pyridyl ring, which may in turn be substituted by 1 or 2 substituents selected from fluorine, chlorine, bromine, methyl, ethyl and trifluoromethyl,
with the proviso that not more than one of the $R^7$ and $R^8$, $R^9$ and $R^{10}$, and $R^7$ and $R^9$ radical pairs at the same time forms a carbo- or heterocycle,
with the proviso that the $R^7$ and $R^9$ radicals are not at the same time both phenyl or 5- or 6-membered heteroaryl,
$R^{11}$ is hydrogen or $(C_1-C_4)$-alkyl,
in which $(C_1-C_4)$-alkyl may be substituted up to five times by fluorine,
$R^{12}$ is hydrogen, $(C_1-C_6)$-alkyl, $(C_3-C_5)$-cycloalkyl or $(C_1-C_4)$-alkylcarbonyl,
in which $(C_1-C_6)$-alkyl may be substituted up to five times by fluorine,
or
$R^{11}$ and $R^{12}$ together with the nitrogen atom to which they are bonded form a 4- to 7-membered azaheterocycle,
in which the 4- to 7-membered azaheterocycle may be substituted by methyl or ethyl,
$R^{13}$ is 5- to 10-membered azaheterocyclyl bonded via a ring carbon atom,
in which 5- to 10-membered azaheterocyclyl bonded via a ring carbon atom may be substituted by 1 or 2 trifluoromethyl, $(C_3-C_7)$-cycloalkyl, oxo and benzyl substituents, and up to four times by $(C_1-C_4)$-alkyl and up to twice by fluorine,
in which 5- to 10-membered azaheterocyclyl may be fused to a phenyl ring or a pyridyl ring, which may in turn be substituted by 1 or 2 substituents selected from fluorine, chlorine, methyl, $(C_1-C_4)$-alkyl and trifluoromethyl,
or
may be amino when $L^2$ is a bond,
in which amino may be substituted by $(C_1-C_4)$-alkyl, $(C_1-C_4)$-alkylcarbonyl, $(C_3-C_6)$-carbocyclyl, 4- to 7-membered heterocyclyl, phenyl or 5- or 6-membered heteroaryl,
in which $(C_1-C_4)$-alkylcarbonyl may be substituted by monoalkylamino or dialkylamino,
in which $(C_3-C_6)$-carbocyclyl and 4- to 7-membered heterocyclyl may be substituted by hydroxyl,
and
in which phenyl and 5- or 6-membered heteroaryl may be substituted by 1 to 3 substituents each independently selected from the group of fluorine, chlorine, methyl and trifluoromethyl,
$R^{14}$ is hydrogen, $(C_1-C_6)$-alkyl, $(C_3-C_7)$-cycloalkyl, $-(C=O)NR^{24}R^{25}$, 5- or 6-membered heteroaryl or phenyl,
in which $(C_1-C_6)$-alkyl may be substituted by 1 or 2 substituents each independently selected from the group of hydroxyl and $(C_1-C_4)$-alkoxy, and may be substituted up to six times by fluorine,
in which $R^{24}$ is hydrogen, $(C_1-C_4)$-alkyl, aryl or naphthyl,
in which $R^{25}$ is hydrogen,
and
in which phenyl and 5- or 6-membered heteroaryl may be substituted by 1 to 3 substituents each independently selected from the group of fluorine, chlorine, bromine, trifluoromethyl, methyl and ethyl,
$R^{15}$ is hydrogen or $(C_1-C_6)$-alkyl,
in which $(C_1-C_4)$-alkyl may be substituted by hydroxyl,
or
$R^{14}$ and $R^{15}$ together with the carbon atom to which they are bonded form a 3- to 7-membered carbocycle,
$R^{16}$ is hydrogen, $(C_1-C_6)$-alkyl or $(C_3-C_7)$-cycloalkyl,
in which $(C_1-C_6)$-alkyl may be substituted by 1 or 2 substituents each independently selected from the group of hydroxyl and $(C_1-C_4)$-alkoxy, and may be substituted up to six times by fluorine,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy,
$R^{17}$ is hydrogen or $(C_1-C_6)$-alkyl,
or
$R^{16}$ and $R^{17}$ together with the carbon atom to which they are bonded form a 3- to 6-membered carbocycle,
in which the 3- to 6-membered carbocycle may be substituted by 1 or 2 substituents each independently selected from the group of fluorine, methyl and ethyl,
or
$R^{14}$ and $R^{16}$ together with the carbon atoms to which they are bonded form a 3- to 7-membered carbocycle or a 4- to 7-membered heterocycle,
with the proviso that not more than one of the $R^{14}$ and $R^{15}$, $R^{16}$ and $R^{17}$, and $R^{14}$ and $R^{16}$ radical pairs at the same time forms a carbo- or heterocycle,
$R^{18}$ is hydrogen or $(C_1-C_4)$-alkyl,
in which $(C_1-C_4)$-alkyl may be substituted by 1 to 5 fluorine substituents,
m is 0 or 1,
n is 0 or 1,
$R^{19}$ is hydrogen, cyano or $(C_1-C_4)$-alkyl, in which $(C_1-C_4)$-alkyl may be substituted by 1 to 5 fluorine substituents,
$R^{20}$ is hydrogen or $(C_1-C_4)$-alkyl,
in which $(C_1-C_4)$-alkyl may be substituted by 1 to 5 fluorine substituents,
$R^{21}$ is hydrogen or $(C_1-C_4)$-alkyl,
in which $(C_1-C_4)$-alkyl may be substituted by 1 to 5 fluorine substituents,
$R^{22}$ is hydrogen or $(C_1-C_4)$-alkyl,
in which $(C_1-C_4)$-alkyl may be substituted by 1 to 5 fluorine substituents,
or
$R^{19}$ and $R^{20}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^{21}$ and $R^{22}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^{19}$ and $R^{21}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
with the proviso that not more than one of the $R^{19}$ and $R^{20}$, $R^{21}$ and $R^{22}$, and $R^{19}$ and $R^{21}$ radical pairs at the same time forms a carbo- or heterocycle,
$R^{23}$ is $(C_1-C_6)$-alkyl, $(C_1-C_6)$-alkoxy, $(C_1-C_4)$-alkoxycarbonyl, hydroxycarbonyl, aminocarbonyl, aminosulphonyl, 5- to 10-membered heterocyclyl bonded via a ring carbon atom, 5- to 10-membered carbocyclyl, phenyl or 5- to 10-membered heteroaryl,
in which $(C_1-C_6)$-alkyl may be substituted by cyano and up to six times by fluorine,
in which $(C_1-C_6)$-alkoxy may be substituted by hydroxyl or $(C_2-C_4)$-alkenyl,
in which aminocarbonyl may be substituted by $(C_1-C_6)$-alkyl or $(C_3-C_6)$-cycloalkyl,
in which aminosulphonyl may be substituted by $(C_1-C_6)$-alkyl or $(C_3-C_6)$-cycloalkyl,
in which phenyl may be substituted by 1 to 3 substituents each independently selected from the group of halogen, cyano, trifluoromethyl, difluoromethyl, $(C_1-C_4)$-alkyl, $(C_1-C_4)$-alkoxy, 5- to 10-membered heteroaryl and 4- to 7-membered heterocyclyl,
in which $(C_1-C_6)$-alkyl may be substituted by 1 or 2 substituents each independently selected from the group of fluorine, trifluoromethoxy, $(C_1-C_4)$-alkoxy, $(C_3-C_6)$-cycloalkyl, hydroxyl and amino,
in which 5- to 10-membered heteroaryl may be substituted by 1 to 3 substituents each independently selected from the group of fluorine, chlorine, cyano, $(C_1-C_4)$-alkyl, trifluoromethyl, $(C_1-C_4)$-alkoxy and amino,
in which $(C_1-C_4)$-alkyl may be substituted by 1 to 3 substituents selected from the group of halogen, cyano, hydroxyl, amino, trifluoromethyl, difluoromethyl, $(C_1-C_4)$-alkoxy, trifluoromethoxy, difluoromethoxy and phenyl,
in which phenyl may be substituted by 1 to 3 halogen substituents,
in which 5- to 10-membered heterocyclyl bonded via a ring carbon atom may be substituted by 1 or 2 substituents each independently selected from the group of oxo, fluorine, trifluoromethyl, hydroxyl and $(C_1-C_4)$-alkyl,
in which 5- to 10-membered heterocyclyl bonded via a ring carbon atom may be fused to a phenyl ring or a pyridyl ring, which may in turn be substituted by 1 to 3 substituents selected from the group of halogen, $(C_1-C_4)$-alkyl, $(C_1-C_4)$-alkoxy and trifluoromethyl,
and
in which 5- to 10-membered carbocyclyl may be substituted by 1 or 2 substituents each independently selected from the group of trifluoromethyl, fluorine, cyano, hydroxyl, hydroxycarbonyl, $(C_1-C_4)$-alkoxycarbonyl, amino and $(C_1-C_4)$-alkyl,
in which 5- to 10-membered carbocyclyl may be fused to a phenyl ring or a pyridyl ring, which may in turn be substituted by 1 to 3 substituents selected from the group of halogen, $(C_1-C_4)$-alkyl, $(C_1-C_4)$-alkoxy and trifluoromethyl,
$R^4$ is hydrogen,
$R^5$ is hydrogen, fluorine, chlorine, bromine, cyano, difluoromethyl, trifluoromethyl, $(C_1-C_4)$-alkyl, $(C_3-C_5)$-cycloalkyl or $(C_2-C_4)$-alkynyl,
$R^6$ is hydrogen or fluorine,
and the N-oxides, salts, solvates, salts of the N-oxides and solvates of the N-oxides or salts thereof.

Preference is given in the context of the present invention to compounds of the formula (I) in which
A is $CH_2$ or $CD_2$,
$R^1$ is $(C_3-C_6)$-cycloalkyl, pyridyl or phenyl,
where $(C_3-C_6)$-cycloalkyl may be substituted by 1 to 2 substituents each independently selected from the group of fluorine, trifluoromethyl, methyl and ethyl,
where pyridyl is substituted by 1 or 2 fluorine substituents, and
where phenyl may be substituted by 1 to 4 substituents each independently selected from the group of halogen, cyano, difluoromethyl, trifluoromethyl, $(C_1-C_4)$-alkyl, $(C_1-C_4)$-alkoxy and $(C_3-C_5)$-cycloalkyl,
$R^2$ is hydrogen, $(C_1-C_4)$-alkyl, cyclopropyl, cyclobutyl, difluoromethyl or trifluoromethyl,
$R^3$ is a group of the formula

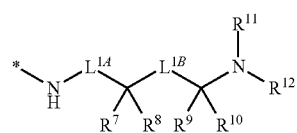

or

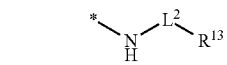

or

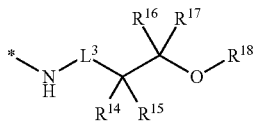

or

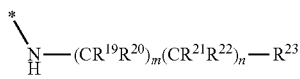

where
* is the attachment site to the carbonyl group,
$L^{1A}$ is a bond, methanediyl, 1,2-ethanediyl or 1,3-propanediyl,
$L^{1B}$ is a bond, methanediyl or 1,2-ethanediyl,
$L^2$ is a bond, methanediyl or 1,2-ethanediyl,
$L^3$ is a bond, methanediyl or 1,2-ethanediyl,
$R^7$ is hydrogen, $(C_1-C_6)$-alkyl, $(C_3-C_7)$-cycloalkyl, 5- or 6-membered heteroaryl or phenyl,
  in which $(C_1-C_6)$-alkyl may be substituted up to five times by fluorine,
  in which phenyl and 5- or 6-membered heteroaryl may be substituted by 1 to 3 substituents each independently selected from the group of fluorine, chlorine, bromine, cyano, nitro, trifluoromethyl, difluoromethyl, methyl, ethyl, methoxy, ethoxy, difluoromethoxy, trifluoromethoxy, methoxycarbonyl and ethoxycarbonyl,
  and
  in which phenyl may be substituted on two adjacent carbon atoms in the phenyl by a methylenedioxy bridge or ethylenedioxy bridge,
  or
  may be fluorine when $L^{1A}$ is not a bond,
$R^8$ is hydrogen or $(C_1-C_4)$-alkyl,
  or
  may be fluorine when $L^{1A}$ is not a bond,
or
$R^7$ and $R^8$ together with the carbon atom to which they are bonded form a 3- to 7-membered carbocycle,
$R^9$ is hydrogen, $(C_1-C_6)$-alkyl, $(C_3-C_5)$-cycloalkyl, cyano, 5- to 10-membered heteroaryl or phenyl,
  in which $(C_1-C_6)$-alkyl may be substituted by $(C_1-C_4)$-alkoxy, $(C_1-C_4)$-alkoxycarbonyl, $(C_1-C_4)$-alkylsulphonyl, $(C_1-C_4)$-alkylthio, benzyloxy, phenoxy, 5- or 6-membered heteroaryl and phenyl, and may be substituted up to five times by fluorine,
    in which benzyloxy, phenoxy, 5- or 6-membered heteroaryl and phenyl may be substituted by 1 to 3 substituents each independently selected from the group of fluorine, chlorine, bromine, methoxy and ethoxy,
  in which $(C_3-C_5)$-cycloalkyl may be substituted by 1 or 2 fluorine, trifluoromethyl, methyl, ethyl, methoxy or ethoxy substituents,
  in which phenyl and 5- to 10-membered heteroaryl may be substituted by 1 to 3 substituents each independently selected from the group of fluorine, chlorine, bromine, cyano, nitro, trifluoromethyl, methyl, ethyl, ethenyl, propenyl, methoxy, ethoxy, difluoromethoxy, trifluoromethoxy, methoxycarbonyl and ethoxycarbonyl,
    in which methoxy and ethoxy may be substituted by hydroxyl,
    and
    in which phenyl may be substituted on two adjacent carbon atoms in the phenyl by a methylenedioxy bridge or ethylenedioxy bridge,
$R^{10}$ is hydrogen or $(C_1-C_4)$-alkyl,
  or
$R^9$ and $R^{10}$ together with the carbon atom to which they are bonded form a 3- to 7-membered carbocycle or a 4- to 7-membered heterocycle,
  or
$R^7$ and $R^9$ together with the carbon atoms to which they are bonded form a 3- to 7-membered carbocycle or a 4- to 7-membered heterocycle,
  in which the 3- to 7-membered carbocycle and the 4- to 7-membered heterocycle may be substituted by 1 or 2 $(C_1-C_4)$-alkyl substituents,
  and
  in which the 3- to 7-membered carbocycle and the 4- to 7-membered heterocycle may be fused to a phenyl ring or a pyridyl ring, which may in turn be substituted by 1 or 2 substituents selected from fluorine, chlorine, bromine, methyl, ethyl and trifluoromethyl,
with the proviso that not more than one of the $R^7$ and $R^8$, $R^9$ and $R^{10}$, and $R^7$ and $R^9$ radical pairs at the same time forms a carbo- or heterocycle,
with the proviso that the $R^7$ and $R^9$ radicals are not at the same time both phenyl or 5- or 6-membered heteroaryl,
$R^{11}$ is hydrogen or $(C_1-C_4)$-alkyl,
  in which $(C_1-C_4)$-alkyl may be substituted up to five times by fluorine,
$R^{12}$ is hydrogen, $(C_1-C_6)$-alkyl, $(C_3-C_5)$-cycloalkyl or $(C_1-C_4)$-alkylcarbonyl,
  in which $(C_1-C_6)$-alkyl may be substituted up to five times by fluorine,
or
$R^{11}$ and $R^{12}$ together with the nitrogen atom to which they are bonded form a 4- to 7-membered azaheterocycle,
  in which the 4- to 7-membered azaheterocycle may be substituted by methyl or ethyl,
$R^{13}$ is 5- to 10-membered azaheterocyclyl bonded via a ring carbon atom or 5- or 6-membered heterocyclyl bonded via a ring nitrogen atom,
  in which 5- to 10-membered azaheterocyclyl bonded via a ring carbon atom may be substituted by 1 or 2 trifluoromethyl, $(C_3-C_7)$-cycloalkyl, oxo and benzyl substituents, and up to four times by $(C_1-C_4)$-alkyl and up to twice by fluorine,
  in which 5- to 10-membered azaheterocyclyl may be fused to a phenyl ring or a pyridyl ring, which may in turn be substituted by 1 or 2 substituents selected from fluorine, chlorine, methyl, $(C_1-C_4)$-alkyl and trifluoromethyl,
  in which 5- or 6-membered heterocyclyl bonded via a ring nitrogen atom may be substituted by $(C_1-C_4)$-alkyl or $(C_1-C_4)$-cycloalkyl,
  or
  may be amino when $L^2$ is a bond,
    in which amino may be substituted by $(C_1-C_4)$-alkyl, $(C_1-C_4)$-alkylcarbonyl, $(C_3-C_6)$-carbocyclyl, 4- to 7-membered heterocyclyl, phenyl or 5- or 6-membered heteroaryl,
      in which $(C_1-C_4)$-alkylcarbonyl may be substituted by monoalkylamino, dialkylamino or 5- or 6-membered heterocyclyl bonded via a ring nitrogen atom, in which 5- or 6-membered heterocyclyl bonded via a ring nitrogen atom may be substituted by oxo, in which $(C_3-C_6)$-carbocyclyl and 4- to 7-membered heterocyclyl may be substituted by hydroxyl, and in which phenyl and 5- or 6-membered heteroaryl may be substituted by 1 to 3 substituents each independently selected from the group of fluorine, chlorine, methyl and trifluoromethyl, $R^{14}$ is hydrogen, $(C_1-C_6)$-alkyl, $(C_3-C_7)$-cycloalkyl, —(C=O)NR$^{24}$R$^{25}$, 5- or 6-membered heteroaryl or phenyl, in which $(C_1-C_6)$-alkyl may be substituted by 1 or 2 substituents each independently selected from the group of hydroxyl and $(C_1-C_4)$-alkoxy, and may be substituted up to six times by fluorine, in which $R^{24}$ is hydrogen, $(C_1-C_4)$-alkyl, aryl or naphthyl, in which $R^{25}$ is hydrogen, and in which phenyl and 5- or 6-membered heteroaryl may be substituted by 1 to 3 substituents each independently selected from the group of fluorine, chlorine, bromine, trifluoromethyl, difluoromethyl, methyl, ethyl and 1-amino-2-methylpropyl, $R^{15}$ is hydrogen or $(C_1-C_6)$-alkyl, in which $(C_1-C_4)$-alkyl may be substituted by hydroxyl, or $R^{14}$ and $R^{15}$ together with the carbon atom to which they are bonded form a 3- to 7-membered carbocycle, $R^{16}$ is hydrogen, $(C_1-C_6)$-alkyl or $(C_3-C_7)$-cycloalkyl, in which $(C_1-C_6)$-alkyl may be substituted by 1 or 2 substituents each independently selected from the group of hydroxyl and $(C_1-C_4)$-alkoxy, and may be substituted up to six times by fluorine, in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy, $R^{17}$ is hydrogen or $(C_1-C_6)$-alkyl, or $R^{16}$ and $R^{17}$ together with the carbon atom to which they are bonded form a 3- to 6-membered carbocycle, in which the 3- to 6-membered carbocycle may be substituted by 1 or 2 substituents each independently selected from the group of fluorine, methyl and ethyl, or $R^{14}$ and $R^{16}$ together with the carbon atoms to which they are bonded form a 3- to 7-membered carbocycle or a 4- to 7-membered heterocycle, with the proviso that not more than one of the $R^{14}$ and $R^{15}$, $R^{16}$ and $R^{17}$, and $R^{14}$ and $R^{16}$ radical pairs at the same time forms a carbo- or heterocycle, $R^{18}$ is hydrogen or $(C_1-C_4)$-alkyl, in which $(C_1-C_4)$-alkyl may be substituted by 1 to 5 fluorine substituents, m is 0 or 1, n is 0 or 1, $R^{19}$ is hydrogen, cyano or $(C_1-C_4)$-alkyl, in which $(C_1-C_4)$-alkyl may be substituted by 1 to 5 fluorine substituents, $R^{20}$ is hydrogen or $(C_1-C_4)$-alkyl, in which $(C_1-C_4)$-alkyl may be substituted by 1 to 5 fluorine substituents, $R^{21}$ is hydrogen or $(C_1-C_4)$-alkyl, in which $(C_1-C_4)$-alkyl may be substituted by 1 to 5 fluorine substituents, $R^{22}$ is hydrogen or $(C_1-C_4)$-alkyl, in which $(C_1-C_4)$-alkyl may be substituted by 1 to 5 fluorine substituents, or $R^{19}$ and $R^{20}$ together with the carbon atom to which they are bonded form a 3- to 7-membered carbocycle or a 4- to 7-membered heterocycle, in which the 3- to 7-membered carbocycle and the 4- to 7-membered heterocycle may in turn be substituted by 1 or 2 substituents each independently selected from the group of fluorine and $(C_1-C_4)$-alkyl, or $R^{21}$ and $R^{22}$ together with the carbon atom to which they are bonded form a 3- to 7-membered carbocycle or a 4- to 7-membered heterocycle, in which the 3- to 7-membered carbocycle and the 4- to 7-membered heterocycle may in turn be substituted by 1 or 2 substituents each independently selected from the group of fluorine and $(C_1-C_4)$-alkyl, or $R^{19}$ and $R^{21}$ together with the carbon atom to which they are bonded form a 3- to 7-membered carbocycle or a 4- to 7-membered heterocycle, in which the 3- to 7-membered carbocycle and the 4- to 7-membered heterocycle may in turn be substituted by 1 or 2 substituents each independently selected from the group of fluorine and $(C_1-C_4)$-alkyl, with the proviso that not more than one of the $R^{19}$ and $R^{20}$, $R^{21}$ and $R^{22}$, and $R^{19}$ and $R^{21}$ radical pairs at the same time forms a carbo- or heterocycle, $R^{23}$ is $(C_1-C_6)$-alkyl, $(C_1-C_6)$-alkoxy, $(C_1-C_4)$-alkoxycarbonyl, hydroxycarbonyl, aminocarbonyl, aminosulphonyl, 5- to 10-membered heterocyclyl bonded via a ring carbon atom, 5- to 10-membered carbocyclyl, phenyl or 5- to 10-membered heteroaryl, in which $(C_1-C_6)$-alkyl may be substituted by cyano and up to six times by fluorine, in which $(C_1-C_6)$-alkoxy may be substituted by hydroxyl or $(C_2-C_4)$-alkenyl, in which aminocarbonyl may be substituted by $(C_1-C_6)$-alkyl or $(C_3-C_6)$-cycloalkyl, in which aminosulphonyl may be substituted by $(C_1-C_6)$-alkyl or $(C_3-C_6)$-cycloalkyl, in which phenyl may be substituted by 1 to 3 substituents each independently selected from the group of halogen, cyano, trifluoromethyl, difluoromethyl, $(C_1-C_4)$-alkyl, $(C_1-C_4)$-alkoxy, 5- to 10-membered heteroaryl and 4- to 7-membered heterocyclyl, in which $(C_1-C_6)$-alkyl may be substituted by 1 or 2 substituents each independently selected from the group of fluorine, trifluoromethoxy, $(C_1-C_4)$-alkoxy, $(C_3-C_6)$-cycloalkyl, hydroxyl and amino, in which 5- to 10-membered heteroaryl may be substituted by 1 to 3 substituents each independently selected from the group of fluorine, chlorine, cyano, $(C_1-C_4)$-alkyl, trifluoromethyl, $(C_1-C_4)$-alkoxy and amino, in which $(C_1-C_4)$-alkyl may be substituted by 1 to 3 substituents each independently selected from the group of halogen, cyano, hydroxyl, amino, trifluoromethyl, difluoromethyl, $(C_1-C_4)$-alkoxy, trifluoromethoxy, difluoromethoxy and phenyl, in which phenyl may be substituted by 1 to 3 halogen substituents, in which 5- to 10-membered heterocyclyl bonded via a ring carbon atom may be substituted by 1 or 2 substituents each independently selected from the group of oxo, fluorine, trifluoromethyl, hydroxyl and ($C_1$-$C_4$)-alkyl, in which 5- to 10-membered heterocyclyl bonded via a ring carbon atom may be fused to a phenyl ring or a pyridyl ring, which may in turn be substituted by 1 to 3 substituents selected from the group of halogen, ($C_1$-$C_4$)-alkyl, ($C_1$-$C_4$)-alkoxy and trifluoromethyl, and in which 5- to 10-membered carbocyclyl may be substituted by 1 or 2 substituents each independently selected from the group of trifluoromethyl, fluorine, cyano, hydroxyl, hydroxycarbonyl, ($C_1$-$C_4$)-alkoxycarbonyl, amino and ($C_1$-$C_4$)-alkyl, in which 5- to 10-membered carbocyclyl may be fused to a phenyl ring or a pyridyl ring, which may in turn be substituted by 1 to 3 substituents selected from the group of halogen, ($C_1$-$C_4$)-alkyl, ($C_1$-$C_4$)-alkoxy and trifluoromethyl, $R^4$ is hydrogen, $R^5$ is hydrogen, fluorine, chlorine, bromine, cyano, difluoromethyl, trifluoromethyl, ($C_1$-$C_4$)-alkyl, methoxy, ($C_3$-$C_5$)-cycloalkyl or ($C_2$-$C_4$)-alkynyl, $R^6$ is hydrogen or fluorine, and the N-oxides, salts, solvates, salts of the N-oxides and solvates of the N-oxides or salts thereof.

Preference is given in the context of the present invention to compounds of the formula (I) in which A is $CH_2$, $R^1$ is cyclohexyl, pyridyl or phenyl,
where cyclohexyl may be substituted by 1 to 2 substituents each independently selected from the group of fluorine and methyl,
where pyridyl is substituted by 1 or 2 F substituents, and
where phenyl may be substituted by 1 to 4 substituents each independently selected from the group of fluorine, chlorine, methyl, methoxy and cyclopropyl, $R^2$ is methyl, cyclopropyl or trifluoromethyl, $R^3$ is a group of the formula

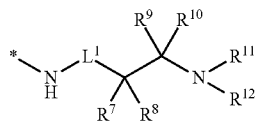

or

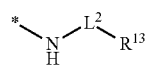

or

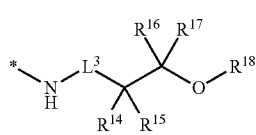

or

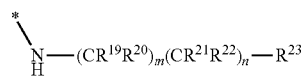

where
* is the attachment site to the carbonyl group,
$L^1$ is a bond,
$L^2$ is a bond,
$L^3$ is a bond,
$R^7$ is hydrogen, ($C_1$-$C_6$)-alkyl or phenyl,
in which ($C_1$-$C_6$)-alkyl may be substituted by 1 to 5 fluorine substituents,
and
in which phenyl may be substituted by 1 to 3 substituents independently of one another selected from the group consisting of fluorine, chlorine, trifluoromethyl, methyl or methoxy,
$R^8$ is hydrogen, methyl or ethyl,
$R^9$ is hydrogen, ($C_1$-$C_6$)-alkyl, cyclopropyl or cyclobutyl,
in which ($C_1$-$C_6$)-alkyl may be substituted by 1 to 5 fluorine substituents,
$R^{10}$ is hydrogen or ($C_1$-$C_4$)-alkyl,
or
$R^9$ and $R^{10}$ together with the carbon atom to which they are bonded form a 3- to 6-membered carbocycle,
$R^{11}$ is hydrogen, methyl or ethyl,
in which ethyl may be substituted by 1 to 3 fluorine substituents,
$R^{12}$ is hydrogen, ($C_1$-$C_4$)-alkyl or ($C_3$-$C_5$)-cycloalkyl,
or
$R^{11}$ and $R^{12}$ together with the nitrogen atom to which they are bonded form a morpholinyl ring or piperidinyl ring,
$R^{13}$ is 9-azabicyclo[3.3.1]nonan-3-yl or piperidin-4-yl,
in which 9-azabicyclo[3.3.1]nonan-3-yl is substituted by methyl,
in which piperidin-4-yl may be substituted by 1 to 5 methyl substituents,
$R^{14}$ is hydrogen, ($C_1$-$C_6$)-alkyl, —(C═O)NR$^{24}$R$^{25}$ or phenyl,
in which ($C_1$-$C_6$)-alkyl may be substituted by a hydroxyl or methoxy radical or up to five times by fluorine,
in which $R^{24}$ is aryl or naphthyl,
in which $R^{25}$ is hydrogen,
and
in which phenyl may be substituted by 1 to 3 substituents independently of one another selected from the group consisting of fluorine, chlorine, trifluoromethyl and methyl,
$R^{15}$ is hydrogen or ($C_1$-$C_4$)-alkyl,
$R^{16}$ is hydrogen, ($C_1$-$C_6$)-alkyl, cyclopropyl or cyclobutyl,
in which ($C_1$-$C_6$)-alkyl may be substituted by 1 to 5 fluorine substituents,
in which cyclopropyl and cyclobutyl may be substituted by 1 or 2 substituents each independently selected from the group of fluorine and methyl,
$R^{17}$ is hydrogen or ($C_1$-$C_4$)-alkyl,
or
$R^{16}$ and $R^{17}$ together with the carbon atom to which they are bonded form a 3- to 6-membered carbocycle,
in which the 3- to 6-membered carbocycle may be substituted by 1 or 2 fluorine or methyl substituents,
$R^{18}$ is hydrogen or ($C_1$-$C_4$)-alkyl,
in which ($C_1$-$C_3$)-alkyl may be substituted by 1 to 5 fluorine substituents,
m is 0 or 1, n is 0 or 1, $R^{19}$ is hydrogen, cyano or methyl,
   in which methyl may be substituted by 1 to 3 fluorine substituents, $R^{20}$ is hydrogen or methyl,
   in which methyl may be substituted by 1 to 3 fluorine substituents, $R^{21}$ is hydrogen or methyl,
   in which methyl may be substituted by 1 to 3 fluorine substituents, $R^{22}$ is hydrogen or methyl,
   in which methyl may be substituted by 1 to 3 fluorine substituents, or $R^{19}$ and $R^{20}$ together with the carbon atom to which they are bonded form a 3- to 5-membered carbocycle, or $R^{19}$ and $R^{21}$ together with the carbon atom to which they are bonded form a cyclopropyl ring, with the proviso that not more than one of the $R^{19}$ and $R^{20}$, and $R^{19}$ and $R^{21}$ radical pairs at the same time forms a carbocycle, $R^{23}$ is $(C_1$-$C_6)$-alkyl, 2-oxopyrrolidin-3-yl, 2-oxotetrahydrofuran-3-yl, cyclopentyl, cyclohexyl, phenyl, indanyl, 1,2,4-oxadiazol-5-yl, 1H-imidazol-2-yl, 1H-pyrazol-4-yl, pyridin-3-yl, pyrimidin-5-yl, quinolin-4-yl or pyrazolo[1,5-a]pyridin-3-yl,
   where $(C_1$-$C_6)$-alkyl may be substituted by cyano or up to three times by fluorine,
   where phenyl may be substituted by 1 to 3 substituents each independently selected from the group of fluorine, chlorine, cyano, trifluoromethyl, methyl, ethyl, methoxy and pyridyl,
   where indanyl may be substituted by hydroxyl,
   where 1,2,4-oxadiazol-5-yl, 1H-imidazol-2-yl, 1H-pyrazol-4-yl, pyridin-3-yl, pyrimidin-5-yl, quinolin-4-yl or pyrazolo[1,5-a]pyridin-3-yl may be substituted by 1 to 3 substituents each independently selected from the group of fluorine, chlorine, trifluoromethyl, $(C_1$-$C_3)$-alkyl, amino and hydroxyl,
      in which $(C_1$-$C_3)$-alkyl may be substituted by fluorine, hydroxyl, amino or trifluoromethyl,
   where cyclopentyl and cyclohexyl are substituted by methoxycarbonyl or ethoxycarbonyl, $R^4$ is hydrogen, $R^5$ is hydrogen, fluorine, chlorine, methyl or ethyl, $R^6$ is hydrogen, and the N-oxides, salts, solvates, salts of the N-oxides and solvates of the N-oxides or salts thereof.

Preference is given in the context of the present invention to compounds of the formula (I) in which A is $CH_2$, $R^1$ is cyclohexyl, pyridyl or phenyl,
   where pyridyl is substituted by 1 or 2 F substituents, and
   where phenyl may be substituted by 1 to 4 substituents each independently selected from the group of fluorine, chlorine, cyano, methyl, ethyl, methoxy, ethoxy and cyclopropyl, $R^2$ is methyl, cyclopropyl, difluoromethyl or trifluoromethyl, $R^3$ is a group of the formula

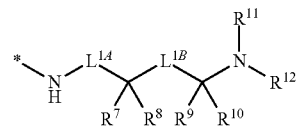

or

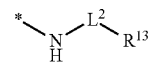

or

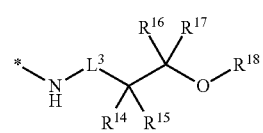

or

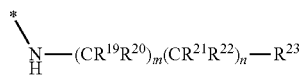

where

* is the attachment site to the carbonyl group, $L^{1A}$ is a bond or methanediyl, $L^{1B}$ is a bond, $L^2$ is a bond, $L^3$ is a bond, $R^7$ is hydrogen, $(C_1$-$C_6)$-alkyl or phenyl,
   in which $(C_1$-$C_6)$-alkyl may be substituted up to five times by fluorine,
   in which phenyl may be substituted by 1 to 3 substituents each independently selected from the group of fluorine, chlorine, bromine, trifluoromethyl, methyl, methoxy, difluoromethoxy and trifluoromethoxy,
   and
   in which phenyl may be substituted on two adjacent carbon atoms in the phenyl by a methylenedioxy bridge or ethylenedioxy bridge,
or
   may be fluorine when $L^{1A}$ is not a bond, $R^8$ is hydrogen, methyl or ethyl,
or
   may be fluorine when $L^{1A}$ is not a bond, $R^9$ is hydrogen, $(C_1$-$C_6)$-alkyl, cyclopropyl or cyclobutyl,
   in which $(C_1$-$C_6)$-alkyl may be substituted up to five times by fluorine,
   in which cyclopropyl and cyclobutyl may be substituted by trifluoromethyl, $R^{10}$ is hydrogen or $(C_1$-$C_4)$-alkyl,
or $R^9$ and $R^{10}$ together with the carbon atom to which they are bonded form a 3- to 7-membered carbocycle, $R^{11}$ is hydrogen, methyl or ethyl,
   in which ethyl may be substituted up to three times by fluorine, $R^{12}$ is hydrogen, $(C_1$-$C_4)$-alkyl, cyclopropyl or cyclobutyl,
   in which $(C_1$-$C_6)$-alkyl may be substituted up to five times by fluorine, or $R^{11}$ and $R^{12}$ together with the nitrogen atom to which they are bonded form a morpholinyl ring, $R^{13}$ is 9-azabicyclo[3.3.1]nonan-3-yl, pyrrolidinyl, piperidin-4-yl, azepanyl or 1,2,3,4-tetrahydroquinolinyl,
  in which piperidin-4-yl may be substituted by 1 to 5 methyl substituents and may be substituted up to twice by fluorine,
  in which 1,2,3,4-tetrahydroquinolinyl may be substituted by 1 to 2 substituents each independently selected from the group of fluorine, oxo, methyl, ethyl, methoxy, ethoxy and trifluoromethyl,
  in which 9-azabicyclo[3.3.1]nonan-3-yl may be substituted by methyl,
  in which pyrrolidinyl may be substituted by 1 to 2 substituents independently of one another selected from the group consisting of fluorine, oxo, methyl and ethyl, $R^{14}$ is hydrogen, $(C_1-C_6)$-alkyl, —(C=O)$NR^{24}R^{25}$ or phenyl,
  in which $(C_1-C_6)$-alkyl may be substituted by hydroxyl or methoxy and up to five times by fluorine,
  in which $R^{24}$ is aryl or naphthyl,
  in which $R^{25}$ is hydrogen,
  and
  in which phenyl may be substituted by 1 or 2 substituents independently of one another selected from the group consisting of fluorine, chlorine, trifluoromethyl and methyl, $R^{15}$ is hydrogen or $(C_1-C_6)$-alkyl, $R^{16}$ is hydrogen, $(C_1-C_6)$-alkyl, cyclopropyl or cyclobutyl,
  in which $(C_1-C_6)$-alkyl may be substituted up to six times by fluorine, $R^{17}$ is hydrogen or $(C_1-C_6)$-alkyl, or $R^{16}$ and $R^{17}$ together with the carbon atom to which they are bonded form a 3- to 6-membered carbocycle,
  in which the 3- to 6-membered carbocycle may be substituted by 1 or 2 substituents each independently selected from the group of fluorine and methyl, $R^{18}$ is hydrogen or $(C_1-C_4)$-alkyl,
  in which $(C_1-C_4)$-alkyl may be substituted by 1 to 5 fluorine substituents, m is 0 or 1, n is 0 or 1, $R^{19}$ is hydrogen, cyano or methyl,
  in which methyl may be substituted by 1 to 3 fluorine substituents, $R^{20}$ is hydrogen or methyl,
  in which methyl may be substituted by 1 to 3 fluorine substituents, $R^{21}$ is hydrogen or methyl,
  in which methyl may be substituted by 1 to 3 fluorine substituents, $R^{22}$ is hydrogen or methyl,
  in which methyl may be substituted by 1 to 3 fluorine substituents, or $R^{19}$ and $R^{20}$ together with the carbon atom to which they are bonded form a 3- to 5-membered carbocycle, or $R^{19}$ and $R^{21}$ together with the carbon atom to which they are bonded form a cyclopropyl ring, with the proviso that not more than one of the $R^{19}$ and $R^{20}$, and $R^{19}$ and $R^{21}$ radical pairs at the same time forms a carbocycle, $R^{23}$ is $(C_1-C_6)$-alkyl, 2-oxopyrrolidin-3-yl, 2-oxotetrahydrofuran-3-yl, cyclopentyl, cyclohexyl, indanyl, 1,2,4-oxadiazol-5-yl, 1H-imidazol-2-yl, 1H-pyrazol-4-yl, pyridin-3-yl, pyrimidin-5-yl, quinolin-4-yl, pyrazolo[1,5-a]pyridin-3-yl, 3,4-dihydro-2H-pyranyl, 1,2,3,4-tetrahydronaphthalenyl, bicyclo[2.2.2]octanyl, chroman-4-yl, 2,3-dihydro-1-benzofuran-3-yl, 2,3-dihydro-1H-indenyl, 3,4-dihydroquinolinyl, 3,4-dihydro-2H-pyrano[2,3-b]pyridinyl or phenyl,
  in which $(C_1-C_6)$-alkyl may be substituted by cyano and up to three times by fluorine,
  in which phenyl may be substituted by 1 to 3 substituents each independently selected from the group of fluorine, chlorine, cyano, trifluoromethyl, methyl, ethyl, methoxy, 1H-imidazol-1-yl and pyridyl,
  in which 1,2,4-oxadiazol-5-yl, 1H-imidazol-2-yl, 1H-pyrazol-4-yl, pyridin-3-yl, pyrimidin-5-yl, quinolin-4-yl or pyrazolo[1,5-a]pyridin-3-yl may be substituted by 1 to 3 substituents each independently selected from the group of fluorine, chlorine, trifluoromethyl, $(C_1-C_3)$-alkyl, amino and hydroxyl,
    in which $(C_1-C_3)$-alkyl may be substituted by fluorine, hydroxyl, amino or trifluoromethyl,
  in which cyclopentyl, cyclohexyl and bicyclo[2.2.2]octanyl may be substituted by methoxycarbonyl, ethoxycarbonyl, hydroxycarbonyl and cyano,
  in which chroman-4-yl, 2,3-dihydro-1-benzofuran-3-yl, 2,3-dihydro-1H-indenyl, 3,4-dihydroquinolinyl and 3,4-dihydro-2H-pyrano[2,3-b]pyridinyl may be substituted by 1 or 2 substituents selected from the group of fluorine, chlorine, methyl, ethyl, methoxy, ethoxy and trifluoromethyl,
  and
  in which 2,3-dihydro-1H-indenyl and indanyl may be substituted by 1 or 2 substituents selected from the group of fluorine, chlorine, methyl, ethyl, methoxy, ethoxy, hydroxyl and trifluoromethyl,
    in which methyl and ethyl may be substituted by hydroxyl, $R^4$ is hydrogen, $R^5$ is hydrogen, fluorine, chlorine, methyl or ethyl, $R^6$ is hydrogen, and the N-oxides, salts, solvates, salts of the N-oxides and solvates of the N-oxides or salts thereof.

Particular preference is given in the context of the present invention to compounds of the formula (I) in which A is $CH_2$, $R^1$ is a phenyl group of the formula

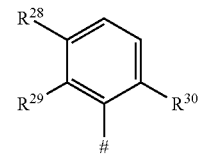

where

\# is the attachment site to A, and $R^{28}$ is hydrogen or fluorine, $R^{29}$ is fluorine, $R^{30}$ is fluorine, $R^2$ is methyl, $R^3$ is a group of the formula

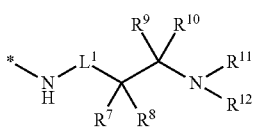

or

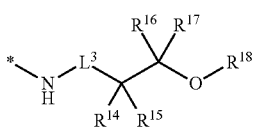

where
* is the attachment site to the carbonyl group,
$L^1$ is a bond,
$L^3$ is a bond,
$R^7$ is hydrogen, $(C_1-C_6)$-alkyl or phenyl,
  in which $(C_1-C_6)$-alkyl may be substituted by 1 to 5 fluorine substituents,
  and
  in which phenyl may be substituted by 1 to 2 chlorine or fluorine substituents,
$R^8$ is hydrogen, methyl or ethyl,
$R^9$ is hydrogen, $(C_1-C_6)$-alkyl, trifluoromethyl or cyclopropyl,
  in which $(C_1-C_6)$-alkyl may be substituted by 1 to 3 fluorine substituents,
$R^{10}$ is hydrogen, methyl or ethyl,
$R^{11}$ is hydrogen,
$R^{12}$ is hydrogen,
$R^{14}$ is hydrogen, $(C_1-C_6)$-alkyl or phenyl,
  in which $(C_1-C_6)$-alkyl may be substituted by a hydroxyl radical or up to five times by fluorine,
  and
  in which phenyl may be substituted by 1 or 2 fluorine substituents,
$R^{15}$ is hydrogen, methyl or ethyl,
$R^{16}$ is hydrogen or $(C_1-C_6)$-alkyl,
$R^{17}$ is hydrogen, methyl or ethyl,
or
$R^{16}$ and $R^{17}$ together with the carbon atom to which they are bonded form a 3- to 6-membered carbocycle,
$R^{18}$ is hydrogen,
$R^4$ is hydrogen,
$R^5$ is hydrogen or methyl,
$R^6$ is hydrogen, PS and the N-oxides, salts, solvates, salts of the N-oxides and solvates of the N-oxides or salts thereof.
Preference is given in the context of the present invention to compounds of the formula (I) in which
A is $CH_2$,
$R^1$ is a phenyl group of the formula

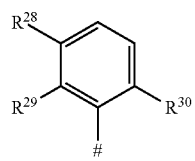

where
# is the attachment site to A,
and $R^{28}$ is hydrogen or fluorine,
$R^{29}$ is fluorine,
$R^{30}$ is fluorine,
$R^2$ is methyl or cyclopropyl,
$R^3$ is a group of the formula

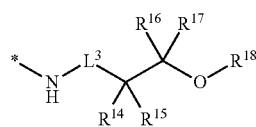

or

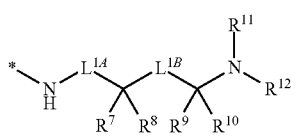

where
* is the attachment site to the carbonyl group,
$L^{1A}$ is a bond,
$L^{1B}$ is a bond,
$R^7$ is hydrogen, $(C_1-C_6)$-alkyl or phenyl,
  in which $(C_1-C_6)$-alkyl may be substituted up to five times by fluorine,
  in which phenyl may be substituted by 1 to 2 chlorine or fluorine substituents,
$R^8$ is hydrogen, methyl or ethyl,
$R^9$ is hydrogen, $(C_1-C_6)$-alkyl or cyclopropyl,
  in which $(C_1-C_6)$-alkyl may be substituted up to five times by fluorine,
$R^{10}$ is hydrogen, methyl or ethyl,
$R^{11}$ is hydrogen,
$R^{12}$ is hydrogen,
$R^{14}$ is hydrogen, $(C_1-C_6)$-alkyl or phenyl,
  in which $(C_1-C_6)$-alkyl may be substituted by hydroxyl and up to five times by fluorine,
  and
  in which phenyl may be substituted by 1 or 2 fluorine substituents,
$R^{15}$ is hydrogen, methyl or ethyl,
$R^{16}$ is hydrogen or $(C_1-C_6)$-alkyl,
$R^{17}$ is hydrogen, methyl or ethyl,
or
$R^{16}$ and $R^{17}$ together with the carbon atom to which they are bonded form a 3- to 6-membered carbocycle,
$R^{18}$ is hydrogen,
$R^4$ is hydrogen,
$R^5$ is hydrogen or methyl,
$R^6$ is hydrogen, PS and the N-oxides, salts, solvates, salts of the N-oxides and solvates of the N-oxides or salts thereof.

In the context of the present invention, preference is also given to compounds of the formula (I) in which
$R^1$ is a phenyl group of the formula

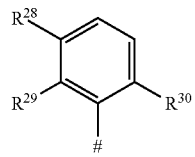

where
# is the attachment site to A,
and
$R^{28}$ is hydrogen or fluorine,
$R^{29}$ is fluorine,
$R^{30}$ is fluorine, PS and the N-oxides, salts, solvates, salts of the N-oxides and solvates of the N-oxides or salts thereof.

In the context of the present invention, preference is also given to compounds of the formula (I) in which
$R^2$ is methyl or cyclopropyl, PS and the N-oxides, salts, solvates, salts of the N-oxides and solvates of the N-oxides or salts thereof.

In the context of the present invention, preference is also given to compounds of the formula (I) in which
$R^2$ is methyl, PS and the N-oxides, salts, solvates, salts of the N-oxides and solvates of the N-oxides or salts thereof.

In the context of the present invention, preference is also given to compounds of the formula (I) in which
$R^2$ is cyclopropyl, PS and the N-oxides, salts, solvates, salts of the N-oxides and solvates of the N-oxides or salts thereof.

In the context of the present invention, preference is also given to compounds of the formula (I) in which
$R^3$ is a group of the formula

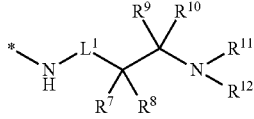

where
* is the attachment site to the carbonyl group,
$L^1$ is a bond, PS and the N-oxides, salts, solvates, salts of the N-oxides and solvates of the N-oxides or salts thereof.

In the context of the present invention, preference is also given to compounds of the formula (I) in which
$R^3$ is a group of the formula

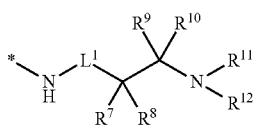

where
* is the attachment site to the carbonyl group,
$R^7$ is hydrogen, $(C_1-C_6)$-alkyl or phenyl,
  in which $(C_1-C_6)$-alkyl may be substituted up to five times by fluorine,
  in which phenyl may be substituted by 1 to 2 chlorine or fluorine substituents, PS and the N-oxides, salts, solvates, salts of the N-oxides and solvates of the N-oxides or salts thereof.

In the context of the present invention, preference is also given to compounds of the formula (I) in which
$R^3$ is a group of the formula

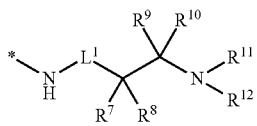

where
* is the attachment site to the carbonyl group,
$R^8$ is hydrogen, PS and the N-oxides, salts, solvates, salts of the N-oxides and solvates of the N-oxides or salts thereof.

In the context of the present invention, preference is also given to compounds of the formula (I) in which
$R^3$ is a group of the formula

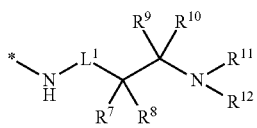

where
* is the attachment site to the carbonyl group,
$R^9$ is hydrogen, $(C_1-C_6)$-alkyl or cyclopropyl,
  in which $(C_1-C_6)$-alkyl may be substituted up to five times by fluorine, PS and the N-oxides, salts, solvates, salts of the N-oxides and solvates of the N-oxides or salts thereof.

In the context of the present invention, preference is also given to compounds of the formula (I) in which
$R^3$ is a group of the formula

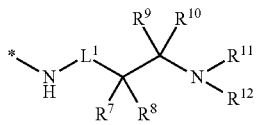

where
* is the attachment site to the carbonyl group,
and
$R^{10}$ is hydrogen or methyl, PS and the N-oxides, salts, solvates, salts of the N-oxides and solvates of the N-oxides or salts thereof.

In the context of the present invention, preference is also given to compounds of the formula (I) in which
$R^3$ is a group of the formula

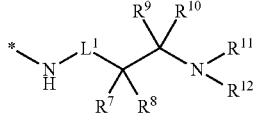

where
* is the attachment site to the carbonyl group,
and
$R^{11}$ is hydrogen, $R^{12}$ is hydrogen, PS and the N-oxides, salts, solvates, salts of the N-oxides and solvates of the N-oxides or salts thereof.

In the context of the present invention, preference is also given to compounds of the formula (I) in which
$R^3$ is a group of the formula

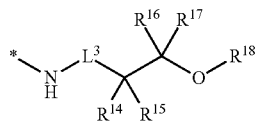

where
* is the attachment site to the carbonyl group,
$L^3$ is a bond, PS and the N-oxides, salts, solvates, salts of the N-oxides and solvates of the N-oxides or salts thereof.

In the context of the present invention, preference is also given to compounds of the formula (I) in which
$R^3$ is a group of the formula

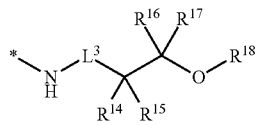

where
* is the attachment site to the carbonyl group,
$R^{14}$ is hydrogen, $(C_1-C_6)$-alkyl or phenyl,
in which $(C_1-C_6)$-alkyl may be substituted by hydroxyl and up to five times by fluorine,
and
in which phenyl may be substituted by 1 or 2 fluorine substituents, PS and the N-oxides, salts, solvates, salts of the N-oxides and solvates of the N-oxides or salts thereof.

In the context of the present invention, preference is also given to compounds of the formula (I) in which
$R^3$ is a group of the formula

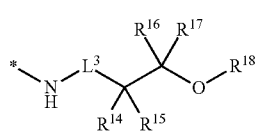

where
* is the attachment site to the carbonyl group,
$R^{15}$ is hydrogen, PS and the N-oxides, salts, solvates, salts of the N-oxides and solvates of the N-oxides or salts thereof.

In the context of the present invention, preference is also given to compounds of the formula (I) in which
$R^3$ is a group of the formula

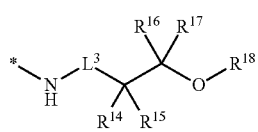

where
* is the attachment site to the carbonyl group,
and
$R^{17}$ is hydrogen or methyl, PS and the N-oxides, salts, solvates, salts of the N-oxides and solvates of the N-oxides or salts thereof.

In the context of the present invention, preference is also given to compounds of the formula (I) in which
$R^3$ is a group of the formula

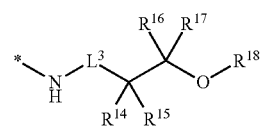

where
* is the attachment site to the carbonyl group,
and
$R^{18}$ is hydrogen, PS and the N-oxides, salts, solvates, salts of the N-oxides and solvates of the N-oxides or salts thereof.

In the context of the present invention, preference is also given to compounds of the formula (I) in which
$R^5$ is hydrogen or methyl, PS and the N-oxides, salts, solvates, salts of the N-oxides and solvates of the N-oxides or salts thereof.

In the context of the present invention, preference is also given to compounds of the formula (I) in which
$R^5$ is methyl, PS and the N-oxides, salts, solvates, salts of the N-oxides and solvates of the N-oxides or salts thereof.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the inventive compounds of the formula (I), characterized in that a compound of the formula (II)

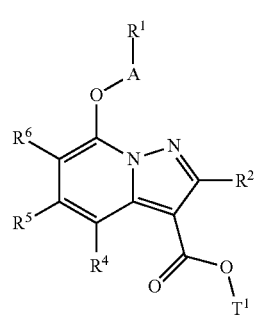

(II)

in which A, $R^1$, $R^2$, $R^4$, $R^5$ and $R^6$ are each as defined above and
$T^1$ is $(C_1-C_4)$-alkyl or benzyl,
is converted in an inert solvent in the presence of a suitable base or acid to a carboxylic acid of the formula (III)

(III)

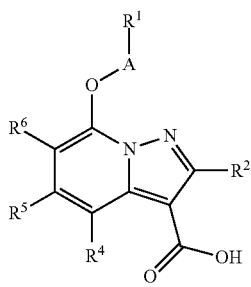

in which A, $R^1$, $R^2$, $R^4$, $R^5$ and $R^6$ are each as defined above, PS and the latter are subsequently reacted, in an inert solvent under amide coupling conditions, with an amine of the formula (IV-A), (IV-B), (IV-C) or (IV-D)

(IV-A)

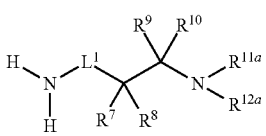

or (IV-B)

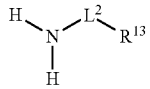

or (IV-C)

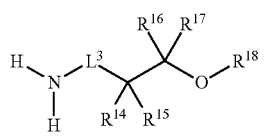

or (IV-D)

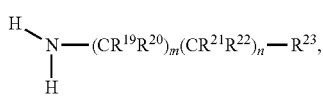

in which $L^1$, $L^2$, $L^3$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each as defined above and
$R^{11A}$ and $R^{12A}$ are each as defined above for $R^{11}$ and $R^{12}$ or are an amino protecting group, for example tert-butoxycarbonyl, benzyloxycarbonyl or benzyl,
then any protecting groups present are detached, and the resulting compounds of the formula (I) are optionally converted with the appropriate (i) solvents and/or (ii) acids or bases to the solvates, salts and/or solvates of the salts thereof.

The preparation process described can be illustrated by way of example by the following synthesis scheme (Scheme 1):

Scheme 1:

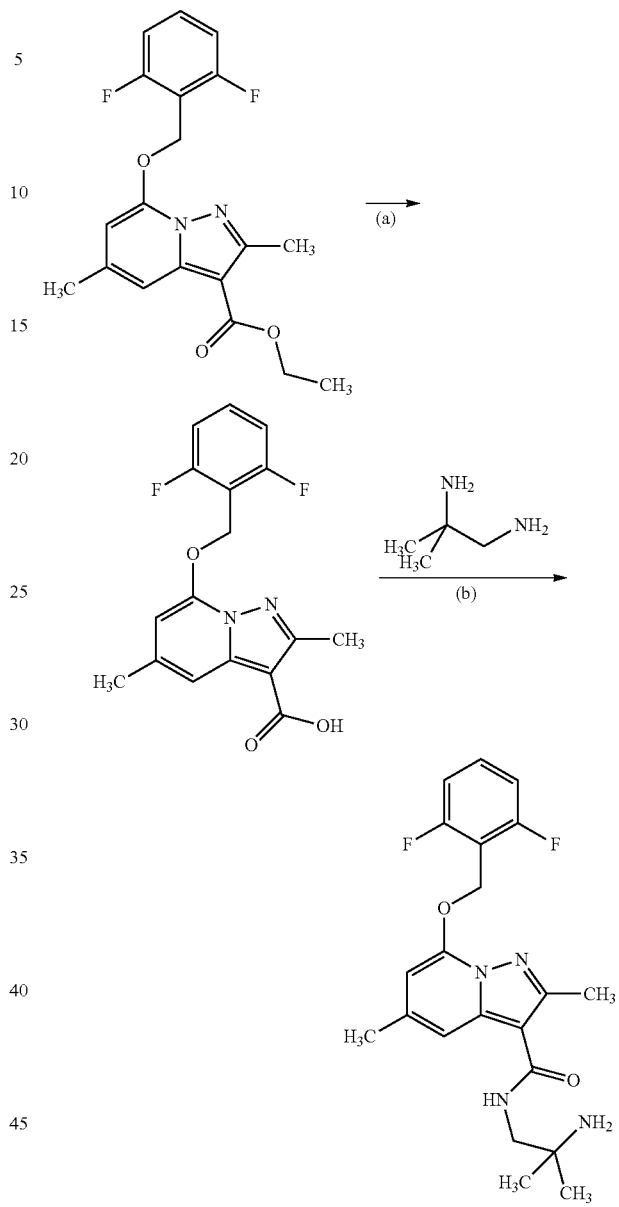

[(a) sodium hydroxide, 1,4-dioxane, 90° C.; (b) HATU, N,N-diisopropylethylamine, DMF, room temperature].

The compounds of the formulae (IV-A), (IV-B), (IV-C) and (IV-D) are commercially available or known from the literature, or can be prepared in analogy to literature processes.

Suitable inert solvents for the process steps (III)+(IV)→(I) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is likewise possible to use mixtures of the solvents mentioned.

Preference is given to dichloromethane, tetrahydrofuran, dimethylformamide or mixtures of these solvents.

Suitable condensing agents for the amide formation in the process steps (III)+(IV)→(I) are carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride (T3P), 1-chloro-N,N,2-trimethylprop-1-en-1-amine, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also, as bases, alkali metal carbonates, for example sodium carbonate or potassium carbonate or sodium hydrogencarbonate or potassium hydrogencarbonate, or organic bases such as trialkylamines, e.g. triethylamine, N-methylmorpholine, N-methylpiperidine or N,N-diisopropylethylamine. Preference is given to using TBTU in combination with N-methylmorpholine, HATU in combination with N,N-diisopropylethylamine or 1-chloro-N,N,2-trimethylprop-1-en-1-amine.

The condensation (III)+(IV)→(I) is generally conducted within a temperature range from −20° C. to +100° C., preferably at 0° C. to +60° C. The conversion can be effected under standard, elevated or reduced pressure (for example from 0.5 to 5 bar). Standard pressure is generally employed.

Alternatively, the carboxylic acid of the formula (III) can also first be converted to the corresponding carbonyl chloride and the latter can then be converted directly or in a separate reaction with an amine of the formula (IV) to the inventive compounds. The formation of carbonyl chlorides from carboxylic acids is effected by the methods known to those skilled in the art, for example by treatment with thionyl chloride, sulphuryl chloride or oxalyl chloride, in the presence of a suitable base, for example in the presence of pyridine, and optionally with addition of dimethylformamide, optionally in a suitable inert solvent.

The hydrolysis of the ester group $T^1$ in the compounds of the formula (II) is effected by customary methods, by treating the esters in inert solvents with acids or bases, in which latter case the salts formed at first are converted to the free carboxylic acids by treating with acid. In the case of the tert-butyl esters, the ester hydrolysis is preferably effected with acids. In the case of the benzyl esters, the ester hydrolysis is preferably effected by hydrogenolysis with palladium on activated carbon or Raney nickel. Suitable inert solvents for this reaction are water or the organic solvents customary for ester hydrolysis. These preferably include alcohols such as methanol, ethanol, n-propanol, isopropanol, n-butanol or tert-butanol, or ethers such as diethyl ether, tetrahydrofuran, 2-methyltetrahydrofuran, dioxane or glycol dimethyl ether, or other solvents such as acetone, dichloromethane, dimethylformamide or dimethyl sulphoxide. It is likewise possible to use mixtures of the solvents mentioned. In the case of a basic ester hydrolysis, preference is given to using mixtures of water with dioxane, tetrahydrofuran, methanol and/or ethanol.

Suitable bases for the ester hydrolysis are the customary inorganic bases. These preferably include alkali metal or alkaline earth metal hydroxides, for example sodium hydroxide, lithium hydroxide, potassium hydroxide or barium hydroxide, or alkali metal or alkaline earth metal carbonates, such as sodium carbonate, potassium carbonate or calcium carbonate. Particular preference is given to sodium hydroxide or lithium hydroxide.

Suitable acids for the ester hydrolysis are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is effected generally within a temperature range from 0° C. to +100° C., preferably at +0° C. to +50° C.

These conversions can be performed at standard, elevated or reduced pressure (for example from 0.5 to 5 bar). In general, standard pressure is employed in each case.

The amino protecting group used is preferably tert-butylcarbonyl (Boc) or benzyloxycarbonyl (Z). Protecting groups used for a hydroxyl or carboxyl function are preferably tert-butyl or benzyl. These protecting groups are detached by customary methods, preferably by reaction with a strong acid such as hydrogen chloride, hydrogen bromide or trifluoroacetic acid in an inert solvent such as dioxane, diethyl ether, dichloromethane or acetic acid; it is optionally also possible to effect the detachment without an additional inert solvent. In the case of benzyl and benzyloxycarbonyl as protecting groups, these may also be removed by hydrogenolysis in the presence of a palladium catalyst. The detachment of the protecting groups mentioned can optionally be undertaken simultaneously in a one-pot reaction or in separate reaction steps.

The compounds of the formula (III) are known from the literature or can be prepared by

[A] reacting a compound of the formula (V)

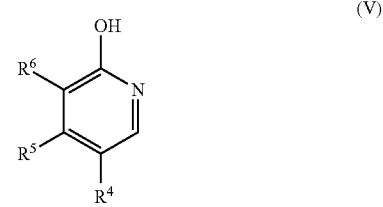

in which $R^4$, $R^5$ and $R^6$ are each as defined above in an inert solvent in the presence of a suitable base with a compound of the formula (VI)

  (VI)

in which A and R¹ are each as defined above and
X¹ is a suitable leaving group, especially chlorine, bromine, iodine, mesylate, triflate or tosylate,
to give a compound of the formula (VII)

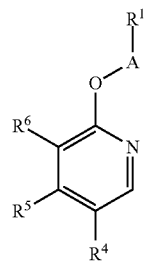  (VII)

in which A, R¹, R⁴, R⁵ and R⁶ are each as defined above,
then converting the latter with O-(2-mesitylenesulphonyl)hydroxylamine (MSH) to a compound (VIII)

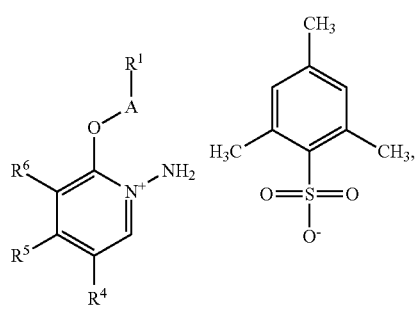  (VIII)

and then reacting this in an inert solvent with a compound of the formula (IX)

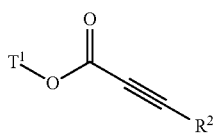  (IX)

in which R² and T¹ are each as defined above,
or
[B] converting a compound of the formula (X)

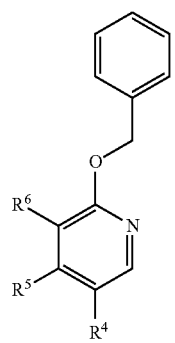  (X)

in which R⁴, R⁵ and R⁶ are each as defined above with O-(2-mesitylenesulphonyl)hydroxylamine (MSH) to a compound (XI)

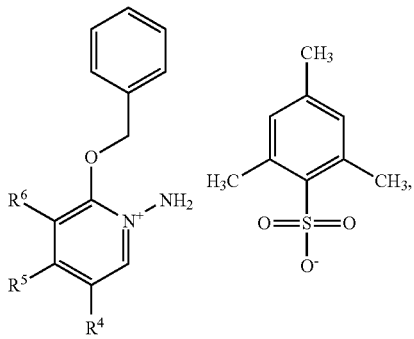  (XI)

then reacting this in an inert solvent with a compound of the formula (IX)

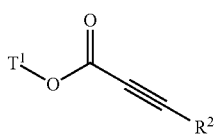  (IX)

in which R² and T¹ are each as defined above to give a compound (XII)

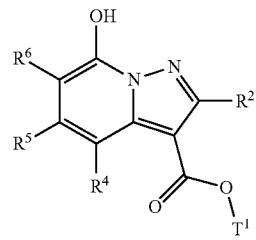  (XIII)

in which R², R⁴, R⁵ and R⁶ are each as defined above and
T¹ is (C₁-C₄)-alkyl or benzyl,
subsequently detaching the benzyl group therefrom by the methods known to those skilled in the art and reacting the resulting compound (XIII)

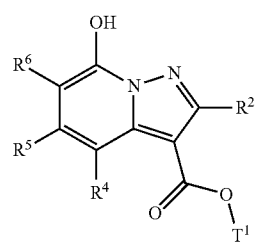  (XIII)

in which R², R⁴, R⁵ and R⁶ are each as defined above and
T¹ is (C₁-C₄)-alkyl or benzyl,
in an inert solvent under Mitsunobu conditions with a compound of the formula (XIV)

(XIV)

$$R^1-A-OH$$

in which A and $R^1$ are each as defined above.

The processes described are illustrated by way of example by the schemes below (Schemes 2 to 3):

Scheme 2:

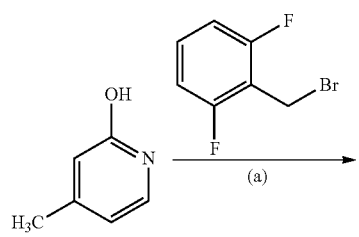

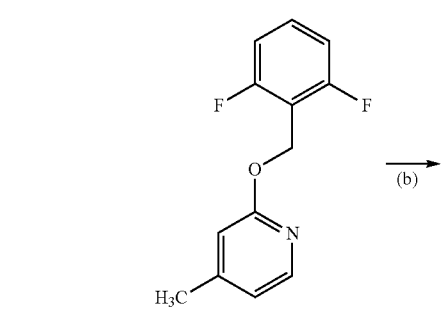

Scheme 3:

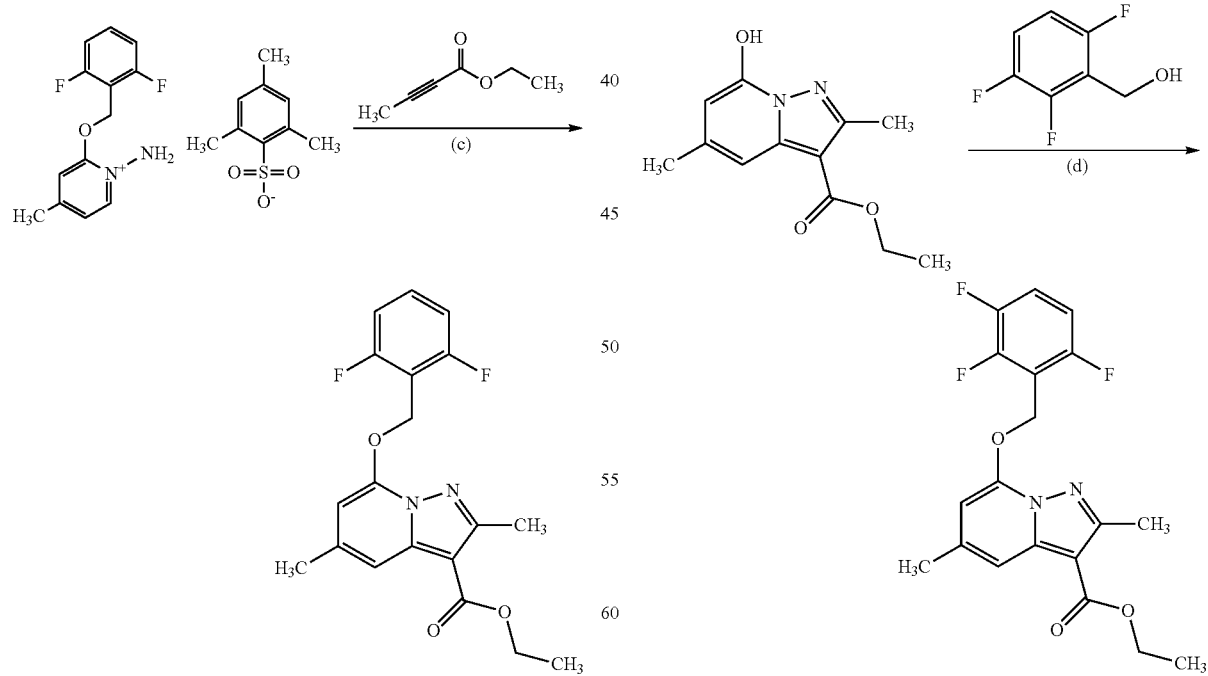

[(a) $Ag_2CO_3$, THF, reflux; (b) O-(2-mesitylenesulphonyl)hydroxylamine (MSH), dichloromethane, room temperature; (c) $K_2CO_3$, DMF, room temperature].

[(a) O-(2-mesitylenesulphonyl)hydroxylamine (MSH), dichloromethane, room temperature; (b) $K_2CO_3$, DMF, room temperature; (c) cyclohexene, Pd/C, ethanol, reflux; (d) triphenylphosphine, diisopropyl (E)-diazene-1,2-dicarboxylate (DIAD), THF, room temperature].

As an alternative to the introduction of $R^1$ by reaction of the compounds (V) with compounds of the formula (VI), as shown in Scheme 2, it is likewise possible—as shown in Scheme 4—to react compounds (XV) with alcohols of the formula (XIV) to give compounds (XVI).

Scheme 4:

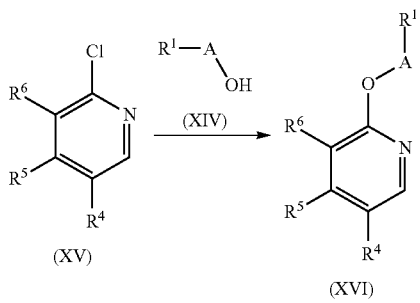

Typical reaction conditions for such reactions can be found in the specialist literature, for example Poon, K. W. C. *Synlet* 2005, 6, 841. Typically, conversion is effected in the presence of a base such as potassium hydroxide and sodium hydroxide, optionally with addition of an 18-crown-6 ether, in an inert solvent, for example THF or toluene, at a temperature between 0° C. and the boiling point of the solvent used.

Inert solvents for the process step (V)+(VI)→(VII) are, for example, ethers such as diethyl ether, dioxane, tetrahydrofuran, dimethoxymethane, glycol dimethyl ether or diethylene glycol dimethyl ether, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP). It is likewise possible to use mixtures of the solvents mentioned. Preference is given to using dimethoxyethane.

Suitable bases for the process step (V)+(VI)→(VII) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, optionally with addition of an alkali metal iodide, for example sodium iodide or potassium iodide, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 4-(N,N-dimethylamino)pyridine (DMAP), 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using sodium tert-butoxide or potassium tert-butoxide.

The reaction is generally effected within a temperature range from 0° C. to +120° C., preferably at +20° C. to +80° C., optionally in a microwave. The reaction can be conducted at standard, elevated or reduced pressure (for example from 0.5 to 5 bar).

Inert solvents for the process step (VII)→(VIII) are, for example, dichloromethane, 1,2-dichloroethane, or other solvents such as acetone, methyl ethyl ketone, ethyl acetate, acetonitrile, N,N-dimethylformamide, N,N-dimethylacetamide, dimethyl sulphoxide, N,N'-dimethylpropyleneurea (DMPU), N-methylpyrrolidone (NMP). It is likewise possible to use mixtures of the solvents mentioned. Preference is given to using dichloromethane.

The reaction is effected generally within a temperature range from 0° C. to +120° C., preferably at +20° C. to +80° C. The reaction can be conducted at standard, elevated or reduced pressure (for example from 0.5 to 5 bar).

Inert solvents for the ring closure to give the imidazo[1,2-a]pyrazine base skeleton (VIII)+(IX)→(II) are the customary organic solvents. These preferably include alcohols such as methanol, ethanol, n-propanol, isopropanol, n-butanol, n-pentanol or tert-butanol, or ethers such as diethyl ether, tetrahydrofuran, 2-methyltetrahydrofuran, dioxane or glycol dimethyl ether, or other solvents such as acetone, dichloromethane, 1,2-dichloroethane, acetonitrile, dimethylformamide or dimethyl sulphoxide. It is likewise possible to use mixtures of the solvents mentioned. Preference is given to using ethanol.

The ring closure is generally effected within a temperature range from +50° C. to +150° C., preferably at +50° C. to +100° C., optionally in a microwave.

The ring closure (VIII)+(IX)→(II) is optionally effected in the presence of dehydrating reaction additives, for example in the presence of molecular sieve (pore size 3 Å or 4 Å) or by means of a water separator. The reaction (VIII)+(IX)→(II) is effected using an excess of the reagent of the formula (VIII), for example with 1 to 20 equivalents of the reagent (VIII), optionally with addition of bases (for example sodium hydrogencarbonate), in which case this addition can be effected all at once or in several portions.

The detachment of the benzyl group in the reaction step (XII)→(XIII) is effected here by customary methods known from protecting group chemistry, preferably by hydrogenolysis in the presence of a palladium catalyst, for example palladium on activated carbon, in an inert solvent, for example ethanol or ethyl acetate [see also, for example, T. W. Greene and P. G. M. Wuts, *Protective Groups in Organic Synthesis*, Wiley, New York, 1999].

The Mitsunobu condensation (XIII)+(XIV)→(II) is effected in the presence of an activating reagent, for example diethyl (E)-diazene-1,2-dicarboxylate (DEAD) or diisopropyl (E)-diazene-1,2-dicarboxylate (DIAD), and of a phosphine reagent, e.g. triphenylphosphine or tributylphosphine, in an inert solvent, e.g. THF, dichloromethane, toluene or DMF, at a temperature between 0° C. and the boiling point of the solvent used.

Further inventive compounds can optionally also be prepared by conversions of functional groups of individual substituents, especially those listed for $R^3$, proceeding from compounds of the formula (I) obtained by above processes. These conversions are performed by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester cleavage, etherification, ether cleavage, formation of carbonamides, and introduction and removal of temporary protective groups.

The inventive compounds have valuable pharmacological properties and can be used for prevention and treatment of diseases in humans and animals. The inventive compounds offer a further treatment alternative and enlarge pharmacy.

The inventive compounds bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the inventive compounds enhance the action of substances which increase the cGMP level, for example EDRF (endothelium-derived relaxing factor), NO donors, protoporphyrin IX, arachidonic acid or phenylhydrazine derivatives.

The inventive compounds are suitable for treatment and/or prophylaxis of cardiovascular, pulmonary, thromboembolic and fibrotic disorders.

The inventive compounds can therefore be used in medicaments for treatment and/or prophylaxis of cardiovascular disorders, for example hypertension, resistant hypertension, acute and chronic heart failure, coronary heart disease, stable and unstable angina pectoris, peripheral and cardiac vascular disorders, arrhythmias, atrial and ventricular arrhythmias and impaired conduction, for example atrioventricular blocks degrees I-III (AB block supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

In the context of the present invention, the term "heart failure" encompasses both acute and chronic forms of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the inventive compounds can also be used for treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity and of combined hyperlipidaemias and metabolic syndrome.

The inventive compounds can additionally be used for treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The inventive compounds are also suitable for treating urological disorders, for example benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic overactive bladder (OAB) and (IC), incontinence (UI), for example mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The inventive compounds are also suitable for treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the inventive compounds for treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

In addition, the inventive compounds are also suitable for treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active ingredients for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The inventive compounds are additionally also suitable for controlling cerebral blood flow and thus represent effective agents for controlling migraine. They are also suitable for the prophylaxis and control of sequelae of cerebral infarct (Apoplexia cerebri) such as stroke, cerebral ischaemias and skull-brain trauma. The inventive compounds can likewise be used for controlling states of pain and tinnitus.

In addition, the inventive compounds have antiinflammatory action and can therefore be used as antiinflammatory agents for treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the inventive compounds can also be used for treatment and/or prophylaxis of autoimmune diseases.

The inventive compounds are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarkoidosis).

The inventive compounds are also suitable for controlling postoperative scarring, for example as a result of glaucoma operations.

The inventive compounds can likewise be used cosmetically for ageing and keratinized skin.

Moreover, the inventive compounds are suitable for treatment and/or prophylaxis of hepatitis, neoplasms, osteoporosis, glaucoma and gastroparesis.

The present invention further provides for the use of the inventive compounds for treatment and/or prophylaxis of disorders, in particular the disorders mentioned above.

The present invention further provides for the use of the inventive compounds for treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the inventive compounds for use in a method for treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the inventive compounds for production of a medicament for treatment and/or prophylaxis of disorders, especially of the aforementioned disorders.

The present invention further provides for the use of the inventive compounds for production of a medicament for treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for treatment and/or prophylaxis of disorders, in particular the disorders mentioned above, using an effective amount of at least one of the inventive compounds.

The present invention further provides a method for treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the inventive compounds.

The inventive compounds can be employed alone or, if required, in combination with other active ingredients. The present invention further provides medicaments comprising at least one of the inventive compounds and one or more further active ingredients, especially for treatment and/or prophylaxis of the aforementioned disorders. Preferred examples of suitable active ingredient combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active ingredients, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or active ingredients which alter lipid metabolism, for example and with preference from the group of the thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the inventive compounds are administered in combination with a platelet aggregation inhibitor, by way of example and with preference aspirin, clopidogrel, ticlopidin or dipyridamole.

In a preferred embodiment of the invention, the inventive compounds are administered in combination with a thrombin inhibitor, by way of example and with preference ximelagatran, dabigatran, melagatran, bivalirudin or clexane.

In a preferred embodiment of the invention, the inventive compounds are administered in combination with a GPIIb/IIIa antagonist such as, by way of example and with preference, tirofiban or abciximab.

In a preferred embodiment of the invention, the inventive compounds are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the inventive compounds are administered in combination with heparin or with a low molecular weight (LMW) heparin derivative.

In a preferred embodiment of the invention, the inventive compounds are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the inventive compounds are administered in combination with a calcium antagonist, by way of example and with preference nifedipine, amlodipine, verapamil or diltiazem.

In a preferred embodiment of the invention, the inventive compounds are administered in combination with an alpha-1-receptor blocker, by way of example and with preference prazosin.

In a preferred embodiment of the invention, the inventive compounds are administered in combination with a beta-receptor blocker, by way of example and with preference propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, by way of example and with preference losartan, candesartan, valsartan, telmisartan or embusartan.

In a preferred embodiment of the invention, the inventive compounds are administered in combination with an ACE inhibitor, by way of example and with preference enalapril, captopril, lisinopril, ramipril, delapril, fosinopril, quinopril, perindopril or trandopril.

In a preferred embodiment of the invention, the inventive compounds are administered in combination with an endothelin antagonist, by way of example and with preference bosentan, darusentan, ambrisentan or sitaxsentan.

In a preferred embodiment of the invention, the inventive compounds are administered in combination with a renin inhibitor, by way of example and with preference aliskiren, SPP-600 or SPP-800.

In a preferred embodiment of the invention, the inventive compounds are administered in combination with a mineralocorticoid receptor antagonist, by way of example and with preference spironolactone or eplerenone.

In a preferred embodiment of the invention, the inventive compounds are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the inventive compounds are administered in combination with a CETP inhibitor, by way of example and with preference dalcetrapib, BAY 60-5521, anacetrapib or CETP vaccine (CETi-1).

In a preferred embodiment of the invention, the inventive compounds are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the inventive compounds are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the inventive compounds are administered in combination with a squalene synthesis inhibitor, by way of example and with preference BMS-188494 or TAK-475.

In a preferred embodiment of the invention, the inventive compounds are administered in combination with an ACAT inhibitor, by way of example and with preference avasimibe, melinamide, pactimibe, eflucimibe or SMP-797.

In a preferred embodiment of the invention, the inventive compounds are administered in combination with an MTP inhibitor, by way of example and with preference implitapide, BMS-201038, R-103757 or JTT-130.

In a preferred embodiment of the invention, the inventive compounds are administered in combination with a PPAR-gamma agonist, by way of example and with preference pioglitazone or rosiglitazone.

In a preferred embodiment of the invention, the inventive compounds are administered in combination with a PPAR-delta agonist, by way of example and with preference GW 501516 or BAY 68-5042.

In a preferred embodiment of the invention, the inventive compounds are administered in combination with a cholesterol absorption inhibitor, by way of example and with preference ezetimibe, tiqueside or pamaqueside.

In a preferred embodiment of the invention, the inventive compounds are administered in combination with a lipase inhibitor, a preferred example being orlistat.

In a preferred embodiment of the invention, the inventive compounds are administered in combination with a polymeric bile acid adsorbent, by way of example and with preference cholestyramine, colestipol, colesolvam, CholestaGel or colestimide.

In a preferred embodiment of the invention, the inventive compounds are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the inventive compounds are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, non-toxic, pharmaceutically suitable excipients, and for the use thereof for the aforementioned purposes.

The inventive compounds may act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The inventive compounds can be administered in administration forms suitable for these administration routes.

Administration forms which function according to the prior art, release the inventive compounds rapidly and/or in a modified manner and contain the inventive compounds in crystalline and/or amorphized and/or dissolved form are suitable for oral administration, for example tablets (non-coated or coated tablets, for example with enteric coatings or coatings that dissolve in a delayed manner or are insoluble and control the release of the compound according to the invention), tablets or films/oblates, films/lyophilizates or capsules which disintegrate rapidly in the oral cavity (for example hard or soft gelatine capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The inventive compounds can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary where appropriate to deviate from the stated amounts, specifically as a function of the body weight, route of administration, individual response to the active ingredient, nature of the preparation and time or interval over which administration takes place. For instance, in some cases, less than the aforementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration figures for liquid/liquid solutions are each based on volume.

A. Examples

Abbreviations and Acronyms

| | |
|---|---|
| abs. | absolute (= dried) |
| aq. | aqueous solution |
| Boc | tert-butyloxycarbonyl |
| br. | broadened signal (NMR coupling pattern) |
| CAS No. | Chemical Abstracts Service number |
| Cbz | benzyloxycarbonyl |
| δ | shift in the NMR spectrum (figure in ppm) |
| d | doublet (NMR coupling pattern) |
| TLC | thin-layer chromatography |
| DCI | direct chemical ionization (in MS) |
| DMAP | 4-N,N-dimethylaminopyridine |
| DMF | dimethylformamide |
| DMSO | dimethyl sulphoxide |
| eq. | equivalent(s) |
| ESI | electrospray ionization (in MS) |
| Et | ethyl |
| h | hour(s) |
| HATU | N-[(dimethylamino)(3H-[1,2,3]triazolo[4,5-b]-pyridin-3-yloxy)methylene]-N-methylmethanaminium hexafluorophosphate |
| HPLC | high-pressure, high-performance liquid chromatography |
| HRMS | high-resolution mass spectrometry |
| conc. | concentrated |
| J | coupling constant (NMR) |
| LC-MS | liquid chromatography-coupled mass spectrometry |
| LiHMDS | lithium hexamethyldisilazide |
| m | multiplet (NMR coupling pattern) |
| Me | methyl |
| min | minute(s) |
| MS | mass spectrometry |
| NMR | nuclear magnetic resonance spectrometry |
| Ph | phenyl |
| q | quartet (NMR coupling pattern) |
| quint. | quintet (NMR coupling pattern) |
| rel | relative stereochemistry |
| $R_F$ | retention factor (in thin-layer chromatography) |
| RT | room temperature |
| $R_t$ | retention time (in HPLC) |
| s | singlet (NMR coupling pattern) |
| t | triplet (NMR coupling pattern) |
| THF | tetrahydrofuran |

| TBTU | (benzotriazol-1-yloxy)bisdimethylaminomethylium fluoroborate |
| UV | ultraviolet spectrometry |
| v/v | volume to volume ratio (of a solution) |

LC-MS and HPLC Methods:

Method 1 (LC-MS):

Instrument: Micromass Quattro Premier with Waters UPLC Acquity; column: Thermo Hypersil GOLD 1.9μ 50×1 mm; eluent A: 1 l water+0.5 ml 50% formic acid, eluent B: 1 l acetonitrile+0.5 ml 50% formic acid; gradient: 0.0 min 90% A→0.1 min 90% A→1.5 min 10% A→2.2 min 10% A; oven: 50° C.; flow rate: 0.33 ml/min; UV detection: 210 nm.

Method 2 (LC-MS):

Instrument: Waters ACQUITY SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 210-400 nm.

Method 3 (LC-MS):

Instrument: Micromass Quattro Premier with Waters UPLC Acquity; column: Thermo Hypersil GOLD 1.9μ 50×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4 (Preparative HPLC):

Column: Chromatorex C18 10μ 250×20 mm Gradient: A=water+0.5% formic acid, B=acetonitrile, 0 min=5% B, 3 min=5% B pre-rinse without substance, then injection, 5 min=5% B, 25 min=30% B, 38 min=30% B, 38.1 min=95% B, 43 min=95% B, 43.01 min=5% B, 48.0 min=5% B flow rate 20 wavelength 210 nm.

Method 5 (Preparative HPLC):

Column: Chromatorex C18 10μ 250×20 mm Gradient: A=water+0.5% formic acid, B=acetonitrile, 0 min=5% B, 3 min=5% B pre-rinse without substance, then injection, 5 min=5% B, 25 min=50% B, 38 min=50% B, 38.1 min=95% B, 43 min=95% B, 43.01 min=5% B, 48.0 min=5% B flow rate 20 ml/min, wavelength 210 nm.

Method 6 (Preparative HPLC):

Column: XBridge Prep. C18 5μ×50×19 mm; gradient: A=water+0.5% ammonium hydroxide, B=acetonitrile, 0 min=5% B, 3 min=5% B pre-rinse without substance, then injection, 5 min=5% B, 25 min=50% B, 38 min=50% B, 38.1 min=95% B, 43 min=95% B, 43.01 min=5% B, 48.0 min=5% B flow rate 15 wavelength 210 nm.

Method 7 (LC-MS):

MS instrument: Waters (Micromass) QM; HPLC instrument: Agilent 1100 series; column: Agilent ZORBAX Extend-C18 3.0×50 mm 3.5 micron; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 8 (LC-MS):

Instrument: Waters ACQUITY SQD UPLC System; column: Waters Acquity UPLC HSS T3 1.8μ 30×2 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.60 ml/min; UV detection: 208-400 nm.

Method 9 (Preparative HPLC):

MS instrument: Waters; HPLC instrument: Waters; Waters X-Bridge C18 column, 18 mm×50 mm, 5 μm, eluent A: water+0.05% triethylamine, eluent B: acetonitrile (ULC)+0.05% triethylamine, with gradient; flow rate: 40 ml/min; UV detection: DAD; 210-400 nm.

or

MS instrument: Waters; HPLC instrument: Waters; Phenomenex Luna 5μ C18 100A column, AXIA Tech. 50×21.2 mm, eluent A: water+0.05% formic acid, eluent B: acetonitrile (ULC)+0.05% formic acid, with gradient; flow rate: 40 ml/min; UV detection: DAD; 210-400 nm.

or

MS instrument: Waters; HPLC instrument: Waters; Waters X-Bridge C18 column, 19 mm×50 mm, 5 μm, eluent A: water+0.05% ammonia, eluent B: acetonitrile (ULC), with gradient; flow rate: 40 ml/min; UV detection: DAD; 210-400 nm.

Method 10 (LC-MS):

MS instrument: Waters SQD; HPLC instrument: Waters UPLC; column: Zorbax SB-Aq (Agilent), 50 mm×2.1 mm, 1.8 μm; eluent A: water+0.025% formic acid, eluent B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 11 (MS):

Instrument: Waters ZQ 2000; electrospray ionization; eluent A: 1 l water+0.25 ml 99% formic acid, eluent B: 1 l acetonitrile+0.25 ml 99% formic acid; 25% A, 75% B; flow rate: 0.25 ml/min.

Method 12 (DCI-MS):

Instrument: Thermo Fisher-Scientific DSQ; chemical ionization; reactant gas $NH_3$; source temperature: 200° C.; ionization energy 70 eV.

Method 13 (LC-MS):

MS instrument: Waters (Micromass) Quattro Micro; HPLC instrument: Agilent 1100 Series; column: YMC-Triart C18 3μ 50×3 mm; eluent A: 1 l water+0.01 mol ammonium carbonate, eluent B: 1 l acetonitrile; gradient: 0.0 min 100% A→2.75 min 5% A→4.5 min 5% A; oven: 40° C.; flow rate: 1.25 ml/min; UV detection: 210 nm.

Method 14 (GC-MS):

Instrument: Thermo Scientific DSQII, Thermo Scientific Trace GC Ultra; column: Restek RTX-35MS, 15 m×200 μm×0.33 μm; constant flow rate of helium: 1.20 ml/min; oven: 60° C.; inlet: 220° C.; gradient: 60° C., 30° C./min→300° C. (hold for 3.33 min).

Method 15 (LC-MS):

Instrument: Acquity UPLC coupled to Quattro Micro mass spectrometer; column: Acquity UPLC BEH C18 (50 mm×2.1 mm ID, packing diameter 1.7 μm); mobile phase A: 10 mM aqueous ammonium hydrogencarbonate solution (adjusted to a pH of 10 with ammonia), mobile phase B: acetonitrile; gradient: 0.0 min 97% A, 3% B, flow rate 1 ml/min; 1.5 min 100% B, flow rate 1 ml/min; 1.9 min 100% B, flow rate 1 ml/min; 2.0 min 97% A, 3% B, flow rate 0.05 ml/min; column temperature: 40° C.; UV detection: from 210 nm to 350 nm; MS conditions: ionization mode: alternating scans, positive and negative electrospray (ES+/ES−); scan range: 100 to 1000 AMU.

Method 16 (LC-MS):

Instrument: Acquity UPLC coupled to Quattro Micro mass spectrometer; column: Acquity UPLC BEH C18 (50 mm×2.1 mm ID, packing diameter 1.7 μm); mobile phase A: 0.1% formic acid in water, mobile phase B: 0.1% formic acid in acetonitrile; gradient: 0.0 min 97% A, 3% B, flow rate 1 ml/min; 1.5 min 100% B, flow rate 1 ml/min; 1.9 min 100%

B, flow rate 1 ml/min; 2.0 min 97% A, 3% B, flow rate 0.05 ml/min; column temperature: 40° C.; UV detection: from 210 nm to 350 nm; MS conditions: ionization mode: alternating scans, positive and negative electrospray (ES+/ES−); scan range: 100 to 1000 AMU.

Method 17 (LC-MS):

Instrument: Waters 2690, Waters 2996 PDA detector, coupled to Quattro Micro mass MS detector; column: Waters SunFire C18 3.5 µm, 2.1×50 mm; mobile phase A: 10 mM aqueous ammonium hydrogencarbonate solution (adjusted to a pH of 10 with ammonia), mobile phase B: acetonitrile; gradient: 0.0 min 95% A, 5% B, flow rate 0.5 ml/min; 3.0 min 95% A, 5% B, flow rate 0.5 ml/min; 17.50 min 5% A, 95% B, flow rate 0.5 ml/min; 19.00 min 5% A, 95% B, flow rate 0.5 ml/min; 19.50 min 95% A, 5% B, flow rate 0.5 ml/min; 20.00 min 95% A, 5% B, flow rate 0.5 ml/min; column temperature: 30° C.; UV detection: from 210 nm to 400 nm; MS conditions: ionization mode: scans, positive and negative electrospray (ES+/ES−); scan range: 130 to 1100 AMU.

Method 18 (LC-MS):

Instrument: Waters 2690, Waters 2996 PDA detector, coupled to Quattro Micro mass MS detector; column: Waters SunFire C18 3.5 µm, 2.1×50 mm; mobile phase A: 0.1% formic acid in water, mobile phase B: 0.1% formic acid in acetonitrile; gradient: 0.0 min 95% A, 5% B, flow rate 0.5 ml/min; 3.0 min 95% A, 5% B, flow rate 0.5 ml/min; 17.50 min 5% A, 95% B, flow rate 0.5 ml/min; 19.00 min 5% A, 95% B, flow rate 0.5 ml/min; 19.50 min 95% A, 5% B, flow rate 0.5 ml/min; 20.00 min 95% A, 5% B, flow rate 0.5 ml/min; column temperature: 30° C.; UV detection: from 210 nm to 400 nm; MS conditions: ionization mode: scans, positive and negative electrospray (ES+/ES−); scan range: 130 to 1100 AMU.

Method 19 (LC-MS):

MS instrument type: Waters ZMD; HPLC instrument type: Waters 1525; column: Phenomenex Luna 3 µm C18(2) 30 mm×4.6 mm; mobile phase A: water 0.1% formic acid, mobile phase B: acetonitrile 0.1% formic acid; gradient: 0.0 min 95% A→0.5 min 95% A→4.5 min 5% A→5.5 min 5% A; flow rate: 2 ml/min; UV detection: DAD.

Method 20 (LC-MS):

MS instrument type: Waters Micromass ZQ2000; HPLC instrument type: Waters Acquity UPLC system; column: Acquity UPLC BEH C18 1.7 µm 100 mm×2.1 mm; mobile phase A: water 0.1% formic acid, mobile phase B: acetonitrile 0.1% formic acid; gradient: 0.0 min 95% A→0.4 min 95% A→6.0 min 5% A→6.8 min 5% A; flow rate: 0.4 ml/min; UV detection: PDA.

Method 21 (LC-MS):

Instrument: Waters 2690, Waters 2996 PDA detector, coupled to Quattro Micro mass MS detector; column: XBridge Prep. MS C18 OBD (150 mm×30 mm ID 5, grain size 4 µm) at room temperature; mobile phase A: 10 mM $NH_4HCO_3$, adjusted to a pH of 10 with ammonia, mobile phase B: acetonitrile; gradient: 0.0 min 97% A, 3% B; 1.0 min 97% A, 3% B; 30 min 0% A, 100% B; 35 min 0% A, 100% B, flow rate 50 ml/min; column temperature: 30° C.; UV detection: from 210 nm to 400 nm; MS conditions: ionization mode: scans, positive and negative electrospray (ES+/ES−); scan range: 100 to 1000 AMU.

Method 22 (LC-MS, Analytical):

Instrument: Agilent MS Quad 6150; HPLC: Agilent 1290; column: Waters Acquity UPLC HSS T3 1.8µ 50×2.1 mm; eluent A: 1 l water+0.25 ml 99% formic acid, eluent B: 1 l acetonitrile+0.25 ml 99% formic acid; gradient: 0.0 min 90% A→1.7 min 5% A→3.0 min 5% A; oven: 50° C.; flow rate: 1.20 ml/min; UV detection: 205-305 nm.

When inventive compounds are purified by preparative HPLC by the above-described methods in which the eluents contain additives, for example trifluoroacetic acid, formic acid or ammonia, the inventive compounds may be obtained in salt form, for example as trifluoroacetate, formate or ammonium salt, if the inventive compounds contain a sufficiently basic or acidic functionality. Such a salt can be converted to the free base or acid by various methods known to the person skilled in the art.

Salts may be present in sub- or superstoichiometric form, especially in the presence of an amine or a carboxylic acid. In addition, in the case of the present pyrazolopyridines, salts are always present under acidic conditions, sometimes in substoichiometric form, although they are not apparent in the $^1$H NMR and they are not specially indicated and identified in the respective IUPAC names and structural formulae.

The multiplicities of proton signals in $^1$H NMR spectra reported in the paragraphs that follow reflect the signal shape observed in each case and do not take account of higher-order signal phenomena.

Starting Materials and Intermediates

Example 1A

2-[(2,6-Difluorobenzyl)oxy]-4-methylpyridine

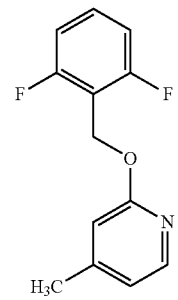 [SMILES: Cc1ccnc(OCc2c(F)cccc2F)c1]

A mixture of 5.00 g (24.2 mmol, 1.0 eq.) of 2,6-difluorobenzyl bromide [CAS No: 85118-00-9] and 3.16 g (29.0 mmol, 1.2 eq.) of 2-hydroxy-4-methylpyridine [CAS No: 13466-41-6] was dissolved in 50 ml of THF. The solution was admixed with 7.99 g (29.0 mmol, 1.2 eq.) of silver carbonate and the mixture was heated to reflux with exclusion of light overnight. Subsequently, the reaction mixture was filtered through kieselguhr and eluted with ethyl acetate, and the filtrate was concentrated. The crude product was purified by means of Biotage Isolera (100 g silica gel cartridge, cyclohexane/ethyl acetate gradient, 0% to 10% ethyl acetate). 3.51 g of the title compound were obtained (61% of theory).

TLC (silica gel, cyclohexane/ethyl acetate 10:1): $R_F$=0.50

LC-MS (Method 2): $R_t$=1.17 min

MS (ESpos): m/z=236 (M+H)$^+$ $^1$H NMR (400 MHz, DMSO-d$_6$): δ [ppm]=2.26 (s, 3H), 5.35 (s, 2H), 6.66 (s, 1H), 6.86 (d, 1H), 7.12-7.21 (m, 2H), 7.47-7.56 (m, 1H), 8.06 (d, 1H).

Example 2A

1-Amino-2-[(2,6-difluorobenzyl)oxy]-4-methylpyridinium 2,4,6-trimethylbenzenesulphonate

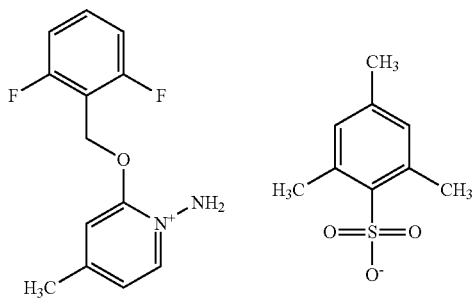

A mixture of 3.4 ml (43.9 mmol, 10 eq.) of trifluoroacetic acid and 0.33 ml water was cooled to −5° C. At this temperature, 1.88 g (6.59 mmol, 1.5 eq.) of ethyl (1E)-N-[(mesitylsulphonyl)oxy]ethanimidoate [CAS No: 38202-27-6] were added in portions. After 1.5 h, 30 ml of ice-water were added, the mixture was stirred briefly, and the precipitated O-(2-mesitylenesulphonyl)hydroxylamine (MSH) was filtered off by means of a precooled frit and washed with 30 ml of ice-water. The water-moist O-(2-mesitylenesulphonyl)hydroxylamine was dissolved in 12 ml of dichloromethane, dried with magnesium sulphate and filtered, and the filtrate was added dropwise directly to a solution of 1.03 g (4.39 mmol, 1.0 eq.) of 2-[(2,6-difluorobenzyl)oxy]-4-methylpyridine from Example 1A in 2 ml of dichloromethane. The mixture was stirred at RT overnight. Subsequently, diethyl ether was added dropwise, and the precipitate obtained was filtered off, washed with diethyl ether and dried. 1.3 g of the title compound were isolated (59% of theory, 90% purity).

$^1$H NMR (400 MHz, DMSO-$d_6$): δ [ppm]=2.17 (s, 3H), 2.46-2.57 (s, 3H and s, 6H obscured by the solvent signal), 5.64 (s, 2H), 6.74 (s, 2H), 7.23-7.48 (m, 4H), 7.60-7.70 (m, 1H), 7.86 (br s, 1H), 8.44 (d, 1H).

Example 3A

Ethyl 7-[(2,6-difluorobenzyl)oxy]-2,5-dimethylpyrazolo[1,5-a]pyridine-3-carboxylate

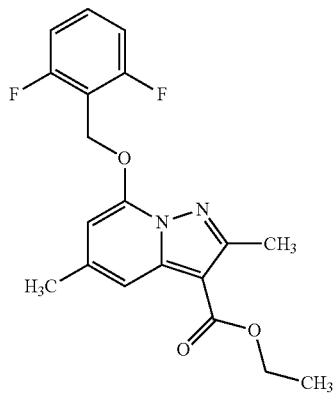 [SMILES: CCOC(=O)c1c(C)nn2c(OCc3c(F)cccc3F)cc(C)cc12]

1.62 g (3.60 mmol, 1.0 eq.) of 1-amino-2-[(2,6-difluorobenzyl)oxy]-4-methylpyridinium 2,4,6-trimethylbenzenesulphonate from Example 2A were dissolved in 36 ml of DMF, and 0.84 ml (7.19 mmol, 2.0 eq.) of ethyl but-2-ynoate [CAS No: 4341-76-8] were added. 0.994 g (7.19 mmol, 2.0 eq.) of potassium carbonate was added and the mixture was stirred at RT for 1.5 h. Subsequently, the mixture was poured onto 150 ml of water and stirred briefly, and the precipitated solids were filtered off, washed with water and dried. 440 mg of the title compound were obtained (45% of theory, 87%).

LC-MS (Method 2): $R_t$=1.22 min
MS (ESpos): m/z=361 (M+H)$^+$

Example 4A

7-[(2,6-Difluorobenzyl)oxy]-2,5-dimethylpyrazolo[1,5-a]pyridine-3-carboxylic Acid

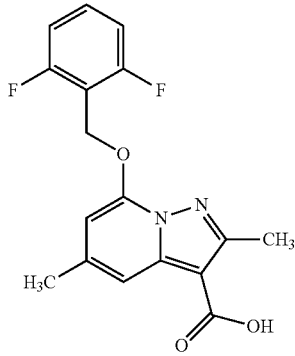 [SMILES: Cc1cc(OCc2c(F)cccc2F)n2nc(C)c(C(=O)O)c2c1]

A solution of 0.440 g (1.22 mmol, 1 eq.) of ethyl 7-[(2,6-difluorobenzyl)oxy]-2,5-dimethylpyrazolo[1,5-a]pyridine-3-carboxylate from Example 3A in 12.7 ml of dioxane was admixed with 4.9 ml (4.88 mmol, 4.0 eq.) of 1 N aqueous sodium hydroxide solution and the mixture was stirred at 90° C. for 36 h. Subsequently, the reaction mixture was concentrated and the precipitated solids were filtered off. The filtrate was acidified with 6 N aqueous hydrochloric acid and stirred briefly, and the precipitated solids were filtered off, washed with water and dried. 248 mg of the title compound were obtained (61% of theory, 60% purity), which was converted further without further purification.

LC-MS (Method 2): $R_t$=0.96 min
MS (ESpos): m/z=333 (M+H)$^+$

Example 5A 2-(Benzyloxy)-4-methylpyridine

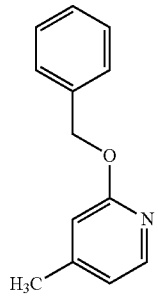

A mixture of 13.6 ml (114 mmol, 1.0 eq.) of benzyl bromide and 15.0 g (137 mmol, 1.2 eq.) of 2-hydroxy-4-methylpyridine [CAS No: 13466-41-6] was dissolved in 470 ml of THF. The solution was admixed with 37.9 g (137 mmol, 1.2 eq.) of silver carbonate and the mixture was heated to reflux with exclusion of light overnight. Subsequently, the reaction mixture was filtered through kieselguhr and eluted with ethyl acetate, and the filtrate was concentrated. The crude product was purified by silica gel chromatography (700 g of silica gel, cyclohexane/ethyl acetate 95:5). 21.4 g of the title compound were obtained (94% of theory).

TLC (silica gel, cyclohexane/ethyl acetate 9:1): $R_F$=0.41

LC-MS (Method 2): $R_t$=1.12 min

MS (ESpos): m/z=200 (M+H)$^+$ $^1$H NMR (400 MHz, DMSO-d$_6$): δ [ppm]=2.27 (s, 3H), 5.33 (s, 2H), 6.70 (s, 1H), 6.83 (d, 1H), 7.27-7.45 (m, 5H), 8.02 (d, 1H).

Example 6A

1-Amino-2-(benzyloxy)-4-methylpyridinium 2,4,6-trimethylbenzenesulphonate

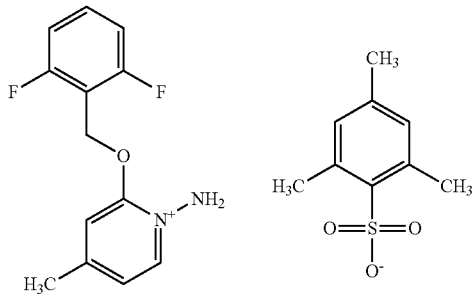

A mixture of 18.0 ml of trifluoroacetic acid (233 mmol, 10 eq.) and 2.66 ml of water was cooled to −5° C. At this temperature, 9.99 g (35.0 mmol, 1.5 eq.) of ethyl (1E)-N-[(mesitylsulphonyl)oxy]ethanimidoate [CAS No: 38202-27-6] were added in portions. After 1.5 h, 150 ml of ice-water were added, and the mixture was stirred briefly and extracted with 100 ml of dichloromethane. The organic phase was dried with magnesium sulphate and filtered, and the resulting solution of O-(2-mesitylenesulphonyl)hydroxylamine (MSH) was added dropwise directly to a solution, cooled to 0° C., of 4.65 g (23.3 mmol, 1.0 eq.) of 2-(benzyloxy)-4-methylpyridine from Example 5A in 50 ml of dichloromethane. The mixture was stirred at RT for 2 h. Subsequently, 1 l of diethyl ether was added dropwise, and precipitated solids were filtered off, washed with 250 ml of diethyl ether and dried. 4.6 g of the title compound were isolated (48% of theory).

LC-MS (Method 2): $R_t$=0.45 min;

MS (ESpos): m/z=215 ($C_{13}H_{15}N_2O$) (M)$^+$; $R_t$=0.57 min;

MS (ESneg): m/z=199 ($C_9H_{11}O_3S$)$^-$;

Example 7A

Ethyl 7-(benzyloxy)-2,5-dimethylpyrazolo[1,5-a]pyridine-3-carboxylate

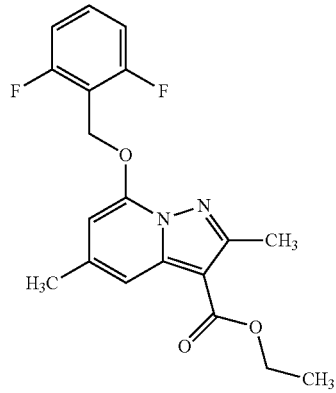 [SMILES: CCOC(=O)c1c(C)nn2c(OCc3c(F)cccc3F)cc(C)cc12]

11.7 g (28.2 mmol, 1.0 eq.) of 1-amino-2-(benzyloxy)-4-methylpyridinium 2,4,6-trimethylbenzenesulphonate from Example 6A were dissolved in 280 ml of DMF, and 6.6 ml (56 mmol, 2.0 eq.) of ethyl but-2-ynoate [CAS No: 4341-76-8] were added. 7.8 g (56 mmol, 2.0 eq.) of potassium carbonate were added and the mixture was stirred at RT for 1 h. Subsequently, 3.9 g (28 mmol, 1 eq.) of potassium carbonate were added and the mixture was stirred at RT for a further 16 h. Then the mixture was poured onto 540 ml of water and stirred briefly, and the precipitated solids were filtered off, washed with 220 ml of water and dried. 3.1 g of the title compound were obtained (34% of theory; 87% purity).

LC-MS (Method 2): $R_t$=1.20 min

MS (ESIpos): m/z=325 (M+H)$^+$ $^1$H NMR (400 MHz, DMSO-d$_6$): δ [ppm]=1.34 (t, 3H), 2.43 (s, 3H), 4.27 (q, 2H), 5.43 (s, 2H), 6.60 (d, 1H), 7.37-7.49 (m, 4H), 7.52-7.59 (m, 2H), [s, 3H beneath solvent signal].

Example 8A

Ethyl 7-hydroxy-2,5-dimethylpyrazolo[1,5-a]pyridine-3-carboxylate

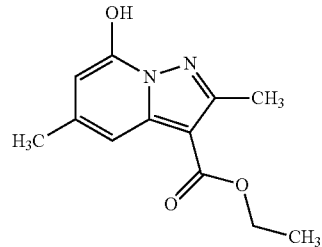 [SMILES: CCOC(=O)c1c(C)nn2c(O)cc(C)cc12]

2 g (5.98 mmol) of ethyl 7-(benzyloxy)-2,5-dimethylpyrazolo[1,5-a]pyridine-3-carboxylate from Example 7A were initially charged in 80 ml of ethanol under argon, and 636 mg (0.59 mmol, 10%) of palladium on activated carbon and 18 ml (179.42 mmol) of cyclohexene were added. The reaction mixture was stirred under reflux for 2.5 hours. Then the reaction mixture was filtered through kieselguhr and washed with ethanol, and the filtrate was concentrated. The residue was taken up in DMSO and acetonitrile and purified by means of preparative HPLC (RP 18 column, eluent:acetonitrile/water gradient with addition of 0.1% TFA). The product fractions were combined, concentrated and lyophilized. 1.2 g of the target compound were obtained (86% of theory).

LC-MS (Method 7): $R_t$=1.60 min
MS (ESIpos): m/z=235 (M+H)$^+$
$^1$H NMR (500 MHz, DMSO-d$_6$): δ=1.33 (t, 3H), 2.35 (s, 3H), 2.54 (s, 3H; hidden under solvent peak), 4.26 (q, 2H), 6.17 (d, 1H), 7.26 (s, 1H).

Example 9A

Ethyl 2,5-dimethyl-7-[(2,3,6-trifluorobenzyl)oxy]pyrazolo[1,5-a]pyridine-3-carboxylate

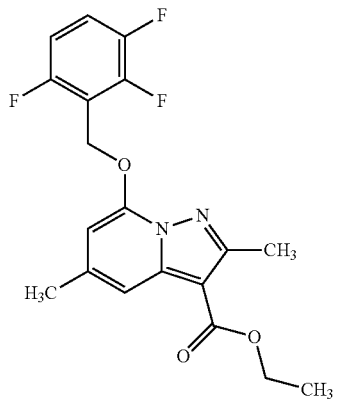 [SMILES: CCOC(=O)c1c(C)nn2c(OCc3c(F)ccc(F)c3F)cc(C)cc12]

1.2 g (5.25 mmol) of ethyl 7-hydroxy-2,5-dimethylpyrazolo[1,5-a]pyridine-3-carboxylate from Example 8A were dissolved in 48 ml of THF. 1.7 g (10.50 mmol) of 2,3,6-trifluorobenzyl alcohol and 2.9 g (11.03 mmol) of triphenylphosphine were added. Subsequently, 2.2 ml (11.03 mmol) of diisopropyl (E)-diazene-1,2-dicarboxylate were added to the solution, which was stirred at RT for 1 h. 120 ml of tert-butyl methyl ether were added, then the mixture was stirred briefly, and the solids formed were filtered off and dried under high vacuum. 1.2 g of the target compound were obtained (62% of theory).

LC-MS (Method 2): $R_t$=1.22 min
MS (ESIpos): m/z=379 (M+H)$^+$
$^1$H NMR (500 MHz, DMSO-d$_6$): δ=1.34 (t, 3H), 2.46 (s, 3H), 2.51 (s, 3H; hidden under solvent peak), 4.28 (d, 2H), 5.51 (s, 2H), 6.70 (s, 1H), 7.29-7.37 (m, 1H), 7.48 (s, 1H), 7.66-7.76 (m, 1H).

Example 10A 2,5-Dimethyl-7-[(2,3,6-trifluorobenzyl)oxy]pyrazolo[1,5-a]pyridine-3-carboxylic Acid

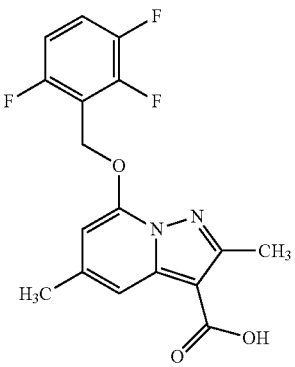 [SMILES: Cc1cc(OCc2c(F)ccc(F)c2F)n2nc(C)c(C(=O)O)c2c1]

700 mg (1.81 mmol) of ethyl 2,5-dimethyl-7-[(2,3,6-trifluorobenzyl)oxy]pyrazolo[1,5-a]pyridine-3-carboxylate from Example 9A were initially charged in 18 ml of dioxane and heated to 90° C. 4.5 ml of dioxane and 7.25 ml (14.50 mmol) of 2 N aqueous sodium hydroxide solution were added, and the reaction mixture was stirred at 90° C. for two days. Another 3.63 ml (7.26 mmol) of 2 N aqueous sodium hydroxide solution were added and the mixture was stirred at 90° C. for a further 2 hours. The reaction solution was admixed with 15 ml of 1 N aqueous hydrochloric acid and stirred for 30 min. In the course of this, solids precipitated out. This suspension was filtered, and the solids filtered off were washed with a little water and dried under high vacuum. 358 mg of the target compound were obtained (54% of theory).

LC-MS (Method 2): $R_t$=0.97 min
MS (ESIpos): m/z=351 (M+H)$^+$

Example 11A rac-Benzyl (2-cyanobutan-2-yl)carbamate

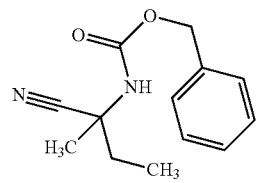

5.00 g (50.94 mmol) of 2-amino-2-methylbutanonitrile [synthesis described in: Lonza A G, U.S. Pat. No. 5,698,704 (1997); Deng, S. L. et al. *Synthesis* 2001, 2445; Hjorringgaard, C. U. et al. *J. Org. Chem.* 2009, 74, 1329; Ogrel, A. et al. *Eur. J. Org. Chem.* 2000, 857] were initially charged in 50 ml of THF and 6.5 ml of water, 21.83 g (157.92 mmol) of potassium carbonate were added, and 7.9 ml (56.04 mmol) of benzyl chlorocarbonate (benzyl chloroformate) were added gradually at 0° C. After adding 8 ml of THF and 3 ml of water, the reaction mixture was stirred overnight, coming gradually to RT. Then water was added, and the reaction mixture was extracted three times with ethyl acetate. The combined organic phases were dried over sodium sulphate and concentrated. The residue was dissolved in diethyl ether and precipitated with petroleum ether. The product was filtered off and the solids were washed with a little petroleum ether and dried under high vacuum. 11.35 g of the target compound were obtained (93% of theory).

LC-MS (Method 2): $R_t$=0.97 min
MS (ESIpos): m/z=233 (M+H)$^+$
$^1$H NMR (400 MHz, DMSO-d$_6$): δ=0.95 (t, 3H), 1.51 (s, 3H), 1.75-1.95 (m, 2H), 5.07 (s, 2H), 7.30-7.43 (m, 4H), 7.88-8.03 (m, 1H).

Example 12A ent-Benzyl (2-cyanobutan-2-yl)carbamate
(Enantiomer A)

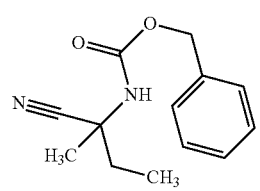 [SMILES: CCC(C)(C#N)NC(=O)OCc1ccccc1]

8 g of rac-benzyl-(2-cyanobutan-2-yl)carbamate from Example 11A were separated into the enantiomers by preparative separation on a chiral phase [column: Daicel Chiralcel OJ-H, 5 μm, 250×20 mm, eluent: 50% isohexane, 50% isopropanol, flow rate: 20 ml/min; 40° C., detection: 220 nm].

Enantiomer A: Yield: 3.23 g (>99% ee)

$R_t$=6.69 min [Daicel Chiralcel OJ-H, 5 μm, 250×4.6 mm; eluent: 50% isohexane, 50% isopropanol; flow rate 1.0 ml/min; 30° C.; detection: 220 nm].

Example 13A ent-Benzyl (2-cyanobutan-2-yl)carbamate
(Enantiomer B)

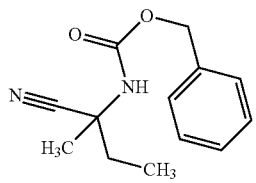

8 g of rac-benzyl-(2-cyanobutan-2-yl)carbamate from Example 11A were separated into the enantiomers by preparative separation on a chiral phase [column: Daicel Chiralcel OJ-H, 5 μm, 250×20 mm, eluent: 50% isohexane, 50% isopropanol, flow rate: 20 ml/min; 40° C., detection: 220 nm].

Enantiomer B: Yield: 3.18 g (>99% ee)

$R_t$=8.29 min [Daicel Chiralcel OJ-H, 5 μm, 250×4.6 mm; eluent: 50% isohexane, 50% isopropanol; flow rate 1.0 ml/min; 30° C.; detection: 220 nm].

Example 14A ent-Benzyl (1-amino-2-methylbutan-2-yl)carbamate
(Enantiomer A)

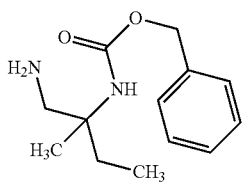 [SMILES: CCC(C)(CN)NC(=O)OCc1ccccc1]

4.00 g (17.22 mmol) of ent-benzyl (2-cyanobutan-2-yl) carbamate from Example 12A were dissolved in 50 ml of a 7 N solution of ammonia in methanol, 5.33 g of Raney nickel were added and hydrogenation was effected at about 25 bar at RT for 24 h. The mixture was filtered through Celite, washed with methanol and concentrated. The crude product was purified by means of silica gel chromatography (eluent:dichloromethane/2N ammonia in methanol=10/0.5). 2.20 g of the target compound were obtained (54% of theory).

LC-MS (Method 2): $R_t$=0.56 min MS (ESIpos): m/z=237 (M+H)⁺

Example 15A ent-Benzyl (1-amino-2-methylbutan-2-yl)carbamate
(Enantiomer B)

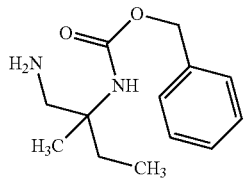 [SMILES: CCC(C)(CN)NC(=O)OCc1ccccc1]

4.00 g (17.22 mmol) of ent-benzyl (2-cyanobutan-2-yl) carbamate from Example 13A were dissolved in 50 ml of 7 N ammoniacal methanol solution, 5.33 g of Raney nickel were added and hydrogenation was effected at about 25 bar at RT for 24 h. The reaction mixture was filtered through Celite, rinsed well with methanol and concentrated. The crude product was purified by means of silica gel chromatography (eluent:dichloromethane/2N ammonia in methanol=10/0.5). 3.56 g of the target compound were obtained (87% of theory).

LC-MS (Method 3): $R_t$=1.40 min

MS (ESIpos): m/z=237 (M+H)⁺

Example 16A rac-Benzyl (2-cyanopentan-2-yl)carbamate

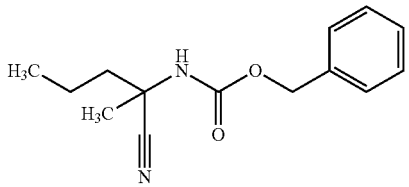 [SMILES: CCCC(C)(C#N)NC(=O)OCc1ccccc1]

20 g (178.3 mmol) of rac-2-amino-2-methylpentanonitrile (described in: Deng, S L. et al., Synthesis 2001, 2445-2449; Freifelder, M. et al., J. Am. Chem. Soc. 1960, 696-698) were initially charged in 2.63 l of THF/water (8/1), and 76.4 g (552.7 mmol) of potassium carbonate were added. Then 27.6 ml (196.1 mmol) of benzyl chloroformate were slowly added dropwise at 0° C. and the mixture was stirred at RT overnight. The reaction mixture was concentrated, and the residue was admixed with water and extracted twice with ethyl acetate. The combined organic phases were dried over sodium sulphate, filtered and concentrated. The residue was purified by means of silica gel chromatography (eluent:cyclohexane/ethyl acetate=4/1). 43.84 g of the target compound were obtained (76% of theory, 76% purity).

LC-MS (Method 2): $R_t$=1.02 min

MS (ESIpos): m/z=247 (M+H)⁺

¹H MR (400 MHz, DMSO-$d_6$): δ=0.90 (t, 3H), 1.31-1.48 (m, 2H), 1.52 (s, 3H), 1.70-1.88 (m, 2H), 5.07 (s, 2H), 7.30-7.42 (m, 5H), 8.00 (br. s, 1H).

Example 17A ent-Benzyl (2-cyanopentan-2-yl)carbamate
(Enantiomer A)

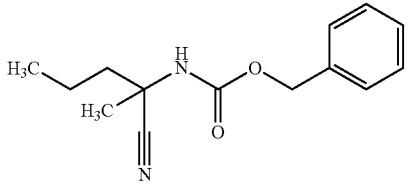 [SMILES: CCCC(C)(C#N)NC(=O)OCc1ccccc1]

43.8 g (135.3 mmol) of rac-benzyl (2-cyanopentan-2-yl) carbamate from Example 16A were separated into the enantiomers by preparative separation on a chiral phase [column: SFC Chiralpak AZ-H, 5 µm, 250×50 mm, eluent: 85% $CO_2$, 15% methanol, flow rate: 250 ml/min; temperature: 28° C., backpressure: 100 bar, detection: 220 nm].

Enantiomer A: Yield: 13.13 g (>99% ee)

$R_t$=2.76 min [SFC Chiralpak AZ-H, 5 µm, 250×4.6 mm; eluent: 90% $CO_2$, 10% methanol; flow rate: 3 ml/min; detection: 220 nm].

Example 18A ent-Benzyl (2-cyanopentan-2-yl)carbamate
(Enantiomer B)

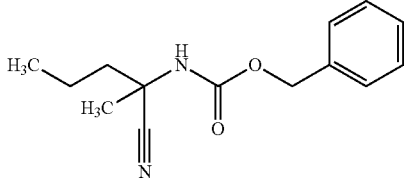 [SMILES: CCCC(C)(C#N)NC(=O)OCc1ccccc1]

43.8 g (135.3 mmol) of rac-benzyl (2-cyanopentan-2-yl) carbamate from Example 16A were separated into the enantiomers by preparative separation on a chiral phase [column: SFC Chiralpak AZ-H, 5 µm, 250×50 mm, eluent: 85% $CO_2$, 15% methanol, flow rate: 250 ml/min; temperature: 28° C., backpressure: 100 bar, detection: 220 nm].

Enantiomer B: Yield: 13.48 g (about 90.4% ee)

$R_t$=3.93 min [SFC Chiralpak AZ-H, 5 µm, 250×4.6 mm; eluent: 90% $CO_2$, 10% methanol; flow rate: 3 ml/min; detection: 220 nm].

Example 19A ent-Benzyl (1-amino-2-methylpentan-2-yl)carbamate
(Enantiomer A)

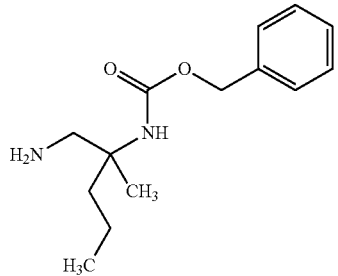 [SMILES: CCCC(C)(CN)NC(=O)OCc1ccccc1]

13.1 g (53.31 mmol) of ent-benzyl (2-cyanopentan-2-yl) carbamate (enantiomer A) from Example 17A were dissolved in 155 ml of 7 N ammonia solution in methanol, and 16.5 g of Raney nickel (50% aqueous slurry) were added under argon. The reaction mixture was hydrogenated in an autoclave at 20-30 bar overnight. The reaction mixture was filtered through Celite, rinsed with methanol, dichloromethane/2 N ammonia in methanol (20/1) and concentrated. The residue was purified by means of silica gel chromatography (eluent: dichloromethane/methanol 40/1 to 20/1). 9.85 g of the target compound were obtained (63% of theory, 86% purity).

LC-MS (Method 2): $R_t$=0.58 min

MS (ESIpos): m/z=251 (M+H)+

$^1$H NMR (400 MHz, DMSO-$d_6$): δ=0.83 (t, 3H), 1.11 (s, 3H), 1.15-1.24 (m, 2H), 1.37 (br. s, 2H), 1.42-1.51 (m, 1H), 1.53-1.63 (m, 1H), 2.46 (d, 1H), 2.66 (d, 1H), 4.97 (s, 2H), 6.69 (br. s, 1H), 7.26-7.40 (m, 5H).

Example 20A ent-Benzyl (1-amino-2-methylpentan-2-yl)carbamate
(Enantiomer B)

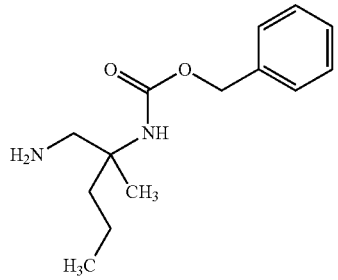 [SMILES: CCCC(C)(CN)NC(=O)OCc1ccccc1]

13.5 g (54.73 mmol) of ent-benzyl (2-cyanopentan-2-yl) carbamate (enantiomer B) from Example 18A were dissolved in 159 ml of 7 N ammonia solution in methanol, and 16.95 g of Raney nickel (50% aqueous slurry) were added under argon. The reaction mixture was hydrogenated in an autoclave at 20-30 bar overnight. The reaction mixture was filtered through Celite, rinsed with methanol, dichloromethane/2 N ammonia in methanol (10/1) and concentrated. The residue was purified by means of silica gel chromatography (eluent:dichloromethane/methanol 40/1 to 20/1). 9.46 g of the target compound were obtained (61% of theory, 88% purity).

LC-MS (Method 2): $R_t$=0.58 min

MS (ESIpos): m/z=251 (M+H)+

$^1$H NMR (400 MHz, DMSO-$d_6$): δ=0.83 (t, 3H), 1.11 (s, 3H), 1.15-1.24 (m, 2H), 1.37 (br. s, 2H), 1.42-1.51 (m, 1H), 1.53-1.63 (m, 1H), 2.46 (d, 1H), 2.66 (d, 1H), 4.97 (s, 2H), 6.69 (br. s., 1H), 7.26-7.40 (m, 5H).

Example 21A ent-Benzyl {1-[({7-[(2,6-difluorobenzyl)oxy]-2,5-dimethylpyrazolo[1,5-a]pyridin-3-yl}carbonyl)amino]-2-methylbutan-2-yl}carbamate (Enantiomer A)

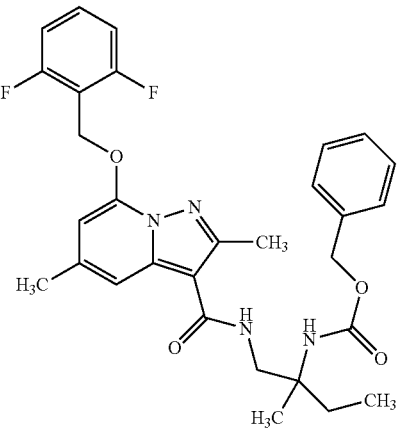 [SMILES: CCC(C)(CNC(=O)c1c(C)nn2c(OCc3c(F)cccc3F)cc(C)cc12)NC(=O)OCc1ccccc1]

A mixture of 74.7 mg (0.225 mmol, 1.0 eq.) of 7-[(2,6-difluorobenzyl)oxy]-2,5-dimethylpyrazolo[1,5-a]pyridine-3-carboxylic acid from Example 4A, 106 mg (0.450 mmol, 2.0 eq.) of ent-benzyl (1-amino-2-methylbutan-2-yl)carbamate from Example 14A (enantiomer A) and 0.196 ml (1.12 mmol, 5.0 eq.) of N,N-diisopropylethylamine in 2.3 ml of DMF was admixed with 111 mg (0.292 mmol, 1.3 eq.) of HATU, and the mixture was stirred at RT for 60 h. Then water was added, and the reaction mixture was extracted three times with ethyl acetate. The combined organic phases were washed with saturated aqueous sodium chloride solution, dried over magnesium sulphate, filtered and concentrated. The crude product was purified by means of Biotage Isolera (10 g silica gel cartridge, cyclohexane/ethyl acetate gradient, 0% to 100% ethyl acetate). 81.7 mg of the title compound were obtained (60% of theory; 91% purity).

TLC (silica gel, cyclohexane/ethyl acetate 10:1): $R_f$=0.33

LC-MS (Method 2): $R_t$=1.24 min

MS (ESIpos): m/z=551 (M+H)$^+$

Example 22A ent-Benzyl {1-[({2,5-dimethyl-7-[(2,3,6-trifluorobenzyl)oxy]pyrazolo[1,5-a]pyridin-3-yl}carbonyl)amino]-2-methylbutan-2-yl}carbamate trifluoroacetate (Enantiomer A)

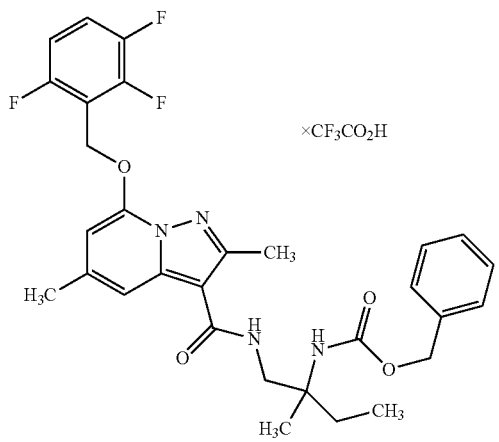 [SMILES: CCC(C)(CNC(=O)c1c(C)nn2c(OCc3c(F)ccc(F)c3F)cc(C)cc12)NC(=O)OCc1ccccc1]

37.8 mg (0.11 mmol) of 2,5-dimethyl-7-[(2,3,6-trifluorobenzyl)oxy]pyrazolo[1,5-a]pyridine-3-carboxylic acid from Example 10A were initially charged together with 49 mg (0.13 mmol) of HATU and 0.1 ml (0.54 mmol) of N,N-diisopropylethylamine in 0.3 ml of DMF, and the mixture was stirred at room temperature for 10 min. Subsequently, 0.5 ml (0.16 mmol) of ent-benzyl (1-amino-2-methylbutan-2-yl) carbamate from Example 14A (enantiomer A) were added to the reaction solution and the mixture was stirred at RT for 2 hours. Another 24.5 mg (0.06 mmol) of HATU were added to the reaction solution and the mixture was stirred at RT overnight. The reaction solution was admixed with TFA and purified by means of preparative HPLC (RP18 column, eluent: acetonitrile/water gradient with addition of 0.1% TFA). 36 mg of the target compound were obtained (41% of theory, 83% purity).

LC-MS (Method 2): $R_t$=1.26 min

MS (ESpos): m/z=569 (M-TFA+H)$^+$

Example 23A ent-Benzyl {1-[({2,5-dimethyl-7-[(2,3,6-trifluorobenzyl)oxy]pyrazolo[1,5-a]pyridin-3-yl}carbonyl)amino]-2-methylpentan-2-yl}carbamate trifluoroacetate (Enantiomer B)

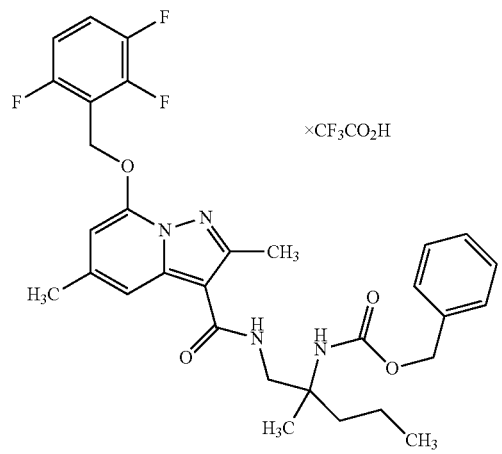 [SMILES: CCCC(C)(CNC(=O)c1c(C)nn2c(OCc3c(F)ccc(F)c3F)cc(C)cc12)NC(=O)OCc1ccccc1]

250 mg (0.68 mmol) of 2,5-dimethyl-7-[(2,3,6-trifluorobenzyl)oxy]pyrazolo[1,5-a]pyridine-3-carboxylic acid from Example 10A were initially charged together with 309 mg (0.81 mmol) of HATU and 0.59 ml (3.39 mmol) of N,N-diisopropylethylamine in 0.9 ml of DMF, and the mixture was stirred at room temperature for 10 min. Subsequently, 255 mg (1.02 mmol) of ent-benzyl (1-amino-2-methylpentan-2-yl) carbamate from Example 20A (enantiomer B) were added to the reaction solution and the mixture was stirred at RT overnight. Then the mixture was diluted with acetonitrile and water, admixed with TFA and purified by means of preparative HPLC (RP18 column, eluent:acetonitrile/water gradient with addition of 0.1% TFA). The product fractions were combined, concentrated and lyophilized. 353 mg of the target compound were obtained (72% of theory).

LC-MS (Method 2): $R_t$=1.31 min

MS (ESpos): m/z=583 (M-TFA+H)$^+$ $^1$H NMR (400 MHz, DMSO-d$_6$): δ=0.85 (t, 3H), 1.20 (s, 3H), 1.23-1.38 (m, 3H), 1.48-1.62 (m, 1H), 1.65-1.79 (m, 1H), 2.39 (s, 3H), 2.51 (s, 3H; under solvent peak), 4.99 (s, 2H), 5.49 (s, 2H), 6.56 (s, 1H), 7.11-7.19 (m, 1H), 7.26-7.44 (m, 8H), 7.66-7.76 (m, 1H).

Example 24A 3,3,4,4,4-Pentafluorobutyl trifluoromethanesulphonate

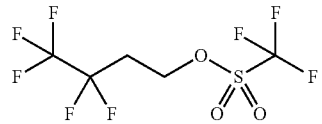 [SMILES: O=S(=O)(OCCC(F)(F)C(F)(F)F)C(F)(F)F]

198.49 g (703.51 mmol) of trifluoromethanesulphonic anhydride were initially charged under argon. The reaction flask was immersed into an oil bath at 70° C. and heated to internal temperature 56° C. 88.2 ml (738.68 mmol) of 3,3,4,4,4-pentafluorobutanol were added dropwise to the reaction mixture within 35 min and the mixture was stirred at bath temperature 70-73° C. and internal temperature 69° C. for two hours. The reaction mixture was concentrated on a rotary evaporator and the residue was taken up in 1500 ml of dichloromethane. The residue was washed once with 300 ml of cold water, once with 300 ml of cold saturated aqueous sodium hydrogencarbonate solution and once with 300 ml of cold water. The organic phase was dried with magnesium sulphate, filtered and concentrated. This gave 192.86 g (92.6% of theory) of the target compound.

$^1$H NMR (400 MHz, DMSO-$d_6$): δ=2.71-2.89 (m, 2H), 4.58 (t, 2H).

Example 25A rac-Methyl 5,5,6,6,6-pentafluoronorleucinate hydrochloride (Racemate)

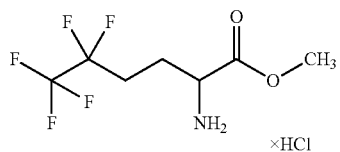

132 g (521.0 mmol) of methyl N-(diphenylmethylene)glycinate [described in: WO2010/123792 A1, 2010; p. 11-13] were initially charged in 1000 ml of THF (anhydrous) under argon and cooled to −40° C. 625.2 ml (625.20 mmol) of bis(trimethylsilyl)lithium amide (1 M in THF) were added dropwise within 30 min. After 10 min at −40° C., the internal temperature was allowed to rise to 0° C. within 35 min 192.86 g (651.25 mmol) of 3,3,4,4,4-pentafluorobutyl trifluoromethanesulphonate from Example 24A, dissolved in 400 ml of THF, were added dropwise to the reaction solution at 0° C. After 10 min, the cooling bath was removed and the mixture was stirred at RT for 3 days. Subsequently, the reaction mixture was cooled to 0° C. and 410 ml (1.33 mol) of 3 N aqueous hydrochloric acid were added dropwise. The cooling bath was removed and the reaction mixture was stirred at RT for two hours. The mixture was subsequently concentrated. This gave 141.5 g of the target compound as a crude mixture (purity unknown), which was used in the subsequent stage without further purification.

Example 26A rac-Methyl N-[(benzyloxy)carbonyl]-5,5,6,6,6-pentafluoronorleucinate (Racemate)

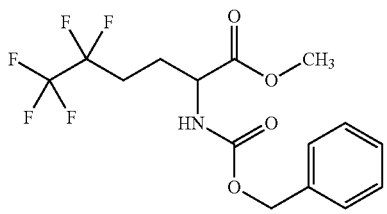 [SMILES: COC(=O)C(CCC(F)(F)C(F)(F)F)NC(=O)OCc1ccccc1]

141.5 g (520.99 mmol) of rac-methyl 5,5,6,6,6-pentafluoronorleucinate hydrochloride from Example 25A were taken up in 850 ml of THF and 850 ml of water under argon, and 223.2 g (1.62 mol) of potassium carbonate were added cautiously at RT. Subsequently, 82 ml (573.09 mmol) of benzyl chloroformate were added dropwise and the suspension was stirred at RT overnight. The reaction mixture was extracted twice with 500 ml of ethyl acetate, and the organic phase was dried with magnesium sulphate, filtered and concentrated. The residue was diluted in 50 ml of dichloromethane and purified by means of silica gel chromatography (eluent:cyclohexane/ethyl acetate 9/1 to 4/1). The isolated product fractions were purified once more by means of preparative HPLC [column: Daiso C18 10 µm Bio 300×100 mm, neutral; eluent: acetonitrile/water gradient; flow rate: 250 ml/min; temperature: RT; wavelength: 210 nm). This gave 27.4 g (14% of theory) of the target compound.

LC-MS (Method 2): $R_t$=1.09 min

MS (ESIpos): m/z=370 (M+H)$^+$.

$^1$H NMR (400 MHz, DMSO-$d_6$): δ=1.78-1.91 (m, 1H), 1.93-2.05 (m, 1H), 2.10-2.30 (m, 1H), 2.30-2.46 (m, 1H), 3.66 (s, 3H), 4.18-4.26 (m, 1H), 5.05 (s, 2H), 7.27-7.40 (m, 5H), 7.89 (d, 1H).

Example 27A rac-Benzyl (6,6,7,7,7-pentafluoro-2-hydroxy-2-methylheptan-3-yl)carbamate (Racemate)

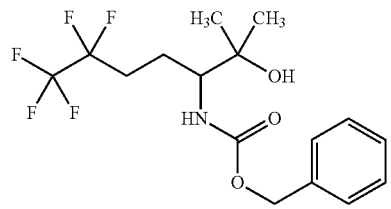 [SMILES: CC(C)(O)C(CCC(F)(F)C(F)(F)F)NC(=O)OCc1ccccc1]

1.7 g (3.68 mmol, 80% pure) of rac-methyl N-[(benzyloxy)carbonyl]-5,5,6,6,6-pentafluoronorleucinate (racemate) from Example 26A were initially charged in THF under argon and the reaction mixture was cooled to 0° C. 4.3 ml (12.89 mmol) of 3M methylmagnesium bromide in diethyl ether were added dropwise and the mixture was stirred at 0° C. for another 15 min. Then the mixture was allowed to warm up gradually to RT and stirred at room temperature overnight. The reaction mixture was admixed cautiously with saturated aqueous ammonium chloride solution and then the reaction solution was concentrated to half the volume. The residue was partitioned between dichloromethane and water, and the organic phase was washed twice with water, dried over sodium sulphate, filtered and concentrated. The residue was purified by means of silica gel chromatography (cyclohexane/ethyl acetate 10:1 to 7:3). This gave 1.31 g (96% of theory) of the target compound.

LC-MS (Method 2): $R_t$=1.03 min

MS (ESIpos): m/z=370 (M+H)$^+$.

¹H NMR (400 MHz, DMSO-d₆): δ=1.01 (s, 3H), 1.08 (s, 3H), 1.43-1.56 (m, 1H), 1.92-2.01 (m, 1H), 2.01-2.19 (m, 2H), 3.36-3.44 (m, 1H), 4.48 (s, 1H), 4.99-5.12 (m, 2H), 7.11 (d, 1H), 7.27-7.38 (m, 5H).

Example 28A ent-Benzyl (6,6,7,7,7-pentafluoro-2-hydroxy-2-methylheptan-3-yl)carbamate (Enantiomer A)

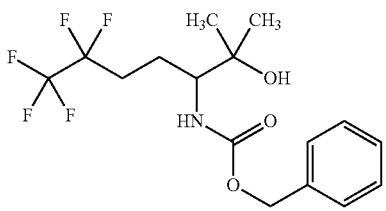 [SMILES: CC(C)(O)C(CCC(F)(F)C(F)(F)F)NC(=O)OCc1ccccc1]

1.31 g of Example 27A were separated into the enantiomers by preparative separation on a chiral phase [column: Daicel Chiralpak AY-H, 5 μm, 250×20 mm, eluent: 90% isohexane, 10% ethanol, flow rate: 15 ml/min; 35° C., detection: 220 nm].

Enantiomer A:

Yield: 459 mg (99% ee) $R_t$=4.31 min [Daicel Chiralpak AY-H, 5 μm, 250×4.6 mm; eluent: 90% isohexane, 10% ethanol; flow rate 1.0 ml/min; 30° C.; detection: 220 nm].

Example 29A ent-3-Amino-6,6,7,7,7-pentafluoro-2-methylheptan-2-ol hydrochloride (Enantiomer A)

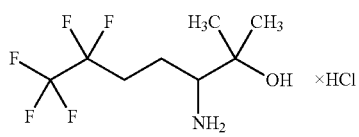

455 mg (1.23 mmol) of ent-benzyl (6,6,7,7,7-pentafluoro-2-hydroxy-2-methylheptan-3-yl)carbamate (enantiomer A) from Example 28A were initially charged in 8.6 ml of ethanol, 131 mg of palladium on charcoal (10%) and 3.74 ml (36.96 mmol) of cyclohexene were added, and the mixture was stirred under reflux for 3 h. The reaction mixture was filtered through a Millipore filter and washed with ethanol. The filtrate was admixed with 1.23 ml of hydrogen chloride (2 N in diethyl ether), concentrated and dried under high vacuum. 335 mg (98% of theory) of the target compound were obtained.

MS (Method 11): m/z=236 (M−HCl+H)⁺

¹H NMR (400 MHz, DMSO-d₆): δ=1.11 (s, 3H), 1.22 (s, 3H), 1.58-1.72 (m, 1H), 1.80-1.92 (m, 1H), 2.27-2.46 (m, 2H, partly hidden by DMSO peak), 2.94-3.04 (m, 1H), 5.35 (s, 1H), 7.80-8.01 (m, 3H).

Example 30A ent-N-[2-Methyl-6-(trifluoromethyl)-1,2,3,4-tetrahydro-1,5-naphthyridin-4-yl]acetamide (Enantiomer A)

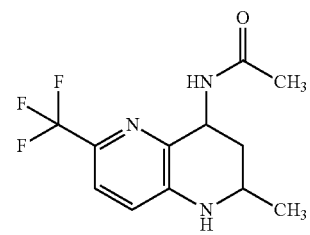 [SMILES: CC(=O)NC1CC(C)Nc2ccc(C(F)(F)F)nc21]

6.00 g (21.96 mmol) of rac-N-[2-methyl-6-(trifluoromethyl)-1,2,3,4-tetrahydro-1,5-naphthyridin-4-yl]acetamide (described in: M.-C. Fernandez et al. Bioorg. Med. Chem. Lett. 2012, 22, 3056-3062) was separated into the enantiomers by preparative separation on a chiral phase [column: SFC Chiralpak AY-H, 20 μm, 360×50 mm, eluent: 90% carbon dioxide, 10% methanol, flow rate: 400 ml/min; temperature: 38° C.; backpressure: 80 bar; detection: 220 nm].

Enantiomer A: Yield: 2.41 g (>99% ee)

$R_t$=2.66 min [Daicel Chiralpak AY-H, 5 μm, 250×4.6 mm; eluent: 90% carbon dioxide, 10% isopropanol; flow rate: 3 ml/min; detection: 210 nm].

Example 31A ent-2-Methyl-6-(trifluoromethyl)-1,2,3,4-tetrahydro-1,5-naphthyridin-4-amine hydrochloride

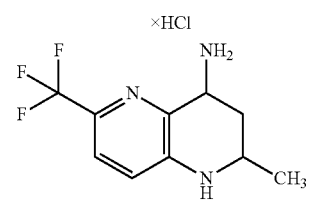 [SMILES: CC1CC(N)c2nc(C(F)(F)F)ccc2N1]

152 mg (0.56 mmol) of ent-N-[2-methyl-6-(trifluoromethyl)-1,2,3,4-tetrahydro-1,5-naphthyridin-4-yl]acetamide (enantiomer A) from Example 30A (described in: M.-C. Fernandez et al. Bioorg. Med. Chem. Lett. 2012, 22, 3056-3062) were admixed with 2.8 ml of saturated hydrogen chloride solution in methanol and stirred in a microwave at 80° C. for 1 hour. The reaction mixture was concentrated and lyophilized. 147 mg of the target compound were obtained (97% of theory, about 98% purity).

LC-MS (Method 2): $R_t$=0.40 min

MS (ESpos): m/z=232 (M−HCl+H)⁺

$^1$H NMR (400 MHz, DMSO-d$_6$): δ=1.23 (d, 3H), 1.59 (q, 1H), 2.25-2.35 (m, 1H), 3.58-3.69 (m, 1H), 4.50-4.61 (m, 1H), 6.97-7.05 (m, 2H), 7.52 (d, 1H), 8.40 (br. s, 3H).

Example 32A rac-2-Amino-4-(benzyloxy)-2-methylbutanonitrile

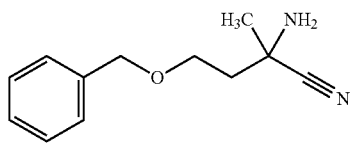

5.31 g (108.3 mmol) of sodium cyanide in 10 ml of water were admixed with 6.37 g (119.1 mmol) of ammonium chloride (dissolved in 15 ml of warm water) and 9 ml (216.6 mmol) of conc. ammonia in water. Subsequently, 19.3 g (108.3 mmol) of 4-(benzyloxy)butan-2-one, dissolved in 3 ml of ethanol, were added. The mixture was stirred at RT for 15 min and at 60° C. for 2 h. Another 4 g (81.6 mmol) of sodium cyanide, 4.8 g (89.7 mmol) of ammonium chloride and 6.5 ml (156.4 mmol) of conc. ammonia in water were added and the mixture was stirred at 60° C. for a further 2 h. Then the reaction solution was cooled and 300 ml each of methylene chloride and water were added thereto. After phase separation, the aqueous phase was extracted with 300 ml of methylene chloride. The combined organic phases were dried and concentrated. The crude product was purified using silica gel (cyclohexane/ethyl acetate gradient 6/4-1/1). 19.9 g of the target compound (77% purity, 69% of theory) were obtained.

LC-MS (Method 13): R$_t$=2.31 min

MS (ESIpos): m/z=205 (M+H)$^+$ $^1$H NMR (400 MHz, DMSO-d$_6$): δ=1.37 (s, 3H), 1.81-1.94 (m, 2H), 2.57 (br. s, 2H), 3.58-3.69 (m, 2H), 4.48 (s, 2H), 7.25-7.38 (m, 5H).

Example 33A rac-4-(Benzyloxy)-2-methylbutane-1,2-diamine

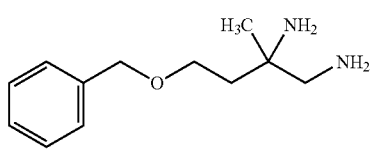

0.5 g (2.45 mmol) of rac-2-amino-4-(benzyloxy)-2-methylbutanonitrile from Example 32A in 25 ml of dry THF were admixed under argon at 0° C. with 1.59 ml (1.59 mmol) of lithium aluminium hydride (1 N solution in diethyl ether). The reaction solution was first stirred at 0° C. for 30 min and then stirred for 1 h, gradually coming to room temperature. Then 245 µl of water, 245 µl of 2 N aqueous sodium hydroxide solution and 490 µl of water were added cautiously. The precipitate was filtered off and washed with THF and methanol, the filtrate was concentrated and the residue was purified by means of silica gel chromatography (eluent:dichloromethane/2 N ammonia in methanol=20/1, isocratic). 0.30 g of the target compound (96% purity, 57% of theory) was obtained.

LC-MS (Method 13): R$_t$=1.94 min

MS (ESIpos): m/z=209 (M+H)$^+$ $^1$H NMR (400 MHz, DMSO-d$_6$): δ=0.90 (s, 3H), 1.56 (t, 2H), 2.27-2.38 (m, 2H), 3.45-3.60 (m, 2H), 4.42 (s, 2H), 7.22-7.36 (m, 5H).

Example 34A rac-3-(3,4-Difluorophenoxy)-2-methylpropane-1,2-diamine

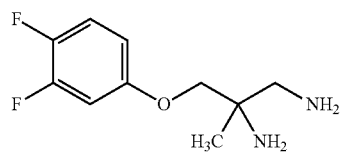

300 mg (1.41 mmol) of rac-2-amino-3-(3,4-difluorophenoxy)-2-methylpropanonitrile were initially charged in 14.4 ml of abs. THF, and 0.92 ml (0.92 mmol) of a 1 N lithium aluminium hydride solution in diethyl ether was added under argon at 0° C. The reaction solution was stirred at 0° C. for 30 min, then allowed to warm up gradually to room temperature and stirred overnight. The reaction mixture was admixed cautiously with 140 µl of water, 140 µl of 2 N aqueous sodium hydroxide solution and 280 µl of water, the precipitate was filtered off and washed with THF and methanol, the filtrate was concentrated and the residue was purified by means of silica gel chromatography (eluent:dichloromethane/2 N ammonia in methanol=20/1). 87 mg of the target compound were obtained (24% of theory, about 84% purity).

LC-MS (Method 7): R$_t$=1.73 min

MS (ESIpos): m/z=217 (M+H)$^+$

Example 35A 3-(Aminomethyl)oxetane-3-amine dihydrochloride

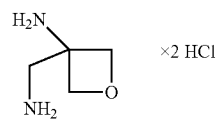

585 mg (2.07 mmol) of 3-(aminomethyl)-N,N-dibenzyloxetane-3-amine [synthesis described in: US2008/103183 A1, 2008; p. 48] were initially charged in ethanol (29.2 ml), and 441 mg (0.41 mmol) of 10% palladium on activated carbon and 6.3 ml (62.2 mmol) of cyclohexene were added. The reaction mixture was stirred under reflux for 8 h. Subsequently, the reaction mixture was filtered through a Millipore® filter and washed with methanol, and the filtrate was admixed with 2.6 ml (5.2 mmol) of 2 M hydrogen chloride in diethyl ether, concentrated and dried under high vacuum. This gave 423 mg (87% of theory, purity 75%) of the target compound.

DCI-MS (Method 12): m/z=103 (M-2HCl+H)$^+$

Example 36A 2-(Trifluoromethyl)piperidine-4-amine hydrochloride

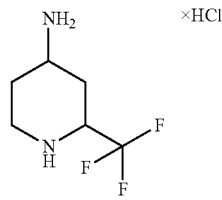 [SMILES: NC1CCNC(C(F)(F)F)C1]

115 mg (0.43 mmol) of tert-butyl [2-(trifluoromethyl)piperidin-4-yl]carbamate were initially charged in 2.2 ml of diethyl ether, 2.14 ml (4.28 mmol) of 2 N hydrochloric acid in diethyl ether were added and the mixture was stirred at RT overnight. The reaction mixture was concentrated and the residue was dried under high vacuum. 89 mg of the target compound were obtained (101% of theory).

Example 37A

Methyl 3-(aminomethyl)adamantane-1-carboxylate

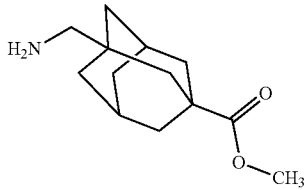

73 mg (0.30 mmol) of 3-(aminomethyl)adamantane-1-carboxylic acid were initially charged in 1.48 ml of methanol, and 1.48 ml of 4 N hydrogen chloride solution in dioxane were added. The mixture was stirred under reflux for 5 h. The mixture was concentrated by evaporation and the residue was admixed with saturated sodium hydrogencarbonate solution. The mixture was extracted three times with ethyl acetate, and the combined organic phases were dried over sodium sulphate and then concentrated by evaporation and dried. 55 mg of the target compound (82% of theory) were obtained, which were used in the subsequent stage without further purification.

Example 38A rac-3-(3,4-Difluorophenyl)-3-(1,3-dioxo-1,3-dihydro-2H-isoindol-2-yl)propanoic Acid

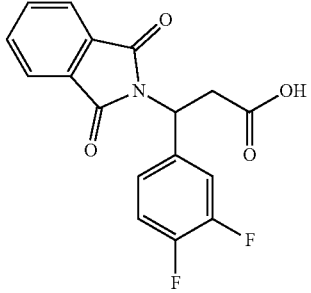 [SMILES: O=C(O)CC(c1ccc(F)c(F)c1)N1C(=O)c2ccccc2C1=O]

1st Stage:

697 g of 3,4-difluorobenzaldehyde (4.76 mol, 1 equivalent) were stirred together with 495 g of malonic acid (4.76 mol, 1 equivalent) and 733 g of ammonium acetate (9.52 mol, 2 equivalents) in 2788 ml of ethanol at reflux under argon for 20 h. Then the mixture was cooled to RT and stirred at RT overnight. The precipitated crystals were filtered off with suction, washed with ethanol and diethyl ether, and dried under reduced pressure. 590 g (62% of theory) of rac-3-amino-3-(3,4-difluorophenyl)propanoic acid were obtained.

rac-3-Amino-3-(3,4-difluorophenyl)propanoic Acid

LC-MS (Method 1): $R_t$=0.27 min

MS (ESIpos): m/z=202.0 (M+H)$^+$ 2 nd Stage:

0.20 g (0.99 mmol) of rac-3-amino-3-(3,4-difluorophenyl)propanoic acid and 0.15 g (0.99 mmol) of phthalic anhydride were dissolved in 0.8 ml of DMF and heated to reflux at 135° C. overnight. The reaction solution was added to about 9 ml of water. The resulting suspension was extracted twice with ethyl acetate. The combined organic phases were washed with water, dried over sodium sulphate, filtered and concentrated. The crude product was purified by means of preparative HPLC (RP18 column, eluent:acetonitrile/water gradient with addition of 0.1% TFA). 0.2 g of the title compound was obtained (61% of theory).

LC-MS (Method 2): $R_t$=0.97 min

MS (ESIpos): m/z=332 (M+H)$^+$ $^1$H NMR (400 MHz, DMSO-d$_6$): δ=3.24-3.3.33 (m, 1H), 3.44-3.52 (m, 1H), 5.63-5.70 (m, 1H), 7.23-7.28 (m, 1H), 7.36-7.47 (m, 1H), 7.49-7.57 (m, 1H), 7.82-7.90 (m, 4H), 12.51 (br s, 1H).

Example 39A rac-tert-Butyl [2-(3,4-difluorophenyl)-2-(1,3-dioxo-1,3-dihydro-2H-isoindol-2-yl)ethyl]carbamate

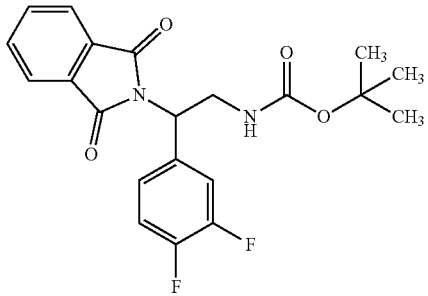 [SMILES: CC(C)(C)OC(=O)NCC(c1ccc(F)c(F)c1)N1C(=O)c2ccccc2C1=O]

Under argon, a solution of 5.0 g of rac-3-(3,4-difluorophenyl)-3-(1,3-dioxo-1,3-dihydro-2H-isoindol-2-yl)propanoic acid (Example 38A, 15.09 mmol) and 3.06 g of triethylamine (30.19 mmol) was initially charged in 65 ml of toluene, 4.36 g of diphenylphosphorus azidate (15.85 mmol) were added and the mixture was stirred at RT for 3.5 h. Subsequently, 65 ml of tert-butanol were added and the mixture was stirred under reflux overnight. After cooling, the reaction solution was concentrated and purified by means of flash chromatography (eluent:petroleum ether/ethyl acetate 2:1, isocratic). 3.1 g of the title compound were obtained (45% of theory).

LC-MS (Method 2): $R_t$=1.19 min

MS (ESIpos): m/z=403 (M+H)$^+$

¹H NMR (400 MHz, DMSO-d₆): δ=1.26 (s, 9H), 3.73-3.90 (m, 2H), 5.32-5.39 (m, 1H), 7.20-7.27 (m, 2H), 7.36-7.46 (m, 1H), 7.48-7.56 (m, 1H), 7.81-7.91 (m, 4H).

Example 40A rac-tert-Butyl [2-amino-2-(3,4-difluorophenyl)ethyl]carbamate

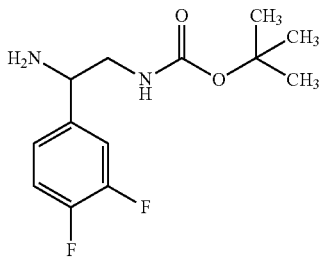 [SMILES: CC(C)(C)OC(=O)NCC(N)c1ccc(F)c(F)c1]

6.13 g of rac-tert-butyl [2-(3,4-difluorophenyl)-2-(1,3-dioxo-1,3-dihydro-2H-isoindol-2-yl)ethyl]carbamate (Example 39A, purity about 60%, about 9.14 mmol) were initially charged in 13.1 ml of 40% aqueous methylamine solution, and the mixture was stirred in a closed vessel at 60° C. overnight. The reaction mixture was concentrated and the residue was purified by means of silica gel chromatography (eluent:dichloromethane:methanol:diethylamine 30:1:0.1; 20:1:0.1). 1.83 g of the title compound were obtained (74% of theory).

LC-MS (Method 1): $R_t$=0.65 min

MS (ESIpos): m/z=273 (M+H)⁺

¹H NMR (400 MHz, DMSO-d₆): δ=1.33 (s, 9H), 1.96 (br s, 2H), 2.92-3.10 (m, 2H), 3.81-3.88 (m, 1H), 6.76-6.82 (m, 1H), 7.11-7.17 (m, 1H), 7.27-7.40 (m, 2H).

Example 41A ent-tert-Butyl [2-amino-2-(3,4-difluorophenyl)ethyl]carbamate
(Enantiomer A)

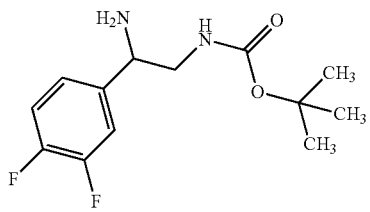 [SMILES: CC(C)(C)OC(=O)NCC(N)c1ccc(F)c(F)c1]

100 mg of rac-tert-butyl [2-amino-2-(3,4-difluorophenyl) ethyl]carbamate (Example 40A) were separated into the enantiomers on a chiral phase [column: Daicel Chiralpak AY-H, 5 μm, 250×20 mm, eluent: 80% isohexane, 20% ethanol+0.2% diethylamine, flow rate 15 ml/min; 30° C., detection: 220 nm].

Yield: 43 mg of enantiomer A (99% purity, >99% ee)

$R_t$=4.58 min [Daicel Chiralpak AY-H, 5 μm, 250×4.6 mm; eluent: 80% isohexane, 20% ethanol+0.2% diethylamine; flow rate 1.0 ml/min; 30° C.; detection: 220 nm].

Example 42A rac-2-Amino-4,4,4-trifluorobutan-1-ol

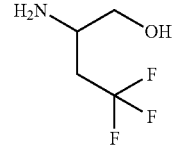

12.9 ml of 2 M of lithium borohydride solution in THF (25.8 mmol, 2.5 equivalents) were initially charged in 20 ml of THF, 6.5 ml of chlorotrimethylsilane (51.1 mmol, 5 equivalents) were added and the mixture was stirred at RT for 5 min. Then 2.0 g of rac-2-amino-4,4,4-trifluorobutanoic acid hydrochloride (10.3 mmol, 1 equivalent) were added in portions and the mixture was stirred at room temperature overnight. Then 20.4 ml of methanol were added dropwise and, on completion of addition, the mixture was concentrated. The residue was admixed with 12 ml of a 20% aqueous potassium hydroxide solution and extracted three times with dichloromethane. The combined organic solutions were dried over sodium sulphate, filtered and concentrated. 1.58 g (96% of theory; 90% purity) of the title compound were obtained.

MS (Method 11): m/z=144.0 (M+H)⁺

¹H NMR (400 MHz, DMSO-d₆): δ=1.54 (br. s, 2H), 1.97-2.15 (m, 1H), 2.28-2.45 (m, 1H), 2.84-2.98 (m, 1H), 3.24 (d, 2H), 4.78 (br. s, 1H).

Example 43A rac-Benzyl (4,4,4-trifluoro-1-hydroxybutan-2-yl)carbamate

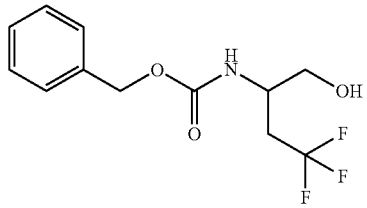 [SMILES: O=C(NC(CO)CC(F)(F)F)OCc1ccccc1]

400 mg of rac-2-amino-4,4,4-trifluorobutan-1-ol (Example 42A, 2.5 mmol, purity about 90%, 1 equivalent) in 36 ml of 1,4-dioxane were admixed at RT with 0.38 ml of 50% aqueous potassium carbonate solution (1.7 mmol, 0.68 equivalent) and 0.54 ml of benzyl chloroformate (3.8 mmol, 1.5 equivalents), and the mixture was stirred at RT for 2 h. Then another 0.11 ml of benzyl chloroformate (0.76 mmol, 0.3 equivalent) and 0.08 ml of 50% aqueous potassium carbonate solution (0.35 mmol, 0.14 equivalent) were added and the mixture was stirred at RT for a further 30 min. Concentration under reduced pressure was followed by purification by means of preparative HPLC (RP18 column, eluent:acetonitrile/water gradient with addition of 0.1% TFA). The resulting crude product was taken up in ethyl acetate and washed twice with saturated aqueous sodium hydrogencarbonate solution. The aqueous phase was extracted with ethyl acetate, and the combined organic phases were dried over sodium sulphate, filtered and concentrated. 490 mg (70% of theory) of the title compound were obtained.

LC-MS (Method 2): $R_t$=0.81 min

MS (ESIpos): m/z=278.1 (M+H)⁺

$^1$H NMR (400 MHz, DMSO-d$_6$): δ=2.20-2.38 (m, 1H), 3.19-3.27 (m, 1H), 3.28-3.42 (m, 2H), 3.72-3.83 (m, 1H), 4.96-5.08 (m, 3H), 7.26-7.39 (m, 5H).

Example 44A rac-Benzyl [1-(1,3-dioxo-1,3-dihydro-2H-isoindol-2-yl)-4,4,4-trifluorobutan-2-yl]carbamate

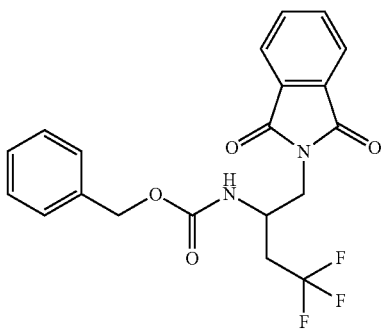 [SMILES: O=C(NC(CN1C(=O)c2ccccc2C1=O)CC(F)(F)F)OCc1ccccc1]

Under argon, 1.58 g of rac-benzyl (4,4,4-trifluoro-1-hydroxybutan-2-yl)carbamate (Example 43A, 5.70 mmol, 1 equivalent), 0.84 g of 1H-isoindole-1,3(2H)-dione (phthalimide, 5.70 mmol, 1 equivalent) and 2.24 g of triphenylphosphine (8.54 mmol, 1.5 equivalents) were dissolved in 28 ml of THF, and 1.84 g of di-tert-butyl (E)-diazene-1,2-dicarboxylate (DIAD, 8.54 mmol, 1.5 equivalents) were added at RT. The mixture was stirred at RT for 30 min and then a water/acetonitrile mixture was added. Purification by means of preparative HPLC (RP18 column, eluent:acetonitrile/water gradient with addition of 0.1% TFA) gave 1.92 g (79% of theory) of the title compound.

LC-MS (Method 2): R$_t$=1.08 min
MS (ESIpos): m/z=407.2 (M+H)$^+$

Example 45A rac-Benzyl (1-amino-4,4,4-trifluorobutan-2-yl)carbamate trifluoroacetate

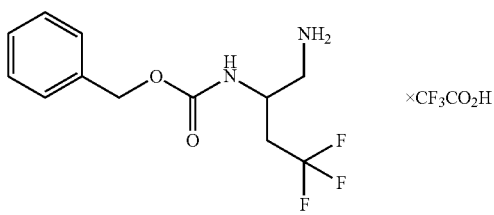 [SMILES: NCC(CC(F)(F)F)NC(=O)OCc1ccccc1]

1.86 g of rac-benzyl [1-(1,3-dioxo-1,3-dihydro-2H-isoindol-2-yl)-4,4,4-trifluorobutan-2-yl]carbamate (Example 44A, 4.35 mmol, 1 equivalent) were dissolved in 15.0 ml of 40% aqueous methylamine solution (174 mmol, 40 equivalents) and the mixture was stirred in a closed flask at 60° C. The reaction mixture was concentrated and the residue was subsequently purified by means of preparative HPLC (RP18 column, eluent:acetonitrile/water gradient with addition of 0.1% TFA). 1.25 g (74% of theory) of the title compound were obtained.

LC-MS (Method 2): R$_t$=0.64 min
MS (ESIpos): m/z=277.2 (M+H)$^+$
$^1$H NMR (400 MHz, DMSO-d$_6$): δ=2.57-2.71 (m, 1H), 2.76-2.89 (m, 1H), 2.93-3.04 (m, 1H), 4.00-4.14 (m, 1H), 5.02 (d, 1H), 5.09 (d, 1H), 7.27-7.42 (m, 5H), 7.47-7.53 (m, 1H), 7.88-8.08 (br. s, 3H), [further signal hidden under DMSO peak].

Example 46A rac-4,4,4-Trifluorobutane-1,2-diamine dihydrochloride

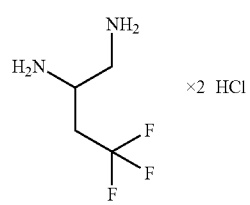

1.99 g (5.10 mmol) of rac-benzyl (1-amino-4,4,4-trifluorobutan-2-yl)carbamate trifluoroacetate (Example 45A) were dissolved in 130 ml of methanol. 543 mg of palladium on charcoal (10%) were added at RT and the mixture was hydrogenated under standard pressure overnight. The reaction mixture was filtered through Celite, and the Celite was washed with methanol. The filtrate was admixed with 5.1 ml of hydrogen chloride solution (2 N in diethyl ether), then concentrated on a rotary evaporator and dried under reduced pressure. 1.10 g (100% of theory) of the title compound were obtained.

MS (Method 11): m/z=143.2 (M-2HCl+H)$^+$
$^1$H NMR (500 MHz, DMSO-d$_6$): δ=2.75-2.88 (m, 1H), 2.90-3.02 (m, 1H), 3.11-3.19 (m, 1H), 3.21-3.29 (m, 1H), 3.78-3.86 (M, 1H), 8.69 (br. s, 6H).

Example 47A

2-Methyl-4-phenyl-2-(trifluoromethyl)-1,3-oxazolidine (Diastereomers)

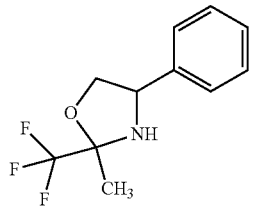 [SMILES: CC1(C(F)(F)F)NC(c2ccccc2)CO1]

55.13 g (492.0 mmol) of 1,1,1-trifluoroacetone in toluene (1.35 l) were admixed with 45 g (328.0 mmol) of rac-2-amino-2-phenylethanol and 8.24 g (32.8 mmol) of pyridinium p-toluenesulphonate. The reaction mixture was boiled under reflux on a water separator for 16 h. The mixture was cooled to 0° C., and the solids formed were filtered off and dried under high vacuum. This gave 68.6 g (77% of theory, purity 85%) of the target compound.

LC-MS (Method 2): R$_t$=0.99 min
MS (ESIpos): m/z=232 (M+H)$^+$
$^1$H NMR (400 MHz, DMSO-d$_6$): δ=1.54 (s, 3H), 3.56 (t, 1H), 3.81 (d, 1H), 4.28 (t, 1H), 4.35-4.43 (m, 1H), 7.29-7.47 (m, 5H).

Example 48A 3,3,3-Trifluoro-2-[(2-hydroxy-1-phenylethyl)amino]-2-methylpropanonitrile (Diastereomers)

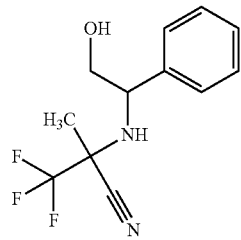 [SMILES: CC(C#N)(NC(CO)c1ccccc1)C(F)(F)F]

52.8 g (228.3 mmol) of 2-methyl-4-phenyl-2-(trifluoromethyl)-1,3-oxazolidine (diastereomers) from Example 47A were initially charged under argon in dichloromethane (2 l) and cooled to 0° C. 42.85 ml (342.5 mmol) of trimethylsilyl cyanide and 42.1 ml (342.5 mmol) of boron trifluoride-diethyl ether complex were added gradually and the mixture was stirred at RT for 16 h. Subsequently, the reaction solution was poured into 1.5 l of saturated sodium hydrogencarbonate solution. Subsequently, another 400 g of sodium hydrogencarbonate were added and the solution was adjusted to pH 10 with conc. sodium hydroxide solution. The aqueous solution was extracted three times with 500 ml of dichloromethane, and the combined organic phases were dried over sodium sulphate, filtered and concentrated. This gave 56.8 g (96% of theory, 2 diastereomers) of the target compound.

LC-MS (Method 2): $R_t$=0.89 min and 0.93 min

MS (ESIneg): m/z=303 (M−H+HCOOH)−

Example 49A

2-[(3-Amino-1,1,1-trifluoro-2-methylpropan-2-yl)amino]-2-phenylethanol (Diastereomers)

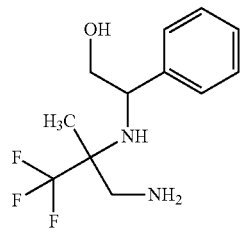 [SMILES: CC(CN)(NC(CO)c1ccccc1)C(F)(F)F]

31 g (120.0 mmol) of 3,3,3-trifluoro-2-[(2-hydroxy-1-phenylethyl)amino]-2-methylpropanonitrile from Example 48A were initially charged in tert-butyl methyl ether (3.1 l) and cooled to 0° C., 18.25 g (480.2 mmol) of lithium aluminium hydride were added and the reaction mixture was stirred at RT for 16 h. Subsequently, the mixture was cooled to 0° C., first quenched with 24 ml of water, then admixed with 24 ml of 15% aqueous potassium hydroxide solution and 48 ml of water. The resulting mixture was filtered through silica gel and washed with tert-butyl methyl ether. The organic phase was separated off, dried over sodium sulphate, filtered and concentrated. This gave 29.2 g (83% of theory, purity 89%) of the target compound.

LC-MS (Method 2): $R_t$=0.52 min

MS (ESIpos): m/z=263 (M+H)+

Example 50A tert-Butyl {3,3,3-trifluoro-2-[(2-hydroxy-1-phenylethyl)amino]-2-methylpropyl}carbamate (Diastereomers)

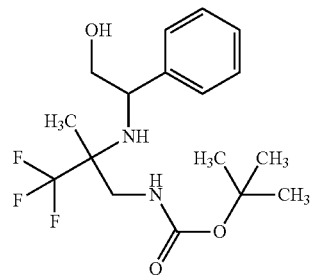 [SMILES: CC(C)(C)OC(=O)NCC(C)(NC(CO)c1ccccc1)C(F)(F)F]

26.2 g (99.9 mmol) of 2-[(3-amino-1,1,1-trifluoro-2-methylpropan-2-yl)amino]-2-phenylethanol (diastereomers) from Example 49A in THF (500 ml) were admixed with 29.1 ml (209.8 mmol) of triethylamine and 23.98 g (109.9 mmol) of di-tert-butyl dicarbonate (dissolved in 286 ml of THF). The reaction mixture was stirred at RT for 16 h. Subsequently, the reaction mixture was concentrated and taken up in 500 ml each of saturated aqueous sodium hydrogencarbonate solution and ethyl acetate. The phases were separated and the organic phase was dried over sodium sulphate, filtered and concentrated. This gave 39.80 g (110% of theory) of the target compound, which were used in the next stage without further purification.

FIA-MS (Method 11, ESpos): m/z=363 (M+H)+

Example 51A rac-tert-Butyl (2-amino-3,3,3-trifluoro-2-methylpropyl)carbamate

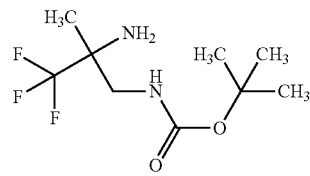 [SMILES: CC(C)(C)OC(=O)NCC(C)(N)C(F)(F)F]

39 g (107.6 mmol) of tert-butyl-{3,3,3-trifluoro-2-[(2-hydroxy-1-phenylethyl)amino]-2-methylpropyl}carbamate from Example 50A were initially charged under argon in ethanol (700 ml), and 5.44 g (53.8 mmol) of palladium(II) hydroxide (20% on activated carbon, water-moist, about 60%) were added. The reaction mixture was hydrogenated at standard pressure for 16 h. Then the reaction mixture was filtered through silica gel and concentrated. The residue was purified by means of silica gel chromatography (cyclohexane/ethyl acetate gradient: 9/1 to 6/4). This gave 15.8 g (61% of theory) of the target compound.

FIA-MS (Method 11, ESpos): m/z=243 (M+H)+

$^1$H NMR (400 MHz, CDCl$_3$): δ=1.22 (s, 3H), 1.45 (s, 9H), 3.13-3.23 (m, 1H), 3.37-3.48 (m, 1H), 4.89 (br. s, 1H).

Example 52A rac-3,3,3-Trifluoro-2-methylpropane-1,2-diamine dihydrochloride

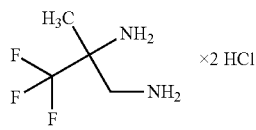

15 g (61.9 mmol) of rac-tert-butyl (2-amino-3,3,3-trifluoro-2-methylpropyl)carbamate from Example 51A in dioxane (188 ml) were admixed with 188 ml of 4 M hydrogen chloride in dioxane. The reaction mixture was stirred at RT for 16 h, then concentrated and stored under argon. This gave 14.4 g (108% of theory) of the target compound, which was not purified any further.

FIA-MS (Method 11, ESpos): m/z=143 (M-2HCl+H)$^+$ $^1$H NMR (400 MHz, D$_2$O): δ=1.40 (s, 3H), 3.21-3.31 (m, 2H).

Example 53A rac-2-Amino-3-fluoro-2-methylpropanonitrile

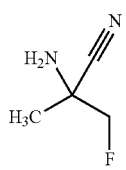

The title compound is known from the literature:

1) McConathy, J. et al., Journal of Medicinal Chemistry 2002, 45, 2240-2249.
2) Bergmann, E. D. et al., Journal of the Chemical Society 1963, 3462-3463.

Further Method:

1.0 g (0.94 ml; 13.15 mmol) of fluoroacetone were initially charged in 11 ml of 2 N ammonia in methanol. At RT, 721 mg (14.72 mmol) of sodium cyanide and 788 mg (14.72 mmol) of ammonium chloride were added successively, and the mixture was stirred at reflux for 2 hours. The reaction solution was cooled, filtered and washed with methylene chloride. A solid precipitated out of the mother liquor, which was filtered off. Methylene chloride and methanol were distilled out of the mother liquor at standard pressure. 1.32 g of the target compound were obtained (89% of theory, about 90% purity). The product was used in the next reaction without further purification.

GC-MS (Method 14): R$_t$=1.64 min

MS (EIpos): m/z=87 (M-CH$_3$)$^+$

Example 54A rac-Benzyl (2-cyano-1-fluoropropan-2-yl)carbamate

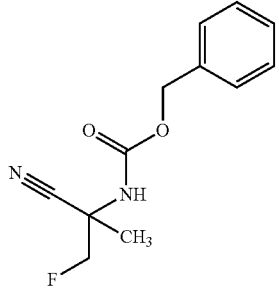 [SMILES: CC(C#N)(CF)NC(=O)OCc1ccccc1]

1.34 g (11.83 mmol, about 90%) of rac-2-amino-3-fluoro-2-methylpropanonitrile from Example 53A in 29 ml of THF/water (9/1) were admixed with 5.07 g (36.67 mmol) of potassium carbonate. At 0° C., 1.69 ml (11.83 mmol) of benzyl chloroformate were slowly added dropwise and the reaction mixture was stirred at RT overnight. The solvent was decanted off and the aqueous phase was twice extracted by shaking with THF and then decanting off the THF. The combined organic phases were dried over sodium sulphate, filtered and concentrated. The residue was separated by means of silica gel chromatography (eluent:cyclohexane/ethyl acetate gradient) and the product fractions were concentrated by evaporation on a rotary evaporator. 1.89 g of the target compound were obtained (66% of theory, 97% purity).

LC-MS (Method 2): R$_t$=0.89 min

MS (ESIpos): m/z=237 (M+H)$^+$ $^1$H NMR (400 MHz, DMSO-d$_6$): δ=1.58 (d, 3H), 4.47-4.78 (m, 2H), 5.10 (s, 2H), 7.30-7.43 (m, 5H), 8.34 (br. s, 1H).

Example 55A ent-Benzyl (2-cyano-1-fluoropropan-2-yl)carbamate (Enantiomer A)

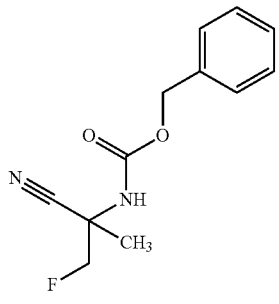 [SMILES: CC(C#N)(CF)NC(=O)OCc1ccccc1]

3.0 g (12.69 mmol) of rac-benzyl (2-cyano-1-fluoropropan-2-yl)carbamate from Example 54A were separated into the enantiomers by preparative separation on a chiral phase [column: Daicel Chiralpak AY-H, 5 µm, 250×20 mm, eluent: 80% isohexane, 20% isopropanol, flow rate: 15 ml/min; 40° C., detection: 220 nm].

Enantiomer A: Yield: 1.18 g (>99% ee)

R$_t$=5.37 min [Daicel Chiralcel AY-H, 5 µm, 250×4.6 mm; eluent: 70% isohexane, 30% 2-propanol; flow rate 1.0 ml/min; 40° C.; detection: 220 nm].

Example 56A ent-Benzyl (2-cyano-1-fluoropropan-2-yl)carbamate (Enantiomer B)

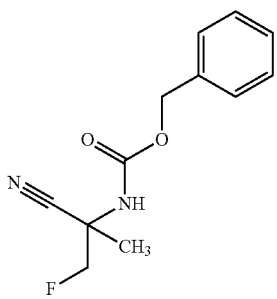 [SMILES: CC(C#N)(CF)NC(=O)OCc1ccccc1]

3.0 g (12.69 mmol) of rac-benzyl-(2-cyano-1-fluoropropan-2-yl)carbamate from Example 54A were separated into the enantiomers by preparative separation on a chiral phase [column: Daicel Chiralpak AY-H, 5 µm, 250×20 mm, eluent: 80% isohexane, 20% isopropanol, flow rate: 15 ml/min; 40° C., detection: 220 nm].

Enantiomer B: Yield: 1.18 g (>99% ee)

$R_t$=6.25 min [Daicel Chiralcel AY-H, 5 µm, 250×4.6 mm; eluent: 70% isohexane, 30% 2-propanol; flow rate 1.0 ml/min; 40° C.; detection: 220 nm].

Example 57A rac-Benzyl (1-amino-3-fluoro-2-methylpropan-2-yl)carbamate

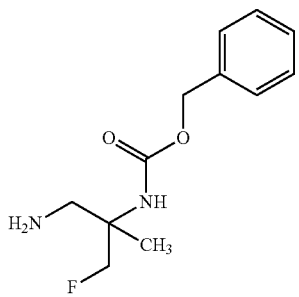 [SMILES: CC(CN)(CF)NC(=O)OCc1ccccc1]

Under argon, 1.2 g (5.08 mmol) of rac-benzyl (2-cyano-1-fluoropropan-2-yl)carbamate from Example 54A in 14.9 ml of 7 N ammonia in methanol were admixed with 1.55 g of Raney nickel (aqueous slurry) and hydrogenated at hydrogen pressure about 25 bar and RT for 24 hours. The reaction mixture was filtered through kieselguhr, washed with methanol and concentrated. 1.2 g of the target compound were obtained (98% of theory).

LC-MS (Method 2): $R_t$=0.49 min

MS (ESIpos): m/z=241 (M+H)$^+$

Example 58A ent-Benzyl (1-amino-3-fluoro-2-methylpropan-2-yl)carbamate (Enantiomer A)

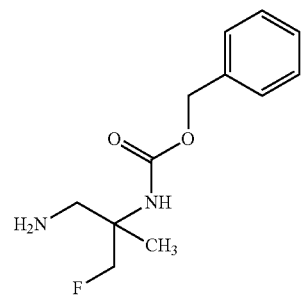 [SMILES: CC(CN)(CF)NC(=O)OCc1ccccc1]

Under argon, 1.2 g (5.08 mmol) of ent-benzyl (2-cyano-1-fluoropropan-2-yl)carbamate (enantiomer A) from Example 55A in 14.9 ml of 7 N ammonia in methanol were admixed with 1.55 g of Raney nickel (aqueous slurry) and hydrogenated at hydrogen pressure about 25 bar and RT for 24 hours. The reaction mixture was filtered through kieselguhr, washed with methanol and concentrated. 700 mg of the target compound were obtained (57% of theory, about 85% purity).

LC-MS (Method 2): $R_t$=0.52 min

MS (ESIpos): m/z=241 (M+H)$^+$

Example 59A ent-Benzyl (1-amino-3-fluoro-2-methylpropan-2-yl)carbamate (Enantiomer B)

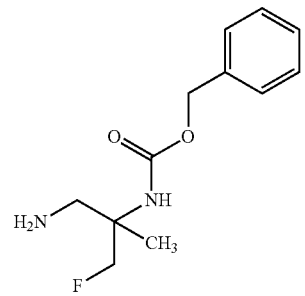 [SMILES: CC(CN)(CF)NC(=O)OCc1ccccc1]

Under argon, 1.2 g (5.08 mmol) of ent-benzyl (2-cyano-1-fluoropropan-2-yl)carbamate (enantiomer B) from Example 56A in 14.9 ml of 7 N ammonia in methanol were admixed with 1.55 g of Raney nickel (aqueous slurry) and hydrogenated at hydrogen pressure about 25 bar and RT for 24 hours. The reaction mixture was filtered through kieselguhr, washed with methanol and concentrated. 1.2 g of the target compound were obtained (98% of theory, about 85% purity).

LC-MS (Method 2): $R_t$=0.50 min

MS (ESIpos): m/z=241 (M+H)$^+$

Example 60A rac-2-Amino-5,5,5-trifluoro-2-methylpentanonitrile

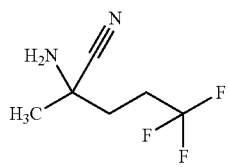

8.0 g (57.1 mmol) of 5,5,5-trifluoropentan-2-one [CAS Registry Number: 1341078-97-4; commercially available, or the methyl ketone can be prepared by literature methods which are known to those skilled in the art, for example via a) two stages from 4,4,4-trifluorobutanal according to Y. Bai et al. Angewandte Chemie 2012, 51, 4112-4116; K. Hiroi et al. Synlett 2001, 263-265; K. Mikami et al. 1982 Chemistry Letters, 1349-1352; b) or from 4,4,4-trifluorobutanoic acid according to A. A. Wube et al. Bioorganic and Medicinal Chemistry 2011, 19, 567-579; G. M. Rubottom et al. Journal of Organic Chemistry 1983, 48, 1550-1552; T. Chen et al. Journal of Organic Chemistry 1996, 61, 4716-4719. The product can be isolated by distillation or chromatography] were initially charged in 47.8 ml of 2 N ammonia in methanol, 3.69 g (75.4 mmol) of sodium cyanide and 4.03 g (75.4 mmol) of ammonium chloride were added at room temperature and the mixture was stirred under reflux for 4 hours. The reaction mixture was cooled, diethyl ether was added and the solids present were filtered off. The solvent was distilled out of the filtrate under standard pressure. 8.7 g of the title compound (92% of theory) were obtained as residue, which was used in the subsequent stage without further purification.

GC-MS (Method 14): $R_t$=1.90 min
MS (ESpos): m/z=151 (M-$CH_3$)$^+$

Example 61A rac-Benzyl (2-cyano-5,5,5-trifluoropentan-2-yl)carbamate

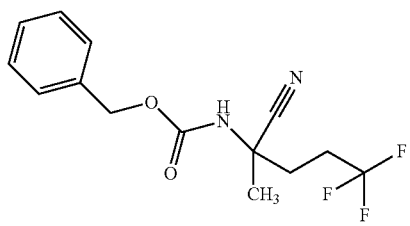 [SMILES: CC(C#N)(CCC(F)(F)F)NC(=O)OCc1ccccc1]

8.7 g (52.36 mmol) of rac-2-amino-5,5,5-trifluoro-2-methylpentanonitrile from Example 60A were initially charged in 128 ml of tetrahydrofuran/water=9/1, and 22.43 g (162.3 mmol) of potassium carbonate were added. At 0° C., 8.93 g (52.36 mmol) of benzyl chloroformate were added dropwise. Then the mixture was allowed to warm up gradually to room temperature and stirred at room temperature overnight. The supernatant solvent was decanted off, the residue was twice stirred with 100 ml each time of tetrahydrofuran, and then the supernatant solvent was decanted off each time. The combined organic phases were concentrated and the crude product was purified by means of silica gel chromatography (eluent:cyclohexane/ethyl acetate gradient 9/1 to 4/1). 11.14 g of the title compound were obtained (68% of theory).

LC-MS (Method 2): $R_t$=1.01 min
MS (ESIpos): m/z=301 (M+H)$^+$
$^1$H NMR (400 MHz, DMSO-$d_6$): δ [ppm]=1.58 (s, 3H), 2.08-2.21 (m, 2H), 2.24-2.52 (m, 2H), 5.09 (s, 2H), 7.29-7.41 (m, 5H), 8.17 (br. s, 1H).

Example 62A ent-Benzyl (2-cyano-5,5,5-trifluoropentan-2-yl)carbamate (Enantiomer A)

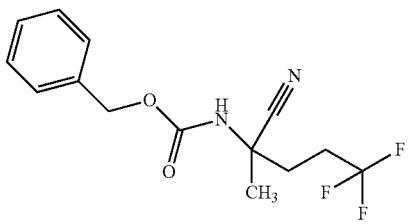 [SMILES: CC(C#N)(CCC(F)(F)F)NC(=O)OCc1ccccc1]

11.14 g of rac-benzyl (2-cyano-5,5,5-trifluoropentan-2-yl) carbamate from Example 61A were separated into the enantiomers by preparative separation on a chiral phase [column: Daicel Chiralpak AZ-H, 5 µm, SFC, 250×50 mm, eluent: 94% carbon dioxide, 6% methanol, flow rate: 200 ml/min, temperature: 38° C., pressure: 135 bar; detection: 210 nm].

Enantiomer A: 4.12 g (about 79% ee)
$R_t$=1.60 min [SFC, Daicel Chiralpak AZ-H, 250×4.6 mm, 5 µm, eluent: 90% carbon dioxide, 10% methanol, flow rate: 3 ml/min, temperature: 30° C., detection: 220 nm].
LC-MS (Method 2): $R_t$=1.01 min
MS (ESIpos): m/z=301 (M+H)$^+$

Example 63A ent-Benzyl (2-cyano-5,5,5-trifluoropentan-2-yl)carbamate (Enantiomer B)

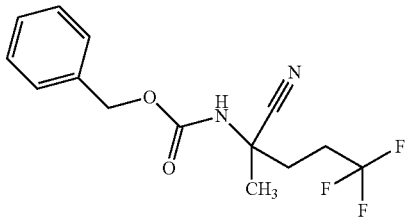 [SMILES: CC(C#N)(CCC(F)(F)F)NC(=O)OCc1ccccc1]

11.14 g of rac-benzyl (2-cyano-5,5,5-trifluoropentan-2-yl) carbamate from Example 61A were separated into the enantiomers by preparative separation on a chiral phase [column: Daicel Chiralpak AZ-H, 5 µm, SFC, 250×50 mm, eluent: 94% carbon dioxide, 6% methanol, flow rate: 200 ml/min, temperature: 38° C., pressure: 135 bar; detection: 210 nm].

Enantiomer B: 4.54 g (about 70% ee, about 89% purity)
$R_t$=1.91 min [SFC, Daicel Chiralpak AZ-H, 250×4.6 mm, 5 µm, eluent: 90% carbon dioxide, 10% methanol, flow rate: 3 ml/min, temperature: 30° C., detection: 220 nm].

LC-MS (Method 2): $R_t$=1.01 min
MS (ESIpos): m/z=301 (M+H)$^+$

Example 64A ent-Benzyl (1-amino-5,5,5-trifluoro-2-methylpentan-2-yl)carbamate (Enantiomer A)

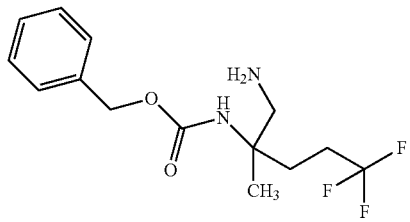 [SMILES: CC(CN)(CCC(F)(F)F)NC(=O)OCc1ccccc1]

4.12 g (13.17 mmol) of ent-benzyl (2-cyano-5,5,5-trifluoropentan-2-yl)carbamate (enantiomer A) from Example 62A were dissolved in 39 ml of 7 N ammonia solution in methanol, and 4 g of Raney nickel (50% aqueous slurry) were added under argon. The reaction mixture was hydrogenated in an autoclave at 20-30 bar overnight. Another 1 g of Raney nickel (50% aqueous slurry) was added and the reaction mixture was hydrogenated in an autoclave at 20-30 bar for 5 h. The reaction mixture was filtered through kieselguhr, rinsed with methanol and concentrated. 3.35 g (56% of theory; purity about 67%) of the target compound were obtained, which were used in the subsequent stage without further purification.

LC-MS (Method 8): $R_t$=1.68 min
MS (ESIpos): m/z=305 (M+H)$^+$
$^1$H NMR (400 MHz, DMSO-$d_6$): δ [ppm]=1.13 (s, 3H), 1.40 (br. s, 2H), 1.70-1.80 (m, 1H), 1.83-1.95 (m, 1H), 2.08-2.2 (m, 2H), 4.98 (s, 2H), 6.85 (br. s, 1H), 7.28-7.41 (m, 5H).

Example 65A ent-Benzyl (1-amino-5,5,5-trifluoro-2-methylpentan-2-yl)carbamate (Enantiomer B)

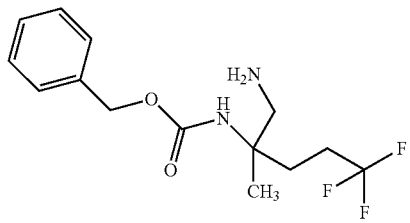 [SMILES: CC(CN)(CCC(F)(F)F)NC(=O)OCc1ccccc1]

4.54 g (13.45 mmol; purity about 89%) of ent-benzyl (2-cyano-5,5,5-trifluoropentan-2-yl)carbamate (enantiomer A) from Example 63A were dissolved in 39 ml of 7 N ammonia solution in methanol, and 5 g of Raney nickel (50% aqueous slurry) were added under argon. The reaction mixture was hydrogenated in an autoclave at 20-30 bar for 3 h. The reaction mixture was filtered through kieselguhr, rinsed with methanol and concentrated. 4.20 g (97% of theory; purity about 95%) of the target compound were obtained, which were used in the subsequent step without further purification.

LC-MS (Method 7): $R_t$=2.19 min
MS (ESIpos): m/z=305 (M+H)$^+$
$^1$H NMR (400 MHz, DMSO-$d_6$): δ [ppm]=1.13 (s, 3H), 1.40 (br. s, 2H), 1.69-1.80 (m, 1H), 1.83-1.96 (m, 1H), 2.07-2.22 (m, 2H), 4.98 (s, 2H), 6.85 (br. s, 1H), 7.27-7.40 (m, 5H).

Example 66A rac-2-[(Diphenylmethylene)amino]-4-fluorobutanonitrile

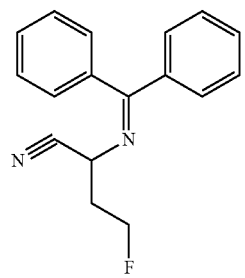 [SMILES: N#CC(CCF)N=C(c1ccccc1)c1ccccc1]

16.5 g (74.91 mmol) of [(diphenylmethylene)amino]acetonitrile were initially charged in 495 ml of abs. THF, and 35.96 ml (89.89 mmol) of n-butyllithium (2.5 N in hexane) were added at −78° C. under argon, and the mixture was stirred at −78° C. for 15 min. Subsequently, the reaction solution was warmed up to 0° C. 13.03 g (74.91 mmol) of 1-iodo-2-fluoroethane were added dropwise to the reaction solution, which was stirred at 0° C. for a further 15 min. The reaction solution was quenched with water at 0° C., ethyl acetate was added and the mixture was washed with saturated aqueous sodium chloride solution. The aqueous phase was reextracted twice with ethyl acetate. The combined organic phases were dried over sodium sulphate, filtered and concentrated by rotary evaporation. The residue was purified by means of silica gel chromatography (eluent:dichloromethane/cyclohexane=1/1 to 2/1). 18.7 g of the target compound were obtained (80% of theory, 85% purity).

LC-MS (Method 3): $R_t$=2.42 min
MS (ESIpos): m/z=267 (M+H)$^+$
$^1$H NMR (400 MHz, DMSO-$d_6$): δ=2.13-2.41 (m, 2H), 4.40 (t, 1H), 4.43-4.71 (m, 2H), 7.25-7.30 (m, 2H), 7.33-7.63 (m, 8H).

Example 67A rac-2-[(Diphenylmethylene)amino]-4,4-difluorobutanonitrile

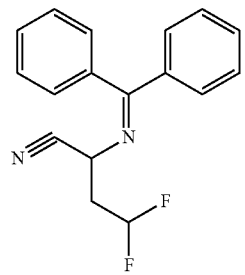 [SMILES: N#CC(CC(F)F)N=C(c1ccccc1)c1ccccc1]

18 g (81.72 mmol) of [(diphenylmethylene)amino]acetonitrile were initially charged in 500 ml of abs. THF, and 39.22 ml (98.06 mmol) of n-butyllithium (2.5 N in hexane) were added at −78° C. under argon, and the mixture was stirred at −78° C. for a further 15 min. Subsequently, the reaction solution was warmed up to 0° C. 17.25 g (89.89 mmol) of 1,1-difluoro-2-iodoethane were added dropwise to the reaction solution, which was stirred at 0° C. for a further 15 min. The reaction solution was quenched with water at 0° C., ethyl acetate was added and the mixture was washed three times with semisaturated aqueous sodium chloride solution. The combined aqueous phases were reextracted twice with ethyl acetate. The combined organic phases were dried over sodium sulphate, filtered and concentrated by rotary evaporation. The residue was purified by means of silica gel chromatography (eluent:dichloromethane/cyclohexane 1/1). 13.57 g of the target compound were obtained (49% of theory, 84% purity).

LC-MS (Method 3): $R_t$=2.48 min

MS (ESIpos): m/z=285 (M+H)$^+$ $^1$H NMR (400 MHz, DMSO-d$_6$): δ=2.53-2.61 (m, 2H; partly obscured by solvent peak), 4.50 (t, 1H), 6.08-6.41 (m, 1H), 7.23-7.33 (m, 2H), 7.38-7.47 (m, 2H), 7.49-7.67 (m, 6H).

Example 68A rac-2-[(Diphenylmethylene)amino]-5-fluoropentanonitrile

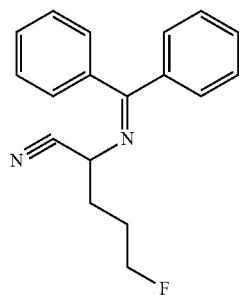 [SMILES: N#CC(CCCF)N=C(c1ccccc1)c1ccccc1]

18 g (81.72 mmol) of [(diphenylmethylene)amino]acetonitrile were initially charged in 500 ml of abs. THF, and 39.22 ml (98.06 mmol) of n-butyllithium (2.5 N in hexane) were added at −78° C. under argon, and the mixture was stirred at −78° C. for a further 15 min. Subsequently, the reaction solution was warmed up to 0° C. and 16.9 g (89.89 mmol) of 1-fluoro-3-iodopropane were added dropwise to the reaction solution, which was stirred at 0° C. for a further 15 min. The reaction solution was quenched with water at 0° C., ethyl acetate was added and the mixture was washed with saturated aqueous sodium chloride solution. The aqueous phase was reextracted twice with ethyl acetate. The combined organic phases were dried over sodium sulphate, filtered and concentrated by rotary evaporation. The residue was purified by means of silica gel chromatography (eluent: 100% toluene, post-purification with dichloromethane/cyclohexane=1/1 to 2/1). A total of 16.73 g of the target compound (73% of theory) were obtained.

LC-MS (Method 3): $R_t$=2.50 min

MS (ESIpos): m/z=281 (M+H)$^+$ $^1$H NMR (400 MHz, DMSO-d$_6$): δ=1.66-1.85 (m, 2H), 1.87-2.00 (m, 2H), 4.26-4.41 (m, 2H), 4.43-4.55 (m, 1H), 7.20-7.33 (m, 2H), 7.38-7.48 (m, 2H), 7.48-7.63 (m, 6H).

Example 69A rac-2-[(Diphenylmethylene)amino]-4-fluoro-2-methylbutanonitrile

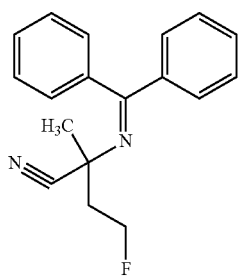 [SMILES: CC(C#N)(CCF)N=C(c1ccccc1)c1ccccc1]

19.94 g (63.64 mmol, 85% purity) of rac-2-[(diphenylmethylene)amino]-4-fluorobutanonitrile from Example 66A were initially charged in 421 ml of abs. THF, and 25.71 ml (64.28 mmol) of n-butyllithium (2.5 N in hexane) were added at −78° C. under argon, and the mixture was stirred at −78° C. for a further 10 min. Subsequently, 36.1 g (254.57 mmol) of iodomethane were added to the reaction solution at −78° C. The reaction mixture was gradually brought to 0° C. over 4.5 h. After complete depletion of the starting material, the reaction solution was quenched with water at 0° C., ethyl acetate was added and the mixture was washed twice with saturated aqueous sodium chloride solution. The organic phase was dried over sodium sulphate, filtered and concentrated by rotary evaporation. The residue was purified by means of silica gel chromatography (eluent:cyclohexane/ethyl acetate=15/1). 17.2 g of the target compound were obtained (78% of theory, 81% purity).

LC-MS (Method 3): $R_t$=2.46 min

MS (ESIpos): m/z=281 (M+H)$^+$ $^1$H NMR (400 MHz, DMSO-d$_6$): δ=1.65-1.67 (s, 3H), 2.30-2.47 (m, 2H), 4.55-4.84 (m, 2H), 7.27-7.32 (m, 2H), 7.37-7.42 (m, 2H), 7.43-7.52 (m, 6H).

Example 70A rac-2-[(Diphenylmethylene)amino]-4,4-difluoro-2-methylbutanonitrile

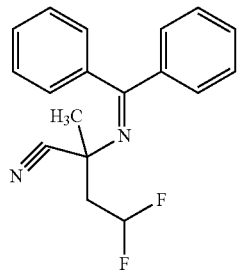 [SMILES: CC(C#N)(CC(F)F)N=C(c1ccccc1)c1ccccc1]

13.07 g (38.62 mmol) of rac-2-[(diphenylmethylene)amino]-4,4-difluorobutanonitrile from Example 67A were initially charged in 255 ml of abs. THF, and 15.6 ml (39.0 mmol) of n-butyllithium (2.5 N in hexane) were added at −78° C. under argon, and the mixture was stirred at −78° C. for a further 10 min. Subsequently, 22.6 g (154.46 mmol) of iodomethane were added to the reaction solution at −78° C. The reaction mixture was gradually brought to 0° C. over 3.5 h. After complete depletion of the starting material, the reaction solution was quenched with water at 0° C., ethyl acetate was added and the mixture was washed twice with saturated aqueous sodium chloride solution. The organic phase was dried over sodium sulphate, filtered and concentrated by rotary evaporation. The residue was purified by means of silica gel chromatography (eluent:cyclohexane/ethyl acetate=15/1). 11.4 g of the target compound were obtained (91% of theory, 92% purity).

LC-MS (Method 3): $R_t$=2.52 min

MS (ESIpos): m/z=299 (M+H)$^+$ $^1$H NMR (400 MHz, DMSO-d$_6$): δ=1.67 (s, 3H), 2.55-2.77 (m, 2H), 6.14-6.48 (m, 1H), 7.28-7.34 (m, 2H), 7.36-7.44 (m, 2H), 7.44-7.54 (m, 6H).

Example 71A rac-2-[(Diphenylmethylene)amino]-5-fluoro-2-methylpentanonitrile

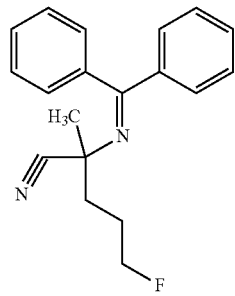 [SMILES: CC(C#N)(CCCF)N=C(c1ccccc1)c1ccccc1]

16.73 g (59.68 mmol) of rac-2-[(diphenylmethylene) amino]-5-fluoropentanonitrile from Example 68A were initially charged in 394 ml of abs. THF, and 24.11 ml (60.27 mmol) of n-butyllithium (2.5 N in hexane) were added at −78° C. under argon, and the mixture was stirred at −78° C. for a further 10 min. Subsequently, 34.93 g (238.70 mmol) of iodomethane were added to the reaction solution at −78° C. The reaction mixture was gradually brought to 0° C. over 4.5 h. The reaction solution was quenched with water at 0° C., ethyl acetate was added and the mixture was washed twice with saturated aqueous sodium chloride solution. The organic phase was dried over sodium sulphate, filtered and concentrated by rotary evaporation. The residue was purified by means of silica gel chromatography (eluent:cyclohexane/ ethyl acetate=15/1). 18.94 g of the target compound were obtained (95% of theory, 88% purity).

LC-MS (Method 3): $R_t$=2.55 min

MS (ESIpos): m/z=295 (M+H)$^+$ $^1$H NMR (400 MHz, DMSO-d$_6$): δ=1.62 (s, 3H), 1.73-1.90 (m, 2H), 1.94-2.03 (m, 1H), 2.04-2.18 (m, 1H), 4.47 (t, 1H), 4.58 (t, 1H), 7.23-7.33 (m, 2H), 7.35-7.43 (m, 2H), 7.44-7.56 (m, 6H).

Example 72A rac-2-Amino-4-fluoro-2-methylbutanonitrile hydrochloride

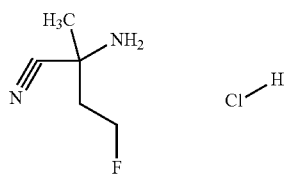

17.45 g (50.45 mmol; 81% purity) of rac-2-[(diphenylmethylene)amino]-4-fluoro-2-methylbutanonitrile from Example 69A were dissolved in 235.6 ml of tetrahydrofuran and 9.1 ml of water, 111 ml (55.46 mmol) of hydrogen chloride solution (0.5 N in diethyl ether) were added and the mixture was stirred at room temperature overnight. The slightly turbid reaction solution was admixed with 25.21 ml (50.42 mmol) of hydrogen chloride solution (2 N in diethyl ether) and concentrated by rotary evaporation. The isolated crude product was reacted further directly without further purification.

LC-MS (Method 3): $R_t$=0.22 min

MS (ESpos): m/z=117 (M−HCl+H)$^+$

Example 73A rac-Benzyl (2-cyano-4-fluorobutan-2-yl)carbamate

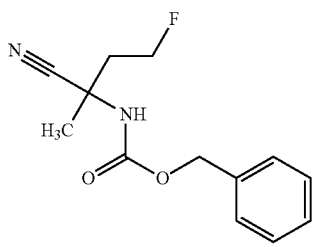 [SMILES: CC(C#N)(CCF)NC(=O)OCc1ccccc1]

The crude rac-2-amino-4-fluoro-2-methylbutanonitrile hydrochloride product from Example 72A was initially charged in 165 ml of tetrahydrofuran/water (1:1), and 28.57 g (206.71 mmol) of potassium carbonate and 9.46 g (55.46 mmol) of benzyl chloroformate were added. The reaction mixture (biphasic mixture) was stirred at room temperature overnight. Another 1.72 g (10.1 mmol) of benzyl chloroformate were added to the reaction and the mixture was stirred at room temperature for a further 2 h. Subsequently, the biphasic system was separated and the aqueous phase was extracted twice with ethyl acetate. The combined organic phases were washed once with saturated aqueous sodium chloride solution, and then dried over sodium sulphate, filtered and concentrated by rotary evaporation. The residue was purified by means of silica gel chromatography (eluent:cyclohexane/ ethyl acetate gradient=20/1 to 5/1). 5.04 g of the target compound were obtained (38% of theory over two stages, 96% purity).

LC-MS (Method 3): $R_t$=1.95 min

MS (ESIpos): m/z=251 (M+H)$^+$

¹H NMR (400 MHz, DMSO-d₆): δ [ppm]=1.59 (s, 3H), 2.20-2.43 (m, 2H), 4.55 (t, 1H), 4.67 (t, 1H), 5.08 (s, 2H), 7.28-7.45 (m, 5H), 8.12 (br. s, 1H).

Example 74A rac-2-Amino-4,4-difluoro-2-methylbutanonitrile hydrochloride

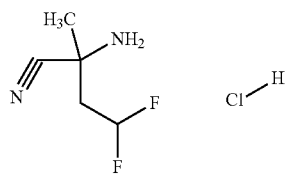

10.84 g (33.43 mmol; 92% purity) of rac-2-[(diphenylmethylene)amino]-4,4-difluoro-2-methylbutanonitrile from Example 70A were dissolved in 156 ml of tetrahydrofuran and 6 ml of water, 73.5 ml (36.77 mmol) of hydrogen chloride solution (0.5 N in diethyl ether) were added and the mixture was stirred at room temperature overnight. The reaction solution was admixed with 16.71 ml (33.43 mmol) of hydrogen chloride solution (2 N in diethyl ether) and concentrated by rotary evaporation. The isolated crude product was reacted further directly without further purification.

LC-MS (Method 3): $R_t$=0.32 min
MS (ESpos): m/z=135 (M−HCl+H)⁺

Example 75A rac-Benzyl (2-cyano-4,4-difluorobutan-2-yl)carbamate

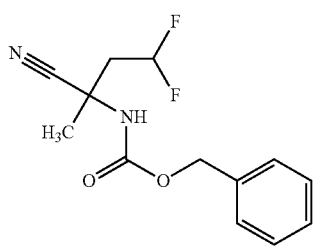 [SMILES: CC(C#N)(CC(F)F)NC(=O)OCc1ccccc1]

The crude rac-2-amino-4,4-difluoro-2-methylbutanonitrile hydrochloride product from Example 74A was initially charged in 109 ml of tetrahydrofuran/water (1:1), and 18.94 g (137.06 mmol) of potassium carbonate and 6.27 g (36.77 mmol) of benzyl chloroformate were added. The reaction mixture (biphasic mixture) was stirred at room temperature overnight. Another 1.14 g (6.69 mmol) of benzyl chloroformate were added to the reaction and the mixture was stirred at room temperature for a further 2 h. Subsequently, the biphasic system was separated and the aqueous phase was extracted twice with ethyl acetate. The combined organic phases were washed once with saturated aqueous sodium chloride solution, and then dried over sodium sulphate, filtered and concentrated by rotary evaporation. The residue was purified by means of silica gel chromatography (eluent:cyclohexane/ethyl acetate gradient=20/1 to 5/1). 7.68 g of the target compound were obtained (61% of theory over two stages, 71% purity).

LC-MS (Method 3): $R_t$=2.04 min
MS (ESIpos): m/z=269 (M+H)⁺
¹H NMR (400 MHz, DMSO-d₆): δ [ppm]=1.65 (s, 3H), 2.51-2.65 (m, 2H), 5.10 (s, 2H), 6.08-6.41 (m, 1H), 7.27-7.44 (m, 5H), 8.24 (br. s, 1H).

Example 76A rac-2-Amino-5-fluoro-2-methylpentanonitrile hydrochloride

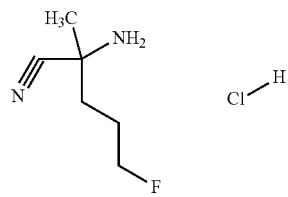

18.94 g (56.62 mmol; 88% purity) of rac-2-[(diphenylmethylene)amino]-5-fluoro-2-methylpentanonitrile from Example 71A were dissolved in 264.6 ml of tetrahydrofuran and 10.2 ml of water, 124.6 ml (62.28 mmol) of hydrogen chloride solution (0.5 N in diethyl ether) were added and the mixture was stirred at room temperature overnight. The reaction solution was admixed with 28.3 ml (56.62 mmol) of hydrogen chloride solution (2 N in diethyl ether) and concentrated by rotary evaporation. The isolated crude product was reacted further directly without further purification.

LC-MS (Method 3): $R_t$=0.25 min
MS (ESpos): m/z=131 (M−HCl+H)⁺

Example 77A rac-Benzyl (2-cyano-5-fluoropentan-2-yl)carbamate

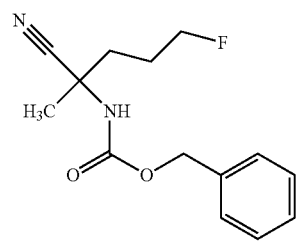 [SMILES: CC(C#N)(CCCF)NC(=O)OCc1ccccc1]

The crude rac-2-amino-5-fluoro-2-methylpentanonitrile hydrochloride product from Example 76A was initially charged in 185 ml of tetrahydrofuran/water (1:1), and 32.09 g (232.18 mmol) of potassium carbonate and 10.63 g (62.29 mmol) of benzyl chloroformate were added. The reaction mixture (biphasic mixture) was stirred at room temperature overnight. Another 1.93 g (11.33 mmol) of benzyl chloroformate were added to the reaction and the mixture was stirred at room temperature for a further 2 h. Subsequently, the biphasic system was separated and the aqueous phase was extracted twice with ethyl acetate. The combined organic phases were washed once with saturated aqueous sodium chloride solution, and then dried over sodium sulphate, filtered and concentrated by rotary evaporation. The residue was purified by means of silica gel chromatography (eluent:cyclohexane/ ethyl acetate gradient=20/1 to 5/1). 11.77 g of the target compound were obtained (72% of theory over two stages, 92% purity).

LC-MS (Method 3): $R_t$=2.03 min

MS (ESIpos): m/z=265 (M+H)$^+$ $^1$H NMR (400 MHz, DMSO-d$_6$): δ [ppm]=1.55 (s, 3H), 1.66-1.85 (m, 2H), 1.86-2.04 (m, 2H), 4.40 (t, 1H), 4.52 (t, 1H), 5.08 (s, 2H), 7.28-7.44 (m, 5H), 8.05 (br. s, 1H).

Example 78A ent-Benzyl (2-cyano-4,4-difluorobutan-2-yl)carbamate (Enantiomer A)

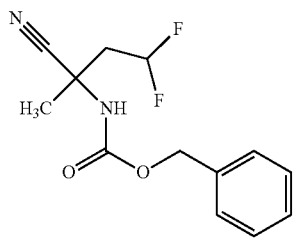 [SMILES: CC(C#N)(CC(F)F)NC(=O)OCc1ccccc1]

7.68 g (20.33 mmol, 71% purity) of rac-benzyl (2-cyano-4,4-difluorobutan-2-yl)carbamate from Example 75A were separated into the enantiomers by preparative separation on a chiral phase [column: Daicel Chiralpak AY-H, 5 μm, 250×20 mm, eluent: 80% isohexane, 20% isopropanol, flow rate: 25 ml/min; temperature: 22° C., detection: 210 nm].

Enantiomer A: Yield: 2.64 g (>99% ee)

$R_t$=6.67 min [Chiralpak AY-H, 5 μm, 250×4.6 mm; eluent: 80% isohexane, 20% isopropanol; flow rate: 3 ml/min; detection: 220 nm].

Example 79A ent-Benzyl (2-cyano-4,4-difluorobutan-2-yl)carbamate (Enantiomer B)

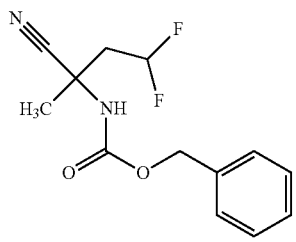 [SMILES: CC(C#N)(CC(F)F)NC(=O)OCc1ccccc1]

7.68 g (20.33 mmol, 71% purity) of rac-benzyl (2-cyano-4,4-difluorobutan-2-yl)carbamate from Example 75A were separated into the enantiomers by preparative separation on a chiral phase [column: Daicel Chiralpak AY-H, 5 μm, 250×20 mm, eluent: 80% isohexane, 20% isopropanol, flow rate: 25 ml/min; temperature: 22° C., detection: 210 nm].

Enantiomer B: Yield: 2.76 g (93% ee)

$R_t$=7.66 min [Chiralpak AY-H, 5 μm, 250×4.6 mm; eluent: 80% isohexane, 20% isopropanol; flow rate: 3 ml/min; detection: 220 nm].

Example 80A ent-Benzyl (2-cyano-5-fluoropentan-2-yl)carbamate (Enantiomer A)

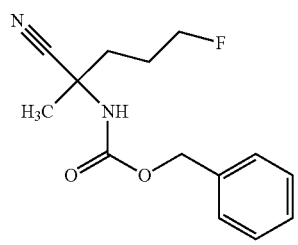 [SMILES: CC(C#N)(CCCF)NC(=O)OCc1ccccc1]

11.77 g (40.97 mmol, 92% purity) of rac-benzyl (2-cyano-5-fluoropentan-2-yl)carbamate from Example 77A were separated into the enantiomers by preparative separation on a chiral phase [column: SFC Daicel Chiralpak AZ-H, 5 μm, 250×30 mm, eluent: 90% $CO_2$, 10% methanol, flow rate: 100 ml/min; temperature: 40° C., detection: 210 nm].

Enantiomer A: Yield: 5.7 g (>99% ee)

$R_t$=1.76 min [SFC Chiralpak AZ-3, 3 μm, 50×4.6 mm; eluent: $CO_2$/methanol gradient (5% to 60% methanol); flow rate: 3 ml/min; detection: 220 nm].

Example 81A ent-Benzyl (2-cyano-5-fluoropentan-2-yl)carbamate (Enantiomer B)

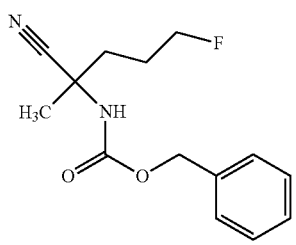 [SMILES: CC(C#N)(CCCF)NC(=O)OCc1ccccc1]

11.77 g (40.97 mmol, 92% purity) of rac-benzyl (2-cyano-5-fluoropentan-2-yl)carbamate from Example 77A were separated into the enantiomers by preparative separation on a chiral phase [column: SFC Daicel Chiralpak AZ-H, 5 μm, 250×30 mm, eluent: 90% $CO_2$, 10% methanol, flow rate: 100 ml/min; temperature: 40° C., detection: 210 nm].

Enantiomer B: Yield: 5.0 g (>99% ee)

$R_t$=1.97 min [SFC Chiralpak AZ-3, 3 μm, 50×4.6 mm; eluent: $CO_2$/methanol gradient (5% to 60% methanol); flow rate: 3 ml/min; detection: 220 nm].

Example 82A ent-Benzyl (1-amino-4,4-difluoro-2-methylbutan-2-yl)carbamate (Enantiomer A)

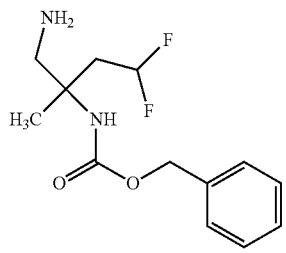

2.3 g (8.57 mmol) of ent-benzyl (2-cyano-4,4-difluorobutan-2-yl)carbamate (enantiomer A) from Example 78A were dissolved in 75 ml of 7 N ammonia solution in methanol, and 2.66 g of Raney nickel (50% aqueous slurry) were added under argon. The reaction mixture was hydrogenated in an autoclave at 20-30 bar for 1.5 h. The reaction mixture was filtered through Celite, rinsed with methanol and 2 N ammonia in methanol, and concentrated. 2.23 g of the target compound were obtained (94% of theory, 98% purity).

LC-MS (Method 3): $R_t$=1.48 min

MS (ESIpos): m/z=273 (M+H)$^+$ $^1$H NMR (400 MHz, DMSO-d$_6$): δ [ppm]=1.19 (s, 3H), 1.48 (br. s, 2H), 2.08-2.40 (m, 2H), 2.53-2.72 (m, 2H; partly obscured by solvent peak), 5.00 (s, 2H), 5.90-6.23 (m, 1H), 6.95 (br. s, 1H), 7.25-7.41 (m, 5H).

Example 83A ent-Benzyl (1-amino-4,4-difluoro-2-methylbutan-2-yl)carbamate (Enantiomer B)

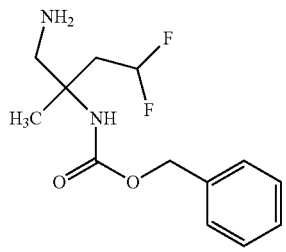 [SMILES: CC(CN)(CC(F)F)NC(=O)OCc1ccccc1]

2.76 g (10.29 mmol) of ent-benzyl (2-cyano-4,4-difluorobutan-2-yl)carbamate (enantiomer B) from Example 79A were dissolved in 90 ml of 7 N ammonia solution in methanol, and 3.19 g of Raney nickel (50% aqueous slurry) were added under argon. The reaction mixture was hydrogenated in an autoclave at 20-30 bar for 1.5 h. The reaction mixture was filtered through Celite, rinsed with methanol and 2 N ammonia in methanol, and concentrated. 2.64 g of the target compound were obtained (88% of theory, 93% purity).

LC-MS (Method 3): $R_t$=1.49 min

MS (ESIpos): m/z=273 (M+H)$^+$ $^1$H NMR (400 MHz, DMSO-d$_6$): δ [ppm]=1.19 (s, 3H), 1.48 (br. s, 2H), 2.08-2.40 (m, 2H), 2.53-2.73 (m, 2H; partly obscured by solvent peak), 5.00 (s, 2H), 5.90-6.24 (m, 1H), 6.95 (br. s, 1H), 7.25-7.41 (m, 5H).

Example 84A ent-Benzyl (1-amino-5-fluoro-2-methylpentan-2-yl)carbamate (Enantiomer A)

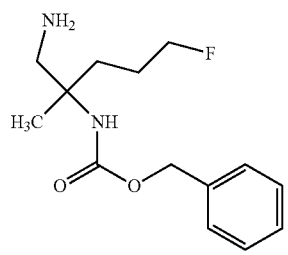 [SMILES: CC(CN)(CCCF)NC(=O)OCc1ccccc1]

5.7 g (21.57 mmol) of ent-benzyl (2-cyano-5-fluoropentan-2-yl)carbamate (enantiomer A) from Example 80A were dissolved in 125 ml of 7 N ammonia solution in methanol, and 6.68 g of Raney nickel (50% aqueous slurry) were added under argon. The reaction mixture was hydrogenated in an autoclave at 20-30 bar for 4.5 h. The reaction mixture was filtered through Celite, rinsed with methanol and 2 N ammonia in methanol, and concentrated. 5.22 g of the target compound were obtained (77% of theory, 85% purity).

LC-MS (Method 3): $R_t$=1.51 min

MS (ESIpos): m/z=269 (M+H)$^+$

Example 85A ent-Benzyl (1-amino-5-fluoro-2-methylpentan-2-yl)carbamate (Enantiomer B)

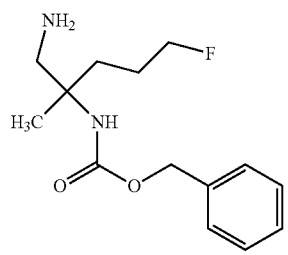 [SMILES: CC(CN)(CCCF)NC(=O)OCc1ccccc1]

5.0 g (18.92 mmol) of ent-benzyl (2-cyano-5-fluoropentan-2-yl)carbamate (enantiomer B) from Example 81A were dissolved in 110 ml of 7 N ammonia solution in methanol, and 5.86 g of Raney nickel (50% aqueous slurry) were added under argon. The reaction mixture was hydrogenated in an autoclave at 20-30 bar for 4.5 h. The reaction mixture was filtered through Celite, rinsed with methanol and 2 N ammonia in methanol, and concentrated. 4.6 g of the target compound were obtained (84% of theory, 93% purity).

LC-MS (Method 3): $R_t$=1.47 min

MS (ESIpos): m/z=269 (M+H)$^+$

Example 86A rac-4-Fluoro-2-methylbutane-1,2-diamine dihydrochloride

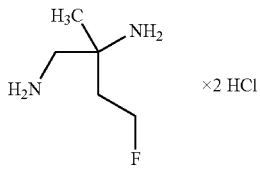

1.00 g (4.00 mmol) of rac-benzyl (2-cyano-4-fluorobutan-2-yl)carbamate from Example 73A were dissolved in 114 ml ethanol/glacial acetic acid (1/1), and 0.85 g of palladium on activated carbon (10%) were added. The reaction mixture was hydrogenated in an autoclave at 30-50 bar for 3 h. The reaction mixture was filtered through a fluted filter, rinsed with ethanol and then filtered once again through a Millipore filter. The filtrate was admixed with 10 ml of hydrogen chloride solution (2 N in diethyl ether) and then concentrated by evaporation. This gave 1.04 g of the target compound which was used in the subsequent stage without further purification.

LC-MS (Method 3): $R_t$=0.19 min
MS (ESpos): m/z=121 (M-2HCl+H)$^+$

Example 87A ent-Benzyl {1-[({7-[(2,6-difluorobenzyl)oxy]-2,5-dimethylpyrazolo[1,5-a]pyridin-3-yl}carbonyl)amino]-2-methylpentan-2-yl}carbamate trifluoroacetate (Enantiomer B)

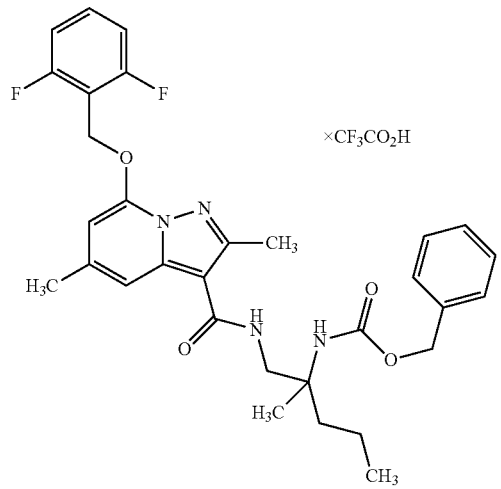 [SMILES: CCCC(C)(CNC(=O)c1c(C)nn2c(OCc3c(F)cccc3F)cc(C)cc12)NC(=O)OCc1ccccc1]

210 mg (0.62 mmol) of 7-[(2,6-difluorobenzyl)oxy]-2,5-dimethylpyrazolo[1,5-a]pyridine-3-carboxylic acid from Example 4A were initially charged together with 259 mg (0.68 mmol) of HATU and 0.324 ml (1.86 mmol) of N,N-diisopropylethylamine in 1.8 ml of DMF, and the mixture was stirred at room temperature for 10 min. Subsequently, 211 mg (0.74 mmol) of ent-benzyl (1-amino-2-methylpentan-2-yl)carbamate (enantiomer B) from Example 20A were added to the reaction solution and the mixture was stirred at RT overnight. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. 190 mg of the target compound were obtained (42% of theory, 92% purity).

LC-MS (Method 2): $R_t$=1.24 min
MS (ESpos): m/z=565 (M-TFA+H)$^+$

Example 88A ent-Benzyl {1-[({7-[(2,6-difluorobenzyl)oxy]-2,5-dimethylpyrazolo[1,5-a]pyridin-3-yl}carbonyl)amino]-3-fluoro-2-methylpropan-2-yl}carbamate trifluoroacetate (Enantiomer A)

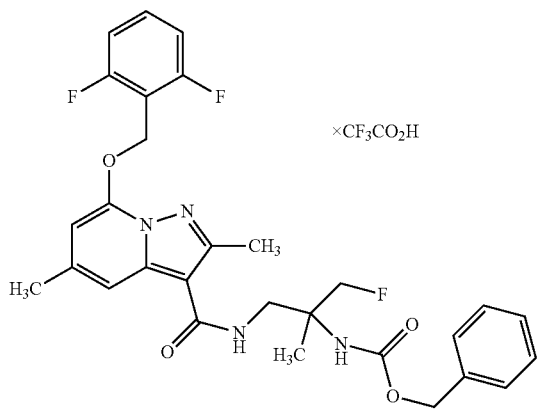 [SMILES: Cc1cc(OCc2c(F)cccc2F)n2nc(C)c(C(=O)NCC(C)(CF)NC(=O)OCc3ccccc3)c2c1]

250 mg (0.56 mmol; about 75% purity) of 7-[(2,6-difluorobenzyl)oxy]-2,5-dimethylpyrazolo[1,5-a]pyridine-3-carboxylic acid from Example 4A were initially charged together with 236 mg (0.62 mmol) of HATU and 0.30 ml (1.69 mmol) of N,N-diisopropylethylamine in 1.68 ml of DMF, the mixture was initially stirred for 20 min, then 192 mg (0.68 mmol, 85%) of ent-benzyl (1-amino-3-fluoro-2-methylpropan-2-yl)carbamate (enantiomer A) from Example 58A were added and the mixture was stirred at RT for 2 h. The reaction solution was admixed with water/TFA and purified by means of preparative HPLC (RP18 column, eluent:acetonitrile/water gradient with addition of 0.1% TFA). The product fractions were concentrated on a rotary evaporator. 231 mg of the target compound were obtained (59% of theory, 95% purity).

LC-MS (Method 2): $R_t$=1.20 min
MS (ESpos): m/z=555 (M-TFA+H)$^+$

Example 89A ent-Benzyl {1-[({7-[(2,6-difluorobenzyl)oxy]-2,5-dimethylpyrazolo[1,5-a]pyridin-3-yl}carbonyl)amino]-3-fluoro-2-methylpropan-2-yl}carbamate trifluoroacetate (Enantiomer B)

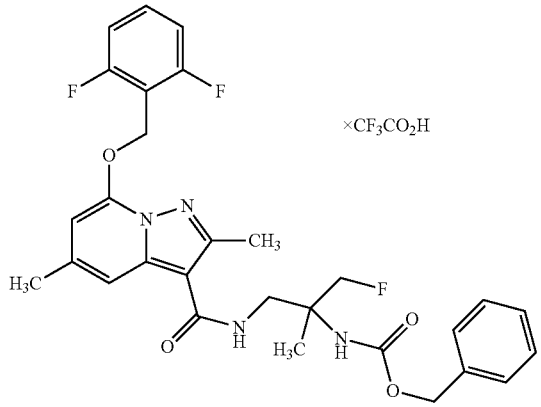 [SMILES: Cc1cc(OCc2c(F)cccc2F)n2nc(C)c(C(=O)NCC(C)(CF)NC(=O)OCc3ccccc3)c2c1]

250 mg (0.56 mmol; about 75% purity) of 7-[(2,6-difluorobenzyl)oxy]-2,5-dimethylpyrazolo[1,5-a]pyridine-3-carboxylic acid from Example 4A were initially charged together with 236 mg (0.62 mmol) of HATU and 0.30 ml (1.69 mmol) of N,N-diisopropylethylamine in 1.68 ml of DMF, the mixture was initially stirred for 20 min, then 192 mg (0.68 mmol, 85%) of ent-benzyl (1-amino-3-fluoro-2-methylpropan-2-yl)carbamate (enantiomer B) from Example 59A were added and the mixture was stirred at RT for 2 h. The reaction solution was admixed with water/TFA and purified by means of preparative HPLC (RP18 column, eluent:acetonitrile/water gradient with addition of 0.1% TFA). The product fractions were concentrated on a rotary evaporator. 240 mg of the target compound were obtained (47% of theory, 74% purity).

LC-MS (Method 2): $R_t$=1.20 min

MS (ESpos): m/z=555 (M-TFA+H)$^+$

Example 90A ent-Benzyl {1-[({7-[(2,6-difluorobenzyl)oxy]-2,5-dimethylpyrazolo[1,5-a]pyridin-3-yl}carbonyl)amino]-5,5,5-trifluoro-2-methylpentan-2-yl}carbamate trifluoroacetate (Enantiomer A)

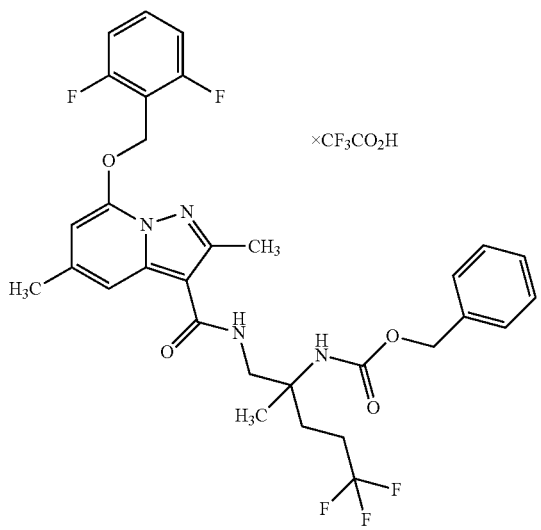 [SMILES: Cc1cc(OCc2c(F)cccc2F)n2nc(C)c(C(=O)NCC(C)(CCC(F)(F)F)NC(=O)OCc3ccccc3)c2c1]

50 mg (0.11 mmol; about 75% purity) of 7-[(2,6-difluorobenzyl)oxy]-2,5-dimethylpyrazolo[1,5-a]pyridine-3-carboxylic acid from Example 4A, 47 mg (0.12 mmol) of HATU and 44 mg (0.34 mmol) of N,N-diisopropylethylamine were initially charged in 0.33 ml of DMF, and the mixture was stirred at RT for 10 min. Subsequently, 62 mg (0.14 mmol; about 67% purity) of ent-benzyl (1-amino-5,5,5-trifluoro-2-methylpentan-2-yl)carbamate (enantiomer A) from Example 64A were added and the mixture was stirred at RT for 2 h. The reaction solution was admixed with water/TFA and purified by means of preparative HPLC (RP18 column, eluent:acetonitrile/water gradient with addition of 0.1% TFA). The product fractions were concentrated on a rotary evaporator. 52 mg (62% of theory) of the title compound were obtained.

LC-MS (Method 2): $R_t$=1.25 min

MS (ESpos): m/z=619 (M-TFA+H)$^+$

Example 91A ent-Benzyl {1-[({7-[(2,6-difluorobenzyl)oxy]-2,5-dimethylpyrazolo[1,5-a]pyridin-3-yl}carbonyl)amino]-5,5,5-trifluoro-2-methylpentan-2-yl}carbamate trifluoroacetate (Enantiomer B)

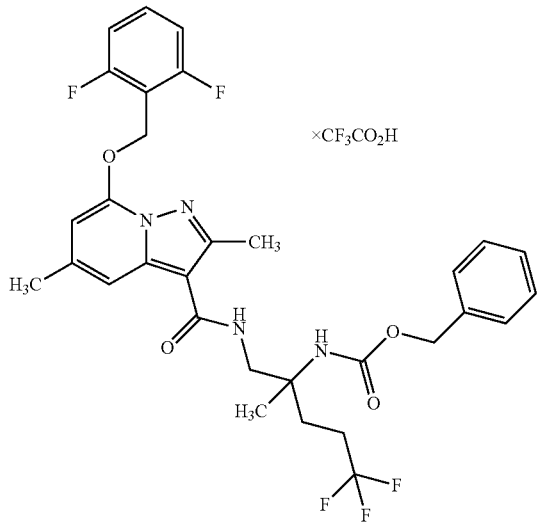 [SMILES: Cc1cc(OCc2c(F)cccc2F)n2nc(C)c(C(=O)NCC(C)(CCC(F)(F)F)NC(=O)OCc3ccccc3)c2c1]

325 mg (0.73 mmol; about 75% purity) of 7-[(2,6-difluorobenzyl)oxy]-2,5-dimethylpyrazolo[1,5-a]pyridine-3-carboxylic acid from Example 4A, 307 mg (0.81 mmol) of HATU and 284 mg (2.20 mmol) of N,N-diisopropylethylamine were initially charged in 2.2 ml of DMF, and the mixture was stirred at RT for 10 min. Subsequently, 282 mg (0.88 mmol; about 95% purity) of ent-benzyl (1-amino-5,5,5-trifluoro-2-methylpentan-2-yl)carbamate (enantiomer B) from Example 65A were added and the mixture was stirred at RT for 2 h. The reaction solution was admixed with water/TFA and purified by means of preparative HPLC (RP18 column, eluent:acetonitrile/water gradient with addition of 0.1% TFA). The product fractions were concentrated on a rotary evaporator. 311 mg (57% of theory) of the title compound were obtained.

LC-MS (Method 2): $R_t$=1.29 min

MS (ESpos): m/z=619 (M-TFA+H)$^+$

Example 92A ent-Benzyl {1-[({7-[(2,6-difluorobenzyl)oxy]-2,5-dimethylpyrazolo[1,5-a]pyridin-3-yl}carbonyl)amino]-5-fluoro-2-methylpentan-2-yl}carbamate trifluoroacetate (Enantiomer A)

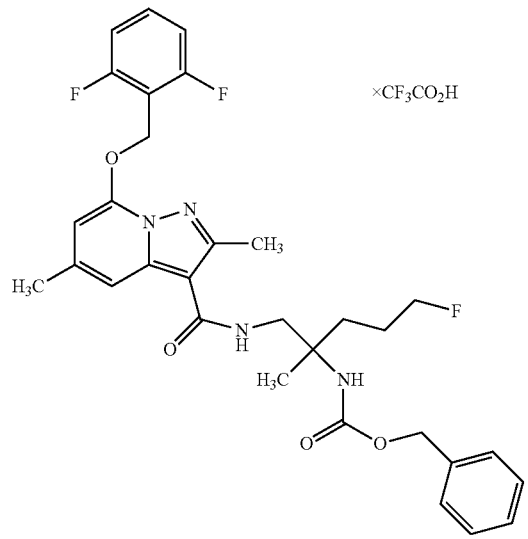 [SMILES: Cc1cc(OCc2c(F)cccc2F)n2nc(C)c(C(=O)NCC(C)(CCCF)NC(=O)OCc3ccccc3)c2c1]

250 mg (0.75 mmol) of 7-[(2,6-difluorobenzyl)oxy]-2,5-dimethylpyrazolo[1,5-a]pyridine-3-carboxylic acid from Example 4A were dissolved in 2.5 ml of DMF, 372 mg (0.98 mmol) of HATU and 0.66 ml (3.76 mmol) of N,N-diisopropylethylamine were added and the mixture was stirred at room temperature for 20 min. Subsequently, 309 mg (0.98 mmol, 85% purity) of ent-benzyl (1-amino-5-fluoro-2-methylpentan-2-yl)carbamate (enantiomer A) from Example 84A were added. After the starting material had been entirely depleted (about 30 min), water was added, and the solids formed were filtered off and washed with water. The residue was purified by means of preparative HPLC (RP18 column, eluent:acetonitrile/water gradient with addition of 0.1% TFA). The product fractions were combined and concentrated. 168 mg of the title compound were obtained (32% of theory).

LC-MS (Method 2): $R_t$=1.17 min
MS (ESpos): m/z=583 (M-TFA+H)$^+$

Example 93A ent-Benzyl {1-[({7-[(2,6-difluorobenzyl)oxy]-2,5-dimethylpyrazolo[1,5-a]pyridin-3-yl}carbonyl)amino]-5-fluoro-2-methylpentan-2-yl}carbamate (Enantiomer B)

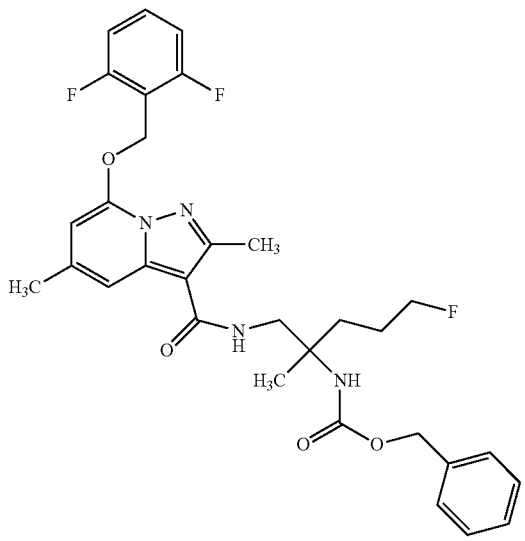 [SMILES: Cc1cc(OCc2c(F)cccc2F)n2nc(C)c(C(=O)NCC(C)(CCCF)NC(=O)OCc3ccccc3)c2c1]

250 mg (0.75 mmol) of 7-[(2,6-difluorobenzyl)oxy]-2,5-dimethylpyrazolo[1,5-a]pyridine-3-carboxylic acid from Example 4A were dissolved in 2.5 ml of DMF, 372 mg (0.98 mmol) of HATU and 0.66 ml (3.76 mmol) of N,N-diisopropylethylamine were added and the mixture was stirred at room temperature for 20 min. Subsequently, 283 mg (0.98 mmol, 93% purity) of ent-benzyl (1-amino-5-fluoro-2-methylpentan-2-yl)carbamate (enantiomer B) from Example 85A were added. After the starting material had been entirely depleted (about 30 min), water was added, and the solids formed were filtered off and washed with water. The residue was purified by means of preparative HPLC (RP18 column, eluent:acetonitrile/water gradient with addition of 0.1% TFA). The product fractions were concentrated and the residue was admixed with 8 ml of 2 M ammonia solution, stirred for 10 min and then concentrated by rotary evaporation. The resulting residue was taken up in dichloromethane and a little methanol and purified by means of silica gel chromatography (eluent:dichloromethane/ethyl acetate:50/1 to dichloromethane/methanol/ethyl acetate:50/1/1). The product fractions were combined and concentrated. 96 mg of the title compound were obtained (21% of theory; 96% purity).

LC-MS (Method 7): $R_t$=2.79 min
MS (ESIpos): m/z=583 (M+H)$^+$

Example 94A ent-Benzyl {1-[({7-[(2,6-difluorobenzyl)oxy]-2,5-dimethylpyrazolo[1,5-a]pyridin-3-yl}carbonyl)amino]-4,4-difluoro-2-methylbutan-2-yl}carbamate (Enantiomer A)

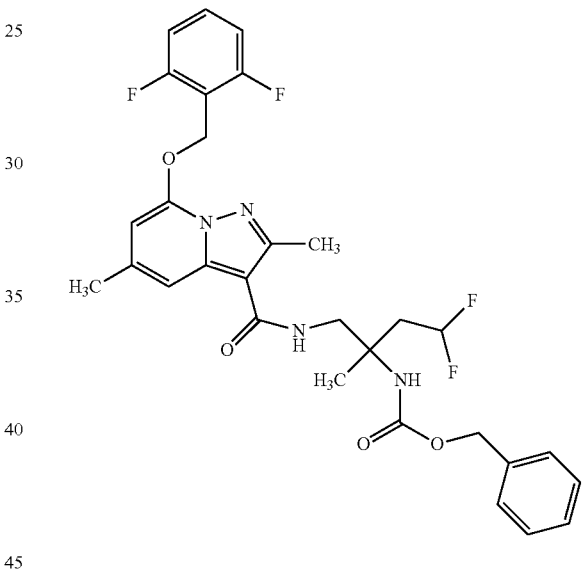

350 mg (1.05 mmol) of 7-[(2,6-difluorobenzyl)oxy]-2,5-dimethylpyrazolo[1,5-a]pyridine-3-carboxylic acid from Example 4A were dissolved in 3.5 ml of DMF, 521 mg (1.37 mmol) of HATU and 0.92 ml (5.27 mmol) of N,N-diisopropylethylamine were added and the mixture was stirred at room temperature for 20 min. Subsequently, 380 mg (1.37 mmol, 98% purity) of ent-benzyl (1-amino-4,4-difluoro-2-methylbutan-2-yl)carbamate (enantiomer A) from Example 82A were added. After the starting material had been entirely depleted (about 60 min), water was added, and the solids formed were filtered off and washed with water. The residue was purified by means of preparative HPLC (RP18 column, eluent:acetonitrile/water gradient with addition of 0.1% TFA). The product fractions were combined and concentrated and repurified once again by means of silica gel chromatography (eluent:cyclohexane/ethyl acetate gradient 2/1 to 1/1). 157 mg of the title compound were obtained (18% of theory; 72% purity).

LC-MS (Method 2): $R_t$=1.18 min
MS (ESIpos): m/z=587 (M+H)$^+$

Example 95A ent-Benzyl-{1-[({7-[(2,6-difluorobenzyl)oxy]-2,5-dimethylpyrazolo[1,5-a]pyridin-3-yl}carbonyl)amino]-4,4-difluoro-2-methylbutan-2-yl}carbamate trifluoroacetate (Enantiomer B)

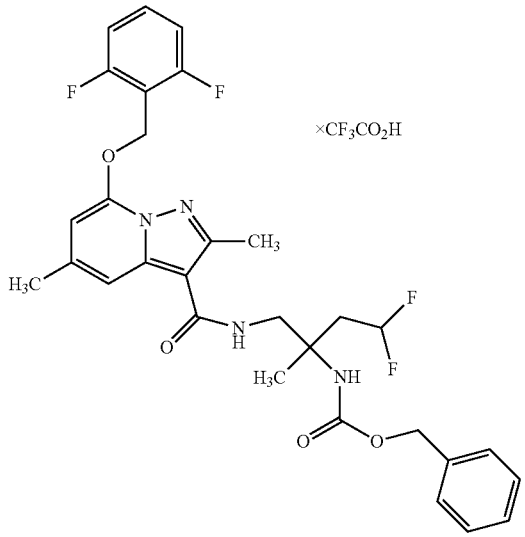 [SMILES: Cc1cc(OCc2c(F)cccc2F)n2nc(C)c(C(=O)NCC(C)(CC(F)F)NC(=O)OCc3ccccc3)c2c1]

350 mg (1.05 mmol) of 7-[(2,6-difluorobenzyl)oxy]-2,5-dimethylpyrazolo[1,5-a]pyridine-3-carboxylic acid from Example 4A were dissolved in 3.5 ml of DMF, 481 mg (1.26 mmol) of HATU and 0.92 ml (5.27 mmol) of N,N-diisopropylethylamine were added and the mixture was stirred at room temperature for 20 min. Subsequently, 366 mg (1.26 mmol, 93% purity) of ent-benzyl (1-amino-4,4-difluoro-2-methylbutan-2-yl)carbamate (enantiomer B) from Example 83A were added. After the starting material had been entirely depleted (about 30 min), water was added, and the solids formed were filtered off and washed with water. The residue was purified by means of preparative HPLC (RP18 column, eluent:acetonitrile/water gradient with addition of 0.1% TFA). The product fractions were combined and concentrated. 281 mg of the title compound were obtained (38% of theory; 99% purity).

LC-MS (Method 2): $R_t$=1.22 min
MS (ESpos): m/z=587 (M-TFA+H)$^+$

Example 96A

Methyl 7-[(2,6-difluorobenzyl)oxy]-5-methyl-2-propylpyrazolo[1,5-a]pyridine-3-carboxylate

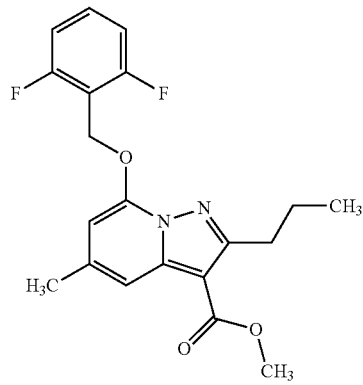 [SMILES: CCCc1nn2c(OCc3c(F)cccc3F)cc(C)cc2c1C(=O)OC]

0.50 g (1.01 mmol) of 1-amino-2-[(2,6-difluorobenzyl)oxy]-4-methylpyridinium 2,4,6-trimethylbenzenesulphonate from Example 2A were dissolved in 3.3 ml of DMF, and 229 mg (1.82 mmol) of methyl hex-2-ynoate were added. 251 mg (1.82 mmol) of potassium carbonate were added and the mixture was stirred at RT for 3 h. Subsequently, the mixture was poured onto 24 ml of water and stirred briefly, and the precipitated solids were filtered off, washed with water and dried. 169 mg of the title compound were obtained (42% of theory; 95% purity).

LC-MS (Method 2): $R_t$=1.25 min
MS (ESIpos): m/z=375 (M+H)$^+$

In analogy to Example 96A, the example compounds shown in Table 1A were prepared by reacting 1-amino-2-[(2,6-difluorobenzyl)oxy]-4-methylpyridinium 2,4,6-trimethylbenzenesulphonate from Example 2A with the appropriate alkynes, which are commercially available or known from the literature, under the conditions described:

TABLE 1A

| Example | IUPAC name/structure (yield) | Analytical data |
|---|---|---|
| 97A | Methyl 7-[(2,6-difluorobenzyl)oxy]-5-methylpyrazolo[1,5-a]pyridine-3-carboxylate (71% of theory; 85% purity) | LC-MS (Method 2): $R_t$ = 1.05 min MS (ESIpos): m/z = 333 (M + H)$^+$ |
| 98A | Ethyl 7-[(2,6-difluorobenzyl)oxy]-5-methyl-2-(trifluoromethyl)pyrazolo[1,5-a]pyridine-3-carboxylate (39% of theory; 86% purity) | LC-MS (Method 2): $R_t$ = 1.26 min MS (ESIpos): m/z = 415 (M + H)$^+$ |

Example 99A

Methyl 2-cyclopropyl-7-[(2,6-difluorobenzyl)oxy]-5-methylpyrazolo[1,5-a]pyridine-3-carboxylate

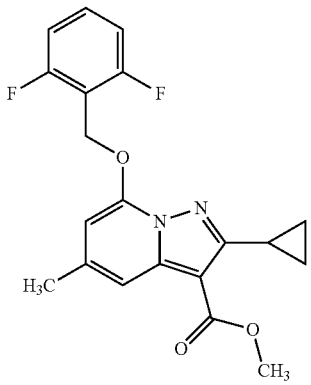 [SMILES: COC(=O)c1c(C2CC2)nn2c(OCc3c(F)cccc3F)cc(C)cc12]

1.0 g (2.22 mmol) of 1-amino-2-[(2,6-difluorobenzyl)oxy]-4-methylpyridinium 2,4,6-trimethylbenzenesulphonate from Example 2A were dissolved in 7.2 ml of DMF, and 496 mg (4.00 mmol) of methyl 3-cyclopropylprop-2-ynoate were added. 552 mg (4.00 mmol) of potassium carbonate were added and the mixture was stirred at RT for 3 h. Subsequently, the mixture was poured onto 50 ml of water and stirred briefly, and the precipitated solids were filtered off, washed with water and dried. 384 mg of the title compound were obtained (46% of theory).

LC-MS (Method 2): $R_t$=1.20 min

MS (ESIpos): m/z=373 (M+H)$^+$ $^1$H NMR (500 MHz, DMSO-$d_6$): δ [ppm]=0.88-0.94 (m, 2H), 0.95-1.00 (m, 2H), 2.43 (s, 3H), 2.70-2.77 (m, 1H), 3.83 (s, 3H), 5.46 (s, 2H), 6.66 (s, 1H), 7.21-7.27 (m, 2H), 7.48 (s, 1H), 7.57-7.64 (m, 1H).

Example 100A

7-[(2,6-Difluorobenzyl)oxy]-5-methyl-2-propylpyrazolo[1,5-a]pyridine-3-carboxylic Acid

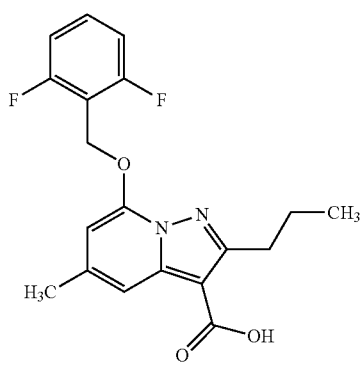 [SMILES: CCCc1nn2c(OCc3c(F)cccc3F)cc(C)cc2c1C(=O)O]

A solution of 169 mg (0.43 mmol; about 95% purity) of methyl 7-[(2,6-difluorobenzyl)oxy]-5-methyl-2-propylpyrazolo[1,5-a]pyridine-3-carboxylate from Example 96A in 4.5 ml of dioxane was admixed with 2.6 ml (2.6 mmol) of 1 N sodium hydroxide solution and reacted at 90° C. for 24 h. Subsequently, another 0.5 ml (0.5 mmol) of 1 N sodium hydroxide solution were added and the mixture was stirred at 90° C. for 1 h. The reaction solution was cooled and adjusted to pH 2 with 1 N hydrochloric acid. The solids that precipitated out were filtered off and dried under high vacuum. 180 mg of the title compound (72% by LC-MS, 84% of theory) were obtained and were converted without further purification.

LC-MS (Method 2): $R_t$=1.04 min

MS (ESIpos): m/z=361 (M+H)$^+$

In analogy to Example 100A, the example compounds shown in Table 2A were prepared by reacting the corresponding carboxylic esters with sodium hydroxide solution (6-10 equivalents) under the conditions described. The reaction temperature was 90 to 100° C.; the reaction time was between 10 h and 24 h:

TABLE 2A

| Example | IUPAC name/ structure (yield) | Analytical data |
|---|---|---|
| 101A | 7-[(2,6-Difluorobenzyl)oxy]-5-methylpyrazolo[1,5-a]pyridine-3-carboxylic acid [1]) | LC-MS (Method 2): $R_t$ = 0.89 min MS (ESIpos): m/z = 319 (M + H)$^+$ |

TABLE 2A-continued

| Example | IUPAC name/ structure (yield) | Analytical data |
|---|---|---|
| | (42% of theory) | |
| 102A | 7-[(2,6-Difluorobenzyl)oxy]-5-methyl-2-(trifluoromethyl)pyrazolo[1,5-a]pyridine-3-carboxylic acid 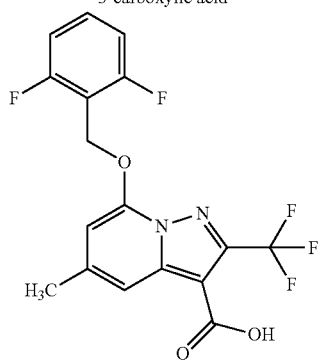 (65% of theory; about 90% purity) | LC-MS (Method 2): $R_t$ = 1.02 min MS (ESIpos): m/z = 387 (M + H)$^+$ |

Example 103A

2-Cyclopropyl-7-[(2,6-difluorobenzyl)oxy]-5-methylpyrazolo[1,5-a]pyridine-3-carboxylic Acid

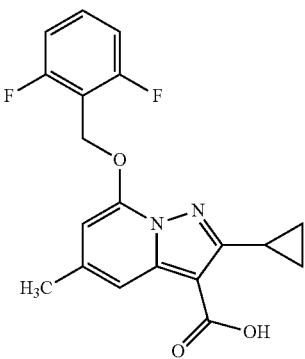 [SMILES: Cc1cc(OCc2c(F)cccc2F)n2nc(C3CC3)c(C(=O)O)c2c1]

A solution of 384 mg (1.02 mmol) of methyl 2-cyclopropyl-7-[(2,6-difluorobenzyl)oxy]-5-methylpyrazolo[1,5-a]pyridine-3-carboxylate from Example 99A in 10.6 ml of dioxane was admixed with 10.2 ml (10.2 mmol) of 1 N sodium hydroxide solution and the mixture was stirred at 100° C. for 7 h. The reaction solution was cooled and adjusted to pH 2 with 1 N hydrochloric acid. The solids that precipitated out were filtered off and dried under high vacuum. The filtrate was admixed once again with 1 N hydrochloric acid. The solids that precipitated out were filtered off and dried under high vacuum together with the previously isolated solids. A total of 361 mg of the title compound (74% by LC-MS, 73% of theory) were obtained and were converted without further purification.

LC-MS (Method 2): $R_t$=1.00 min
MS (ESIpos): m/z=359 (M+H)$^+$
$^1$H NMR (400 MHz, DMSO-d$_6$): δ [ppm]=0.87-0.99 (m, 4H), 2.42 (s, 3H), 2.73-2.82 (m, 1H), 5.45 (s, 2H), 6.61 (s, 1H), 7.20-7.28 (m, 2H), 7.48 (s, 1H), 7.55-7.65 (m, 1H), 12.29 (br. s, 1H).

Example 104A ent-Benzyl {1-[({7-[(2,6-difluorobenzyl)oxy]-5-methyl-2-propylpyrazolo[1,5-a]pyridin-3-yl}carbonyl)amino]-2-methylpentan-2-yl}carbamate trifluoroacetate (Enantiomer B)

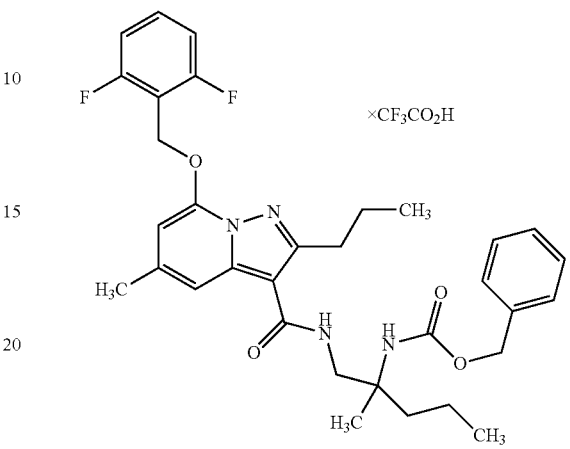

90 mg (0.19 mmol, about 75% purity) of 7-[(2,6-difluorobenzyl)oxy]-5-methyl-2-propylpyrazolo[1,5-a]pyridine-3-carboxylic acid from Example 100A were initially charged together with 78 mg (0.21 mmol) of HATU and 0.1 ml (0.56 mmol) of N,N-diisopropylethylamine in 0.6 ml of DMF, and the mixture was stirred at room temperature for 10 min. Subsequently, 64 mg (0.23 mmol) of ent-benzyl (1-amino-2-methylpentan-2-yl)carbamate (enantiomer B) from Example 20A were added to the reaction solution and the mixture was stirred at RT overnight. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. 54 mg of the target compound were obtained (41% of theory).

LC-MS (Method 2): $R_t$=1.34 min
MS (ESpos): m/z=593.6 (M-TFA+H)$^+$

In analogy to Example 104A, the example compounds shown in Table 3A were prepared by reacting the corresponding carboxylic acids with ent-benzyl (1-amino-2-methylpentan-2-yl)carbamate (enantiomer B) from Example 20A (1.1-1.5 equivalents), HATU (1.1-3 equivalents) and N,N-diisopropylethylamine (3-5 equivalents) under the reaction conditions described (reaction time: 0.5-24 h; temperature: RT).

Illustrative Workup of the Reaction Mixture:

The reaction mixture was diluted with water, TFA or formic acid and purified by means of preparative HPLC (RP18 column, eluent:acetonitrile/water gradient with addition of 0.1% TFA or 0.05% formic acid). The crude product was additionally or alternatively purified by means of thick-layer chromatography or silica gel chromatography (eluent:dichloromethane/methanol or dichloromethane/2 M ammonia in methanol). The product-containing fractions were concentrated.

The product-containing fractions from the preparative HPLC were optionally concentrated, and the residue was taken up in dichloromethane and washed with saturated aqueous sodium hydrogencarbonate solution. The aqueous phase was extracted twice with dichloromethane, and the combined organic phases were dried over sodium sulphate, filtered, concentrated and lyophilized.

TABLE 3A

| Example | IUPAC name/ structure (yield) | Analytical data |
|---|---|---|
| 105A | ent-Benzyl {1-[({7-[(2,6-difluorobenzyl)oxy]-5-methyl-2-(trifluoromethyl)pyrazolo[1,5-a]pyridin-3-yl}carbonyl)amino]-2-methylpentan-2-yl}carbamate trifluoroacetate (enantiomer B)<br>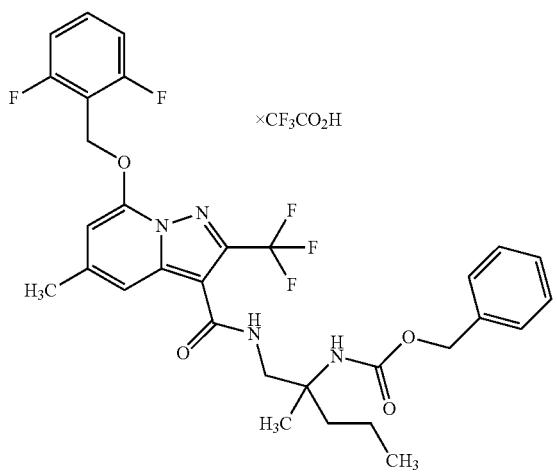 [SMILES: CCCC(C)(CNC(=O)c1c(C(F)(F)F)nn2c(OCc3c(F)cccc3F)cc(C)cc12)NC(=O)OCc1ccccc1]<br>(53% of theory) | LC-MS (Method 2):<br>$R_t$ = 1.30 min<br>MS (ESpos):<br>m/z = 619 (M−TFA + H)+ |
| 106A | ent-Benzyl {1-[({7-[(2,6-difluorobenzyl)oxy]-5-methylpyrazolo[1,5-a]pyridin-3-yl}carbonyl)amino]-2-methylpentan-2-yl}carbamate trifluoroacetate (enantiomer B)<br>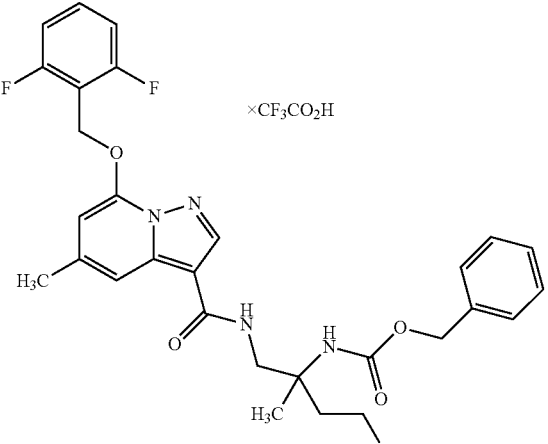<br>(63% of theory) | LC-MS (Method 2):<br>$R_t$ = 1.29 min<br>MS (ESpos):<br>m/z = 551 (M−TFA + H)+ |

Example 107A ent-Benzyl {1-[({2-cyclopropyl-7-[(2,6-difluorobenzyl)oxy]-5-methylpyrazolo[1,5-a]pyridin-3-yl}carbonyl)amino]-2-methylbutan-2-yl}carbamate trifluoroacetate (Enantiomer A)

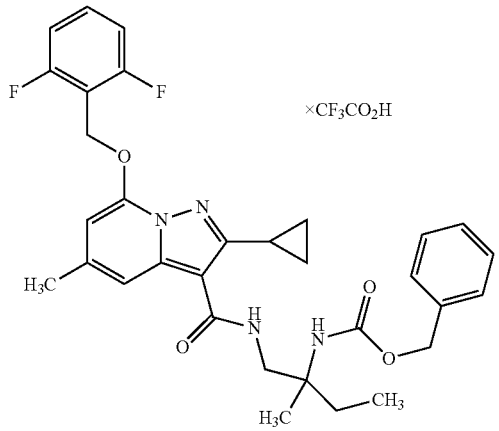 [SMILES: CCC(C)(CNC(=O)c1c(C2CC2)nn2c(OCc3c(F)cccc3F)cc(C)cc12)NC(=O)OCc1ccccc1]

70 mg (0.15 mmol, about 74% purity) of 2-cyclopropyl-7-[(2,6-difluorobenzyl)oxy]-5-methylpyrazolo[1,5-a]pyridine-3-carboxylic acid from Example 103A were initially charged together with 71 mg (0.19 mmol) of HATU and 0.13 ml (0.72 mmol) of N,N-diisopropylethylamine in 0.5 ml of DMF, and the mixture was stirred at room temperature for 20 min. Subsequently, 44 mg (0.19 mmol) of ent-benzyl (1-amino-2-methylbutan-2-yl)carbamate (enantiomer A) from Example 14A were added to the reaction solution and the mixture was stirred at RT for 1 h. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. 57 mg of the target compound were obtained (51% of theory, 90% purity).

LC-MS (Method 2): $R_t$=1.26 min
MS (ESpos): m/z=577 (M-TFA+H)$^+$

Example 108A ent-Benzyl {1-[({2-cyclopropyl-7-[(2,6-difluorobenzyl)oxy]-5-methylpyrazolo[1,5-a]pyridin-3-yl}carbonyl)amino]-2-methylpentan-2-yl}carbamate trifluoroacetate (Enantiomer B)

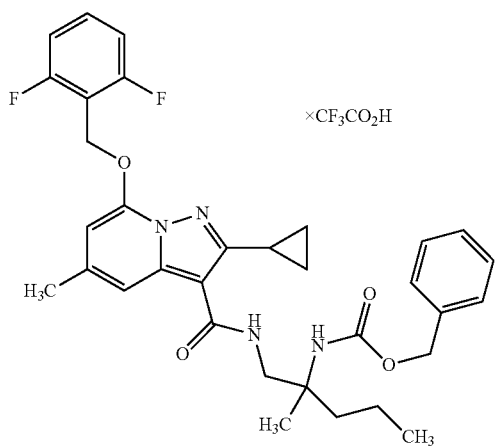 [SMILES: CCCC(C)(CNC(=O)c1c(C2CC2)nn2c(OCc3c(F)cccc3F)cc(C)cc12)NC(=O)OCc1ccccc1]

107 mg (0.22 mmol, about 74% purity) of 2-cyclopropyl-7-[(2,6-difluorobenzyl)oxy]-5-methylpyrazolo[1,5-a]pyridine-3-carboxylic acid from Example 103A were initially charged together with 125 mg (0.33 mmol) of HATU and 0.16 ml (0.90 mmol) of N,N-diisopropylethylamine in 1.0 ml of DMF, and the mixture was stirred at room temperature for 10 min. Subsequently, 82 mg (0.29 mmol; 88% purity) of ent-benzyl (1-amino-2-methylpentan-2-yl)carbamate (enantiomer B) from Example 20A were added to the reaction solution and the mixture was stirred at RT for 1 h. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. 88 mg of the target compound were obtained (57% of theory).

LC-MS (Method 2): $R_t$=1.31 min
MS (ESpos): m/z=591 (M-TFA+H)$^+$

Example 109A ent-Benzyl {1-[({2-cyclopropyl-7-[(2,6-difluorobenzyl)oxy]-5-methylpyrazolo[1,5-a]pyridin-3-yl}carbonyl)amino]-5,5,5-trifluoro-2-methylpentan-2-yl}carbamate trifluoroacetate (Enantiomer B)

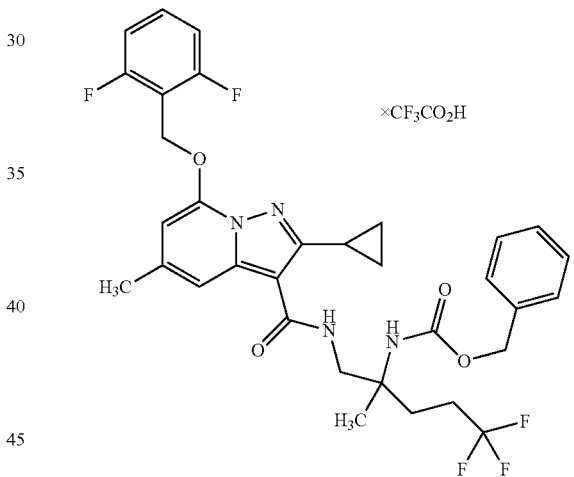

100 mg (0.21 mmol, about 74% purity) of 2-cyclopropyl-7-[(2,6-difluorobenzyl)oxy]-5-methylpyrazolo[1,5-a]pyridine-3-carboxylic acid from Example 103A were initially charged together with 102 mg (0.27 mmol) of HATU and 0.18 ml (1.03 mmol) of N,N-diisopropylethylamine in 0.7 ml of DMF, and the mixture was stirred at room temperature for 10 min. Subsequently, 86 mg (0.27 mmol; 95% purity) of ent-benzyl (1-amino-5,5,5-trifluoro-2-methylpentan-2-yl)carbamate (enantiomer B) from Example 65A were added to the reaction solution and the mixture was stirred at RT for 0.5 h. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. 97 mg of the target compound were obtained (61% of theory).

LC-MS (Method 2): $R_t$=1.32 min
MS (ESpos): m/z=645 (M-TFA+H)$^+$

Example 110A ent-Benzyl {1-[({2-cyclopropyl-7-[(2,6-difluorobenzyl)oxy]-5-methylpyrazolo[1,5-a]pyridin-3-yl}carbonyl)amino]-4,4-difluoro-2-methylbutan-2-yl}carbamate trifluoroacetate (Enantiomer A)

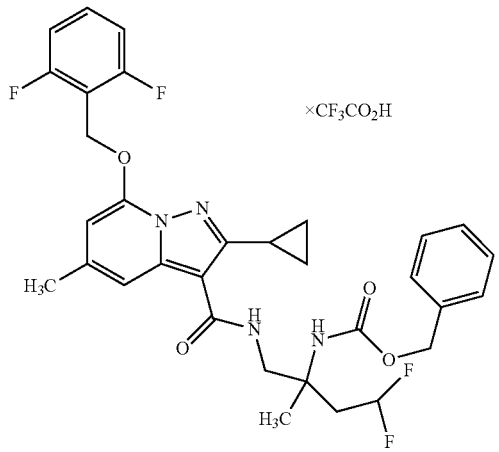 [SMILES: Cc1cc(OCc2c(F)cccc2F)n2nc(C3CC3)c(C(=O)NCC(C)(CC(F)F)NC(=O)OCc3ccccc3)c2c1]

60 mg (0.12 mmol, about 74% purity) of 2-cyclopropyl-7-[(2,6-difluorobenzyl)oxy]-5-methylpyrazolo[1,5-a]pyridine-3-carboxylic acid from Example 103A were initially charged together with 61 mg (0.16 mmol) of HATU and 0.11 ml (0.62 mmol) of N,N-diisopropylethylamine in 0.4 ml of DMF, and the mixture was stirred at room temperature for 20 min. Subsequently, 58 mg (0.21 mmol; 98% purity) of ent-benzyl (1-amino-4,4-difluoro-2-methylbutan-2-yl)carbamate (enantiomer A) from Example 82A were added to the reaction solution and the mixture was stirred at RT for 1 h. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. 55 mg of the target compound were obtained (58% of theory, 95% purity).

LC-MS (Method 2): $R_t$=1.26 min
MS (ESpos): m/z=613 (M-TFA+H)$^+$

Example 111A ent-Benzyl {1-[({2-cyclopropyl-7-[(2,6-difluorobenzyl)oxy]-5-methylpyrazolo[1,5-a]pyridin-3-yl}carbonyl)amino]-4,4-difluoro-2-methylbutan-2-yl}carbamate trifluoroacetate (Enantiomer B)

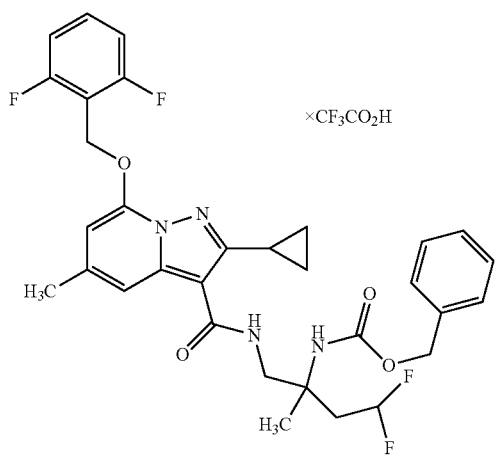 [SMILES: Cc1cc(OCc2c(F)cccc2F)n2nc(C3CC3)c(C(=O)NCC(C)(CC(F)F)NC(=O)OCc3ccccc3)c2c1]

60 mg (0.12 mmol, about 74% purity) of 2-cyclopropyl-7-[(2,6-difluorobenzyl)oxy]-5-methylpyrazolo[1,5-a]pyridine-3-carboxylic acid from Example 103A were initially charged together with 61 mg (0.16 mmol) of HATU and 0.11 ml (0.62 mmol) of N,N-diisopropylethylamine in 0.4 ml of DMF, and the mixture was stirred at room temperature for 20 min. Subsequently, 50 mg (0.16 mmol; 93% purity) of ent-benzyl (1-amino-4,4-difluoro-2-methylbutan-2-yl)carbamate (enantiomer B) from Example 83A were added to the reaction solution and the mixture was stirred at RT for 0.5 h. The mixture was admixed with water and stirred at RT for 0.5 h. The solids obtained were filtered off and washed with water. The solids were admixed with acetonitrile, water and TFA and purified by means of preparative HPLC (RP18 column, eluent:acetonitrile/water gradient with addition of 0.1% TFA). The product fractions were combined and concentrated. 54 mg of the target compound were obtained (49% of theory, 82% purity).

LC-MS (Method 2): $R_t$=1.26 min
MS (ESpos): m/z=613 (M-TFA+H)$^+$

Example 112A tert-Butyl {3-[({7-[(2,6-difluorobenzyl)oxy]-2,5-dimethylpyrazolo[1,5-a]pyridin-3-yl}carbonyl)amino]-2,2-difluoropropyl}carbamate trifluoroacetate

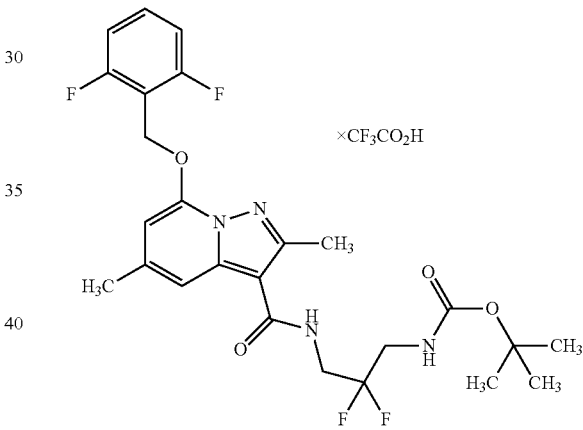

80 mg (0.18 mmol, about 75% purity) of 7-[(2,6-difluorobenzyl)oxy]-2,5-dimethylpyrazolo[1,5-a]pyridine-3-carboxylic acid from Example 4A were initially charged together with 89 mg (0.24 mmol) of HATU and 94 µl (0.54 mmol) of N,N-diisopropylethylamine in 0.6 ml of DMF, and the mixture was stirred at room temperature for 20 min. Subsequently, 49 mg (0.24 mmol) of tert-butyl (3-amino-2,2-difluoropropyl)carbamate were added to the reaction solution and the mixture was stirred at RT for 30 min. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. 77 mg of the target compound were obtained (66% of theory).

LC-MS (Method 2): $R_t$=1.21 min
MS (ESpos): m/z=525 (M-TFA+H)$^+$

In analogy to Example 112A, the example compounds shown in Table 4A were prepared by reacting 7-[(2,6-difluorobenzyl)oxy]-2,5-dimethylpyrazolo[1,5-a]pyridine-3-carboxylic acid from Example 4A with the appropriate amines which are commercially available or known from the literature (1.1-1.5 equivalents), HATU (1.1-3 equivalents) and N,N-diisopropylethylamine (3-5 equivalents) under the reaction conditions described (reaction time: 0.5-24 h; temperature: RT or 60° C.).

Illustrative Workup of the Reaction Mixture:

The reaction mixture was diluted with water, TFA or formic acid and purified by means of preparative HPLC (RP18 column, eluent:acetonitrile/water gradient with addition of 0.1% TFA or 0.05% formic acid). The crude product was additionally or alternatively purified by means of thick-layer chromatography or silica gel chromatography (eluent:dichloromethane/methanol or dichloromethane/2 M ammonia in methanol). The product-containing fractions were concentrated.

The product-containing fractions from the preparative HPLC were optionally concentrated, and the residue was taken up in dichloromethane and washed with saturated aqueous sodium hydrogencarbonate solution. The aqueous phase was extracted twice with dichloromethane, and the combined organic phases were dried over sodium sulphate, filtered, concentrated and lyophilized.

Alternatively, the reaction solution was admixed with water and the precipitated solids were stirred at room temperature for about 30 min. Subsequently, the solids were filtered off, washed well with water and dried under high vacuum.

TABLE 4A

| Example | IUPAC name/ structure (yield) | Analytical data |
|---|---|---|
| 113A | rac-tert-Butyl 2-{[({7-[(2,6-difluorobenzyl)oxy]-2,5-dimethylpyrazolo[1,5-a]pyridin-3-yl}carbonyl)amino]methyl}-3,4-dihydroquinoline-1(2H)-carboxylate trifluoroacetate<br><br>(44% of theory) | LC-MS (Method 2):<br>$R_t$ = 1.25 min<br>MS (ESpos):<br>m/z = 577 (M-TFA + H)$^+$ |
| 114A | rac-Ethyl 6-{2-[(tert-butoxycarbonyl)amino]-1-[({7-[(2,6-difluorobenzyl)oxy]-2,5-dimethylpyrazolo[1,5-a]pyridin-3-yl}carbonyl)amino]ethyl}pyridine-2-carboxylate trifluoroacetate<br><br>(8% of theory) | LC-MS (Method 7):<br>$R_t$ = 2.77 min<br>MS (ESpos):<br>m/z = 624 (M-TFA + H)$^+$ |

TABLE 4A-continued

| Example | IUPAC name/ structure (yield) | Analytical data |
|---|---|---|
| 115A | rac-tert-Butyl {2-(4-cyanophenyl)-2-[({7-[(2,6-difluorobenzyl)oxy]-2,5-dimethylpyrazolo[1,5-a]pyridin-3-yl}carbonyl) amino]ethyl}carbamate trifluoroacetate<br />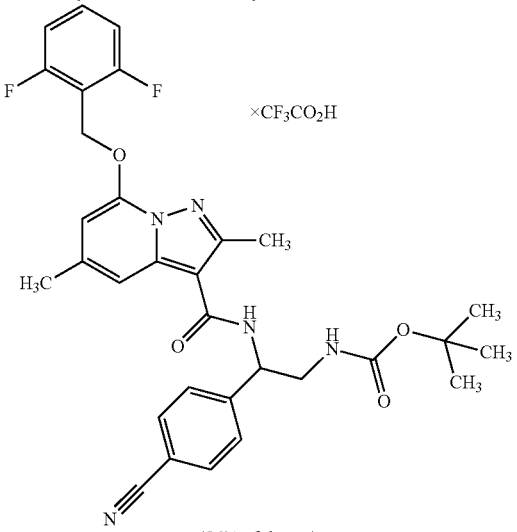<br />(56% of theory) | LC-MS (Method 2):<br />$R_t = 1.14$ min<br />MS (ESpos): m/z = 576 (M-TFA + H)$^+$ |

Example 116A

7-[(2,3-Difluorobenzyl)oxy]-2,5-dimethylpyrazolo[1,5-a]pyridine-3-carboxylic Acid ethyl Ester

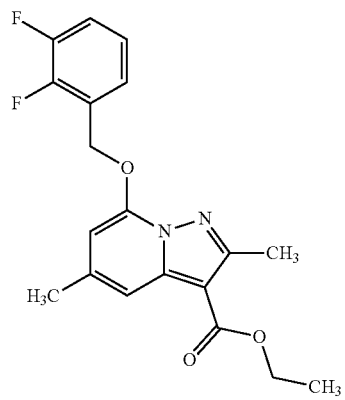 [SMILES: CCOC(=O)c1c(C)nn2c(OCc3cccc(F)c3F)cc(C)cc12]

A solution of 180 mg (0.768 mmol) of 7-hydroxy-2,5-dimethylpyrazolo[1,5-a]pyridine-3-carboxylic acid ethyl ester from Example 8A in 7 ml of dry tetrahydrofuran was admixed with 221.5 mg (1.537 mmol) of (2,3-difluorophenyl)methanol (CAS 75853-18-8), 423.2 mg (1.614 mmol) of triphenylphosphine and 0.32 ml (1.614 mmol) of diethyl azodicarboxylate. The resulting mixture was stirred at room temperature for 1 h, some of the solvent was drawn off under reduced pressure and the residue was admixed with 5 ml of tert-butyl methyl ether. The resulting precipitate was filtered off and dried under reduced pressure, which gave 190 mg (67% of theory, 97% pure) of the target compound.

LC-MS (Method 16): $R_t$=1.29 min
MS (ESpos): m/z=361.24 (M+H)$^+$
$^1$H NMR (300 MHz, DMSO-d$_6$): δ [ppm]=1.32 (t, 3H), 2.43 (s, 3H), 2.49 (s, 3H), 4.20-3.32 (m, 2H), 5.52 (s, 2H), 6.65 (s, 1H), 7.26-7.38 (m, 1H), 7.41-7.65 (m, 3H).

Example 117A

7-[(2,3-Difluorobenzyl)oxy]-2,5-dimethylpyrazolo[1,5-a]pyridine-3-carboxylic Acid

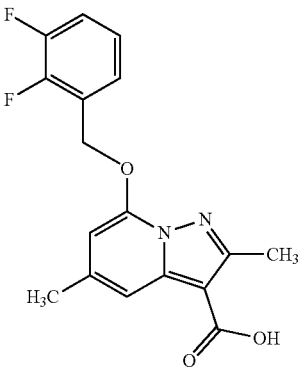

A solution of 190 mg (0.527 mmol) of 7-[(2,3-difluorobenzyl)oxy]-2,5-dimethylpyrazolo[1,5-a]pyridine-3-carboxylic acid ethyl ester from Example 116A in 5 ml of dioxane was admixed with 2.1 ml of 2 N sodium hydroxide solution. The resulting mixture was stirred at 90° C. for 15 h. Owing to incomplete mixing, 1 ml of dimethyl sulphoxide was added, followed by further 2 N sodium hydroxide solution (1 ml). The resulting mixture was stirred for a further 2 h. After the reaction had ended, the solvent was removed under reduced pressure. The residue was admixed with acetonitrile (5 ml), followed by the dropwise addition of trifluoroacetic acid (2 ml). The resulting precipitate was filtered off and dried under reduced pressure, which gave 130 mg (71% of theory, 93% pure) of the target compound.

LC-MS (Method 16): $R_t$=1.01 min

MS (ESpos): m/z=333.2 (M+H)$^+$ $^1$H NMR (300 MHz, DMSO-d$_6$): δ [ppm]=2.40 (s, 3H), 2.49 (s, 3H), 5.50 (s, 2H), 6.65 (s, 1H), 7.25-7.35 (m, 1H), 7.42-7.57 (m, 3H).

Example 118A rac-{1-[({7-[(2,3-Difluorobenzyl)oxy]-2,5-dimethylpyrazolo[1,5-a]pyridin-3-yl}carbonyl)amino]-2-methylpentan-2-yl}carbamic Acid tert-butyl Ester

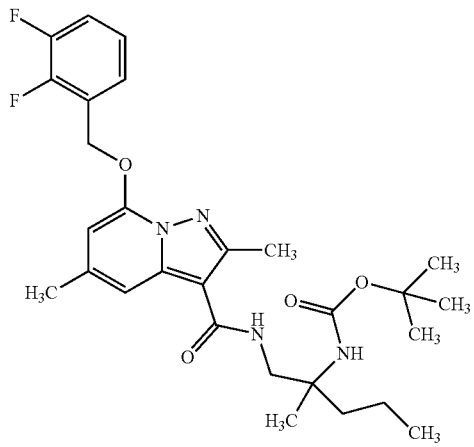 [SMILES: CCCC(C)(CNC(=O)c1c(C)nn2c(OCc3cccc(F)c3F)cc(C)cc12)NC(=O)OC(C)(C)C]

A solution of 120 mg (0.336 mmol) of 7-[(2,3-difluorobenzyl)oxy]-2,5-dimethylpyrazolo[1,5-a]pyridine-3-carboxylic acid from Example 117A in 2 ml of DMF was admixed with 70.8 mg (0.437 mmol) of 1,1'-carbonyldiimidazole and 36 mg (0.235 mmol) of 1-hydroxybenzotriazole. After stirring at room temperature for 15 min, 94.4 mg (0.437 mmol) of rac-(1-amino-2-methylpentan-2-yl)carbamic acid tert-butyl ester from Example 152A were added, followed by 0.117 ml (0.672 mmol) of N,N-diisopropylethylamine. The tubes were sealed and introduced into a Biotage Initiator with microwave irradiation at 100° C. for 20 minutes. The reaction mixture was partitioned between ethyl acetate (10 ml) and water (10 ml), the phases were separated and the aqueous phase was acidified to pH=5 with 2 N aqueous hydrochloric acid and extracted with dichloromethane (2×15 ml). The combined organic phases were concentrated under reduced pressure and the residue was purified by flash chromatography using a prepacked silica gel cartridge (eluent:cyclohexane-ethyl acetate 10:1 to 1:1), which gave 35 mg (15% of theory, 78% pure) of the target compound.

LC-MS (Method 16): $R_t$=1.37 min

MS (ESpos): m/z=531.5 (M+H)$^+$

Example 119A 7-(Cyclohexylmethoxy)-2,5-dimethylpyrazolo[1,5-a]pyridine-3-carboxylic Acid ethyl Ester

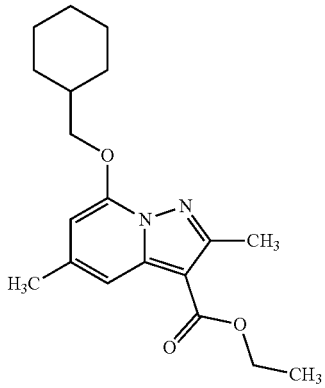 [SMILES: CCOC(=O)c1c(C)nn2c(OCC3CCCCC3)cc(C)cc12]

A solution of 180 mg (0.768 mmol) of 7-hydroxy-2,5-dimethylpyrazolo[1,5-a]pyridine-3-carboxylic acid ethyl ester from Example 8A in 7 ml of dry tetrahydrofuran was admixed with 0.189 ml (537 mmol) of cyclohexylmethanol, 423.2 mg (1.614 mmol) of triphenylphosphine and 0.32 ml (1.614 mmol) of diethyl azodicarboxylate. The resulting mixture was stirred at room temperature for 1 h. Some of the solvent was drawn off under reduced pressure and the residue was admixed with 5 ml of tert-butyl methyl ether. The resulting precipitate was filtered off and the mother liquor was partitioned between dichloromethane (15 ml) and water (10 ml). The organic phase was removed and concentrated under reduced pressure. The residue was purified by flash chromatography using a prepacked silica gel cartridge (eluent:cyclohexane-ethyl acetate 10:1 to 1:1), which gave 220 mg (60% of theory, 71% pure) of the target compound.

LC-MS (Method 23): $R_t$=1.46 min

MS (ESpos): m/z=331.31 (M+H)$^+$

Example 120A 7-(Cyclohexylmethoxy)-2,5-dimethylpyrazolo[1,5-a]pyridine-3-carboxylic Acid

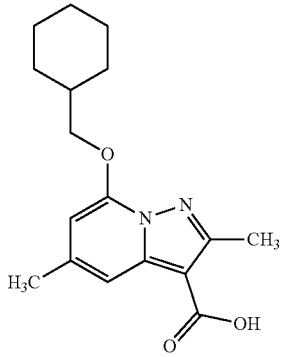 [SMILES: Cc1cc(OCC2CCCCC2)n2nc(C)c(C(=O)O)c2c1]

A solution of 220 mg (0.469 mmol, 71% pure) of 7-(cyclohexylmethoxy)-2,5-dimethylpyrazolo[1,5-a]pyridine-3-carboxylic acid ethyl ester from Example 119A in 4 ml of dioxane was admixed with 2 ml of 2 N sodium hydroxide solution. The resulting mixture was stirred at 100° C. for 15 h. The solvent was drawn off under reduced pressure and acetonitrile (5 ml) was added to the residue, and then trifluoroacetic acid (2 ml) was added dropwise. The resulting precipitate was filtered off and dried under reduced pressure, which gave 110 mg (74% of theory, 95% pure) of the target compound.

LC-MS (Method 16): $R_t$=1.17 min
MS (ESpos): m/z=303.22 (M+H)$^+$

Example 121A rac-[1-({[7-(Cyclohexylmethoxy)-2,5-dimethylpyrazolo[1,5-a]pyridin-3-yl]carbonyl}amino)-2-methylpentan-2-yl]carbamic Acid tert-butyl Ester

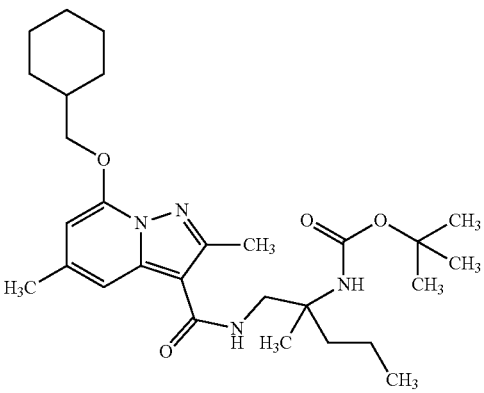 [SMILES: CCCC(C)(CNC(=O)c1c(C)nn2c(OCC3CCCCC3)cc(C)cc12)NC(=O)OC(C)(C)C]

A solution of 110 mg (0.364 mmol) of 7-(cyclohexylmethoxy)-2,5-dimethylpyrazolo[1,5-a]pyridine-3-carboxylic acid from Example 120A in 1 ml of thionyl chloride was stirred at 100° C. for 1 h. After the reaction had ended, the solvent was drawn off under reduced pressure and the residue was suspended in 3 ml of dichloromethane and then added to a solution of 102.3 mg (0.473 mmol) of rac-(1-amino-2-methylpentan-2-yl)carbamic acid tert-butyl ester from Example 152A in 2 ml of dry dichloromethane. The resulting solution was stirred at room temperature overnight. The solvent was drawn off under reduced pressure and the residue was purified by flash chromatography using a prepacked silica gel cartridge (eluent:cyclohexane-ethyl acetate 10:1 to 1:1), which gave 40 mg (13% of theory, 59% pure) of the target compound.

LC-MS (Method 16): $R_t$=1.51 min
MS (ESpos): m/z=501.55 (M+H)$^+$

Example 122A 2,5-Dimethyl-7-(3-methylbutoxy)pyrazolo[1,5-a]pyridine-3-carboxylic Acid ethyl Ester

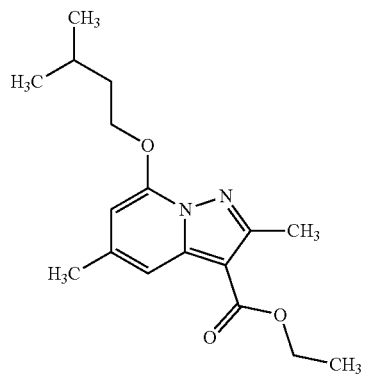 [SMILES: CCOC(=O)c1c(C)nn2c(OCCC(C)C)cc(C)cc12]

A solution of 180 mg (0.768 mmol) of 7-hydroxy-2,5-dimethylpyrazolo[1,5-a]pyridine-3-carboxylic acid ethyl ester from Example 8A in 7 ml of dry tetrahydrofuran was admixed with 0.167 ml (1.537 mmol) of 3-methylbutan-1-ol (CAS 123-51-3), 423.2 mg (1.614 mmol) of triphenylphosphine and 0.32 ml (1.614 mmol) of diethyl azodicarboxylate. The resulting mixture was stirred at room temperature for 1 h. Some of the solvent was drawn off under reduced pressure and the residue was admixed with 5 ml of tert-butyl methyl ether. The resulting precipitate was filtered off and the mother liquor was partitioned between dichloromethane (15 ml) and water (10 ml). The organic phase was removed and concentrated under reduced pressure. The residue was purified by flash chromatography using a prepacked silica gel cartridge (eluent:cyclohexane-ethyl acetate 10:1 to 1:1), which gave 225 mg (69% of theory, 72% pure) of the target compound.

LC-MS (Method 16): $R_t$=1.35 min
MS (ESpos): m/z=305.28 (M+H)$^+$

Example 123A 2,5-Dimethyl-7-(3-methylbutoxy)pyrazolo[1,5-a]pyridine-3-carboxylic Acid

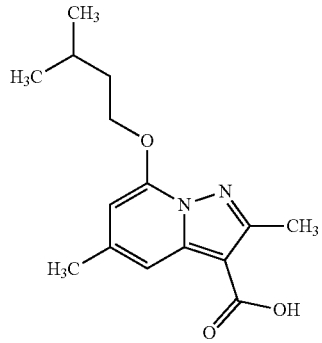 [SMILES: Cc1cc(OCCC(C)C)n2nc(C)c(C(=O)O)c2c1]

A solution of 220 mg (0.469 mmol, 72% pure) of 2,5-dimethyl-7-(3-methylbutoxy)pyrazolo[1,5-a]pyridine-3-carboxylic acid ethyl ester from Example 122A in 4 ml of dioxane was admixed with 2 ml of 2 N sodium hydroxide solution. The resulting mixture was stirred at 100° C. for 15 h. The solvent was removed under reduced pressure. The residue was admixed with acetonitrile (5 ml), followed by the dropwise addition of trifluoroacetic acid (2 ml). The resulting precipitate was filtered off and dried under reduced pressure, which gave 45 mg (28% of theory, 90% pure) of the target compound.

LC-MS (Method 16): $R_t$=1.06 min
MS (ESpos): m/z=277.26 (M+H)$^+$
$^1$H NMR (300 MHz, DMSO-$d_6$): δ [ppm]=0.95 (d, 6H), 1.68-1.89 (m, 1H), 2.39 (s, 3H), 2.48 (s, 3H), 4.31 (s, 2H), 6.44 (s, 1H), 7.39 (s, 1H).

Example 124A rac-[1-({[2,5-Dimethyl-7-(3-methylbutoxy)pyrazolo[1,5-a]pyridin-3-yl]carbonyl}amino)-2-methylpentan-2-yl]carbamic Acid tert-butyl Ester

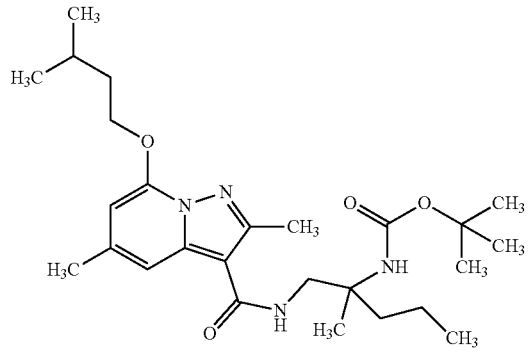 [SMILES: CCCC(C)(CNC(=O)c1c(C)nn2c(OCCC(C)C)cc(C)cc12)NC(=O)OC(C)(C)C]

A solution of 45 mg (0.163 mmol) of 2,5-dimethyl-7-(3-methylbutoxy)pyrazolo[1,5-a]pyridine-3-carboxylic acid from Example 8A in 3 ml of tetrahydrofuran was admixed with 30 mg (0.177 mmol) of 1-hydroxybenzotriazole and 30 mg (0.177 mmol) of 1-(3-dimethylaminopropyl)-3-ethylcarbodiimide. The resulting solution was stirred at room temperature for 15 min, and then 45.7 mg (0.212 mmol) of rac-(1-amino-2-methylpentan-2-yl)carbamic acid tert-butyl ester from Example 152A were added, followed by 0.85 ml (0.212 mmol) of N,N-diisopropylethylamine. The mixture was stirred at room temperature for a further 18 h. The solvent was drawn off under reduced pressure and the residue was partitioned between ethyl acetate (10 ml) and water (10 ml). The organic phase was removed and washed with water and aqueous sodium chloride solution, dried with a phase separation cartridge and dried further under reduced pressure, which gave 80 mg (61% of theory, 54% pure) of the target compound.

LC-MS (Method 16): $R_t$=1.43 min

MS (ESpos): m/z=475.45 (M+H)$^+$

Example 125A rac-{1-[({7-[(2,6-Difluoro-3-methoxybenzyl)oxy]-2,5-dimethylpyrazolo[1,5-a]pyridin-3-yl}carbonyl)amino]-2-methylpentan-2-yl}carbamic Acid tert-butyl Ester

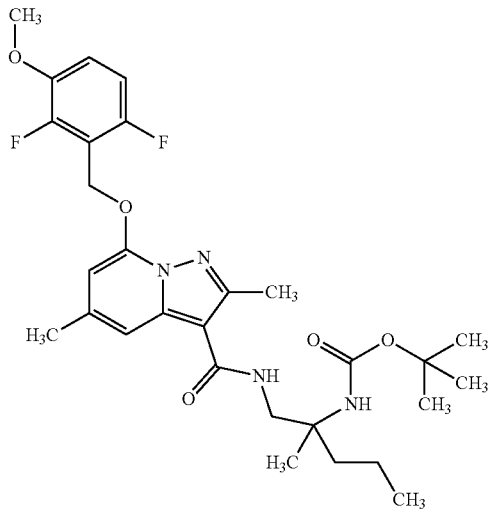 [SMILES: CCCC(C)(CNC(=O)c1c(C)nn2c(OCc3c(F)ccc(OC)c3F)cc(C)cc12)NC(=O)OC(C)(C)C]

A solution of 80 mg (0.20 mmol) of rac-(1-{[(7-hydroxy-2,5-dimethylpyrazolo[1,5-a]pyridin-3-yl)carbonyl]amino}-2-methylpentan-2-yl)carbamic acid tert-butyl ester from Example 141A and 38 mg (0.20 mmol) of 2-(chloromethyl)-1,3-difluoro-4-methoxybenzene from Example 133A in 2 ml of DMF was admixed with 129 mg (0.396 mmol) of caesium carbonate. The resulting suspension was stirred at RT for 72 h. The reaction mixture was diluted with dichloromethane (15 ml) and extracted with saturated aqueous sodium hydrogencarbonate solution (10 ml). The organic phase was concentrated under reduced pressure, which gave a crude material that contained the target compound in a multicomponent mixture (30% pure). The crude material was used in the next step without further purification.

LC-MS (Method 16): $R_t$=1.36 min

MS (ESpos): m/z=561.42 (M+H)$^+$

Example 126A rac-{{1-[({7-[(3-Cyano-2,6-difluorobenzyl)oxy]-2,5-dimethylpyrazolo[1,5-a]pyridin-3-yl}carbonyl)amino]-2-methylpentan-2-yl}carbamic Acid tert-butyl Ester

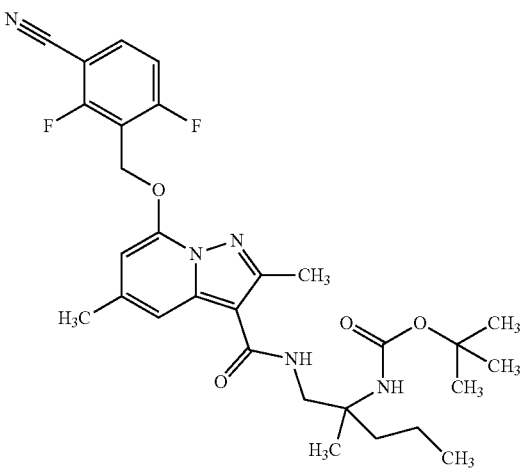 [SMILES: CCCC(C)(CNC(=O)c1c(C)nn2c(OCc3c(F)ccc(C#N)c3F)cc(C)cc12)NC(=O)OC(C)(C)C]

A solution of 80 mg (0.20 mmol) of rac-(1-{[(7-hydroxy-2,5-dimethylpyrazolo[1,5-a]pyridin-3-yl)carbonyl]amino}-2-methylpentan-2-yl)carbamic acid tert-butyl ester from Example 141A and 56 mg (0.27 mmol) of 3-(chloromethyl)-2,4-difluorobenzonitrile from Example 135A in 3 ml of DMF was admixed with 129 mg (0.396 mmol) of caesium carbonate. The resulting suspension was stirred at RT for 72 h and then diluted with dichloromethane (15 ml) and extracted with saturated aqueous sodium hydrogencarbonate solution (10 ml). The organic phase was concentrated under reduced pressure, which gave a crude product that contained the target compound in a multicomponent mixture (20% pure). This crude material was used in the next step without further purification.

LC-MS (Method 16): $R_t$=1.33 min

MS (ESpos): m/z=556.39 (M+H)$^+$

Example 127A

2-[(2,6-Difluorobenzyl)oxy]pyridine

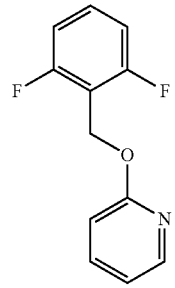 [SMILES: Fc1cccc(F)c1COc1ccccn1]

A solution of 2 ml (18.0 mmol) of (2,6-difluorophenyl)methanol in 15 ml of dry tetrahydrofuran stirred at 0° C. was admixed with 865.9 mg (21.6 mmol) of sodium hydride (60% in mineral oil), followed by 1.72 ml (18.0 mmol) of 2-bromopyridine. The resulting solution was stirred at room temperature for 15 h. The reaction mixture was diluted with water (15 ml) and extracted with dichloromethane (2×20 ml). The organic phase was removed, dried with a phase separation cartridge and concentrated under reduced pressure. The residue was purified by flash chromatography using a prepacked silica gel cartridge (eluent:cyclohexane-ethyl acetate 10:1 to 1:1), which gave 800 mg (15% of theory, 77% pure) of the target compound.

LC-MS (Method 16): R$_t$=1.17 min
MS (ESpos): m/z=222.13 (M+H)$^+$

Example 128A

1-Amino-2-[(2,6-difluorobenzyl)oxy]pyridinium 2,4,6-trimethylbenzenesulphonate

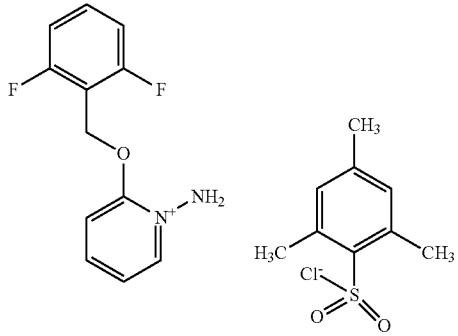

1.1 g (4.01 mmol) of O-(2-mesitylenesulphonyl)acetohydroxamic acid ethyl ester (CAS 38202-27-6) was added in portions to a precooled mixture of trifluoroacetic acid (3 ml) and water (0.5 ml) at −5° C. The resulting mixture was stirred at −5° C. for 1.5 hours and diluted with 10 ml of ice/water. The mixture was extracted with dichloromethane (10 ml). The organic phase was dried over sodium sulphate, filtered and added to a precooled solution of 800 mg (2.67 mmol, 77% pure) of 2-[(2,6-difluorobenzyl)oxy]pyridine from Example 127A in dichloromethane (2 ml) at 0° C. The mixture was stirred at room temperature for 18 hours. The mixture was added dropwise to diethyl ether (500 ml) while stirring over the course of 40 minutes. The mixture was stirred at room temperature for 1 further hour, which gave a precipitate, which was filtered off and washed with diethyl ether (50 ml), which gave 540 mg (36% of theory, 81% pure) of the target compound.

LC-MS (Method 16): R$_t$=0.56 min
MS (ESpos): m/z=237.16 (M+H)$^+$

Example 129A

7-[(2,6-Difluorobenzyl)oxy]-2-methylpyrazolo[1,5-a]pyridine-3-carboxylic Acid ethyl Ester

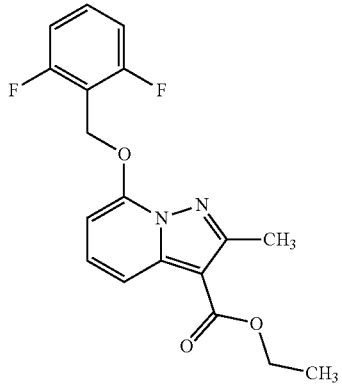 [SMILES: CCOC(=O)c1c(C)nn2c(OCc3c(F)cccc3F)cccc12]

A stirred solution of 540 mg (1.00 mmol, 81% pure) of 1-amino-2-[(2,6-difluorobenzyl)oxy]pyridinium-2,4,6-trimethylbenzenesulphonate from Example 128A in DMF (10 ml) at 0° C. was admixed with 0.35 ml (3.06 mmol) of ethyl 2-butynoate and 623 mg (4.51 mmol) of potassium carbonate. The reaction mixture was stirred at room temperature overnight and added dropwise to 20 ml of water while stirring. The resulting suspension was extracted with ethyl acetate (2×20 ml). The combined organic phases were dried with a phase separation cartridge and concentrated under reduced pressure. The residue was purified by flash chromatography using a prepacked silica gel cartridge (eluent:cyclohexane-ethyl acetate 10:1 to 1:1), which gave 200 mg (25% of theory, 43% pure) of the target compound.

LC-MS (Method 16): R$_t$=1.23 min
MS (ESpos): m/z=347.21 (M+H)$^+$

Example 130A

7-[(2,6-Difluorobenzyl)oxy]-2-methylpyrazolo[1,5-a]pyridine-3-carboxylic Acid

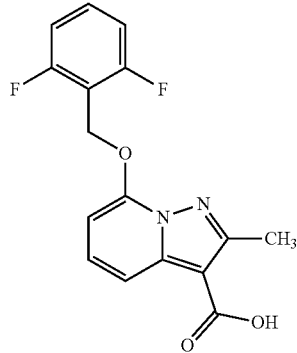 [SMILES: Cc1nn2c(OCc3c(F)cccc3F)cccc2c1C(=O)O]

A solution of 200 mg (0.228 mmol, 43% pure) of 7-[(2,6-difluorobenzyl)oxy]-2-methylpyrazolo[1,5-a]pyridine-3-carboxylic acid ethyl ester from Example 129A in 3 ml of dioxane was admixed with 1 ml of 2 N sodium hydroxide solution. The resulting mixture was stirred at room temperature for 72 h. The solvent was drawn off under reduced pressure and the residue was purified by flash chromatography using a prepacked silica gel cartridge (eluent:dichloromethane-methanol 100:1 to 10:1), which gave 100 mg (77% of theory, 61% pure) of the target compound.

LC-MS (Method 16): R$_t$=0.94 min
MS (ESpos): m/z=319.15 (M+H)$^+$

Example 131A rac-{1-[({7-[(2,6-Difluorobenzyl)oxy]-2-methylpyrazolo[1,5-a]pyridin-3-yl}carbonyl)amino]-2-methylpentan-2-yl}carbamic Acid tert-butyl Ester

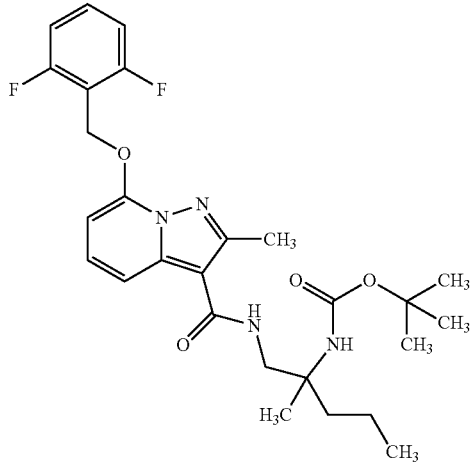 [SMILES: CCCC(C)(CNC(=O)c1c(C)nn2c(OCc3c(F)cccc3F)cccc12)NC(=O)OC(C)(C)C]

A solution of 100 mg (0.19 mmol, 61% pure) of 7-[(2,6-difluorobenzyl)oxy]-2-methylpyrazolo[1,5-a]pyridine-3-carboxylic acid from Example 130A in 4 ml of tetrahydrofuran was admixed with 39.1 mg (0.287 mmol) of 1-hydroxybenzotriazole and 74.3 mg (0.287 mmol) of 1-(3-dimethylaminopropyl)-3-ethylcarbodiimide hydrochloride. The resulting solution was stirred at room temperature for 15 min, and then 62.2 mg (0.287 mmol) of rac-(1-amino-2-methylpentan-2-yl)carbamic acid tert-butyl ester from Example 152A were added, followed by 0.1 ml (0.575 mmol) of N,N-diisopropylethylamine After the addition, the mixture was stirred at room temperature for a further 15 h. The solvent was drawn off under reduced pressure and the residue was partitioned between dichloromethane (10 ml) and water (10 ml). The organic phase was removed and washed with water and saturated aqueous sodium chloride solution, dried with a phase separation cartridge and concentrated under reduced pressure, which gave 45 mg (24% of theory, 53% pure) of the target compound.

LC-MS (Method 16): $R_t$=1.32 min

MS (ESpos): m/z=517.37 (M+H)$^+$

Example 132A (2,6-Difluoro-3-methoxyphenyl)methanol

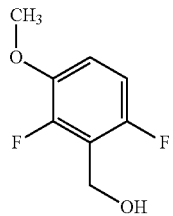

A stirred solution of 600 mg (3.48 mmol) of 2,6-difluoro-3-methoxybenzaldehyde (CAS 149949-30-4) in 8 ml of ethanol at 0° C. was admixed with 65.9 mg (1.74 mmol) of sodium borohydride in portions. After stirring at 0° C. for 30 min, the reaction mixture was quenched with water and extracted three times with methyl tert-butyl ether. The combined organic extracts were washed with water and saturated aqueous sodium chloride solution, and dried with a phase separation cartridge. The solvent was drawn off to dryness under reduced pressure, which gave 550 mg (89% of theory) of the target compound.

$^1$H NMR (300 MHz, DMSO-d$_6$): δ [ppm]=3.80 (s, 3H), 4.48 (d, 2H), 5.23 (t, 1H), 6.91-7.02 (m, 1H), 7.03-7.14 (m, 1H).

Example 133A 2-(Chloromethyl)-1,3-difluoro-4-methoxybenzene

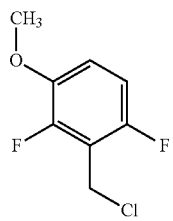

A solution of 120 mg (0.689 mmol) of 2,6-difluoro-3-methoxyphenyl)methanol from Example 132A in 3 ml of dichloromethane and 1 ml of thionyl chloride was stirred at room temperature overnight. The solvent was evaporated off under reduced pressure and the residue was purified by flash chromatography using a prepacked silica gel cartridge (eluent:cyclohexane-ethyl acetate 10:1 to 1:1), which gave 50 mg (38% of theory) of the target compound.

$^1$H NMR (300 MHz, DMSO-d$_6$): δ [ppm]=3.82 (s, 3H), 4.75 (s, 2H), 7.06-7.13 (m, 1H), 7.16-7.25 (m, 1H).

Example 134A 2,4-Difluoro-3-(hydroxymethyl)benzonitrile

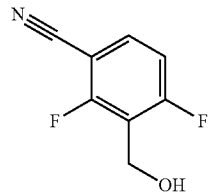 [SMILES: N#Cc1ccc(F)c(CO)c1F]

A stirred solution of 300 mg (3.48 mmol) of 2,4-difluoro-3-formylbenzonitrile (CAS 149489-14-5) in 10 ml of ethanol at 0° C. was admixed with 34 mg (0.89 mmol) of sodium borohydride in portions. After stirring at 0° C. for 1 h, the reaction mixture was mixed with water and extracted three times with methyl tert-butyl ether. The combined organic extracts were washed with water and saturated aqueous sodium chloride solution, and dried with a phase separation cartridge. The solvent was drawn off to dryness under reduced pressure, which gave 280 mg (82% of theory) of the target compound.

$^1$H NMR (300 MHz, DMSO-d$_6$): δ [ppm]=4.51 (d, 2H), 5.45 (t, 1H), 7.34 (t, 1H), 7.98 (dd, 1H).

Example 135A

3-Chloromethyl-2,4-difluorobenzonitrile

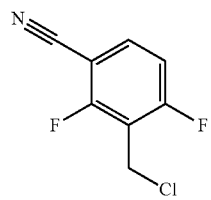 [SMILES: N#Cc1ccc(F)c(CCl)c1F]

A solution of 120 mg (0.710 mmol) of 2,4-difluoro-3-(hydroxymethyl)benzonitrile from Example 134A in 3 ml of dichloromethane and 1 ml of thionyl chloride was stirred at room temperature for 3 h. The solvent was evaporated off under reduced pressure and the residue was purified by flash chromatography using a prepacked silica gel cartridge (eluent:cyclohexane-ethyl acetate 10:1 to 1:1), which gave 60 mg (45% of theory) of the target compound.

$^1$H NMR (300 MHz, DMSO-d$_6$): δ [ppm]=4.82 (s, 2H), 7.45 (t, 1H), 8.10 (dd, 1H).

Example 136A

7-[(2-Chloro-6-fluorobenzyl)oxy]-2,5-dimethylpyrazolo[1,5-a]pyridine-3-carboxylic Acid ethyl Ester

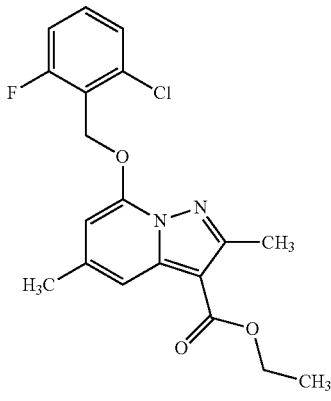 [SMILES: CCOC(=O)c1c(C)nn2c(OCc3c(F)cccc3Cl)cc(C)cc12]

A solution of 180 mg (0.76 mmol) of 7-hydroxy-2,5-dimethylpyrazolo[1,5-a]pyridine-3-carboxylic acid ethyl ester (Example 8A) in 7 ml of tetrahydrofuran was admixed with 247 mg (1.52 mmol) of 2-chloro-6-fluorobenzyl alcohol, 419 mg (1.60 mmol) of triphenylphosphine and 0.32 ml (1.60 mmol) of diisopropyl azodicarboxylate. The reaction mixture was stirred at room temperature for 1 h and concentrated under reduced pressure. The residue was purified by flash chromatography using a prepacked silica gel cartridge (mobile phase: cyclohexane-ethyl acetate, gradient 10% to 30%), which gave 280 mg (84% yield, 84% pure) of the target compound.

LC-MS (Method 16): $R_t$=1.34 min; m/z=377.22 (M+H)$^+$ $^1$H NMR (500 MHz, CDCl$_3$) δ [ppm]=1.42 (m, 3H), 2.46 (s, 3H), 2.67 (s, 3H), 4.38 (m, 2H), 5.52 (d, 2H), 6.26 (s, 1H), 7.08 (m, 1H), 7.29 (s, 1H), 7.35 (m, 1H), 7.57 (s, 1H).

Example 137A 7-(2-Chloro-6-fluorobenzyloxy)-2,5-dimethylpyrazolo[1,5-a]pyridine-3-carboxylic Acid

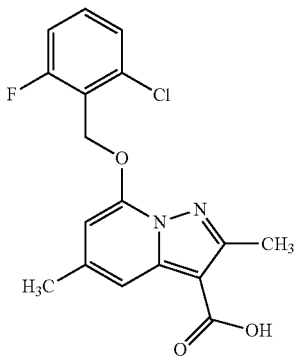 [SMILES: Cc1cc(OCc2c(F)cccc2Cl)n2nc(C)c(C(=O)O)c2c1]

A solution of 198 mg (0.62 mmol) of 7-(2-chloro-6-fluorobenzyloxy)-2,5-dimethylpyrazolo[1,5-a]pyridine-3-carboxylic acid ethyl ester (Example 136A) in 6.7 ml of 1,4-dioxane was admixed with 2 M sodium hydroxide solution (2.5 ml). The mixture was stirred at 90° C. for a further 18 hours. The reaction mixture was admixed with 0.8 ml of dimethyl sulphoxide and stirred at 90° C. for a further 6 hours. The reaction mixture was concentrated under reduced pressure. The residue was admixed with acetonitrile (5 ml) and trifluoroacetic acid (0.8 ml), and then with water and dichloromethane. The organic phase was removed and concentrated under reduced pressure. The residue was purified by flash chromatography using a prepacked silica gel cartridge (mobile phase: dichloromethane/methanol, gradient 80% to 100%), which gave 105 mg (27% yield, 56% pure) of the target compound, which was used in the next step without further purification.

LC-MS (Method 16): $R_t$=1.05 min; m/z=349.15 (M+H)$^+$

Example 138A rac-{1-[({7-[(2-Chloro-6-fluorobenzyl)oxy]-2,5-dimethylpyrazolo[1,5-a]pyridin-3-yl}carbonyl)amino]-2-methylpentan-2-yl}carbamic Acid tert-butyl Ester

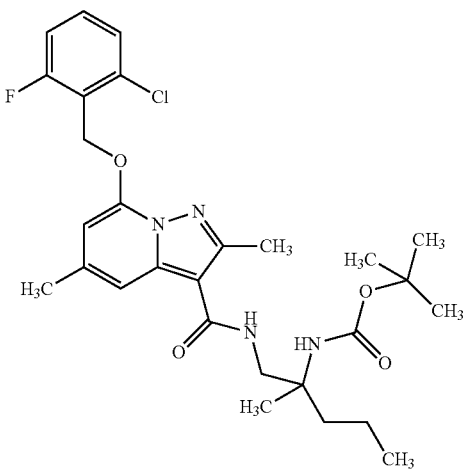 [SMILES: CCCC(C)(CNC(=O)c1c(C)nn2c(OCc3c(F)cccc3Cl)cc(C)cc12)NC(=O)OC(C)(C)C]

A solution of 26 mg (0.074 mmol) of 7-(2-chloro-6-fluorobenzyloxy)-2,5-dimethylpyrazolo[1,5-a]pyridine-3-carboxylic acid (Example 137A) in 3 ml of tetrahydrofuran was admixed with 17 mg (0.09 mmol) of 1-(3-dimethylaminopropyl)-3-ethylcarbodiimide hydrochloride, 14 mg (0.09 mmol) of 1-hydroxybenzotriazole, 21 mg (0.096 mmol) of rac-(1-aminomethyl-1-methylbutyl)carbamic acid tert-butyl ester from Example 152A and 0.039 ml (0.222 mmol) of N,N-diisopropylethylamine. The mixture was stirred at room temperature for a further 18 hours. The reaction mixture was then heated to 60° C. for 3 hours. After concentration under reduced pressure, the residue was partitioned between dichloromethane and water. The organic phase was removed and concentrated under reduced pressure, which gave 40 mg (99% yield) of the target compound.

LC-MS (Method 16): $R_t$=1.42 min; m/z=547.35 (M+H)$^+$ $^1$H NMR (500 MHz, CDCl$_3$): δ [ppm]=0.94 (t, 3H), 1.25 (s, 3H), 1.33-1.41 (m, 2H), 1.42-1.44 (m, 9H), 1.53-1.61 (m, 1H), 1.68-1.78 (m, 1H), 2.43 (s, 3H), 2.69 (s, 3H), 3.73 (qd, 2H), 4.64 (br. s, 1H), 5.51 (s, 2H), 6.21 (s, 1H), 6.90 (br. s., 1H), 7.07 (t, 1H), 7.27-7.29 (m, 1H), 7.35 (td, 1H), 7.65 (s, 1H).

$^{13}$C NMR (126 MHz, CDCl$_3$): δ [ppm]=14.5, 14.8, 16.8, 21.9, 23.8, 28.4, 40.4, 46.8, 56.0, 62.8, 79.5, 94.3, 103.9, 110.0, 114.4, 120.3, 125.7, 131.5, 136.9, 137.9, 143.4, 149.0, 151.1, 162.3, 165.1.

Example 139A

7-Benzyloxy-2,5-dimethylpyrazolo[1,5-a]pyridine-3-carboxylic Acid

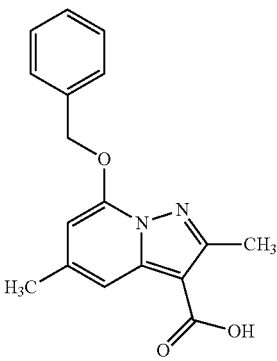 [SMILES: Cc1cc(OCc2ccccc2)n2nc(C)c(C(=O)O)c2c1]

A solution of 390 mg (1.13 mmol) of 7-benzyloxy-2,5-dimethylpyrazolo[1,5-a]pyridine-3-carboxylic acid ethyl ester (Example 7A) in 6 ml of 1,4-dioxane was admixed with 4 ml of 2 M sodium hydroxide solution. The mixture was stirred at 100° C. for a further 18 hours. The reaction mixture was cooled under reduced pressure and then concentrated under reduced pressure. The residue was admixed with acetonitrile (10 ml) and water (2 ml), followed by 2 ml of trifluoroacetic acid, which was added dropwise. The resulting precipitate was filtered off and dried under reduced pressure, which gave 262 mg (72% yield, 92% pure) of the target compound.

LC-MS (Method 15): $R_t$=0.65 min; m/z=297.21 $(M+H)^+$
$^1$H NMR (300 MHz, DMSO-d$_6$) δ [ppm]=2.40 (s, 3H), 2.50 (s, 3H), 5.41 (s, 2H), 6.56 (d, 1H), 7.37-7.56 (m, 6H), 12.21 (br.s, 1H).

Example 140A rac-[1-({[7-(Benzyloxy)-2,5-dimethylpyrazolo[1,5-a]pyridin-3-yl]carbonyl}amino)-2-methylpentan-2-yl]carbamic Acid tert-butyl Ester

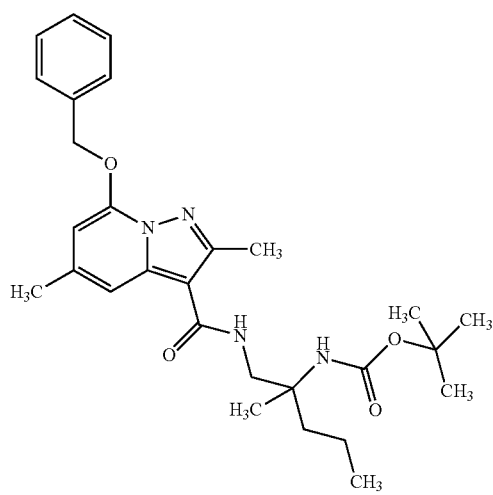 [SMILES: CCCC(C)(CNC(=O)c1c(C)nn2c(OCc3ccccc3)cc(C)cc12)NC(=O)OC(C)(C)C]

A solution of 240 mg (0.81 mmol) of 7-benzyloxy-2,5-dimethylpyrazolo[1,5-a]pyridine-3-carboxylic acid (Example 139A) in 12 ml of tetrahydrofuran was admixed with 132 mg (0.97 mmol) of 1-hydroxy-7-azabenzotriazole and 186 mg (0.97 mmol) of 1-(3-dimethylaminopropyl)-3-ethylcarbodiimide hydrochloride. The reaction mixture was stirred at room temperature for 10 minutes. The resulting mixture was admixed with 0.422 ml (2.43 mmol) of N,N-diisopropylethylamine and 210 mg (0.97 mmol) of rac-(1-aminomethyl-1-methylbutyl)carbamic acid tert-butyl ester from Example 152A. The mixture was stirred at room temperature for a further 18 hours, and the contents were then concentrated under reduced pressure. The residue was partitioned between dichloromethane and water. The organic phase was removed and washed with water and aqueous sodium chloride solution, dried over sodium sulphate, filtered and concentrated under reduced pressure. The residue was purified by flash chromatography using a prepacked silica gel cartridge (mobile phase: cyclohexane/ethyl acetate, gradient 0% to 50%), which gave 370 mg (65% yield, 71% pure) of the target compound, which was used in the next step without further purification.

LC-MS (Method 15): $R_t$=1.36 min; m/z=495.39 $(M+H)^+$

Example 141A rac-(1-{[(7-Hydroxy-2,5-dimethylpyrazolo[1,5-a]pyridin-3-yl)carbonyl]amino}-2-methylpentan-2-yl)carbamic Acid tert-butyl Ester

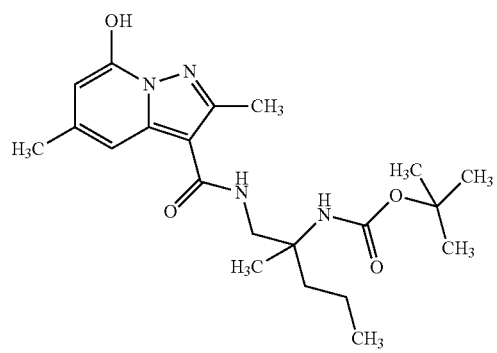 [SMILES: CCCC(C)(CNC(=O)c1c(C)nn2c(O)cc(C)cc12)NC(=O)OC(C)(C)C]

A solution of 207 mg (0.418 mmol) of rac-[1-{[7-benzyloxy-2,5-dimethylpyrazolo[1,5-a]pyridine-3-carbonyl]amino}methyl}-1-methylbutyl)carbamic acid tert-butyl ester (Example 140A) in 6 ml of absolute ethanol was admixed with 47 mg of palladium on charcoal (loading 10% by weight, activated) and 1.3 ml of cyclohexene. The reaction mixture was heated to reflux under an argon atmosphere for 2.5 hours. The resulting mixture was cooled to room temperature, filtered through a layer of Celite and concentrated under reduced pressure, which gave 206 mg (99% yield, 81% pure) of the target compound.

LC-MS (Method 15): $R_t$=0.84 min; m/z=405.35 $(M+H)^+$

Example 142A rac-[1-[({2,5-Dimethyl-7-[4,4,4-trifluoro-3-(trifluoromethyl)butoxy]pyrazolo[1,5-a]pyridin-3-yl}carbonyl)amino]-2-methylpentan-2-yl}carbamic Acid tert-butyl Ester

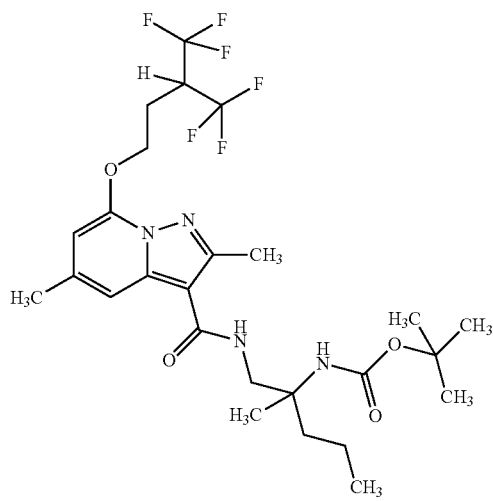 [SMILES: CCCC(C)(CNC(=O)c1c(C)nn2c(OCCC(C(F)(F)F)C(F)(F)F)cc(C)cc12)NC(=O)OC(C)(C)C]

A solution of 40 mg (0.10 mmol) of rac-[1-{[7-hydroxy-2,5-dimethylpyrazolo[1,5-a]pyridine-3-carbonyl)amino]}-1-methylbutyl)carbamic acid tert-butyl ester (Example 141A) in 1 ml of DMF was admixed with 65 mg (0.2 mmol) of caesium carbonate and 78 mg (0.3 mmol) of 4-bromo-1,1,1-trifluoro-2-(trifluoromethyl)butane (CAS: 203303-02-0). The reaction mixture was stirred at room temperature for 18 hours. The solvent was evaporated off under reduced pressure. The residue was partitioned between dichloromethane and water, the phases were separated and the organic phase was concentrated under reduced pressure, which gave 55 mg (51% yield, 54% pure) of the target compound, which was used in the next step without further purification.

LC-MS (Method 15): $R_t$=1.40 min; m/z=583.37 (M+H)$^+$

Example 143A

2-Bromomethyl-3-fluoropyridine

A solution of 285 mg (2.242 mmol) of (3-fluoropyridin-2-yl)methanol (CAS: 31181-79-0) in dry dichloromethane (9 ml) in an ice-water bath and under an argon atmosphere was admixed with 882 mg (3.36 mmol) of triphenylphosphine and 1.12 g (3.36 mmol) of tetrabromomethane. The reaction mixture was stirred at room temperature for 22 hours. The solvent was evaporated off and the residue was purified by flash chromatography using a prepacked silica gel cartridge (mobile phase: cyclohexane-ethyl acetate, gradient 15% to 30%), which gave 156 mg (11% yield, 98% pure) of the target compound.

LC-MS (Method 16): $R_t$=0.79 min; m/z=192.01 (M+H)$^+$

Example 144A rac-{1-[({7-[(3-Fluoropyridin-2-yl)methoxy]-2,5-dimethylpyrazolo[1,5-a]pyridin-3-yl}carbonyl)amino]-2-methylpentan-2-yl}carbamic Acid tert-butyl Ester

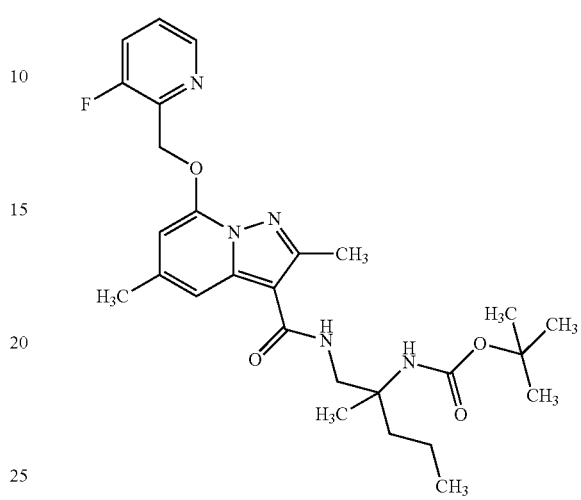

A solution of 49 mg (0.12 mmol) of rac-[1-{[7-hydroxy-2,5-dimethylpyrazolo[1,5-a]pyridine-3-carbonyl)amino]}-1-methylbutyl)carbamic acid tert-butyl ester (Example 141A) in 2.1 ml of DMF was admixed with 78 mg (0.24 mmol) of caesium carbonate and 69 mg (0.360 mmol) of 2-bromomethyl-3-fluoropyridine (Example 143A). The reaction mixture was stirred at room temperature for 18 hours. The solvent was evaporated off under reduced pressure and the residue was partitioned between dichloromethane and water. The organic phase was removed and concentrated under reduced pressure. The residue was purified by preparative HPLC chromatography (Method 21), which gave 21 mg (33% yield, 96% pure) of the target compound.

LC-MS (Method 15): $R_t$=1.22 min; m/z=514.34 (M+H)$^+$

Example 145A

4-Bromo-2-[(2,6-difluorobenzyl)oxy]pyridine

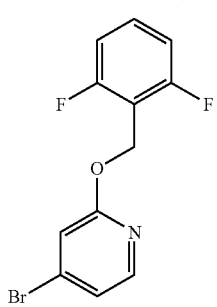 [SMILES: Fc1cccc(F)c1COc1cc(Br)ccn1]

15.5 ml (15.5 mmol) of a 1 M solution of potassium tert-butoxide in tetrahydrofuran was added dropwise at 0° C. to a solution of 1.72 ml (15.5 mmol) of (2,6-difluorophenyl)methanol and 1.6 ml (15.5 mmol) of 4-bromo-2-fluoropyridine in 50 ml of anhydrous tetrahydrofuran. The reaction mixture was stirred at room temperature for 18 h. The reaction mixture was partitioned between ethyl acetate and water. The organic phase was removed and washed with water and saturated aqueous sodium chloride solution, dried over sodium sulphate, filtered and concentrated. The residue was purified by chromatography on silica gel (40 g silica gel cartridge, mobile phase: cyclohexane/ethyl acetate, gradient 0% to 100%). This gave 4.12 g of the target compound (88% of theory).

LC-MS (Method 19): $R_t$=4.17 min; m/z=300 and 302 (M+H)⁺

Example 146A

4-Cyclopropyl-2-[(2,6-difluorobenzyl)oxy]pyridine

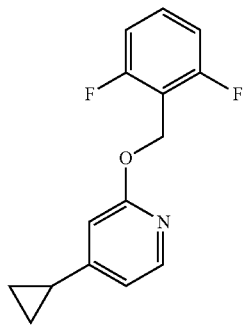 [SMILES: Fc1cccc(F)c1COc1cc(C2CC2)ccn1]

A mixture of 500 mg (1.66 mmol) of 4-bromo-2-[(2,6-difluorobenzyl)oxy]pyridine (Example 145A), 365 µl (2.0 mmol) of 2-cyclopropyl-4,4,5,5-tetramethyl-1,3,2-dioxaborolane, 139 mg (0.17 mmol) of 1,1'-bis(diphenylphosphino)ferrocenepalladium(II) dichloride-dichloromethane complex and 1.63 g (5.0 mmol) of caesium carbonate in 0.5 ml of water and 4 ml of dioxane was degassed with argon for 5 min and stirred in a sealed tube at 100° C. for 2 h. The reaction mixture was cooled to room temperature and the residue was partitioned between ethyl acetate and water. The organic phase was removed and washed with saturated aqueous sodium chloride solution, dried over sodium sulphate, filtered and concentrated. The residue was purified by chromatography on silica gel (40 g silica gel cartridge, mobile phase: methanol/ethyl acetate, gradient 0% to 25%). This gave 350 mg of the target compound (80% of theory).

LC-MS (Method 19): $R_t$=3.93 min; m/z=262 (M+H)⁺

Example 147A

1-Amino-4-cyclopropyl-2-[(2,6-difluorobenzyl)oxy]pyridinium 2,4,6-trimethylbenzenesulphonate

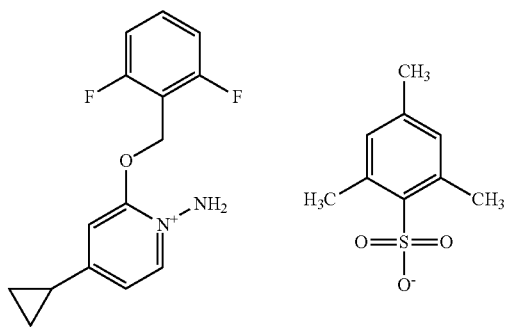

767 mg (2.7 mmol) of O-(2-mesitylenesulphonyl)acetohydroxamic acid ethyl ester was added in portions to a precooled mixture of 1.4 ml of trifluoroacetic acid and 0.2 ml of water at −5° C. The resulting mixture was stirred at −5° C. for 1.5 h and diluted with 10 ml of ice/water. The mixture was extracted with 4 ml of dichloromethane. The organic phase was dried over saturated aqueous potassium carbonate solution, filtered and added to a precooled solution of 470 mg (1.8 mmol) of 4-cyclopropyl-2-[(2,6-difluorobenzyl)oxy]pyridine (Example 146A) in 4 ml of dichloromethane at 5° C. The mixture was stirred at room temperature for 18 h and then concentrated. The residue was poured into 100 ml of diethyl ether, filtered, washed with diethyl ether and dried overnight. This gave 543 mg of the target compound (63% of theory).

LC-MS (Method 19): $R_t$=0.31, 1.85 and 2.00 min; m/z=277 (M+H)⁺

Example 148A

5-Cyclopropyl-7-[(2,6-difluorobenzyl)oxy]-2-methylpyrazolo[1,5-a]pyridine-3-carboxylic Acid ethyl Ester

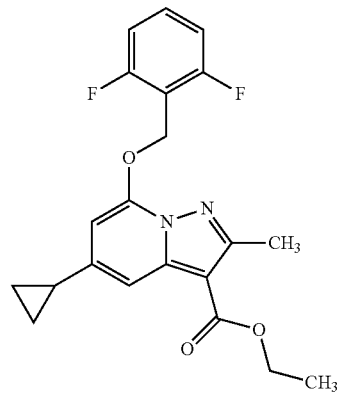 [SMILES: CCOC(=O)c1c(C)nn2c(OCc3c(F)cccc3F)cc(C3CC3)cc12]

468 mg (3.4 mmol) of potassium carbonate were added to a mixture of 264 µl (2.3 mmol) of ethyl but-2-ynoate and 540 mg (1.1 mmol) of 1-amino-4-cyclopropyl-2-[(2,6-difluorobenzyl)oxy]pyridinium 2,4,6-trimethylbenzenesulphonate (Example 147A) in 10 ml of DMF. The reaction mixture was stirred at room temperature for 2 h and then poured into 25 ml of water precooled to 5° C. The precipitate was filtered off, washed with water and dried.

This gave 138 mg of the target compound (31% of theory).

LC-MS (Method 19): Rt=3.87 min; m/z=387 (M+H)⁺

The filtrate was extracted with ethyl acetate (×2). The combined organic extracts were washed with water and saturated aqueous sodium chloride solution, dried over sodium sulphate, filtered and concentrated. The residue was purified by chromatography on silica gel (40 g silica gel cartridge, mobile phase: methanol/ethyl acetate, gradient 0% to 25%). This gave a further 48 mg of the target compound (11% of theory).

LC-MS (Method 19): $R_t$=3.87 min; m/z=387 (M+H)⁺

Example 149A

5-Cyclopropyl-7-[(2,6-difluorobenzyl)oxy]-2-methylpyrazolo[1,5-a]pyridine-3-carboxylic Acid

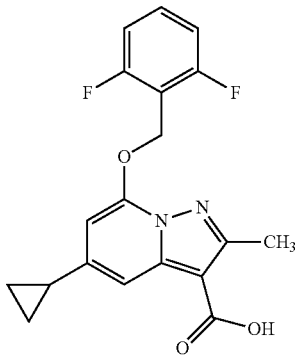 [SMILES: Cc1nn2c(OCc3c(F)cccc3F)cc(C3CC3)cc2c1C(=O)O]

1.8 ml (1.8 mmol) of a 1 M aqueous solution of sodium hydroxide were added to a solution of 180 mg (0.47 mmol) of 5-cyclopropyl-7-(2,6-difluorobenzyloxy)-2-methylpyrazolo[1,5-a]pyridine-3-carboxylic acid ethyl ester (Example 148A) in 18 ml of methanol. The reaction was stirred at reflux for 18 h and concentrated under reduced pressure. The residue was taken up in 4 ml of tetrahydrofuran, and 70 mg (0.55 mmol) of potassium trimethylsilanolate were added. The reaction mixture was stirred at 65° C. for 18 h and concentrated under reduced pressure, which gave the target compound, which was used directly in the next step.

LC-MS (Method 19): $R_t$=3.33 min; m/z=359 (M+H)$^+$

Example 150A rac-{1-[({5-Cyclopropyl-7-[(2,6-difluorobenzyl)oxy]-2-methylpyrazolo[1,5-a]pyridin-3-yl}carbonyl)amino]-2-methylpentan-2-yl}carbamic Acid tert-butyl Ester

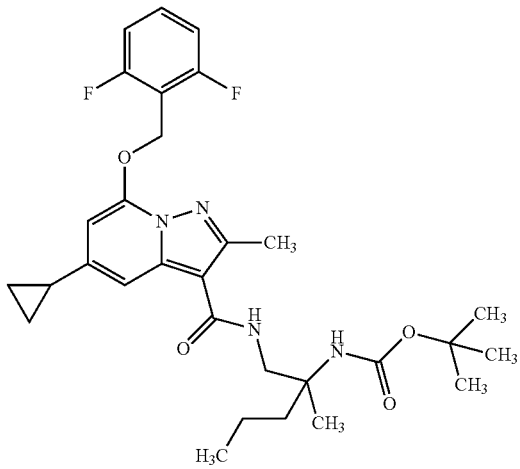 [SMILES: CCCC(C)(CNC(=O)c1c(C)nn2c(OCc3c(F)cccc3F)cc(C3CC3)cc12)NC(=O)OC(C)(C)C]

76 mg (0.6 mmol) of 1-hydroxy-7-azabenzotriazole and 107 mg (0.6 mmol) of 1-(3-dimethylaminopropyl)-3-ethylcarbodiimide hydrochloride were added to a solution of 167 mg (0.5 mmol) of 5-cyclopropyl-7-[(2,6-difluorobenzyl)oxy]-2-methylpyrazolo[1,5-a]pyridine-3-carboxylic acid (Example 149A), 244 µl (1.4 mmol) of N,N-diisopropylethylamine and 121 mg (0.6 mmol) of rac-(1-amino-2-methylpentan-2-yl)carbamic acid tert-butyl ester from Example 152A in 5 ml of tetrahydrofuran. The mixture was stirred at room temperature for 18 h and concentrated under reduced pressure. The residue was partitioned between ethyl acetate and water. The organic phase was removed and washed with water and saturated aqueous sodium chloride solution, dried over sodium sulphate, filtered and concentrated. The residue was purified by chromatography on silica gel (40 g silica gel cartridge, mobile phase: cyclohexane/ethyl acetate, gradient 0% to 100%). This gave 125 mg of the target compound (48% of theory).

LC-MS (Method 26): $R_t$=4.31 min; m/z=557 (M+H)$^+$ $^1$H NMR (400 MHz, DMSO-$d_6$): δ [ppm]=0.80-0.86 (m, 2H), 0.94 (dd, 3H), 1.04 (ddd, 2H), 1.25 (s, 3H), 1.30-1.40 (m, 2H), 1.42 (s, 9H), 1.56 (ddd, 1H), 1.73 (ddd, 1H), 1.91-1.99 (m, 1H), 2.68 (s, 3H), 3.65-3.79 (m, 2H), 4.63 (s, 1H), 5.46 (s, 2H), 6.06 (d, 1H), 6.95 (dd, 2H), 7.37 (tdd, 1H), 7.56 (d, 1H).

Example 151A rac-tert-Butyl (2-cyanopentan-2-yl)carbamate-2-methylpropan-2-ol

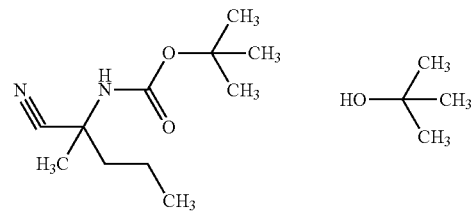

64.21 g (294.18 mmol) of di-tert-butyl dicarbonate were initially charged in a round-bottom flask, and 30 g (267.44 mmol) of rac-2-amino-2-methylpentanenitrile were added very gradually at RT (internal thermometer, maximum temperature 30° C.), and stirring of the mixture was continued at room temperature overnight. The reaction mixture was admixed with dichloromethane and washed twice with 1 N sodium hydroxide solution. The organic phase was dried over sodium sulphate, filtered and concentrated (at bath temperature 30° C.). 76.33 g (quantitative yield) of the target compound were obtained.

Example 152A rac-tert-Butyl (1-amino-2-methylpentan-2-yl)carbamate

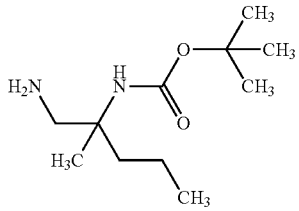

61.0 g (212.98 mmol) of rac-tert-butyl (2-cyanopentan-2-yl)carbamate-2-methylpropan-2-ol from Example 151A were dissolved in 618 ml of 7 N ammoniacal methanol and admixed under argon with 66 g of Raney nickel (50% aqueous slurry). Subsequently, the reaction mixture was hydrogenated in an autoclave at 20-30 bar overnight. The reaction mixture was filtered through Celite, rinsed well with methanol and concentrated. 43.70 g (95% of theory) of the target compound were obtained.

LC-MS (Method 7): $R_t$=1.95 min
MS (ESIpos): m/z=217 (M+H)$^+$

Example 153A ent-Benzyl {1-[({2,5-dimethyl-7-[(2,3,6-trifluorobenzyl)oxy]pyrazolo[1,5-a]pyridin-3-yl}carbonyl)amino]-5,5,5-trifluoro-2-methylpentan-2-yl}carbamate trifluoroacetate (Enantiomer B)

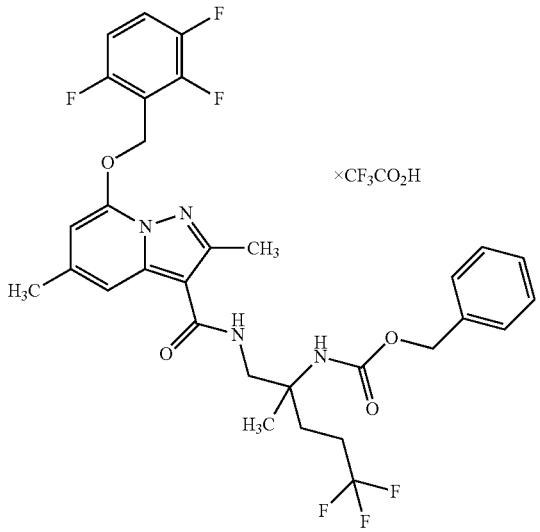 [SMILES: Cc1cc(OCc2c(F)ccc(F)c2F)n2nc(C)c(C(=O)NCC(C)(CCC(F)(F)F)NC(=O)OCc3ccccc3)c2c1]

100 mg (0.25 mmol; purity about 87%) of 2,5-dimethyl-7-[(2,3,6-trifluorobenzyl)oxy]pyrazolo[1,5-a]pyridine-3-carboxylic acid from Example 10A, 103 mg (0.32 mmol; purity about 95%) of ent-benzyl (1-amino-5,5,5-trifluoro-2-methylpentan-2-yl)carbamate (enantiomer B) from Example 65A and 123 mg (0.32 mmol) of HATU were initially charged in 0.8 ml of DMF and stirred at RT for 10 min. Subsequently, 0.22 ml (0.11 mmol) of N,N-diisopropylethylamine were added and the mixture was stirred at RT for 1 h. The reaction solution was admixed with acetonitrile/water/TFA and purified by means of preparative HPLC (RP18 column, eluent: acetonitrile/water gradient with addition of 0.1% TFA). The product fractions were concentrated on a rotary evaporator. 61 mg (25% of theory; 75% purity) of the title compound were obtained.
LC-MS (Method 2): $R_t$=1.23 min
MS (ESpos): m/z=637 (M-TFA+H)$^+$ Example 154A 4-Methyl-2-[(2,3,6-trifluorobenzyl)oxy]pyridine

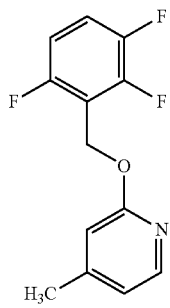 [SMILES: Cc1ccnc(OCc2c(F)ccc(F)c2F)c1]

A mixture of 8.32 g (36.96 mmol) of 2-(bromomethyl)-1,3,4-trifluorobenzene and 4.84 g (44.35 mmol) of 2-hydroxy-4-methylpyridine [CAS No.: 13466-41-6] was dissolved in 227 ml of THF. The solution was admixed with 12.23 g (44.35 mmol) of silver carbonate and the mixture was heated to reflux with exclusion of light overnight. Subsequently, the reaction mixture was filtered through kieselguhr and washed with ethyl acetate, and the filtrate was concentrated. The crude product was purified by means of silica gel chromatography (eluent:cyclohexane/dichloromethane gradient: 10/0 to 1/1). 1.45 g of the title compound were obtained (15% of theory).
LC-MS (Method 22): $R_t$=1.44 min
MS (ESIpos): m/z=254 (M+H)$^+$
$^1$H NMR (400 MHz, DMSO-$d_6$): δ [ppm]=2.27 (s, 3H), 5.38 (s, 2H), 6.67 (s, 1H), 6.87 (d, 1H), 7.16-7.25 (m, 1H), 7.51-7.62 (m, 1H), 8.05 (d, 1H).

Example 155A

1-Amino-4-methyl-2-[(2,3,6-trifluorobenzyl)oxy]pyridinium 2,4,6-trimethylbenzenesulphonate

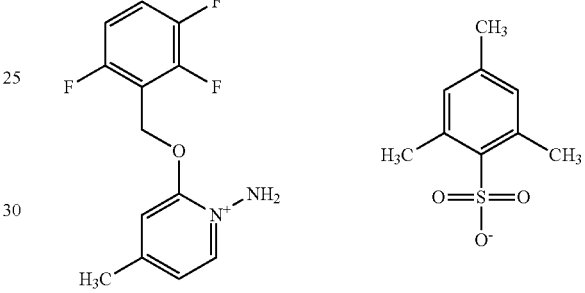

1) A mixture of 5.8 ml (75.82 mmol) of trifluoroacetic acid and 0.59 ml of water was cooled to −5° C. At this temperature, 3.25 g (11.37 mmol) of ethyl (1E)-N-[(mesitylsulphonyl)oxy]ethanimidoate [CAS No: 38202-27-6] were added in portions. After 1.5 h, the mixture was added to 51 ml of ice-water and extracted with 41 ml of dichloromethane. The organic phase was dried over sodium sulphate and a frit was used to filter the sodium sulphate off. The resulting solution of O-(2-mesitylenesulphonyl)hydroxylamine (MSH) was added dropwise directly to a solution of 1.92 g (7.58 mmol) of 4-methyl-2-[(2,3,6-trifluorobenzyl)oxy]pyridine from Example 154A in 5.1 ml of dichloromethane at 0° C. The mixture was stirred at RT for 2 h.

2) Once again, a mixture of 5.8 ml (75.82 mmol) of trifluoroacetic acid and 0.59 ml of water was cooled down to −5° C. At this temperature, 3.25 g (11.37 mmol) of ethyl (1E)-N-[(mesitylsulphonyl)oxy]ethanimidoate [CAS No: 38202-27-6] were added in portions. After 1.5 h, the mixture was added to 51 ml of ice-water and extracted with 41 ml of dichloromethane. The organic phase was dried over sodium sulphate and a frit was used to filter the sodium sulphate off. The resulting solution of O-(2-mesitylenesulphonyl)hydroxylamine (MSH) was added dropwise directly to the reaction solution (described in 1)).

Stirring of the reaction mixture continued at RT overnight. Subsequently, 250 ml of diethyl ether were added dropwise, and the precipitate obtained was filtered off, washed with diethyl ether and dried. 2.5 g of the title compound were isolated (69% of theory, 98% purity).
LC-MS (Method 3): $R_t$=1.28 and 1.38 min (double peak)
MS (ESpos): m/z (peak at 1.28 min)=269 (M)$^+$ of the cation $^1$H NMR (400 MHz, DMSO-d$_6$): δ [ppm]=2.17 (s, 3H), 2.46-2.57 (s, 3H and s, 6H obscured by the solvent signal), 5.68 (s, 2H), 6.74 (s, 2H), 7.29-7.36 (m, 1H), 7.37-7.44 (m, 3H), 7.67-7.78 (m, 1H), 7.85 (s, 1H), 8.44 (d, 1H).

Example 156A

Methyl 2-cyclopropyl-5-methyl-7-[(2,3,6-trifluorobenzyl)oxy]pyrazolo[1,5-a]pyridine-3-carboxylate

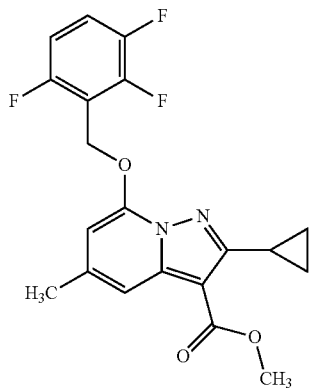 [SMILES: COC(=O)c1c(C2CC2)nn2c(OCc3c(F)ccc(F)c3F)cc(C)cc12]

1.45 g (3.00 mmol, purity 98%) of 1-amino-4-methyl-2-[(2,3,6-trifluorobenzyl)oxy]pyridinium 2,4,6-trimethylbenzenesulphonate from Example 155A were dissolved in 9.7 ml of DMF and admixed with 670 mg (5.40 mmol) of methyl 3-cyclopropylprop-2-ynoate. 747 mg (5.40 mmol) of potassium carbonate was added and the mixture was stirred at RT for 3 h. Subsequently, the mixture was poured onto 73 ml of water and stirred briefly, and the precipitated solids were filtered off, washed with water and dried. 462 mg of the title compound were obtained (33% of theory; 85% purity).

LC-MS (Method 7): R$_t$=2.90 min
MS (ESIpos): m/z=391 (M+H)$^+$

Example 157A

2-Cyclopropyl-5-methyl-7-[(2,3,6-trifluorobenzyl)oxy]pyrazolo[1,5-a]pyridine-3-carboxylic Acid

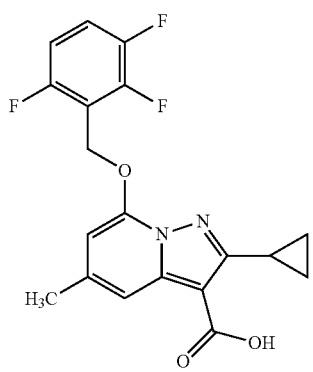 [SMILES: Cc1cc(OCc2c(F)ccc(F)c2F)n2nc(C3CC3)c(C(=O)O)c2c1]

A solution of 462 mg (1.01 mmol; purity 85%) of methyl 2-cyclopropyl-5-methyl-7-[(2,3,6-trifluorobenzyl)oxy]pyrazolo[1,5-a]pyridine-3-carboxylate from Example 156A in 10.5 ml of dioxane and 3 ml of DMSO was admixed with 5.55 ml (11.10 mmol) of 2 N sodium hydroxide solution, and the mixture was stirred at 100° C. for 6.5 h. Another 1 ml (2 mmol) of 2 N sodium hydroxide solution was added and the mixture was stirred at 100° C. for a further 2.5 h. The reaction solution was cooled down to 0° C. and adjusted to pH 2 with 1 N hydrochloric acid. The solids that precipitated out were stirred for 30 min, filtered off and dried under high vacuum. 300 mg of the title compound were obtained (74% of theory, 93% purity) and were converted without further purification.

LC-MS (Method 2): R$_t$=1.00 min
MS (ESIpos): m/z=377 (M+H)$^+$ $^1$H NMR (400 MHz, DMSO-d$_6$): δ [ppm]=0.87-0.99 (m, 4H), 2.42 (s, 3H), 2.74-2.82 (m, 1H), 5.50 (s, 2H), 6.62 (s, 1H), 7.25-7.33 (m, 1H), 7.50 (s, 1H), 7.62-7.73 (m, 1H), 12.29 (br. s, 1H).

Example 158A ent-Benzyl {1-[({2-cyclopropyl-5-methyl-7-[(2,3,6-trifluorobenzyl)oxy]pyrazolo[1,5-a]pyridin-3-yl}carbonyl)amino]-2-methylpentan-2-yl}carbamate trifluoroacetate (Enantiomer B)

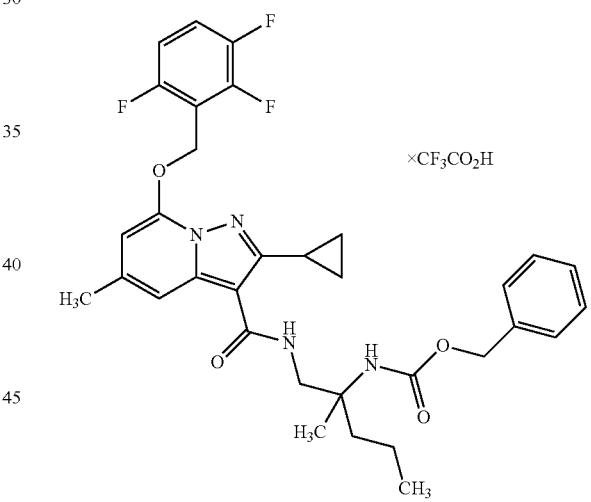

90 mg (0.22 mmol; 93% purity) of 2-cyclopropyl-5-methyl-7-[(2,3,6-trifluorobenzyl)oxy]pyrazolo[1,5-a]pyridine-3-carboxylic acid from Example 157A, 110 mg (0.29 mmol) of HATU and 0.19 ml (1.11 mmol) of N,N-diisopropylethylamine were initially charged in 0.74 ml of DMF, and the mixture was stirred at RT for 10 min. Subsequently, 82 mg (0.29 mmol; about 88% purity) of ent-benzyl (1-amino-2-methylpentan-2-yl)carbamate (enantiomer B) from Example 20A were added and the mixture was stirred at RT for 1 h. The reaction solution was admixed with water/TFA and purified by means of preparative HPLC (RP18 column, eluent:acetonitrile/water gradient with addition of 0.1% TFA). The product fractions were concentrated on a rotary evaporator. 82 mg (51% of theory) of the title compound were obtained.

LC-MS (Method 2): R$_t$=1.30 min
MS (ESpos): m/z=609 (M-TFA+H)$^+$

Example 159A ent-Benzyl {1-[({2-cyclopropyl-5-methyl-7-[(2,3,6-trifluorobenzyl)oxy]pyrazolo[1,5-a]pyridin-3-yl}carbonyl)amino]-5,5,5-trifluoro-2-methylpentan-2-yl}carbamate trifluoroacetate (Enantiomer B)

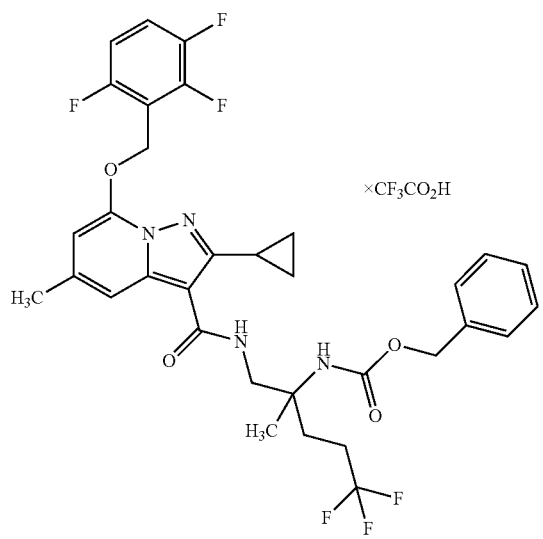 [SMILES: Cc1cc(OCc2c(F)ccc(F)c2F)n2nc(C3CC3)c(C(=O)NCC(C)(CCC(F)(F)F)NC(=O)OCc3ccccc3)c2c1]

90 mg (0.22 mmol; 93% purity) of 2-cyclopropyl-5-methyl-7-[(2,3,6-trifluorobenzyl)oxy]pyrazolo[1,5-a]pyridine-3-carboxylic acid from Example 157A, 110 mg (0.29 mmol) of HATU and 0.19 ml (1.11 mmol) of N,N-diisopropylethylamine were initially charged in 0.74 ml of DMF, and the mixture was stirred at RT for 10 min. Subsequently, 93 mg (0.29 mmol; about 95% purity) of ent-benzyl (1-amino-5,5,5-trifluoro-2-methylpentan-2-yl)carbamate (enantiomer B) from Example 65A were added and the mixture was stirred at RT for 1 h. The reaction solution was admixed with water/TFA and purified by means of preparative HPLC (RP18 column, eluent:acetonitrile/water gradient with addition of 0.1% TFA). The product fractions were concentrated on a rotary evaporator. 79 mg (45% of theory) of the title compound were obtained.

LC-MS (Method 2): $R_t$=1.29 min
MS (ESpos): m/z=663 (M-TFA+H)$^+$

Example 160A

2-[(2,6-Difluorobenzyl)oxy]-4-methoxypyridine

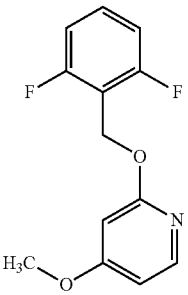 [SMILES: COc1ccnc(OCc2c(F)cccc2F)c1]

To a solution of 3.5 g (27.53 mmol) of 2-fluoro-4-methoxypyridine (CAS: 175965-83-0) and 3.97 g (27.53 mmol) of 2,6-difluorobenzyl alcohol in 97 ml of dry tetrahydrofuran, cooled beforehand to 0° C., were added dropwise 27.5 ml (27.53 mmol) of a 1M solution of potassium tert-butoxide in tetrahydrofuran. The resulting mixture was stirred at room temperature for 18 hours. The solvent was evaporated off and the residue was partitioned between water and ethyl acetate. The organic phase was removed, washed with water and aqueous sodium chloride solution, dried over sodium sulphate, filtered and concentrated under reduced pressure, which gave 5.77 g (66% yield, 79% purity) of the product.

LC-MS (Method 15): $R_t$=1.17 min; m/z=252.14 (M+H)$^+$
$^1$H NMR (300 MHz, DMSO-d$_6$) δ [ppm]=3.78 (s, 3H), 5.35 (s, 2H), 6.38 (d, J=2.17 Hz, 1H), 6.61-6.64 (m, 1H), 7.16 (m, 2H), 7.46-7.54 (m, 1H), 7.99 (d, J=5.96 Hz, 1H).

Example 161A

1-Amino-2-[(2,6-difluorobenzyl)oxy]-4-methoxypyridinium 2,4,6-trimethylbenzenesulphonate

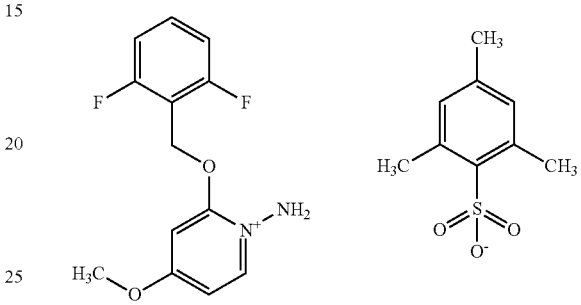

7.76 g (27.2 mmol) of O-(2-mesitylenesulphonyl)acetohydroxamic acid ethyl ester (CAS 38202-27-6) were added in portions to a precooled mixture of 14.0 ml of trifluoroacetic acid and 2.5 ml of water at −5° C. The resulting mixture was stirred at −5° C. for 1.5 hours and diluted with 170 ml of ice/water. The mixture was extracted with 110 ml of dichloromethane. The organic phase was dried over sodium sulphate, filtered and added to a precooled solution of 5.77 g (18.13 mmol, 80% pure) of 2-[(2,6-difluorobenzyl)oxy]-4-methoxypyridine (Example 160A) in 60 ml of dichloromethane at 0° C. The mixture was stirred at room temperature for 18 hours and added dropwise to a stirred solution of diethyl ether (500 ml). The mixture was stirred for a further hour, in the course of which the solvent was allowed to evaporate off. The resulting precipitate was filtered off, washed with 100 ml of diethyl ether and dried under reduced pressure, which gave 3.99 g (34% yield, 72% purity) of product.

LC-MS (Method 15): $R_t$=0.60 min; m/z=267.18 (M+H)$^+$

Example 162A

7-[(2,6-Difluorobenzyl)oxy]-5-methoxy-2-methylpyrazolo[1,5-a]pyridine-3-carboxylic Acid ethyl Ester

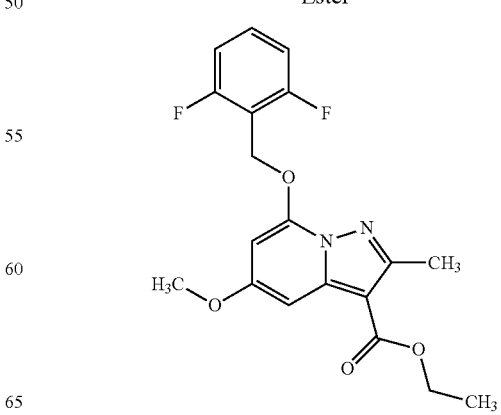

A solution of 3.99 g (6.15 mmol, 72% purity) of 1-amino-2-[(2,6-difluorobenzyl)oxy]-4-methoxypyridinium 2,4,6-trimethylbenzenesulphonate (Example 161A) in 70 ml of N,N-dimethylformamide was admixed with 1.38 g (12.31 mmol) of ethyl 2-butynoate (CAS: 4341-76-8) and 2.55 g (18.46 mmol) of potassium carbonate. The reaction mixture was stirred at room temperature for 18 hours and added dropwise to 150 ml of water. The resulting precipitate was filtered off and dried under reduced pressure, which gave 477 mg (12% yield, 57% purity) of product.

LC-MS (Method 15): $R_t$=1.24 min; m/z=377.54 (M+H)$^+$

Example 163A

7-[(2,6-Difluorobenzyl)oxy]-5-methoxy-2-methylpyrazolo[1,5-a]pyridine-3-carboxylic Acid

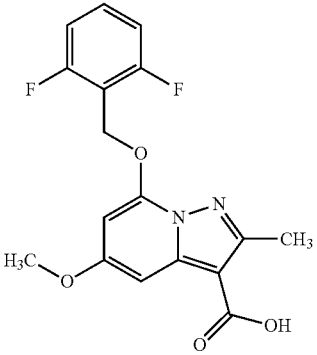 [SMILES: COc1cc(OCc2c(F)cccc2F)n2nc(C)c(C(=O)O)c2c1]

A solution of 375 mg (0.57 mmol, 57% purity) of 7-[(2,6-difluorobenzyl)oxy]-5-methoxy-2-methylpyrazolo[1,5-a]pyridine-3-carboxylic acid ethyl ester (Example 162A) in 8.0 ml of 1,4-dioxane was admixed with 6.0 ml of aqueous 2M sodium hydroxide solution. The mixture was stirred at 100° C. for a further 18 hours. The reaction mixture was concentrated under reduced pressure. The residue was admixed with 4 ml of acetonitrile and 2 ml of water, followed by 0.8 ml of trifluoroacetic acid. The resulting precipitate was filtered off and dried under reduced pressure, which gave 172 mg (65% yield, 75% purity) of product.

LC-MS (Method 15): $R_t$=0.64 min; m/z=349.11 (M+H)$^+$
$^1$H NMR (300 MHz, DMSO-$d_6$) δ [ppm]=2.45 (s, 3H), 3.90 (s, 3H), 5.46 (s, 2H), 6.47 (d, J=2.43 Hz, 1H), 7.03 (d, J=2.39 Hz, 1H), 7.23-7.30 (m, 2H), 7.57-7.65 (m, 1H), 12.18 (br. s., 1H).

Example 164A rac-{1-[({7-[(2,6-Difluorobenzyl)oxy]-5-methoxy-2-methylpyrazolo[1,5-a]pyridin-3-yl}carbonyl)amino]-2-methylpentan-2-yl}carbamic Acid tert-butyl Ester

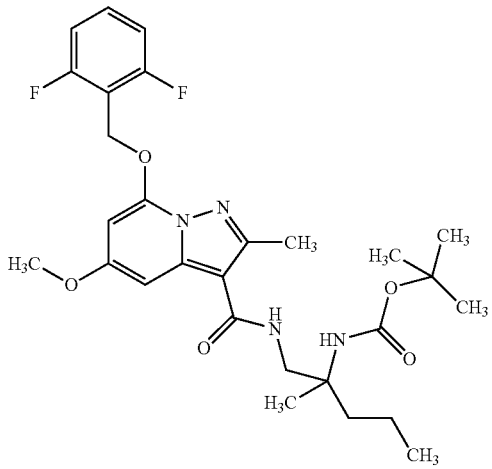 [SMILES: CCCC(C)(CNC(=O)c1c(C)nn2c(OCc3c(F)cccc3F)cc(OC)cc12)NC(=O)OC(C)(C)C]

A solution of 170 mg (0.366 mmol, 75% purity) of 7-[(2,6-difluorobenzyl)oxy]-5-methoxy-2-methylpyrazolo[1,5-a]pyridine-3-carboxylic acid (Example 163A) in 8 ml of tetrahydrofuran was admixed with 84 mg (0.44 mmol) of 1-(3-dimethylaminopropyl)-3-ethylcarbodiimide hydrochloride (CAS: 25952-53-8) and 60 mg (0.44 mmol) of 1-hydroxy-7-azabenzotriazole (CAS: 39968-33-7). The solution was stirred at room temperature for 20 minutes. The reaction mixture was admixed with 0.191 ml (1.01 mmol) of N,N-diisopropylethylamine and 158 mg (0.732 mmol) of rac-(1-amino-2-methylpentan-2-yl)carbamic acid tert-butyl ester (Example 152A). The mixture was stirred at room temperature for a further 18 hours, and the reaction mixture was then concentrated under reduced pressure. The residue was partitioned between dichloromethane and water. The organic phase was removed, extracted with a saturated aqueous sodium hydrogencarbonate solution, water and aqueous sodium chloride solution, dried over sodium sulphate, filtered and concentrated under reduced pressure. The remaining residue was purified by flash chromatography using a prepacked silica gel cartridge (eluent:dichloromethane/methanol, gradient 0% to 10%), which gave 120 mg (44% yield, 73% purity) of product.

LC-MS (Method 15): $R_t$=1.33 min; m/z=547.36 (M+H)$^+$

Example 165A

2-[(2,6-Difluorobenzyl)oxy]-4-ethylpyridine

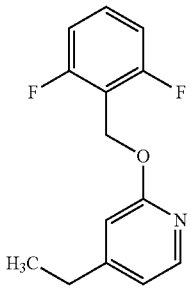 [SMILES: CCc1ccnc(OCc2c(F)cccc2F)c1]

A solution of 3.8 g (9.24 mmol, 73% purity) of 4-bromo-2-[(2,6-difluorobenzyl)oxy]pyridine (Example 145A) in 54 ml of 1,4-dioxane and 13 ml of water was degassed under argon for 10 minutes. The solution was admixed with 9.04 g (27.73 mmol) of caesium carbonate, 0.82 g (11.09 mmol) of ethylboronic acid (CAS: 4433-63-0) and 0.75 g (0.924 mmol) of (1,1)-bis(diphenylphosphino)ferrocenedichloropalladium (II) complex with dichloromethane (CAS: 95464-05-4). The reaction vessel was closed and the contents were stirred at 100° C. for 18 hours. The solvent was evaporated off and the residue was partitioned between water and ethyl acetate. The organic phase was removed and concentrated under reduced pressure. The residue was purified by flash chromatography using a prepacked silica gel cartridge (eluent:cyclohexane/ethyl acetate, gradient 0% to 5%), which gave 1.38 g (41% yield, 69% purity) of product.

LC-MS (Method 15): $R_t$=1.31 min; m/z=250.19 (M+H)$^+$
$^1$H NMR (300 MHz, DMSO-$d_6$) δ [ppm]=1.19 (t, J=7.58 Hz, 3H), 2.58 (q, J=7.63 Hz, 2H), 5.41 (s, 2H), 6.57-6.58 (m, 1H), 6.72-6.75 (m, 1H), 6.91 (t, J=7.45 Hz, 2H), 7.26-7.32 (m, 1H), 8.05 (d, J=5.20 Hz, 1H).

Example 166A

1-Amino-2-[(2,6-difluorobenzyl)oxy]-4-ethylpyridinium 2,4,6-trimethylbenzenesulphonate

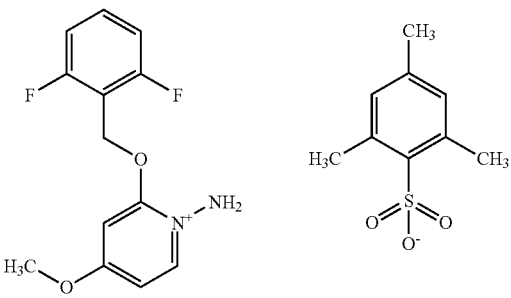

1.74 g (6.08 mmol) of O-(2-mesitylenesulphonyl)acetohydroxamic acid ethyl ester (CAS 38202-27-6) was added in portions to a precooled mixture of 3.1 ml of trifluoroacetic acid and 0.6 ml of water at −5° C. The resulting mixture was stirred at −5° C. for 1.5 hours and diluted with 40 ml of ice/water. The mixture was extracted with 20 ml of dichloromethane. The organic phase was dried over sodium sulphate, filtered and added to a precooled solution of 1.46 g (4.05 mmol, 69% pure) of 2-[(2,6-difluorobenzyl)oxy]-4-ethylpyridine (Example 165A) in 12 ml of dichloromethane at 0° C. The mixture was stirred at room temperature for 18 hours and added dropwise to a stirred solution of diethyl ether (150 ml). The solution was concentrated under reduced pressure, which gave 1.88 g (38% yield, 38% purity) of product, which were used in the next step without further purification.

LC-MS (Method 15): $R_t$=0.73 min; m/z=265.19 (M+H)$^+$

Example 167A

7-[(2,6-Difluorobenzyl)oxy]-5-ethyl-2-methylpyrazolo[1,5-a]pyridine-3-carboxylic Acid ethyl Ester

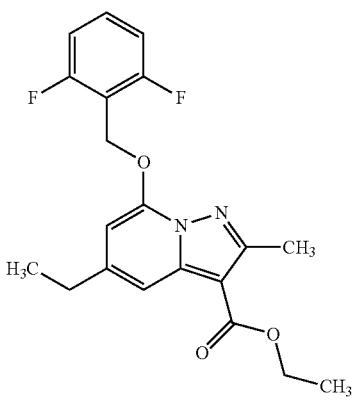 [SMILES: CCOC(=O)c1c(C)nn2c(OCc3c(F)cccc3F)cc(CC)cc12]

A solution of 1.88 g (1.54 mmol, 38% purity) of 1-amino-2-[(2,6-difluorobenzyl)oxy]-4-ethylpyridinium 2,4,6-trimethylbenzenesulphonate (Example 166A) in 12 ml of N,N-Dimethylformamide was admixed with 0.35 g (3.08 mmol) of ethyl 2-butynoate (CAS: 4341-76-8) and 0.64 g (4.61 mmol) of potassium carbonate. The reaction mixture was stirred at room temperature for 3 hours. The solvent was concentrated and the residue was partitioned between water and ethyl acetate. The organic phase was removed, washed with aqueous sodium chloride solution and concentrated under reduced pressure. The residue was purified by flash chromatography using a prepacked silica gel cartridge (eluent:cyclohexane/ethyl acetate, gradient 0% to 10%), which gave 0.29 g (35% yield, 70% purity) of product.

LC-MS (Method 15): $R_t$=1.35 min; m/z=375.26 (M+H)$^+$ $^1$H NMR (300 MHz, CDCl$_3$) δ [ppm]=1.33 (t, J=7.60 Hz, 3H), 1.39-1.45 (m, 3H), 2.66 (s, 3H), 2.65-2.77 (m, 2H), 4.33-4.40 (m, 2H), 5.47 (br. s., 2H), 6.27 (d, J=1.60 Hz, 1H), 6.91-6.98 (m, 2H), 7.32-7.40 (m, 1H), 7.57-7.58 (m, 1H).

Example 168A

7-[(2,6-Difluorobenzyl)oxy]-5-ethyl-2-methylpyrazolo[1,5-a]pyridine-3-carboxylic Acid

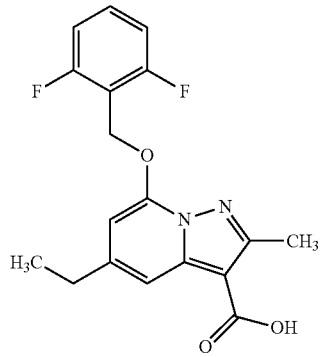 [SMILES: CCc1cc(OCc2c(F)cccc2F)n2nc(C)c(C(=O)O)c2c1]

A solution of 287 mg (0.54 mmol, 70% purity) of 7-[(2,6-difluorobenzyl)oxy]-5-ethyl-2-methylpyrazolo[1,5-a]pyridine-3-carboxylic acid ethyl ester (Example 167A) in 5.5 ml of 1,4-dioxane was admixed with 2.7 ml of aqueous 2M sodium hydroxide solution. The mixture was stirred at 90° C. for a further 18 hours. The reaction mixture was concentrated under reduced pressure. The residue was admixed with water and the pH was adjusted to 7. The resulting precipitate was filtered off and dried under reduced pressure, which gave 280 mg (35% yield, 23% purity) of product, which were used in the next step without purification.

LC-MS (Method 15): $R_t$=0.70 min; m/z=347.21 (M+H)$^+$

Example 169A rac-{1-[({7-[(2,6-Difluorobenzyl)oxy]-5-ethyl-2-methylpyrazolo[1,5-a]pyridin-3-yl}carbonyl)amino]-2-methylpentan-2-yl}carbamic Acid tert-butyl Ester

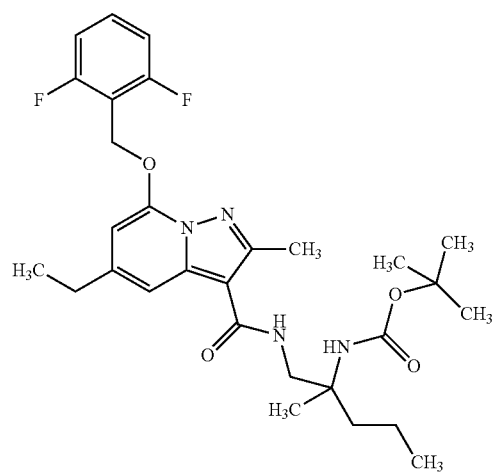 [SMILES: CCCC(C)(CNC(=O)c1c(C)nn2c(OCc3c(F)cccc3F)cc(CC)cc12)NC(=O)OC(C)(C)C]

A solution of 280 mg (0.19 mmol, 23% purity) of 7-[(2,6-difluorobenzyl)oxy]-5-ethyl-2-methylpyrazolo[1,5-a]pyridine-3-carboxylic acid (Example 168A) in 4 ml of tetrahydrofuran was admixed with 43 mg (0.22 mmol) of 1-(3-dimethylaminopropyl)-3-ethylcarbodiimide hydrochloride (CAS: 25952-53-8) and 30 mg (0.22 mmol) of 1-hydroxy-7-azabenzotriazole (CAS: 39968-33-7). The solution was stirred at room temperature for 20 minutes. The reaction mixture was admixed with 0.097 ml (0.56 mmol) of N,N-diisopropylethylamine and 48 mg (0.22 mmol) of rac-(1-amino-2-methylpentan-2-yl)carbamic acid tert-butyl ester (Example 152A). The mixture was stirred at room temperature for a further 24 hours, and the reaction mixture was then concentrated under reduced pressure. The residue was partitioned between dichloromethane and water. The organic phase was removed and concentrated under reduced pressure. The residue was purified by preparative HPLC chromatography (Method 21), which gave 19 mg (19% yield, 95% purity) of product.

LC-MS (Method 15): $R_t$=1.41 min; m/z=545.44 (M+H)$^+$

Example 170A (2S)-2-Amino-2-(2-thienyl)ethanol

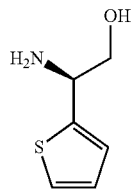

1.59 ml (3.18 mmol) of lithium borohydride (2 M in THF) were initially charged in 2.5 ml of dry THF, 0.80 ml (6.30 mmol) of chlorotrimethylsilane were added at RT and the mixture was stirred at RT for 5 min. Subsequently, 200 mg (1.27 mmol) of (2S)-amino(2-thienyl)acetic acid were added in portions and the reaction mixture was stirred at RT overnight. 2.5 ml of methanol were added dropwise to the reaction mixture, and the mixture was concentrated. The residue was admixed with 1.5 ml of a 20% aqueous potassium hydroxide solution and extracted three times with dichloromethane. The combined organic phases were dried over sodium sulphate, filtered and concentrated. 173 mg of the target compound were obtained (90% of theory).

LC-MS (Method 7): $R_t$=1.13 min; m/z=127 (M-NH$_3$+H)$^+$
$^1$H NMR (400 MHz, DMSO-d$_6$): δ=2.00 (br. s, 2H), 3.28-3.36 (m, 1H; obscured by solvent signal), 3.46-3.56 (m, 1H), 4.08-4.14 (m, 1H), 4.89 (t, 1H), 6.91-6.96 (m, 2H), 7.29-7.34 (m, 1H).

In analogy to Example 170A, the example compounds shown in Table 5A were prepared by reacting lithium borohydride (1.7-2.5 equivalents) and chlorotrimethylsilane (3.4-5 equivalents) with the appropriate amino acids which are commercially available or known from the literature under the reaction conditions described:

TABLE 5A

| Example | IUPAC name/ structure (yield) | Analytical data |
|---|---|---|
| 171A | (2S)-2-Amino-2-(5-methyl-2-furyl)ethanol (88% of theory) | $^1$H NMR (400 MHz, DMSO-d$_6$): δ = 1.65-1.78 (m, 2H), 2.21 (s, 3H), 3.30- |

TABLE 5A-continued

| Example | IUPAC name/ structure (yield) | Analytical data |
|---|---|---|
| | | 3.39 (m, 1H; obscured by solvent signal), 3.51-3.61 (m, 1H), 3.71-3.79 (m, 1H), 4.71 (br. s, 1H), 5.92 (d, 1H), 6.06 (d, 1H). LC-MS (Method 7): $R_t$ = 1.23 min; m/z = 125 (M-NH$_3$ + H)$^+$ |
| 172A | (2R)-2-Amino-2-(5-methyl-2-furyl)ethanol (79% of theory) | $^1$H NMR (400 MHz, DMSO-d$_6$): δ = 1.65-1.77 (m, 2H), 2.21 (s, 3H), 3.30-3.39 (m, 1H; obscured by solvent signal), 3.51-3.61 (m, 1H), 3.71-3.80 (m, 1H), 4.71 (br. s, 1H), 5.92 (d, 1H), 6.06 (d, 1H). LC-MS (Method 7): $R_t$ = 1.24 min; m/z = 125 (M-NH$_3$ + H)$^+$ |

Example 173A tert-Butyl [(1S)-1-{5-[(1S)-1-amino-2-hydroxyethyl]-1,3,4-oxadiazol-2-yl}-2-methylpropyl]carbamate acetate

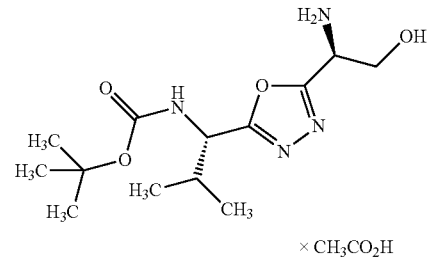 [SMILES: CC(C)[C@H](NC(=O)OC(C)(C)C)c1nnc([C@@H](N)CO)o1]

The target compound can be prepared in two stages analogously to E. Ko et al. Journal of the American Chemical Society 2011, 133, 3, 462-477.

Stage 1: Reaction of tert-butyl [(2S)-1-hydrazino-3-methyl-1-oxobutan-2-yl]carbamate [CAS: 72039-28-2], O-benzyl-N-[(benzyloxy)carbonyl]-L-serine [CAS: 20806-43-3] with 1-ethyl-3-(3-dimethylaminopropyl)carbodiimide hydrochloride (EDC, CAS: 25952-53-8) and then with iodine, triethylamine and triphenylphosphine gives benzyl [(1S)-2-(benzyloxy)-1-(5-{(1S)-1-[(tert-butoxycarbonyl)amino]-2-methylpropyl}-1,3,4-oxadiazol-2-yl)ethyl]carbamate.

Stage 2: Reaction of benzyl [(1S)-2-(benzyloxy)-1-(5-{(1S)-1-[(tert-butoxycarbonyl)amino]-2-methylpropyl}-1,3,4-oxadiazol-2-yl)ethyl]carbamate with hydrogen, palladium/activated carbon in acetic acid or acetic acid/ethanol or acetic acid/methanol at RT, 40° C., 60° C. or 78° C.

LC-MS (Method 7): $R_t$=1.73 min
MS (ESpos): m/z=301 (M–HOAc+H)$^+$

Example 174A tert-Butyl [(1S)-1-(5-{(1S)-1-[({7-[(2,6-difluorobenzyl)oxy]-2,5-dimethylpyrazolo[1,5-a]pyridin-3-yl}carbonyl)amino]-2-hydroxyethyl}-1,3,4-oxadiazol-2-yl)-2-methylpropyl]carbamate trifluoroacetate

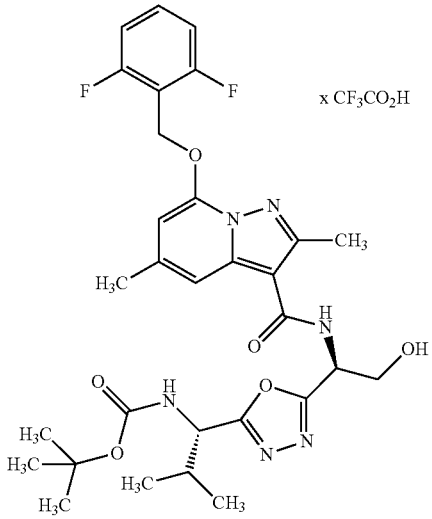 [SMILES: Cc1cc(OCc2c(F)cccc2F)n2nc(C)c(C(=O)N[C@@H](CO)c3nnc([C@@H](NC(=O)OC(C)(C)C)C(C)C)o3)c2c1]

124 mg (0.37 mmol) of 7-[(2,6-difluorobenzyl)oxy]-2,5-dimethylpyrazolo[1,5-a]pyridine-3-carboxylic acid from Example 4A were initially charged together with 184 mg (0.49 mmol) of HATU and 0.52 ml (3.00 mmol) of N,N-diisopropylethylamine in 1.24 ml of DMF, and the mixture was stirred at room temperature for 10 min. Subsequently, 175 mg (0.49 mmol) of tert-butyl [(1S)-1-{5-[(1S)-1-amino-2-hydroxyethyl]-1,3,4-oxadiazol-2-yl}-2-methylpropyl]carbamate acetate from Example 173A were added to the reaction solution and the mixture was stirred at RT for 1 h. Then the mixture was diluted with acetonitrile and water, admixed with TFA and purified by means of preparative HPLC (RP18 column, eluent:acetonitrile/water gradient with addition of 0.1% TFA). 211 mg of the target compound were obtained (73% of theory, 94% purity).

LC-MS (Method 2): $R_t$=1.05 min

MS (ESpos): m/z=615 (M-TFA+H)$^+$

Working Examples

Example 1

N-(2-Amino-2-methylpropyl)-7-[(2,6-difluorobenzyl)oxy]-2,5-dimethylpyrazolo[1,5-a]pyridine-3-carboxamide formate

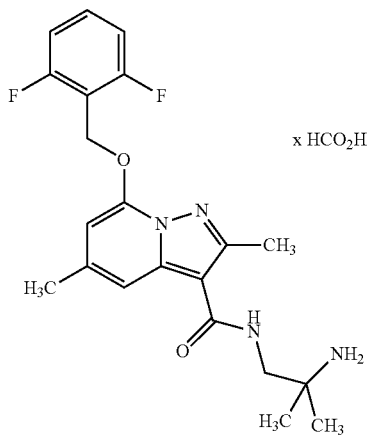 [SMILES: Cc1cc(OCc2c(F)cccc2F)n2nc(C)c(C(=O)NCC(C)(C)N)c2c1]

A mixture of 78.0 mg (0.235 mmol, 1.0 eq.) of 7-[(2,6-difluorobenzyl)oxy]-2,5-dimethylpyrazolo[1,5-a]pyridine-3-carboxylic acid from Example 4A, 49 μl (0.47 mmol, 2.0 eq.) of 1,2-diamino-2-methylpropane [CAS No.: 811-93-8] and 0.20 ml (1.2 mmol, 5.0 eq.) of N,N-diisopropylethylamine in 2.4 ml of DMF was admixed with 116 mg of HATU (0.305 mmol, 1.3 eq.) and stirred at RT for 6 h. Subsequently, water was added and the mixture was extracted three times with ethyl acetate. The combined organic phases were washed with saturated aqueous sodium chloride solution, dried over magnesium sulphate, filtered and concentrated. The residue was stirred with water, and the precipitated solids were filtered off and purified by means of preparative HPLC (Method 4). 22.3 mg of the title compound were obtained (24% of theory).

LC-MS (Method 2): $R_t$=0.75 min

MS (ESIpos): m/z=403 (M+H)$^+$ $^1$H NMR (400 MHz, DMSO-d$_6$) δ [ppm]=1.21 (s, 6H) 2.42 (s, 3H), 2.53 (s, 3H), 3.37 (d, 2H) 5.45 (s, 2H) 6.57 (s, 1H) 7.21-7.32 (m, 2H) 7.41 (s, 1H) 7.58-7.68 (m, 1H), 7.68-7.75 (m, 1H), 8.36 (br. s, 1H).

Example 2 ent-N-(2-Amino-2-methylbutyl)-7-[(2,6-difluorobenzyl)oxy]-2,5-dimethylpyrazolo[1,5-a]pyridine-3-carboxamide formate (Enantiomer A)

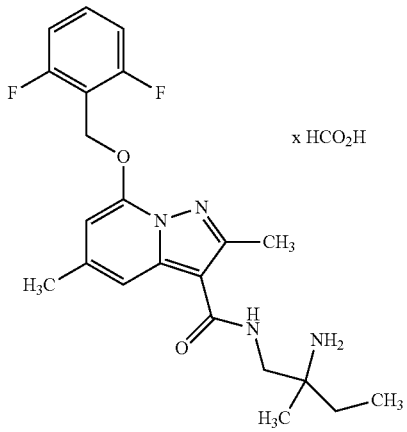 [SMILES: CCC(C)(N)CNC(=O)c1c(C)nn2c(OCc3c(F)cccc3F)cc(C)cc12]

A mixture of 81.0 mg of ent-benzyl {1-[({7-[(2,6-difluorobenzyl)oxy]-2,5-dimethylpyrazolo[1,5-a]pyridin-3-yl}carbonyl)amino]-2-methylbutan-2-yl}carbamate (0.147 mmol, 1.0 eq.) from Example 21A (enantiomer A) and 10 mg (0.015 mmol, 0.1 eq) of 20% palladium hydroxide on activated carbon in 5.0 ml of ethanol was hydrogenated at RT and standard pressure for 4.5 h. Subsequently, the mixture was filtered through kieselguhr and washed with methanol and dichloromethane, and the filtrate was concentrated. The crude product was purified by means of preparative HPLC (Method 5), giving 30 mg of the title compound (49% of theory).

LC-MS (Method 2): $R_t$=0.76 min

MS (ESIpos): m/z=417 (M+H)$^+$ $^1$H NMR (400 MHz, DMSO-d$_6$): δ [ppm]=0.91 (t, 3H), 1.11 (s, 3H), 1.38-1.61 (m, 2H), 2.41 (s, 3H), 2.52 (s, 3H), 3.27-3.41 (m, 2H) 5.45 (s, 2H) 6.57 (s, 1H) 7.22-7.31 (m, 2H), 7.41 (s, 1H) 7.53-7.68 (m, 2H), 8.34 (br. s, 1H).

Example 3 ent-N-(2-Amino-2-methylbutyl)-2,5-dimethyl-7-[(2,3,6-trifluorobenzyl)oxy]pyrazolo[1,5-a]pyridine-3-carboxamide (Enantiomer A)

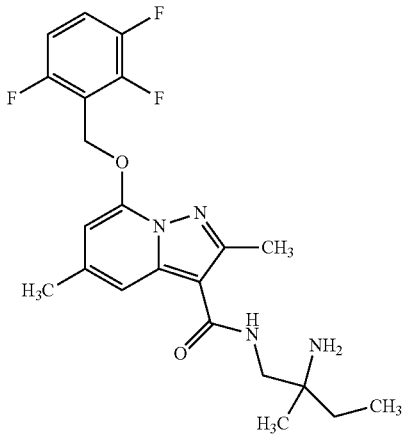 [SMILES: CCC(C)(N)CNC(=O)c1c(C)nn2c(OCc3c(F)ccc(F)c3F)cc(C)cc12]

36 mg (0.04 mmol, 83% purity) of ent-benzyl {1-[({2,5-dimethyl-7-[(2,3,6-trifluorobenzyl)-oxy]pyrazolo pyridin-3-yl}carbonyl)amino]-2-methylbutan-2-yl}carbamate trifluoroacetate from Example 22A (enantiomer A) were dissolved under argon in 2 ml of ethanol, 3 mg (0.004 mmol) of 20% palladium(II) hydroxide on activated carbon were added and hydrogenation was effected at standard pressure for 5 hours. The reaction solution was filtered through a Millipore filter, washed through with ethanol and concentrated under reduced pressure. The residue was purified by means of preparative HPLC (RP18 column, eluent:acetonitrile/water gradient with addition of 0.05% TFA). The product fractions were combined and concentrated. Subsequently, the residue was taken up in dichloromethane and washed with 0.5 ml of saturated aqueous sodium hydrogencarbonate solution. The aqueous phase was reextracted twice with dichloromethane. The combined organic phases were dried over sodium sulphate, filtered, concentrated and lyophilized. 12 mg of the target compound were obtained (62% of theory).

LC-MS (Method 2): $R_t$=0.74 min

MS (ESIpos): m/z=435 (M+H)$^+$ $^1$H NMR (500 MHz, DMSO-d$_6$): δ=0.86 (t, 3H), 0.97 (s, 3H), 1.28-1.41 (m, 2H), 1.48 (br. s, 2H), 2.40 (s, 3H), 2.51 (s, 3H), 3.09-3.24 (m, 2H), 5.49 (s, 2H), 6.55 (s, 1H), 7.20 (t, 1H), 7.28-7.35 (m, 1H), 7.41 (s, 1H), 7.65-7.73 (m, 1H).

Example 4 ent-N-(2-Amino-2-methylpentyl)-2,5-dimethyl-7-[(2,3,6-trifluorobenzyl)oxy]pyrazolo[1,5-a]pyridine-3-carboxamide (Enantiomer B)

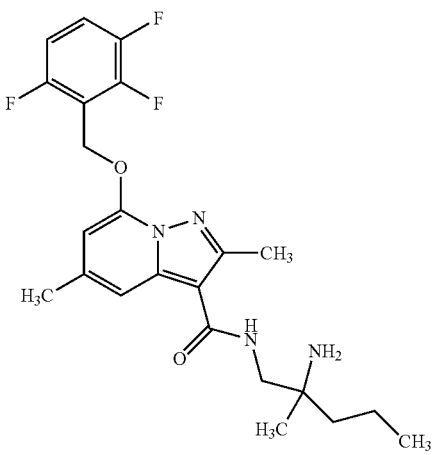 [SMILES: CCCC(C)(N)CNC(=O)c1c(C)nn2c(OCc3c(F)ccc(F)c3F)cc(C)cc12]

59 mg (0.08 mmol, 93% purity) of ent-benzyl {1-[({2,5-dimethyl-7-[(2,3,6-trifluorobenzyl)-oxy]pyrazolo pyridin-3-yl}carbonyl)amino]-2-methylpentan-2-yl}carbamate trifluoroacetate from Example 23A (enantiomer B) were dissolved in 3.7 ml of ethanol, 5.5 mg (0.01 mmol) of 20% palladium(II) hydroxide on activated carbon were added and hydrogenation was effected at standard pressure for a total of 5 hours. The reaction solution was filtered by means of a Millipore filter and the filtrate was concentrated by rotary evaporation. The residue was purified by means of preparative HPLC (RP18 column, eluent:acetonitrile/water gradient with addition of 0.1% TFA). The product fractions were combined and concentrated. The mixed product fractions were concentrated and purified once again by means of preparative HPLC (RP18 column, eluent:acetonitrile/water gradient with addition of 0.1% TFA). All the product fractions were combined and concentrated. Subsequently, the residue was taken up in dichloromethane and a little methanol, and washed with 0.5 ml of saturated aqueous sodium hydrogencarbonate solution. The aqueous phase was reextracted twice with dichloromethane. The combined organic phases were dried over sodium sulphate, filtered, concentrated and lyophilized. 15 mg of the target compound were obtained (42% of theory).

LC-MS (Method 2): $R_t$=0.83 min

MS (ESIpos): m/z=449 (M+H)$^+$ $^1$H NMR (400 MHz, DMSO-d$_6$): δ=0.87 (t, 3H), 0.98 (s, 3H), 1.25-1.42 (m, 4H), 1.72 (br. s, 2H), 2.42 (s, 3H), 2.52 (s, 3H), 3.09-3.24 (m, 2H), 5.49 (s, 2H), 6.56 (s, 1H), 7.24 (t, 1H), 7.28-7.35 (m, 1H), 7.40 (s, 1H), 7.66-7.74 (m, 1H).

Example 5

N-[2-(1-Hydroxycyclopentyl)ethyl]-2,5-dimethyl-7-[(2,3,6-trifluorobenzyl)oxy]pyrazolo[1,5-a]pyridine-3-carboxamide

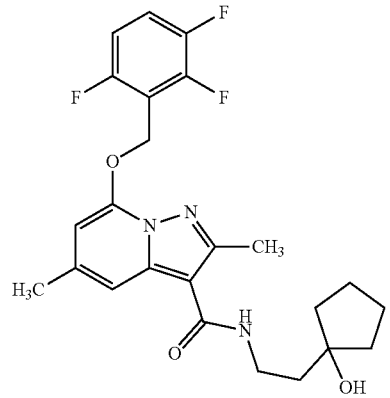 [SMILES: Cc1cc(OCc2c(F)ccc(F)c2F)n2nc(C)c(C(=O)NCCC3(O)CCCC3)c2c1]

12.9 mg (0.1 mmol) of 1-(2-aminoethyl)cyclopentanol were initially charged in a 96-well deep well multititre plate. A solution of 35 mg (0.1 mmol) of 2,5-dimethyl-7-[(2,3,6-trifluorobenzyl)oxy]pyrazolo[1,5-a]pyridine-3-carboxylic acid from Example 10A in 0.2 ml of DMF and a solution of 45.6 mg (0.12 mol) of HATU in 0.2 ml of DMF were added successively. After adding 20.2 mg (0.2 mmol) of 4-methylmorpholine and 0.2 ml of dichloromethane, the mixture was shaken at RT overnight. Then the dichloromethane was evaporated off, the residue was filtered and the target compound was isolated by preparative LC-MS (Method 9). The product-containing fractions were concentrated under reduced pressure using a centrifugal dryer. The residue of each product fraction was dissolved in 0.6 ml of DMSO. These were combined and finally freed of the solvent in a centrifugal dryer. 5 mg (10% of theory) were obtained.

LC-MS (Method 10): $R_t$=1.08 min
MS (ESIpos): m/z=462 (M+H)$^+$

In analogy to Example 5, the example compounds shown in Table 1 were prepared by reacting 2,5-dimethyl-7-[(2,3,6-trifluorobenzyl)oxy]pyrazolo[1,5-a]pyridine-3-carboxylic acid from Example 10A with the appropriate amines, which are commercially available or have been described above, under the conditions described:

TABLE 1

| Example | IUPAC name/ structure (yield) | Analytical data |
|---|---|---|
| 6 | N-(2-Hydroxy-2,3-dihydro-1H-inden-1-yl)-2,5-dimethyl-7-[(2,3,6-trifluorobenzyl)oxy]pyrazolo[1,5-a]pyridine-3-carboxamide<br><br>(17% of theory) | LC-MS (Method 10):<br>$R_t$ = 1.10 min<br>MS (ESIpos):<br>m/z = 482 (M + H)$^+$ |
| 7 | N-[(2S)-3-Hydroxy-1-(2-naphthylamino)-1-oxopropan-2-yl]-2,5-dimethyl-7-[(2,3,6-trifluorobenzyl)oxy]pyrazolo[1,5-a]pyridine-3-carboxamide<br><br>(12% of theory) | LC-MS (Method 10):<br>$R_t$ = 1.12 min<br>MS (ESIpos):<br>m/z = 563 (M + H)$^+$ |

TABLE 1-continued

| Example | IUPAC name/ structure (yield) | Analytical data |
|---|---|---|
| 8 | N-(2-Amino-2-ethylbutyl)-2,5-dimethyl-7-[(2,3,6-trifluorobenzyl)oxy]pyrazolo[1,5-a]pyridine-3-carboxamide<br>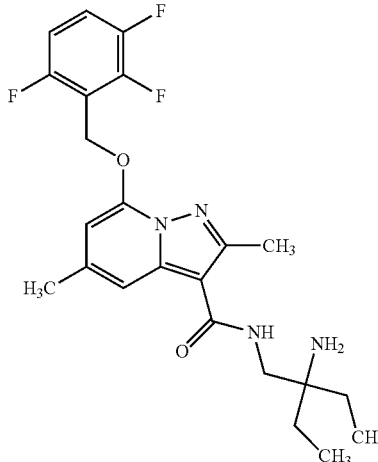<br>(31% of theory) | LC-MS (Method 10):<br>$R_t$ = 0.78 min<br>MS (ESIpos):<br>m/z = 449 (M + H)$^+$ |
| 9 | 2,5-Dimethyl-N-(2,2,6,6-tetramethylpiperidin-4-yl)-7-[(2,3,6-trifluorobenzyl)oxy]pyrazolo[1,5-a]pyridine-3-carboxamide<br>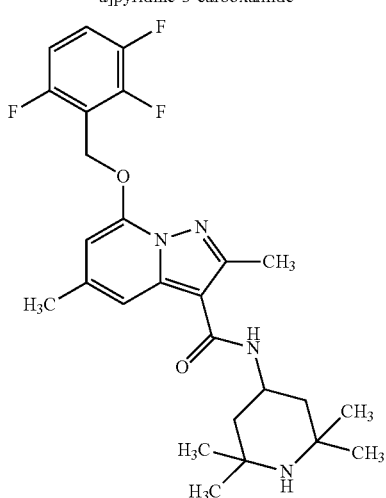<br>(54% of theory) | LC-MS (Method 10):<br>$R_t$ = 0.77 min<br>MS (ESIpos):<br>m/z = 489 (M + H)$^+$ |

TABLE 1-continued

| Example | IUPAC name/ structure (yield) | Analytical data |
|---|---|---|
| 10 | rac-2,5-Dimethyl-N-(2-phenylcyclopropyl)-7-[(2,3,6-trifluorobenzyl)oxy]pyrazolo[1,5-a]pyridine-3-carboxamide<br>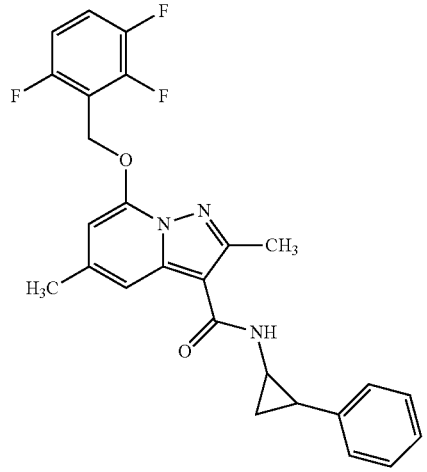 [SMILES: Cc1cc(OCc2c(F)ccc(F)c2F)n2nc(C)c(C(=O)NC3CC3c3ccccc3)c2c1]<br>(24% of theory) | LC-MS (Method 10):<br>$R_t$ = 1.19 min<br>MS (ESIpos):<br>m/z = 466 (M + H)$^+$ |
| 11 | N-[1-(2-Hydroxyethyl)-3,5-dimethyl-1H-pyrazol-4-yl]-2,5-dimethyl-7-[(2,3,6-trifluorobenzyl)oxy]pyrazolo[1,5-a]pyridine-3-carboxamide<br>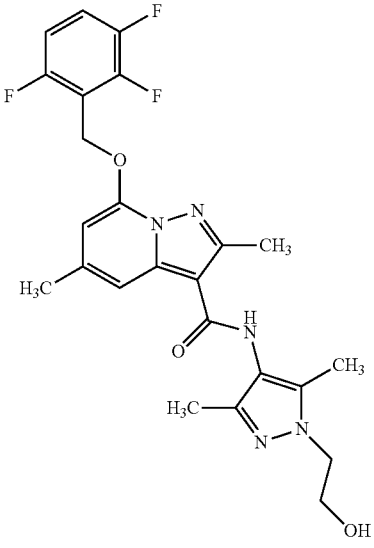 [SMILES: Cc1cc(OCc2c(F)ccc(F)c2F)n2nc(C)c(C(=O)Nc3c(C)nn(CCO)c3C)c2c1]<br>(14% of theory) | LC-MS (Method 10):<br>$R_t$ = 0.95 min<br>MS (ESIpos):<br>m/z = 488 (M + H)$^+$ |

TABLE 1-continued

| Example | IUPAC name/ structure (yield) | Analytical data |
|---|---|---|
| 12 | N-[2-(Dimethylamino)ethyl]-2,5-dimethyl-7-[(2,3,6-trifluorobenzyl)oxy]pyrazolo[1,5-a]pyridine-3-carboxamide<br />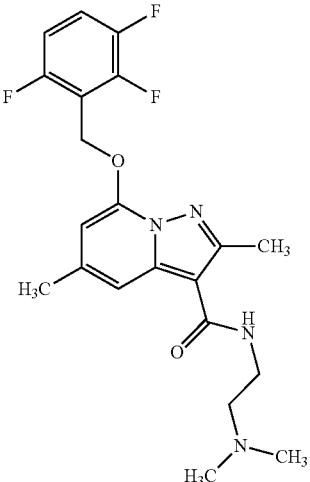 [SMILES: Cc1cc(OCc2c(F)ccc(F)c2F)n2nc(C)c(C(=O)NCCN(C)C)c2c1]<br />(7% of theory) | LC-MS (Method 10):<br />$R_t$ = 0.73 min<br />MS (ESIpos):<br />m/z = 421 (M + H)$^+$ |
| 13 | rac-N-(2-Amino-2-cyclopropylpropyl)-2,5-dimethyl-7-[(2,3,6-trifluorobenzyl)oxy]pyrazolo[1,5-a]pyridine-3-carboxamide<br />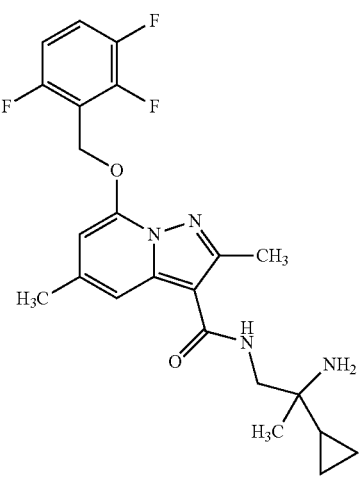 [SMILES: Cc1cc(OCc2c(F)ccc(F)c2F)n2nc(C)c(C(=O)NCC(C)(N)C3CC3)c2c1]<br />(28% of theory) | LC-MS (Method 10):<br />$R_t$ = 0.76 min<br />MS (ESIpos):<br />m/z = 447 (M + H)$^+$ |

TABLE 1-continued

| Example | IUPAC name/ structure (yield) | Analytical data |
|---|---|---|
| 14 | 2,5-Dimethyl-N-[2-(pyridin-3-yl)benzyl]-7-[(2,3,6-trifluorobenzyl)oxy]pyrazolo[1,5-a]pyridine-3-carboxamide<br>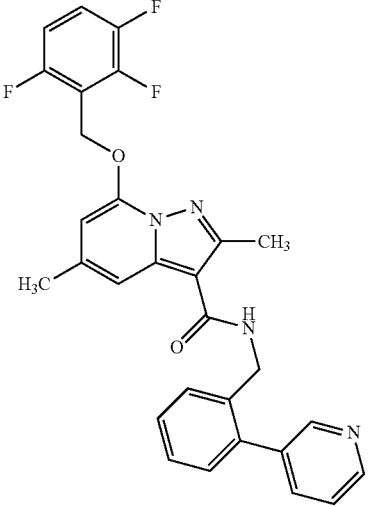 [SMILES: Cc1cc(OCc2c(F)ccc(F)c2F)n2nc(C)c(C(=O)NCc3ccccc3-c3cccnc3)c2c1]<br>(28% of theory) | LC-MS (Method 10):<br>$R_t$ = 1.07 min<br>MS (ESIpos):<br>m/z = 517 (M + H)$^+$ |
| 15 | 2,5-Dimethyl-N-[2-(morpholin-4-yl)ethyl]-7-[(2,3,6-trifluorobenzyl)oxy]pyrazolo[1,5-a]pyridine-3-carboxamide<br>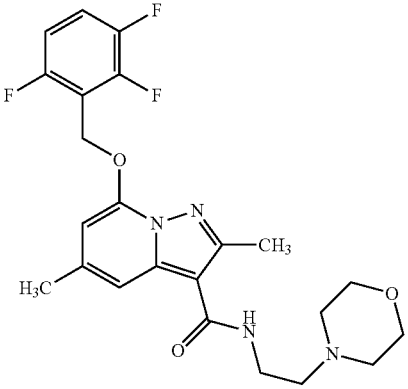 [SMILES: Cc1cc(OCc2c(F)ccc(F)c2F)n2nc(C)c(C(=O)NCCN3CCOCC3)c2c1]<br>(61% of theory) | LC-MS (Method 10):<br>$R_t$ = 0.73 min<br>MS (ESIpos):<br>m/z = 463 (M + H)$^+$ |

TABLE 1-continued

| Example | IUPAC name/ structure (yield) | Analytical data |
|---|---|---|
| 16 | N-[1-(4-Fluorobenzyl)-3,5-dimethyl-1H-pyrazol-4-yl]-2,5-dimethyl-7-[(2,3,6-trifluorobenzyl)oxy]pyrazolo[1,5-a]pyridine-3-carboxamide<br />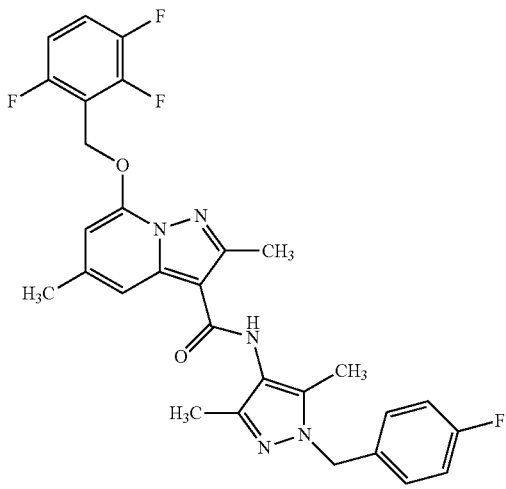 [SMILES: Cc1cc(OCc2c(F)ccc(F)c2F)n2nc(C)c(C(=O)Nc3c(C)nn(Cc4ccc(F)cc4)c3C)c2c1]<br />(12% of theory) | LC-MS (Method 10):<br />$R_t$ = 1.14 min<br />MS (ESIpos):<br />m/z = 552 (M + H)$^+$ |
| 17 | 2,5-Dimethyl-7-[(2,3,6-trifluorobenzyl)oxy]-N-[1-(2,2,2-trifluoroethyl)-1H-pyrazol-4-yl]pyrazolo[1,5-a]pyridine-3-carboxamide<br />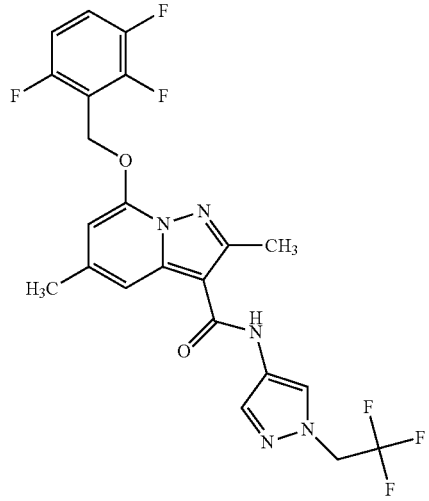 [SMILES: Cc1cc(OCc2c(F)ccc(F)c2F)n2nc(C)c(C(=O)Nc3cnn(CC(F)(F)F)c3)c2c1]<br />(27% of theory) | LC-MS (Method 10):<br />$R_t$ = 1.10 min<br />MS (ESIpos):<br />m/z = 498 (M + H)$^+$ |

TABLE 1-continued

| Example | IUPAC name/ structure (yield) | Analytical data |
|---|---|---|
| 18 | N-(1H-Imidazol-2-ylmethyl)-2,5-dimethyl-7-[(2,3,6-trifluorobenzyl)oxy]pyrazolo[1,5-a]pyridine-3-carboxamide<br />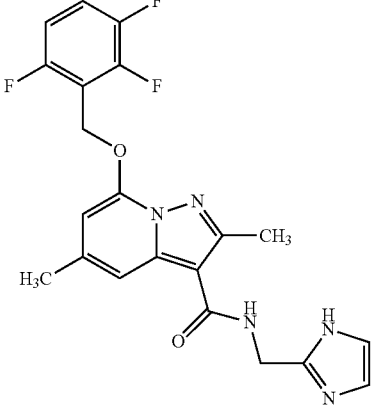<br />(44% of theory) | LC-MS (Method 10):<br />$R_t = 0.72$ min<br />MS (ESIpos):<br />m/z = 430 (M + H)$^+$ |
| 19 | rac-2,5-Dimethyl-7-[(2,3,6-trifluorobenzyl)oxy]-N-{1-[3-(trifluoromethyl)-1,2,4-oxadiazol-5-yl]ethyl}pyrazolo[1,5-a]pyridine-3-carboxamide<br />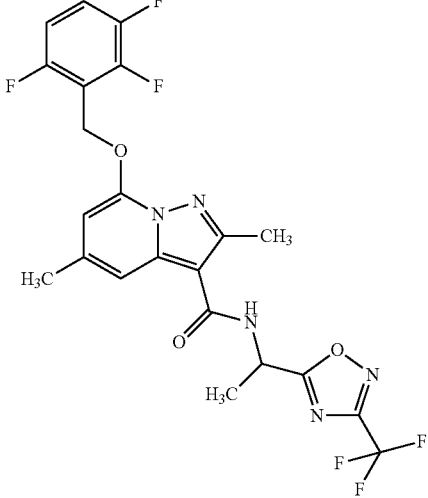<br />(31% of theory) | LC-MS (Method 10):<br />$R_t = 1.19$ min<br />MS (ESIpos):<br />m/z = 514 (M + H)$^+$ |

TABLE 1-continued

| Example | IUPAC name/ structure (yield) | Analytical data |
|---|---|---|
| 20 | 2,5-Dimethyl-N-[5-methyl-3-(trifluoromethyl)-1H-pyrazol-4-yl]-7-[(2,3,6-trifluorobenzyl)oxy]pyrazolo[1,5-a]pyridine-3-carboxamide<br />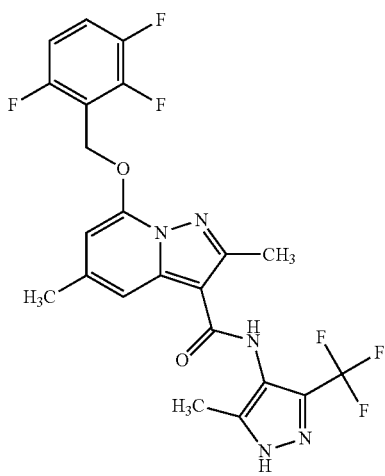 [SMILES: Cc1cc(OCc2c(F)ccc(F)c2F)n2nc(C)c(C(=O)Nc3c(C(F)(F)F)n[nH]c3C)c2c1]<br />(7% of theory) | LC-MS (Method 10):<br />$R_t$ = 1.05 min<br />MS (ESIpos):<br />m/z = 498 (M + H)$^+$ |
| 21 | N-[(6-Chloropyridin-3-yl)methyl]-2,5-dimethyl-7-[(2,3,6-trifluorobenzyl)oxy]pyrazolo[1,5-a]pyridine-3-carboxamide<br />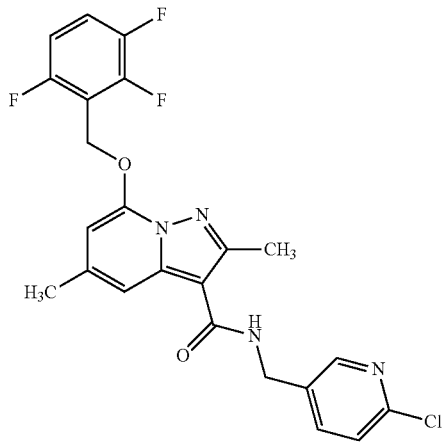 [SMILES: Cc1cc(OCc2c(F)ccc(F)c2F)n2nc(C)c(C(=O)NCc3ccc(Cl)nc3)c2c1]<br />(2% of theory) | LC-MS (Method 10):<br />$R_t$ = 1.10 min<br />MS (ESIpos):<br />m/z = 475 (M + H)$^+$ |

TABLE 1-continued

| Example | IUPAC name/ structure (yield) | Analytical data |
|---|---|---|
| 22 | ent-2,5-Dimethyl-N-(6,6,7,7,7-pentafluoro-2-hydroxy-2-methylheptan-3-yl)-7-[(2,3,6-trifluorobenzyl)oxy]pyrazolo[1,5-a]pyridine-3-carboxamide<br>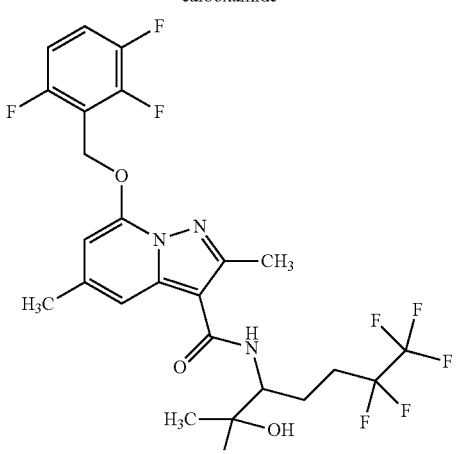<br>(18% of theory) | LC-MS (Method 10):<br>$R_t$ = 1.16 min<br>MS (ESIpos):<br>m/z = 568 (M + H)$^+$ |
| 23 | 2,5-Dimethyl-N-(pyrazolo[1,5-a]pyridin-3-yl)-7-[(2,3,6-trifluorobenzyl)oxy]pyrazolo[1,5-a]pyridine-3-carboxamide<br>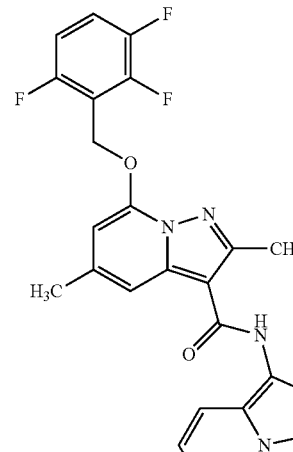<br>(14% of theory) | LC-MS (Method 10):<br>$R_t$ = 1.10 min<br>MS (ESIpos):<br>m/z = 466 (M + H)$^+$ |

TABLE 1-continued

| Example | IUPAC name/ structure (yield) | Analytical data |
|---|---|---|
| 24 | rac-2,5-Dimethyl-7-[(2,3,6-trifluorobenzyl)oxy]-N-[1-(2,2,2-trifluoroethoxy)propan-2-yl]pyrazolo[1,5-a]pyridine-3-carboxamide<br>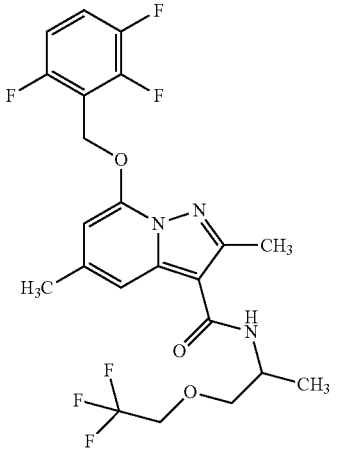 [SMILES: Cc1cc(OCc2c(F)ccc(F)c2F)n2nc(C)c(C(=O)NC(C)COCC(F)(F)F)c2c1]<br>(13% of theory) | LC-MS (Method 10):<br>$R_t$ = 1.15 min<br>MS (ESIpos):<br>m/z = 490 (M + H)$^+$ |
| 25 | N-[(1-Hydroxycyclopropyl)methyl]-2,5-dimethyl-7-[(2,3,6-trifluorobenzyl)oxy]pyrazolo[1,5-a]pyridine-3-carboxamide<br>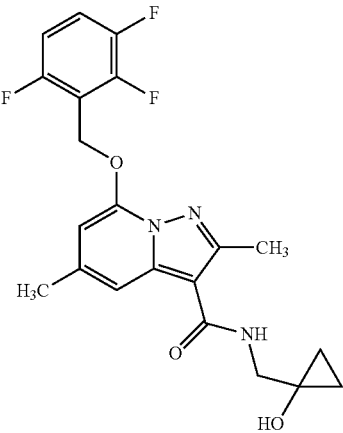 [SMILES: Cc1cc(OCc2c(F)ccc(F)c2F)n2nc(C)c(C(=O)NCC3(O)CC3)c2c1]<br>(40% of theory) | LC-MS (Method 10):<br>$R_t$ = 0.98 min<br>MS (ESIpos):<br>m/z = 420 (M + H)$^+$ |

TABLE 1-continued

| Example | IUPAC name/ structure (yield) | Analytical data |
|---|---|---|
| 26 | N-{2-[Cyclopropyl(2,2-difluoroethyl)amino]ethyl]-2,5-dimethyl-7-[(2,3,6-trifluorobenzyl)oxy]pyrazolo[1,5-a]pyridine-3-carboxamide<br>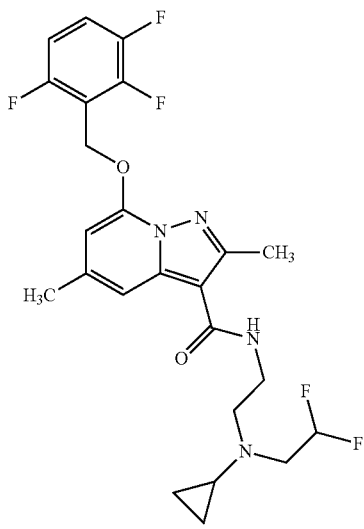 [SMILES: Cc1cc(OCc2c(F)ccc(F)c2F)n2nc(C)c(C(=O)NCCN(CC(F)F)C3CC3)c2c1]<br>(26% of theory) | LC-MS (Method 10):<br>$R_t = 1.15$ min<br>MS (ESIpos):<br>m/z = 497 (M + H)$^+$ |
| 27 | 2,5-Dimethyl-N-[(3S)-2-oxotetrahydrofuran-3-yl]-7-[(2,3,6-trifluorobenzyl)oxy]pyrazolo[1,5-a]pyridine-3-carboxamide<br>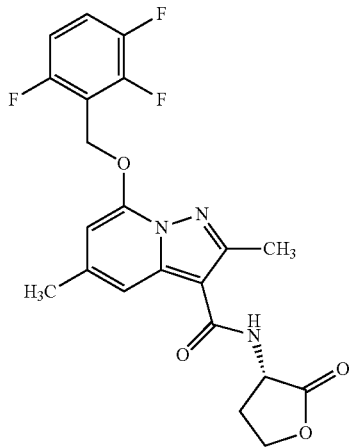 [SMILES: Cc1cc(OCc2c(F)ccc(F)c2F)n2nc(C)c(C(=O)N[C@H]3CCOC3=O)c2c1]<br>(40% of theory) | LC-MS (Method 10):<br>$R_t = 1.00$ min<br>MS (ESIpos):<br>m/z = 434 (M + H)$^+$ |

TABLE 1-continued

| Example | IUPAC name/ structure (yield) | Analytical data |
|---|---|---|
| 28 | N-[1-Hydroxy-2-(hydroxymethyl)butan-2-yl]-2,5-dimethyl-7-[(2,3,6-trifluorobenzyl)oxy]pyrazolo[1,5-a]pyridine-3-carboxamide<br />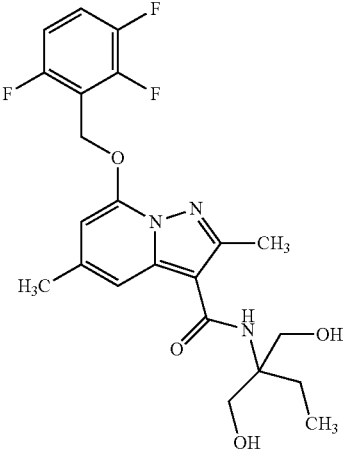 [SMILES: CCC(CO)(CO)NC(=O)c1c(C)nn2c(OCc3c(F)ccc(F)c3F)cc(C)cc12]<br />(38% of theory) | LC-MS (Method 10):<br />$R_t$ = 1.00 min<br />MS (ESIpos):<br />m/z = 452 (M + H)$^+$ |
| 29 | 2,5-Dimethyl-N-(9-methyl-9-azabicyclo[3.3.1]non-3-yl)-7-[(2,3,6-trifluorobenzyl)oxy]pyrazolo[1,5-a]pyridine-3-carboxamide<br />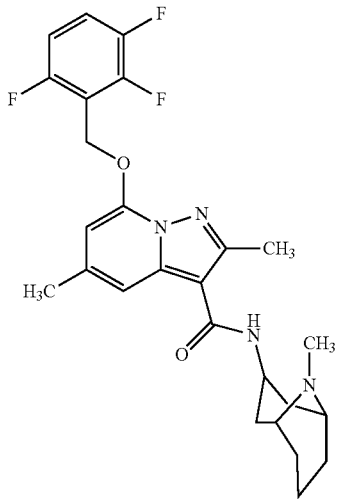<br />(66% of theory) | LC-MS (Method 10):<br />$R_t$ = 0.77 min<br />MS (ESIpos):<br />m/z = 487 (M + H)$^+$ |

TABLE 1-continued

| Example | IUPAC name/ structure (yield) | Analytical data |
|---|---|---|
| 30 | rac-N-[1-(4-Fluorophenyl)-2-hydroxyethyl]-2,5-dimethyl-7-[(2,3,6-trifluorobenzyl)oxy]pyrazolo[1,5-a]pyridine-3-carboxamide<br>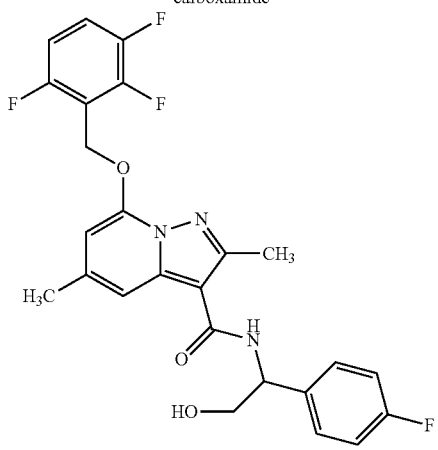<br>(40% of theory) | LC-MS (Method 10):<br>$R_t$ = 1.07 min<br>MS (ESIpos):<br>m/z = 488 (M + H)$^+$ |
| 31 | N-[1-(4-Chlorophenyl)cyclopentyl]-2,5-dimethyl-7-[(2,3,6-trifluorobenzyl)oxy]pyrazolo[1,5-a]pyridine-3-carboxamide<br>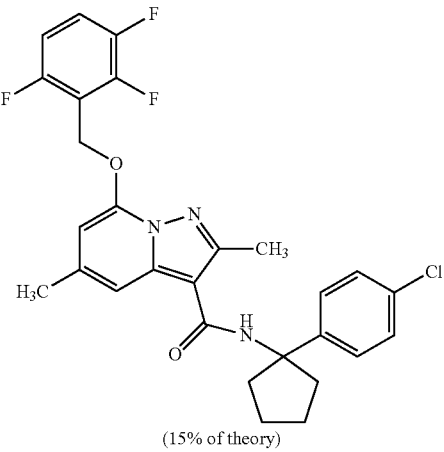<br>(15% of theory) | LC-MS (Method 10):<br>$R_t$ = 1.26 min<br>MS (ESIpos):<br>m/z = 528 (M + H)$^+$ |
| 32 | N-[2-(1H-Imidazol-1-yl)benzyl]-2,5-dimethyl-7-[(2,3,6-trifluorobenzyl)oxy]pyrazolo[1,5-a]pyridine-3-carboxamide<br>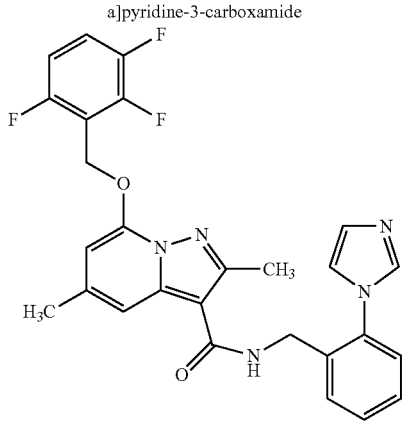<br>(56% of theory) | LC-MS (Method 10):<br>$R_t$ = 0.82 min<br>MS (ESIpos):<br>m/z = 506 (M + H)$^+$ |

TABLE 1-continued

| Example | IUPAC name/structure (yield) | Analytical data |
|---|---|---|
| 33 | N-[1-(2-Hydroxyethyl)-1H-pyrazol-4-yl]-2,5-dimethyl-7-[(2,3,6-trifluorobenzyl)oxy]pyrazolo[1,5-a]pyridine-3-carboxamide<br>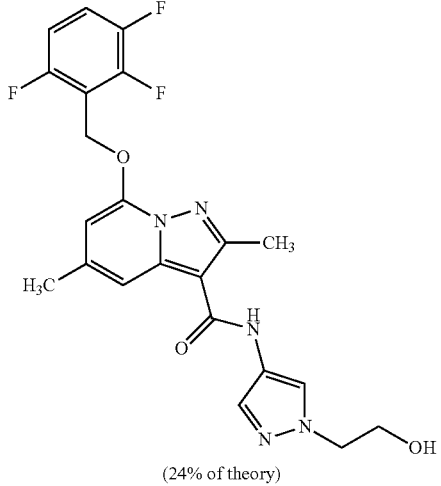<br>(24% of theory) | LC-MS (Method 10):<br>$R_t = 0.94$ min<br>MS (ESIpos):<br>m/z = 460 (M + H)$^+$ |
| 34 | N-[(4-Chlorophenyl)(cyano)methyl]-2,5-dimethyl-7-[(2,3,6-trifluorobenzyl)oxy]pyrazolo[1,5-a]pyridine-3-carboxamide<br>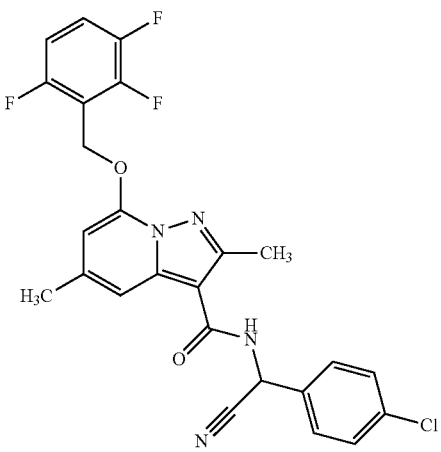 [SMILES: Cc1cc(OCc2c(F)ccc(F)c2F)n2nc(C)c(C(=O)NC(C#N)c3ccc(Cl)cc3)c2c1]<br>(9% of theory) | LC-MS (Method 10):<br>$R_t = 1.20$ min<br>MS (ESIpos):<br>m/z = 499 (M + H)$^+$ |

Example 35

Methyl trans-4-{[({7-[(2,6-difluorobenzyl)oxy]-2,5-dimethylpyrazolo[1,5-a]pyridin-3-yl}carbonyl)amino]methyl}cyclohexanecarboxylate

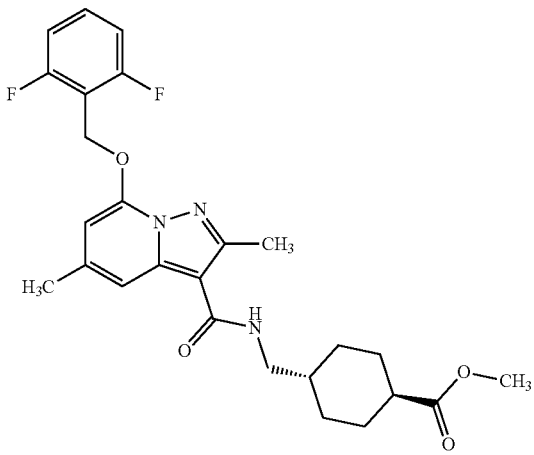 [SMILES: COC(=O)[C@H]1CC[C@H](CNC(=O)c2c(C)nn3c(OCc4c(F)cccc4F)cc(C)cc23)CC1]

A mixture of 100 mg (0.30 mmol, 1.0 eq.) of 7-[(2,6-difluorobenzyl)oxy]-2,5-dimethylpyrazolo[1,5-a]pyridine-3-carboxylic acid from Example 4A, 116 mg of TBTU (0.36 mmol, 1.2 eq.) and 0.132 ml (1.2 mmol, 4.0 eq.) of 4-methylmorpholine in 2.2 ml of DMF was admixed with 103 mg (0.60 mmol, 2.0 eq.) of methyl trans-4-(aminomethyl)cyclohexanecarboxylate, and the mixture was stirred at RT overnight. The reaction mixture was admixed with water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 67 mg of the target compound were obtained (46% of theory).

LC-MS (Method 2): $R_t$=0.93 min
MS (ESIpos): m/z=486 (M+H)$^+$

Example 36 trans-4-{[({7-[(2,6-Difluorobenzyl)oxy]-2,5-dimethylpyrazolo[1,5-a]pyridin-3-yl}carbonyl)amino]methyl}cyclohexanecarboxylic Acid

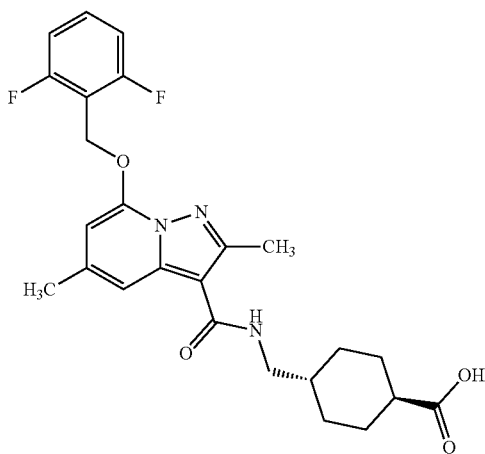 [SMILES: Cc1cc(OCc2c(F)cccc2F)n2nc(C)c(C(=O)NC[C@H]3CC[C@H](C(=O)O)CC3)c2c1]

90 mg (0.19 mmol, 1.0 eq.) of methyl trans-4-{[({7-[(2,6-difluorobenzyl)oxy]-2,5-dimethylpyrazolo[1,5-a]pyridin-3-yl}carbonyl)amino]methyl}cyclohexanecarboxylate from Example 35 were dissolved in 5.5 ml of THF/methanol (5/1) and admixed with 1.3 ml of 1 N aqueous lithium hydroxide solution. The mixture was stirred at RT for 3 days. Subsequently, another 2 ml of 1 N lithium hydroxide solution were added and the mixture was stirred at 60° C. for 7 days. After cooling, the mixture was acidified to pH=3 with 1 N hydrochloric acid and freed of the organic solvents on a rotary evaporator. The resulting aqueous phase was extracted three times with dichloromethane and the combined organic phases were washed with water, then dried with sodium sulphate, filtered and concentrated. The residue was purified by means of thick-layer chromatography (eluent:dichloromethane/methanol=20/1). 46 mg of the target compound were obtained (53% of theory).

LC-MS (Method 2): $R_t$=0.94 min
MS (ESIpos): m/z=472 (M+H)$^+$
$^1$H NMR (500 MHz, DMSO-$d_6$) δ [ppm]=0.92-1.01 (m, 2H) 1.21-1.34 (m, 2H), 1.46-1.57 (m, 1H), 1.75-1.84 (m, 2H), 1.86-1.96 (m, 2H), 2.09-2.18 (m, 1H), 2.40 (s, 3H), 2.47 (s, 3H), 3.12 (t, 2H), 5.44 (s, 2H) 6.53 (s, 1H) 7.22-7.30 (m, 2H), 7.34 (s, 1H), 7.39-7.44 (m, 1H), 7.58-7.66 (m, 1H), 11.97 (br. s, 1H).

Example 37 tert-Butyl (3R)-3-[({7-[(2,6-difluorobenzyl)oxy]-2,5-dimethylpyrazolo[1,5-a]pyridin-3-yl}carbonyl)amino]-5-methylhexanoate

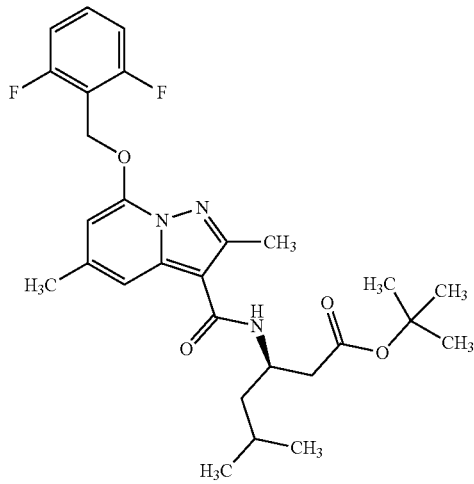 [SMILES: Cc1cc(OCc2c(F)cccc2F)n2nc(C)c(C(=O)N[C@@H](CC(=O)OC(C)(C)C)CC(C)C)c2c1]

A mixture of 100 mg (0.30 mmol, 1.0 eq.) of 7-[(2,6-difluorobenzyl)oxy]-2,5-dimethylpyrazolo[1,5-a]pyridine-3-carboxylic acid from Example 4A, 116 mg of TBTU (0.36 mmol, 1.2 eq.) and 0.132 ml (1.2 mmol, 4.0 eq.) of 4-methylmorpholine in 2.2 ml of DMF was admixed with 121 mg (0.60 mmol, 2.0 eq.) of tert-butyl (3R)-3-amino-5-methylhexanoate, and the mixture was stirred at RT overnight. The reaction mixture was admixed with water and TFA and purified by means of preparative HPLC (RP18 column, eluent: acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 88 mg of the target compound were obtained (57% of theory).

LC-MS (Method 2): $R_t$=1.30 min
MS (ESIpos): m/z=516 (M+H)$^+$

Example 38

(3R)-3-[({7-[(2,6-Difluorobenzyl)oxy]-2,5-dimethylpyrazolo[1,5-a]pyridin-3-yl}carbonyl)amino]-5-methylhexanoic Acid

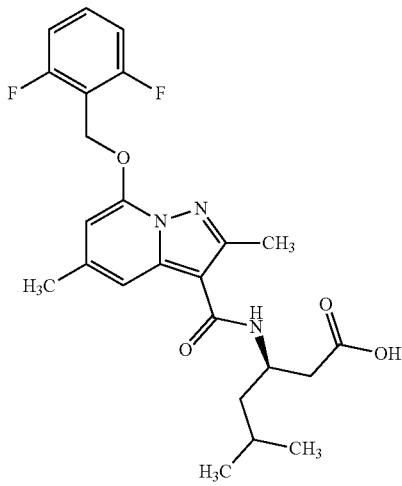 [SMILES: Cc1cc(OCc2c(F)cccc2F)n2nc(C)c(C(=O)N[C@@H](CC(=O)O)CC(C)C)c2c1]

88 mg (0.17 mmol) of tert-butyl (3R)-3-[({7-[(2,6-difluorobenzyl)oxy]-2,5-dimethylpyrazolo[1,5-a]pyridin-3-yl}carbonyl)amino]-5-methylhexanoate from Example 37 were suspended in 2 ml of diethyl ether and admixed with 2.56 ml of 2 N hydrogen chloride solution, and the mixture was stirred at RT overnight. Subsequently, 2 ml of 2 N hydrogen chloride solution in diethyl ether were added and the mixture was stirred at RT for 4 h. The reaction mixture was concentrated, admixed with water and TFA and purified by means of preparative HPLC (RP18 column, eluent:acetonitrile/water gradient with addition of 0.1% TFA). The product fractions were combined, concentrated and lyophilized. 57 mg of the target compound were obtained (73% of theory).

LC-MS (Method 2): $R_t$=1.04 min
MS (ESIpos): m/z=460 (M+H)$^+$
$^1$H NMR (500 MHz, DMSO-d$_6$) δ [ppm]=0.90 (dd, 6H) 1.25-1.33 (m, 1H), 1.52-1.60 (m, 1H), 1.61-1.70 (m, 1H), 2.35-2.49 (m, 8H), 4.34-4.44 (m, 1H), 5.44 (s, 2H) 6.52 (s, 1H) 7.21-7.33 (m, 4H), 7.58-7.67 (m, 1H), 12.18 (br. s, 1H).

Example 39 ent-N-(2-Amino-2-methylpentyl)-7-[(2,6-difluorobenzyl)oxy]-2,5-dimethylpyrazolo[1,5-a]pyridine-3-carboxamide (Enantiomer B)

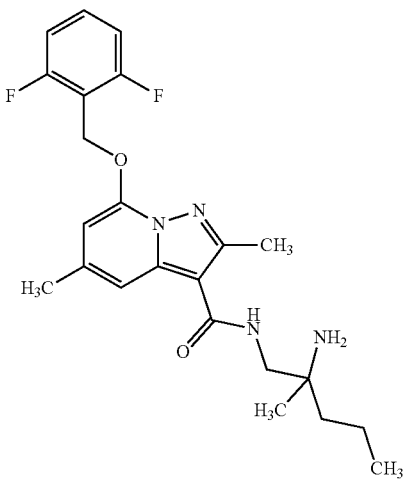 [SMILES: CCCC(C)(N)CNC(=O)c1c(C)nn2c(OCc3c(F)cccc3F)cc(C)cc12]

190 mg (0.26 mmol, 92% purity) of ent-benzyl {1-[({7-[(2,6-difluorobenzyl)oxy]-2,5-dimethylpyrazolo[1,5-a]pyridin-3-yl}carbonyl)amino]-2-methylpentan-2-yl}carbamate trifluoroacetate from Example 87A (enantiomer B) were dissolved in 6.9 ml of ethanol, 8.6 mg (0.01 mmol) of 10% palladium on activated carbon were added and hydrogenation was effected at standard pressure for 1.5 hours. The reaction solution was filtered by means of a Millipore filter and the filtrate was concentrated by rotary evaporation. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 79 mg of the target compound were obtained (70% of theory).

LC-MS (Method 2): $R_t$=0.74 min
MS (ESIpos): m/z=431 (M+H)$^+$
$^1$H NMR (400 MHz, DMSO-d$_6$): δ=0.87 (t, 3H), 0.98 (s, 3H), 1.25-1.41 (m, 4H), 1.49 (br. s, 2H), 2.40 (s, 3H), 2.50 (s, 3H; beneath solvent peak), 3.09-3.23 (m, 2H), 5.44 (s, 2H), 6.54 (s, 1H), 7.18-7.30 (m, 3H), 7.38 (s, 1H), 7.57-7.67 (m, 1H).

Example 40 ent-N-(2-Amino-3-fluoro-2-methylpropyl)-7-[(2,6-difluorobenzyl)oxy]-2,5-dimethylpyrazolo[1,5-a]pyridine-3-carboxamide (Enantiomer A)

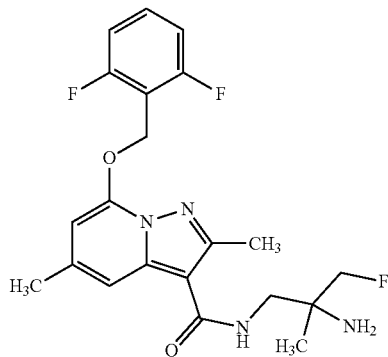 [SMILES: Cc1cc(OCc2c(F)cccc2F)n2nc(C)c(C(=O)NCC(C)(N)CF)c2c1]

Under argon, 231 mg (0.33 mmol, 95%) of ent-benzyl{1-[({7-[(2,6-difluorobenzyl)oxy]-2,5-dimethylpyrazolo[1,5-a]pyridin-3-yl}carbonyl)amino]-3-fluoro-2-methylpropan-2-yl}carbamate trifluoroacetate (enantiomer A) from Example 88A were dissolved in 8.5 ml of ethanol, 70 mg (0.07 mmol) of palladium on activated carbon (10%) were added and the reaction mixture was hydrogenated at standard pressure for 2.5 hours. The reaction mixture was filtered through Celite and washed well with ethanol, and the filtrate was then concentrated. The residue was purified by means of preparative HPLC (RP18 column, eluent:acetonitrile/water gradient with addition of 0.1% TFA). The collected product fractions were taken up in dichloromethane and a little methanol, and washed twice with saturated aqueous sodium hydrogencarbonate solution. The combined organic phases were reextracted twice with dichloromethane. The combined organic phases were dried over sodium sulphate, filtered and concentrated. 90 mg of the target compound were obtained (65% of theory, 99% purity).

LC-MS (Method 2): $R_t$=0.67 min

MS (ESIpos): m/z=421 (M+H)$^+$ $^1$H NMR (500 MHz, DMSO-$d_6$): δ=1.03 (s, 3H), 1.63 (br. s, 2H), 2.41 (s, 3H), 2.51 (s, 3H; obscured by solvent peak), 3.20-3.36 (m, 2H; obscured by water peak), 4.08-4.15 (m, 1H), 4.18-4.25 (m, 1H), 5.45 (s, 2H), 6.55 (s, 1H), 7.22-7.31 (m, 3H), 7.39 (s, 1H), 7.58-7.66 (m, 1H).

Example 41 ent-N-(2-Amino-3-fluoro-2-methylpropyl)-7-[(2,6-difluorobenzyl)oxy]-2,5-dimethylpyrazolo[1,5-a]pyridine-3-carboxamide (Enantiomer B)

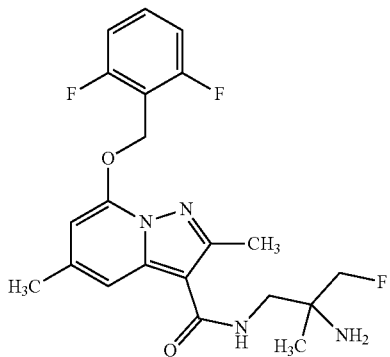 [SMILES: Cc1cc(OCc2c(F)cccc2F)n2nc(C)c(C(=O)NCC(C)(N)CF)c2c1]

Under argon, 240 mg (0.27 mmol, 74%) of ent-benzyl{1-[({7-[(2,6-difluorobenzyl)oxy]-2,5-dimethylpyrazolo[1,5-a]pyridin-3-yl}carbonyl)amino]-3-fluoro-2-methylpropan-2-yl}carbamate trifluoroacetate (enantiomer B) from Example 89A were dissolved in 6.8 ml of ethanol, 56 mg (0.05 mmol) of palladium on activated carbon (10%) were added and the reaction mixture was hydrogenated at standard pressure for 8 hours. The reaction mixture was filtered through Celite and washed well with ethanol, and the filtrate was then concentrated. The residue was taken up in acetonitrile/water, TFA was added and the mixture was purified by means of preparative HPLC (RP18 column, eluent:acetonitrile/water gradient with addition of 0.1% TFA). The collected product fractions were concentrated. The residue was taken up in dichloromethane and a little methanol, and washed twice with saturated aqueous sodium hydrogencarbonate solution. The combined organic phases were reextracted twice with dichloromethane. The combined organic phases were dried over sodium sulphate, filtered and concentrated. 66 mg of the target compound were obtained (59% of theory, 99% purity).

LC-MS (Method 2): $R_t$=0.67 min

MS (ESIpos): m/z=421 (M+H)$^+$ $^1$H NMR (500 MHz, DMSO-$d_6$): δ=1.03 (s, 3H), 1.68 (br. s, 2H), 2.41 (s, 3H), 2.51 (s, 3H; obscured by solvent peak), 3.20-3.36 (m, 2H; obscured by water peak), 4.08-4.15 (m, 1H), 4.18-4.25 (m, 1H), 5.44 (s, 2H), 6.55 (s, 1H), 7.22-7.31 (m, 3H), 7.39 (s, 1H), 7.58-7.67 (m, 1H).

Example 42 ent-N-(2-Amino-5,5,5-trifluoro-2-methylpentyl)-7-[(2,6-difluorobenzyl)oxy]-2,5-dimethylpyrazolo[1,5-a]pyridine-3-carboxamide (Enantiomer A)

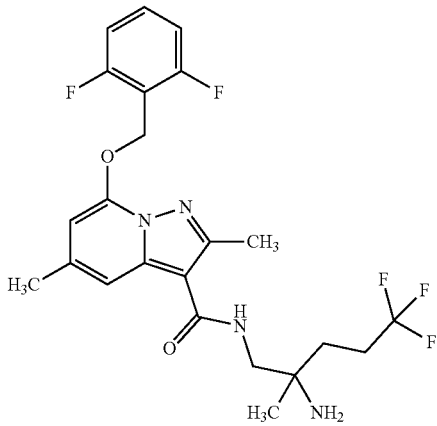 [SMILES: Cc1cc(OCc2c(F)cccc2F)n2nc(C)c(C(=O)NCC(C)(N)CCC(F)(F)F)c2c1]

A mixture of 52 mg (0.07 mmol) of ent-benzyl {1-[({7-[(2,6-difluorobenzyl)oxy]-2,5-dimethylpyrazolo[1,5-a]pyridin-3-yl}carbonyl)amino]-5,5,5-trifluoro-2-methylpentan-2-yl}carbamate trifluoroacetate (enantiomer A) from Example 90A and 15 mg of palladium on activated carbon (10%) in 1.8 ml of ethanol was hydrogenated at room temperature and standard pressure for 2 h. Subsequently, the mixture was filtered through Celite and washed with ethanol, and the filtrate was concentrated. The crude product was admixed with acetonitrile, water and TFA and purified by means of preparative HPLC (RP-C18, eluent:acetonitrile/water gradient with addition of 0.1% TFA). The product fractions were taken up in dichloromethane and washed twice with saturated aqueous sodium hydrogencarbonate solution. The combined aqueous phases were extracted twice with dichloromethane. The combined organic phases were dried over sodium sulphate, filtered and concentrated. 4 mg of the title compound were obtained (12% of theory; 99% purity).

LC-MS (Method 2): $R_t$=0.77 min

MS (ESIpos): m/z=485 (M+H)$^+$ $^1$H NMR (500 MHz, DMSO-$d_6$): δ [ppm]=1.02 (s, 3H), 1.46-1.58 (m, 2H), 1.67 (br. s, 2H), 2.24-2.47 (m, 5H), 2.50 (s, 3H; obscured by the solvent peak), 3.14-3.25 (m, 2H), 5.44 (s, 2H), 6.54 (s, 1H), 7.21-7.30 (m, 2H), 7.34 (s, 1H), 7.40 (t, 1H), 7.58-7.66 (m, 1H).

Example 43 ent-N-(2-Amino-5,5,5-trifluoro-2-methylpentyl)-7-[(2,6-difluorobenzyl)oxy]-2,5-dimethylpyrazolo[1,5-a]pyridine-3-carboxamide (Enantiomer B)

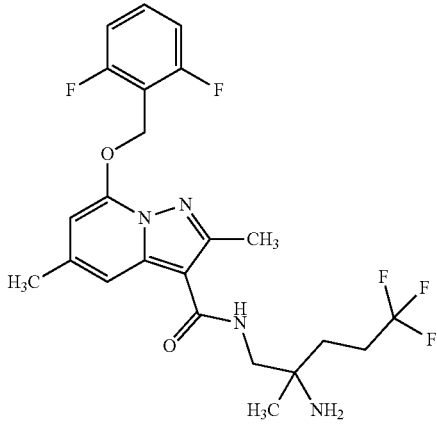 [SMILES: Cc1cc(OCc2c(F)cccc2F)n2nc(C)c(C(=O)NCC(C)(N)CCC(F)(F)F)c2c1]

A mixture of 311 mg (0.42 mmol) of ent-benzyl {1-[({7-[(2,6-difluorobenzyl)oxy]-2,5-dimethylpyrazolo[1,5-a]pyridin-3-yl}carbonyl)amino]-5,5,5-trifluoro-2-methylpentan-2-yl}carbamate trifluoroacetate (enantiomer B) from Example 91A and 13 mg of palladium on activated carbon (10%) in 10.7 ml of ethanol was hydrogenated at room temperature and standard pressure for 2.5 h. Subsequently, the mixture was filtered through a Millipore filter and washed with ethanol, and the filtrate was concentrated. The crude product was admixed with acetonitrile, water and TFA and purified by means of preparative HPLC (RP-C18, eluent: acetonitrile/water gradient with addition of 0.1% TFA). The product fractions were taken up in dichloromethane and washed twice with saturated aqueous sodium hydrogencarbonate solution. The combined aqueous phases were extracted twice with dichloromethane. The combined organic phases were dried over sodium sulphate, filtered and concentrated. 159 mg of the title compound were obtained (77% of theory; 98% purity).

LC-MS (Method 2): $R_t$=0.77 min

MS (ESIpos): m/z=485 (M+H)$^+$ $^1$H NMR (400 MHz, DMSO-d$_6$): δ [ppm]=1.02 (s, 3H), 1.46-1.67 (m, 4H), 2.24-2.47 (m, 5H), 2.50 (s, 3H; obscured by solvent peak), 3.14-3.25 (m, 2H), 5.44 (s, 2H), 6.54 (s, 1H), 7.21-7.30 (m, 2H), 7.34 (s, 1H), 7.39 (t, 1H), 7.57-7.67 (m, 1H).

Enantiomer B: about 70% ee $R_t$=5.31 min [Daicel Chiralpak AZ-H, 5 μm, 250×4.6 mm; eluent: 50% isohexane, 50% ethanol+0.2% diethylamine; flow rate 1.0 ml/min; temperature: 35° C.; detection: 220 nm].

Example 44 ent-N-(2-Amino-5-fluoro-2-methylpentyl)-7-[(2,6-difluorobenzyl)oxy]-2,5-dimethylpyrazolo[1,5-a]pyridine-3-carboxamide (Enantiomer A)

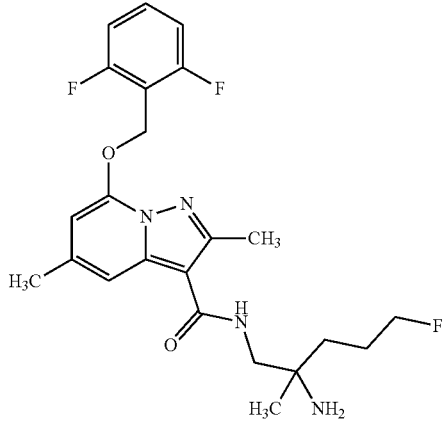 [SMILES: Cc1cc(OCc2c(F)cccc2F)n2nc(C)c(C(=O)NCC(C)(N)CCCF)c2c1]

A mixture of 82 mg (0.12 mmol) of ent-benzyl {1-[({7-[(2,6-difluorobenzyl)oxy]-2,5-dimethylpyrazolo[1,5-a]pyridin-3-yl}carbonyl)amino]-5-fluoro-2-methylpentan-2-yl}carbamate trifluoroacetate (enantiomer A) from Example 92A and 3.7 mg of palladium on activated carbon (10%) in 3 ml of ethanol was hydrogenated at room temperature and standard pressure for 2 h. Subsequently, the mixture was filtered through a Millipore filter and washed with ethanol, and the filtrate was concentrated. The crude product was admixed with acetonitrile, water and TFA and purified by means of preparative HPLC (RP-C18, eluent:acetonitrile/water gradient with addition of 0.1% TFA). The product fractions were taken up in dichloromethane and a little methanol, and washed twice with saturated aqueous sodium hydrogencarbonate solution. The combined aqueous phases were extracted twice with dichloromethane. The combined organic phases were dried over sodium sulphate, filtered and concentrated. 39 mg of the title compound were obtained (73% of theory; 98% purity).

LC-MS (Method 2): $R_t$=0.73 min

MS (ESIpos): m/z=449 (M+H)$^+$ $^1$H NMR (400 MHz, DMSO-d$_6$): δ [ppm]=1.00 (s, 3H), 1.31-1.45 (m, 2H), 1.47-1.85 (m, 4H), 2.40 (s, 3H), 2.50 (s, 3H; obscured by the solvent peak), 3.12-3.25 (m, 2H), 4.32-4.39 (m, 1H), 4.44-4.51 (m, 1H), 5.44 (s, 2H), 6.56 (s, 1H), 7.21-7.33 (m, 3H), 7.38 (s, 1H), 7.57-7.67 (m, 1H).

Example 45 ent-N-(2-Amino-5-fluoro-2-methylpentyl)-7-[(2,6-difluorobenzyl)oxy]-2,5-dimethylpyrazolo[1,5-a]pyridine-3-carboxamide (Enantiomer B)

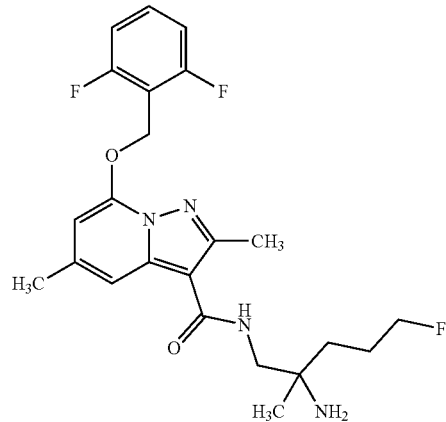 [SMILES: Cc1cc(OCc2c(F)cccc2F)n2nc(C)c(C(=O)NCC(C)(N)CCCF)c2c1]

A mixture of 109 mg (0.15 mmol; 96% purity) of ent-benzyl {1-[({7-[(2,6-difluorobenzyl)oxy]-2,5-dimethylpyrazolo[1,5-a]pyridin-3-yl}carbonyl)amino]-5-fluoro-2-methylpentan-2-yl}carbamate (enantiomer B) from Example 93A, 5 mg of palladium on activated carbon (10%) in 4 ml of ethanol was hydrogenated at room temperature and standard pressure for 6 h. Subsequently, the mixture was filtered through a Millipore filter and washed with ethanol, and the filtrate was concentrated. The crude product was admixed with acetonitrile, water and TFA and purified by means of preparative HPLC (RP-C18, eluent:acetonitrile/water gradient with addition of 0.1% TFA). The product fractions were taken up in dichloromethane and a little methanol, and washed twice with saturated aqueous sodium hydrogencarbonate solution. The combined organic phases were extracted twice with dichloromethane. The combined organic phases were dried over sodium sulphate, filtered and concentrated. 40 mg of the title compound were obtained (58% of theory; 97% purity).

LC-MS (Method 2): $R_t$=0.73 min

MS (ESIpos): m/z=449 (M+H)$^+$ $^1$H NMR (500 MHz, DMSO-d$_6$): δ [ppm]=1.00 (s, 3H), 1.32-1.44 (m, 2H), 1.47-1.84 (m, 4H), 2.40 (s, 3H), 2.50 (s, 3H; obscured by the solvent peak), 3.12-3.24 (m, 2H), 4.34-4.39 (m, 1H), 4.44-4.49 (m, 1H), 5.44 (s, 2H), 6.56 (s, 1H), 7.22-7.32 (m, 3H), 7.38 (s, 7.58-7.66 (m, 1H).

Example 46 ent-N-(2-Amino-4,4-difluoro-2-methylbutyl)-7-[(2,6-difluorobenzyl)oxy]-2,5-dimethylpyrazolo[1,5-a]pyridine-3-carboxamide (Enantiomer A)

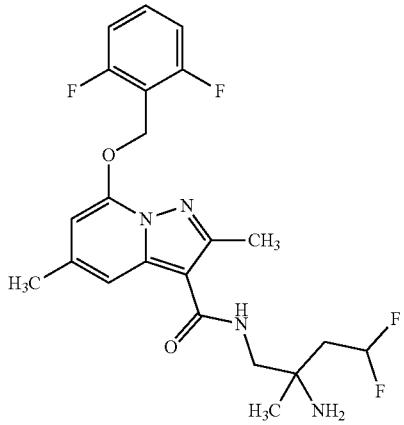 [SMILES: Cc1cc(OCc2c(F)cccc2F)n2nc(C)c(C(=O)NCC(C)(N)CC(F)F)c2c1]

A mixture of 157 mg (0.19 mmol; 72% purity) of ent-benzyl {1-[({7-[(2,6-difluorobenzyl)oxy]-2,5-dimethylpyrazolo[1,5-a]pyridin-3-yl}carbonyl)amino]-4,4-difluoro-2-methylbutan-2-yl}carbamate (enantiomer A) from Example 94A, 6.2 mg of palladium on activated carbon (10%) and 22 μl of TFA in 5 ml of ethanol was hydrogenated at room temperature and standard pressure for 4.5 h. Subsequently, the mixture was filtered through a Millipore filter and washed with ethanol, and the filtrate was concentrated. The crude product was admixed with acetonitrile, water and TFA and purified by means of preparative HPLC (RP-C18, eluent: acetonitrile/water gradient with addition of 0.1% TFA). The product fractions were taken up in dichloromethane and a little methanol, and washed twice with saturated aqueous sodium hydrogencarbonate solution. The combined aqueous phases were extracted twice with dichloromethane. The combined organic phases were dried over sodium sulphate, filtered and concentrated. 58 mg of the title compound were obtained (65% of theory; 98% purity).

LC-MS (Method 2): $R_t$=0.73 min
MS (ESIpos): m/z=453 (M+H)$^+$
$^1$H NMR (500 MHz, DMSO-d$_6$): δ [ppm]=1.07 (s, 3H), 1.69 (br. s, 2H), 1.84-1.96 (m, 2H), 2.40 (s, 3H), 2.50 (s, 3H; obscured by the solvent peak), 3.18-3.29 (m, 2H), 5.44 (s, 2H), 6.10-6.38 (m, 1H), 6.56 (s, 1H), 7.22-7.30 (m, 2H), 7.34-7.40 (m, 2H), 7.57-7.67 (m, 1H).

Example 47 ent-N-(2-Amino-4,4-difluoro-2-methylbutyl)-7-[(2,6-difluorobenzyl)oxy]-2,5-dimethylpyrazolo[1,5-a]pyridine-3-carboxamide (Enantiomer B)

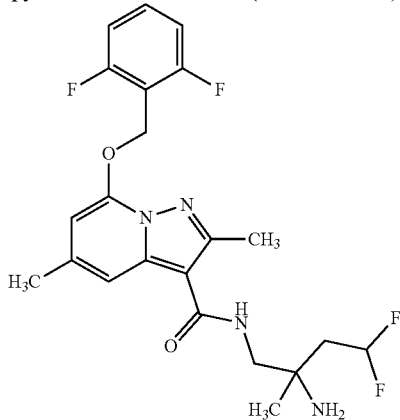

A mixture of 281 mg (0.40 mmol; purity 99%) of ent-benzyl {1-[({7-[(2,6-difluorobenzyl)oxy]-2,5-dimethylpyrazolo[1,5-a]pyridin-3-yl}carbonyl)amino]-4,4-difluoro-2-methylbutan-2-yl}carbamate trifluoroacetate (enantiomer B) from Example 95A and 13 mg of palladium on activated carbon (10%) in 10.2 ml of ethanol was hydrogenated at room temperature and standard pressure for 3.5 h. Subsequently, the mixture was filtered through a Millipore filter and washed with ethanol, and the filtrate was concentrated. The crude product was admixed with acetonitrile, water and TFA and purified by means of preparative HPLC (RP-C18, eluent: acetonitrile/water gradient with addition of 0.1% TFA). The product fractions were taken up in dichloromethane and a little methanol, and washed twice with saturated aqueous sodium hydrogencarbonate solution. The combined aqueous phases were extracted twice with dichloromethane. The combined organic phases were dried over sodium sulphate, filtered and concentrated. 145 mg of the title compound were obtained (80% of theory; 99% purity).

LC-MS (Method 2): $R_t$=0.67 min
MS (ESIpos): m/z=453 (M+H)$^+$
$^1$H NMR (500 MHz, DMSO-d$_6$): δ [ppm]=1.07 (s, 3H), 1.69 (br. s, 2H), 1.84-1.96 (m, 2H), 2.40 (s, 3H), 2.50 (s, 3H; obscured by the solvent peak), 3.18-3.29 (m, 2H), 5.45 (s, 2H), 6.10-6.38 (m, 1H), 6.56 (s, 1H), 7.22-7.29 (m, 2H), 7.34-7.40 (m, 2H), 7.57-7.67 (m, 1H).

Example 48 rac-N-(2-Amino-4-fluoro-2-methylbutyl)-7-[(2,6-difluorobenzyl)oxy]-2,5-dimethylpyrazolo[1,5-a]pyridine-3-carboxamide

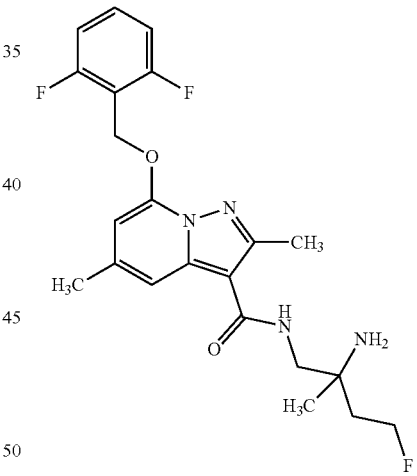

200 mg (0.45 mmol, about 75% purity) of 7-[(2,6-difluorobenzyl)oxy]-5-methyl-2-propylpyrazolo[1,5-a]pyridine-3-carboxylic acid from Example 4A were initially charged together with 274 mg (0.72 mmol) of HATU and 0.42 ml (2.41 mmol) of N,N-diisopropylethylamine in 2.8 ml of DMF, and the mixture was stirred for 20 min. A solution of 330 mg (1.27 mmol assuming a purity of about 75%) of rac-4-fluoro-2-methylbutane-1,2-diamine dihydrochloride from Example 86A in 1.4 ml of DMF and 0.63 ml (3.61 mmol) of N,N-diisopropylethylamine was added to the first reaction mixture and the mixture was stirred at RT for 1 h. The reaction solution was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 75 mg of the target compound were obtained (37% of theory, 98% purity).

LC-MS (Method 2): $R_t$=0.71 min

MS (ESIpos): m/z=435 (M+H)$^+$ $^1$H NMR (400 MHz, DMSO-d$_6$): δ=1.03 (s, 3H), 1.48-1.83 (m, 4H), 2.40 (s, 3H), 2.50 (s, 3H; obscured by the solvent peak), 3.14-3.28 (m, 2H), 4.55-4.62 (m, 1H), 4.66-4.73 (m, 1H), 5.45 (s, 2H), 6.55 (s, 1H), 7.20-7.32 (m, 3H), 7.38 (s, 1H), 7.58-7.67 (m, 1H).

Example 49 ent-N-(2-Amino-4-fluoro-2-methylbutyl)-7-[(2,6-difluorobenzyl)oxy]-2,5-dimethylpyrazolo[1,5-a]pyridine-3-carboxamide (Enantiomer A)

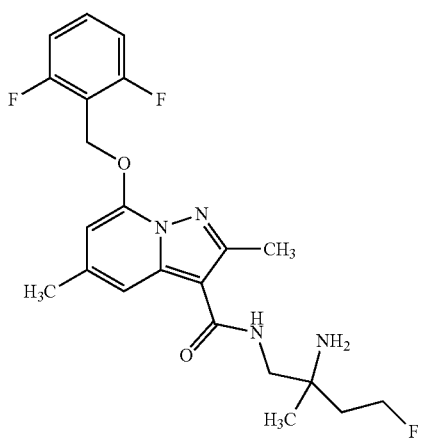 [SMILES: Cc1cc(OCc2c(F)cccc2F)n2nc(C)c(C(=O)NCC(C)(N)CCF)c2c1]

70 mg (0.16 mmol, 98% purity) of rac-N-(2-amino-4-fluoro-2-methylbutyl)-7-[(2,6-difluorobenzyl)oxy]-2,5-dimethylpyrazolo[1,5-a]pyridine-3-carboxamide from Example 48 were separated into the enantiomers by preparative separation on a chiral phase [column: Daicel Chiralpak IF, 5 μm, 250×20 mm, eluent: 100% ethanol+0.2% diethylamine, flow rate: 15 ml/min; temperature: 45° C., detection: 220 nm].

The product fractions were collected on dry ice and concentrated (bath temperature: 30° C.) and lyophilized.

Enantiomer A: Yield: 28 mg (>99% ee)

$R_t$=6.76 min [Chiralpak AZ-H, 5 μm, 250×4.6 mm; eluent: 100% ethanol+0.2% diethylamine; flow rate: 1 ml/min; detection: 270 nm].

Example 50 ent-N-(2-Amino-4-fluoro-2-methylbutyl)-7-[(2,6-difluorobenzyl)oxy]-2,5-dimethylpyrazolo[1,5-a]pyridine-3-carboxamide (Enantiomer B)

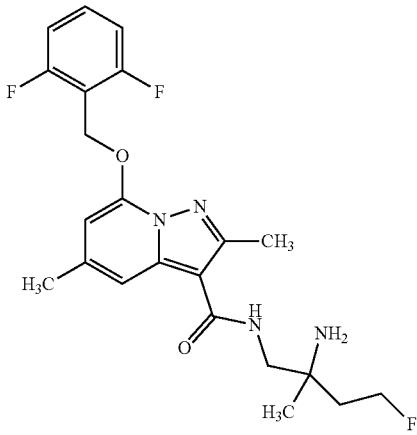 [SMILES: Cc1cc(OCc2c(F)cccc2F)n2nc(C)c(C(=O)NCC(C)(N)CCF)c2c1]

90 mg (0.16 mmol, 98% purity) of rac-N-(2-amino-4-fluoro-2-methylbutyl)-7-[(2,6-difluorobenzyl)oxy]-2,5-dimethylpyrazolo[1,5-a]pyridine-3-carboxamide from Example 48 were separated into the enantiomers by preparative separation on a chiral phase [column: Daicel Chiralpak IF, 5 μm, 250×20 mm, eluent: 100% ethanol+0.2% diethylamine, flow rate: 15 ml/min; temperature: 45° C., detection: 220 nm].

The product fractions were collected on dry ice and concentrated (bath temperature: 30° C.) and lyophilized.

Enantiomer B: Yield: 33 mg (94% ee)

$R_t$=7.84 min [Chiralpak AZ-H, 5 μm, 250×4.6 mm; eluent: 100% ethanol+0.2% diethylamine; flow rate: 1 ml/min; detection: 270 nm].

Example 51 ent-N-(2-Amino-2-methylpentyl)-7-[(2,6-difluorobenzyl)oxy]-5-methyl-2-propylpyrazolo[1,5-a]pyridine-3-carboxamide (Enantiomer B)

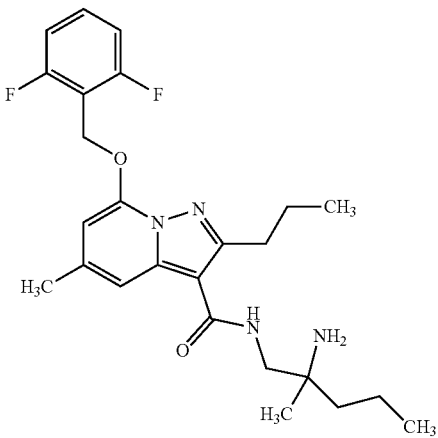 [SMILES: CCCc1nn2c(OCc3c(F)cccc3F)cc(C)cc2c1C(=O)NCC(C)(N)CCC]

54 mg (0.08 mmol) of ent-benzyl {1-[({7-[(2,6-difluorobenzyl)oxy]-5-methyl-2-propylpyrazolo[1,5-a]pyridin-3-yl}carbonyl)amino]-2-methylpentan-2-yl}carbamate trifluoroacetate (enantiomer B) from Example 104A were dissolved in 2 ml of ethanol, 4 mg of 10% palladium on activated carbon were added and hydrogenation was effected at standard pressure for 0.5 hour. The reaction mixture was filtered by means of a Millipore filter and the filtrate was concentrated by rotary evaporation. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 20 mg of the target compound were obtained (56% of theory).

LC-MS (Method 2): $R_t$=0.79 min

MS (ESIpos): m/z=459 $(M+H)^+$

In analogy to Example 51, the example compounds shown in Table 2 were prepared by hydrogenating the protected Cbz-amines with 10% palladium on activated carbon (0.03-0.1 equivalent) under the reaction conditions described (reaction time: 1-6 h; temperature: RT; standard pressure).

Illustrative Workup of the Reaction Mixture:

The reaction mixture was diluted with water, TFA or formic acid and purified by means of preparative HPLC (RP18 column, eluent:acetonitrile/water gradient with addition of 0.1% TFA or 0.05% formic acid). The crude product was additionally or alternatively purified by means of thick-layer chromatography or silica gel chromatography (eluent:dichloromethane/methanol or dichloromethane/2 M ammonia in methanol). The product-containing fractions were concentrated.

The residue was, if necessary, taken up in dichloromethane and washed with saturated aqueous sodium hydrogencarbonate solution. The aqueous phase was extracted twice with dichloromethane, and the combined organic phases were dried over sodium sulphate, filtered, concentrated and lyophilized.

TABLE 2

| Example | IUPAC name/structure (yield) | Analytical data |
|---|---|---|
| 52 | ent-N-(2-Amino-2-methylpentyl)-7-[(2,6-difluorobenzyl)oxy]-5-methyl-2-(trifluoromethyl)pyrazolo[1,5-a]pyridine-3-carboxamide trifluoroacetate (enantiomer B) 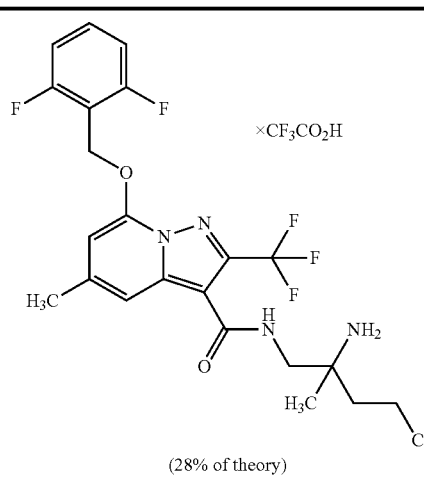 (28% of theory) | LC-MS (Method 2): $R_t$ = 0.83 min MS (ESIpos): m/z = 485 $(M+H)^+$ |
| 53 | ent-N-(2-Amino-2-methylpentyl)-7-[(2,6-difluorobenzyl)oxy]-5-methylpyrazolo[1,5-a]pyridine-3-carboxamide (enantiomer B) 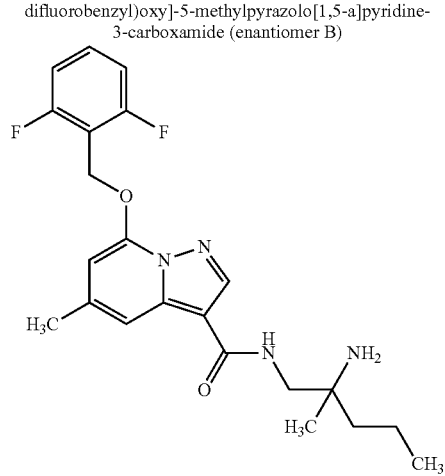 (60% of theory) | LC-MS (Method 2): $R_t$ = 0.74 min MS (ESIpos): m/z = 417 $(M+H)^+$ |

Example 54 ent-N-(2-Amino-2-methylbutyl)-2-cyclopropyl-7-[(2,6-difluorobenzyl)oxy]-5-methylpyrazolo[1,5-a]pyridine-3-carboxamide (Enantiomer A)

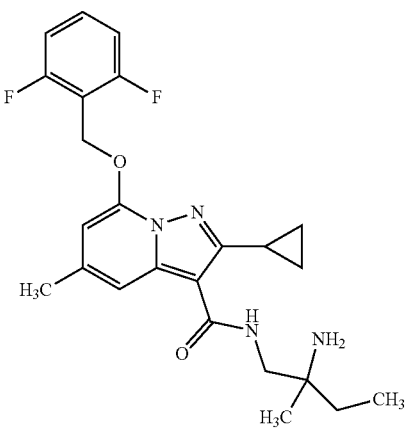 [SMILES: CCC(C)(N)CNC(=O)c1c(C2CC2)nn2c(OCc3c(F)cccc3F)cc(C)cc12]

57 mg (0.07 mmol; 90% purity) of ent-benzyl {1-[({2-cyclopropyl-7-[(2,6-difluorobenzyl)oxy]-5-methylpyrazolo[1,5-a]pyridin-3-yl}carbonyl)amino]-2-methylbutan-2-yl}carbamate trifluoroacetate (enantiomer A) from Example 107A were dissolved in 2.1 ml of ethanol, 3 mg of 10% palladium on activated carbon were added and hydrogenation was effected at standard pressure for 3.5 hour. The reaction mixture was filtered by means of a Millipore filter and the filtrate was concentrated by rotary evaporation. The residue was dissolved in 2.1 ml of ethanol, admixed with 13 μl of TFA and 3 mg of 10% palladium on activated carbon, and hydrogenated at standard pressure for 1 hour. The reaction mixture was filtered by means of a Millipore filter and the filtrate was concentrated by rotary evaporation. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 26 mg of the target compound were obtained (79% of theory).

LC-MS (Method 2): $R_t$=0.75 min

MS (ESIpos): m/z=443 (M+H)$^+$ $^1$H NMR (500 MHz, DMSO-d$_6$): δ=0.83-0.93 (m, 5H), 0.95-1.02 (m, 5H), 1.29-1.43 (m, 2H), 1.50 (br. s, 2H), 2.31-2.42 (m, 4H), 3.13-3.25 (m, 2H), 5.44 (s, 2H), 6.53 (s, 1H), 7.21-7.28 (m, 2H), 7.36 (t, 1H), 7.47 (s, 1H), 7.57-7.64 (m, 1H).

Example 55 ent-N-(2-Amino-2-methylpentyl)-2-cyclopropyl-7-[(2,6-difluorobenzyl)oxy]-5-methylpyrazolo[1,5-a]pyridine-3-carboxamide (Enantiomer B)

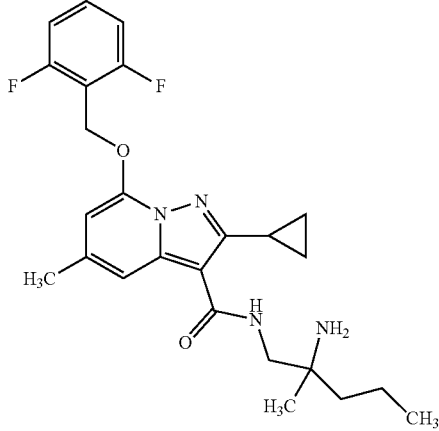 [SMILES: CCCC(C)(N)CNC(=O)c1c(C2CC2)nn2c(OCc3c(F)cccc3F)cc(C)cc12]

88 mg (0.12 mmol) of ent-benzyl {1-[({2-cyclopropyl-7-[(2,6-difluorobenzyl)oxy]-5-methylpyrazolo pyridin-3-yl}carbonyl)amino]-2-methylpentan-2-yl}carbamate trifluoroacetate (enantiomer B) from Example 108A were dissolved in 3.2 ml of ethanol, 4 mg of 10% palladium on activated carbon were added and hydrogenation was effected at standard pressure for 2 hours. The reaction mixture was filtered by means of a Millipore filter and the filtrate was concentrated by rotary evaporation. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 41 mg of the target compound were obtained (72% of theory).

LC-MS (Method 2): $R_t$=0.78 min

MS (ESIpos): m/z=457 (M+H)$^+$ $^1$H NMR (500 MHz, DMSO-d$_6$): δ=0.83-0.93 (m, 5H), 0.96-1.02 (m, 5H), 1.25-1.40 (m, 4H), 1.70 (br. s, 2H), 2.32-2.42 (m, 4H), 3.12-3.25 (m, 2H), 5.44 (s, 2H), 6.53 (s, 1H), 7.21-7.29 (m, 2H), 7.39 (t, 1H), 7.45 (s, 1H), 7.57-7.65 (m, 1H).

Example 56 ent-N-(2-Amino-4,4-difluoro-2-methylbutyl)-2-cyclopropyl-7-[(2,6-difluorobenzyl)oxy]-5-methylpyrazolo[1,5-a]pyridine-3-carboxamide (Enantiomer A)

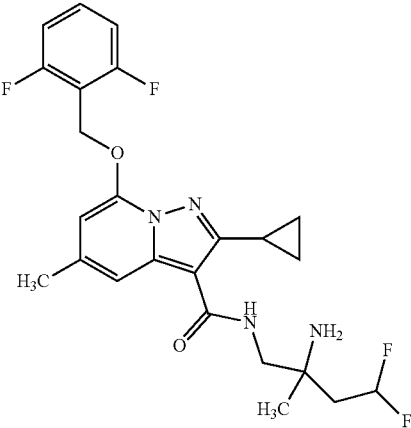 [SMILES: Cc1cc(OCc2c(F)cccc2F)n2nc(C3CC3)c(C(=O)NCC(C)(N)CC(F)F)c2c1]

55 mg (0.07 mmol; 95% purity) of ent-benzyl {1-[({2-cyclopropyl-7-[(2,6-difluorobenzyl)oxy]-5-methylpyrazolo[1,5-a]pyridin-3-yl}carbonyl)amino]-4,4-difluoro-2-methylbutan-2-yl}carbamate trifluoroacetate (enantiomer A) from Example 110A were dissolved in 1.8 ml of ethanol, 2.3 mg of 10% palladium on activated carbon were added and hydrogenation was effected at standard pressure for 3 hours. The reaction mixture was filtered by means of a Millipore filter. The mixture was admixed with 20 μl (0.22 mmol) of TFA and 23 mg of 10% palladium on activated carbon, and hydrogenated at standard pressure for 1.5 hours. The reaction mixture was filtered by means of a Millipore filter and the filtrate was concentrated. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 30 mg of the target compound were obtained (85% of theory).

LC-MS (Method 2): $R_t$=0.79 min

MS (ESIpos): m/z=479 (M+H)$^+$ $^1$H NMR (400 MHz, DMSO-d$_6$): δ [ppm]=0.86-0.93 (m, 2H), 0.94-1.01 (m, 2H), 1.08 (s, 3H), 1.70 (br. s, 2H), 1.85-

1.99 (m, 2H), 2.34-2.43 (m, 4H), 3.20-3.29 (m, 2H; partly obscured by solvent peak), 5.45 (s, 2H), 6.08-6.42 (m, 1H), 6.53 (s, 1H), 7.19-7.29 (m, 2H), 7.42 (s, 1H), 7.49 (t, 1H) 7.55-7.65 (m, 1H).

obscured by solvent peak), 5.45 (s, 2H), 6.08-6.42 (m, 1H), 6.53 (s, 1H), 7.20-7.29 (m, 2H), 7.42 (s, 1H), 7.49 (t, 1H), 7.55-7.65 (m, 1H).

Example 57 ent-N-(2-Amino-4,4-difluoro-2-methylbutyl)-2-cyclopropyl-7-[(2,6-difluorobenzyl)oxy]-5-methylpyrazolo[1,5-a]pyridine-3-carboxamide (Enantiomer B)

Example 58 ent-N-(2-Amino-5,5,5-trifluoro-2-methylpentyl)-2-cyclopropyl-7-[(2,6-difluorobenzyl)oxy]-5-methylpyrazolo[1,5-a]pyridine-3-carboxamide (Enantiomer B)

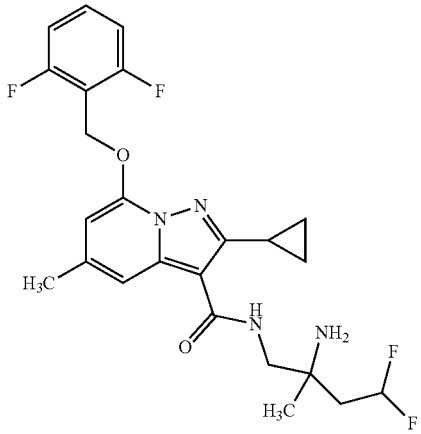 [SMILES: Cc1cc(OCc2c(F)cccc2F)n2nc(C3CC3)c(C(=O)NCC(C)(N)CC(F)F)c2c1]

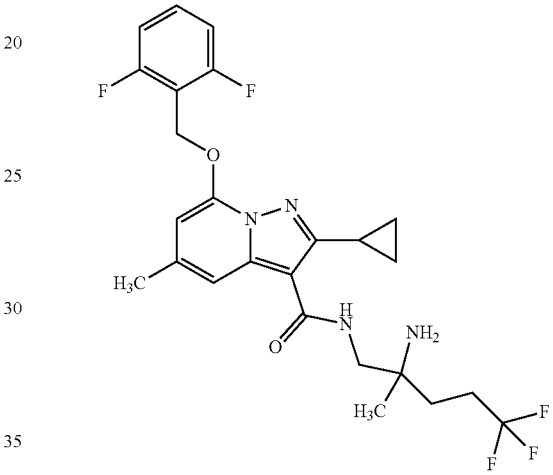

54 mg (0.06 mmol; 82% purity) of ent-benzyl {1-[({2-cyclopropyl-7-[(2,6-difluorobenzyl)oxy]-5-methylpyrazolo[1,5-a]pyridin-3-yl}carbonyl)amino]-4,4-difluoro-2-methylbutan-2-yl}carbamate trifluoroacetate (enantiomer B) from Example 111A were dissolved in 1.6 ml of ethanol, 2 mg of 10% palladium on activated carbon were added and hydrogenation was effected at standard pressure for 4.5 hours. The reaction mixture was filtered by means of a Millipore filter. The mixture was admixed with 5 μl (0.06 mmol) of TFA and 2 mg of 10% palladium on activated carbon, and hydrogenated at standard pressure for 1 hour. The reaction mixture was filtered by means of a Millipore filter and the filtrate was concentrated. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 17 mg of the target compound were obtained (58% of theory).

LC-MS (Method 2): $R_t$=0.79 min

MS (ESIpos): m/z=479 (M+H)$^+$ $^1$H NMR (400 MHz, DMSO-d$_6$): δ [ppm]=0.87-0.93 (m, 2H), 0.94-1.01 (m, 2H), 1.08 (s, 3H), 1.72 (br. s, 2H), 1.86-1.99 (m, 2H), 2.34-2.43 (m, 4H), 3.20-3.29 (m, 2H; partly 97 mg (0.13 mmol; 82% purity) of ent-benzyl {1-[({2-cyclopropyl-7-[(2,6-difluorobenzyl)oxy]-5-methylpyrazolo[1,5-a]pyridin-3-yl}carbonyl)amino]-5,5,5-trifluoro-2-methylpentan-2-yl}carbamate trifluoroacetate (enantiomer B) from Example 109A were dissolved in 3.2 ml of ethanol, 4 mg of 10% palladium on activated carbon were added and hydrogenation was effected at standard pressure for 4.5 hours. The reaction mixture was filtered by means of a Millipore filter and the filtrate was concentrated. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 51 mg of the target compound were obtained (78% of theory).

LC-MS (Method 2): $R_t$=0.80 min

MS (ESIpos): m/z=511 (M+H)$^+$ $^1$H NMR (400 MHz, DMSO-d$_6$): δ [ppm]=0.87-0.92 (m, 2H), 0.93-0.99 (m, 2H), 1.02 (s, 3H), 1.48-1.64 (m, 4H), 2.24-2.45 (m, 6H), 3.17-3.28 (m, 2H), 5.44 (s, 2H), 6.08-6.42 (m, 1H), 6.52 (s, 1H), 7.20-7.29 (m, 2H), 7.39 (s, 1H), 7.50 (t, 1H), 7.56-7.65 (m, 1H).

Example 59 rac-N-(2-Amino-2-cyanoethyl)-7-[(2,6-difluorobenzyl)oxy]-2,5-dimethylpyrazolo[1,5-a]pyridine-3-carboxamide

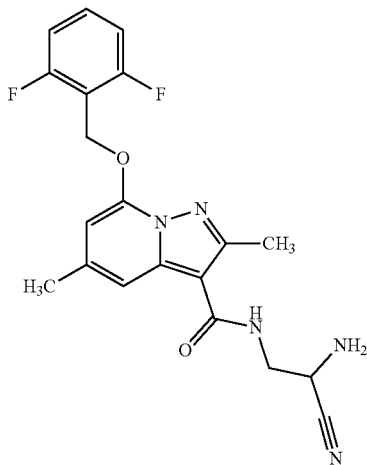 [SMILES: Cc1cc(OCc2c(F)cccc2F)n2nc(C)c(C(=O)NCC(N)C#N)c2c1]

80 mg (0.18 mmol; about 75% purity) of 7-[(2,6-difluorobenzyl)oxy]-2,5-dimethylpyrazolo[1,5-a]pyridine-3-carboxylic acid from Example 4A were initially charged together with 76 mg (0.20 mmol) of HATU and 0.21 ml (1.17 mmol) of N,N-diisopropylethylamine in 0.74 ml of DMF, and the mixture was stirred at room temperature for 10 min. Subsequently, 33 mg (0.21 mmol) of rac-2,3-diaminopropanonitrile dihydrochloride were added to the reaction solution at 0° C. and the mixture was stirred at RT overnight. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. 55 mg of the target compound were obtained (75% of theory).

LC-MS (Method 2): $R_t$=0.76 min
MS (ESIpos): m/z=400 (M+H)$^+$
$^1$H NMR (400 MHz, DMSO-$d_6$): δ=2.40 (s, 3H), 2.42-2.54 (m, 5H; obscured by solvent peak), 3.39-3.55 (m, 2H), 3.91-4.04 (m, 1H), 5.44 (s, 2H), 6.57 (s, 1H), 7.19-7.30 (m, 2H), 7.38 (s, 1H), 7.57-7.67 (m, 1H), 7.72 (t, 1H).

In analogy to Example 59, the example compounds shown in Table 3 were prepared by reacting 7-[(2,6-difluorobenzyl)oxy]-2,5-dimethylpyrazolo[1,5-a]pyridine-3-carboxylic acid from Example 4A with the appropriate amines [hydrazines, hydrazides, hydroxylamines] which are commercially available or have been described above (1.1-5 equivalents), HATU (1.1-4.5 equivalents) and N,N-diisopropylethylamine (3-12 equivalents) in DMF or in DMF/dichloromethane (1/1) under the reaction conditions described (reaction time: 1-48 h; temperature: 0° C.-RT, −20° C., RT or 60° C.).

Illustrative Workup of the Reaction Mixture:
The reaction solution was admixed with water and the precipitated solids were stirred at room temperature for about 30 min. Subsequently, the solids were filtered off, washed well with water and dried under high vacuum.

Alternatively, the reaction mixture was diluted with water, TFA or formic acid and purified by means of preparative HPLC (RP18 column, eluent:acetonitrile/water gradient with addition of 0.1% TFA or 0.05% formic acid). The crude product was additionally or alternatively purified by means of thick-layer chromatography or silica gel chromatography (eluent:dichloromethane/methanol or dichloromethane/2 M ammonia in methanol). The product-containing fractions were concentrated.

The product fractions from the purifications were, if necessary, taken up in dichloromethane and washed with saturated aqueous sodium hydrogencarbonate solution. The aqueous phase was extracted twice with dichloromethane, and the combined organic phases were dried over sodium sulphate, filtered, concentrated and lyophilized.

TABLE 3

| Example | IUPAC name/structure (yield) | Analytical data |
|---|---|---|
| 60 | N-[(3-Aminooxetan-3-yl)methyl]-7-[(2,6-difluorobenzyl)oxy]-2,5-dimethylpyrazolo[1,5-a]pyridine-3-carboxamide<br><br>(23% of theory) | LC-MS (Method 2):<br>$R_t$ = 0.65 min<br>MS (ESIpos):<br>m/z = 417 (M + H)$^+$ |

TABLE 3-continued

| Example | IUPAC name/structure (yield) | Analytical data |
|---|---|---|
| 61 | 7-[(2,6-Difluorobenzyl)oxy]-2,5-dimethyl-N-(2-sulphamoylethyl)pyrazolo[1,5-a]pyridine-3-carboxamide<br>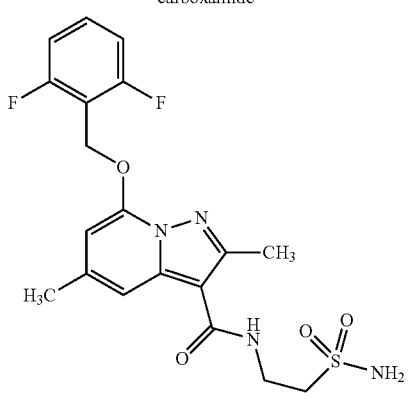<br>(39% of theory) | LC-MS (Method 2):<br>$R_t$ = 0.83 min<br>MS (ESIpos):<br>m/z = 439 (M + H)$^+$ |
| 62 | N-[(4-Cyanocyclohexyl)methyl]-7-[(2,6-difluorobenzyl)oxy]-2,5-dimethylpyrazolo[1,5-a]pyridine-3-carboxamide (cis-/trans mixture)<br>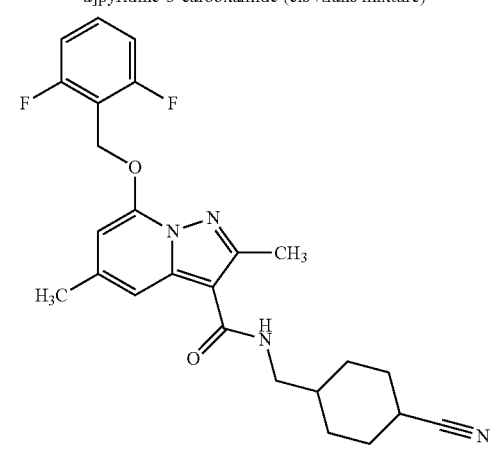<br>(50% of theory) | LC-MS (Method 2):<br>$R_t$ = 1.02 min<br>MS (ESIpos):<br>m/z = 453 (M + H)$^+$ |
| 63 | N-(5-Cyanopentyl)-7-[(2,6-difluorobenzyl)oxy]-2,5-dimethylpyrazolo[1,5-a]pyridine-3-carboxamide<br>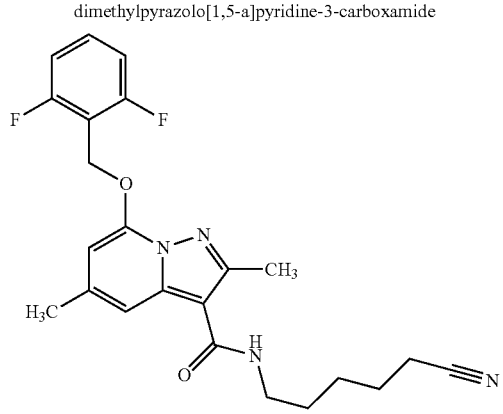<br>(85% of theory) | LC-MS (Method 2):<br>$R_t$ = 0.97 min<br>MS (ESIpos):<br>m/z = 427 (M + H)$^+$ |

TABLE 3-continued

| Example | IUPAC name/structure (yield) | Analytical data |
|---|---|---|
| 64 | 7-[(2,6-Difluorobenzyl)oxy]-N-(2-hydroxyethoxy)-2,5-dimethylpyrazolo[1,5-a]pyridine-3-carboxamide trifluoroacetate<br />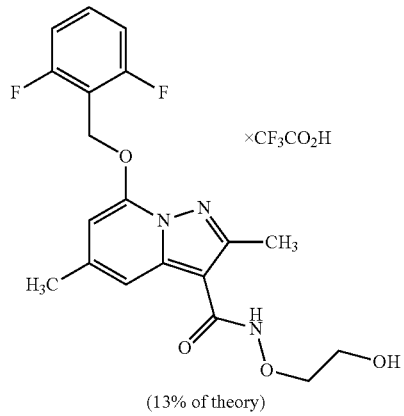<br />(13% of theory) | LC-MS (Method 2):<br />$R_t$ = 0.80 min<br />MS (ESpos):<br />m/z = 392 (M-TFA + H)+ |
| 65 | N-(Allyloxy)-7-[(2,6-difluorobenzyl)oxy]-2,5-dimethylpyrazolo[1,5-a]pyridine-3-carboxamide trifluoroacetate<br />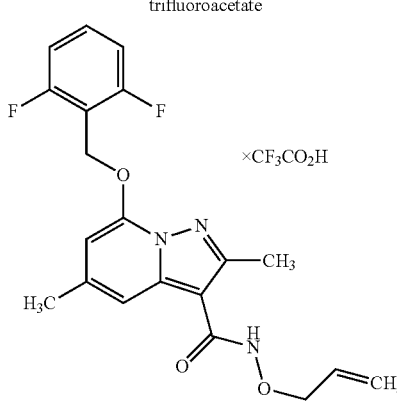<br />(25% of theory; 94% purity) | LC-MS (Method 2):<br />$R_t$ = 0.95 min<br />MS (ESpos):<br />m/z = 388 (M-TFA + H)+ |
| 66 | 7-[(2,6-Difluorobenzyl)oxy]-N'-(4-fluorophenyl)-2,5-dimethylpyrazolo[1,5-a]pyridine-3-carbohydrazide trifluoroacetate<br />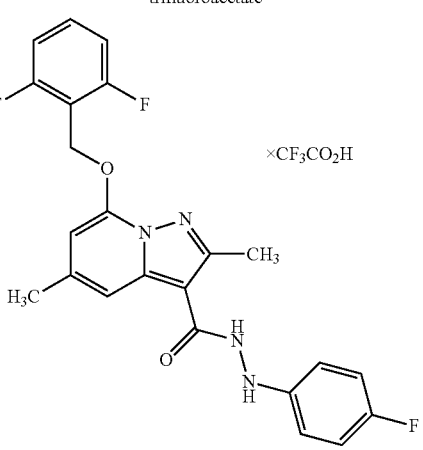<br />(3% of theory; 90% purity) [1] | LC-MS (Method 7):<br />$R_t$ = 2.54 min<br />MS (ESpos):<br />m/z = 441 (M-TFA + H)+ |

TABLE 3-continued

| Example | IUPAC name/structure (yield) | Analytical data |
|---|---|---|
| 67 | 7-[(2,6-Difluorobenzyl)oxy]-N'-[(dimethylamino)acetyl]-2,5-dimethylpyrazolo[1,5-a]pyridine-3-carbohydrazide<br>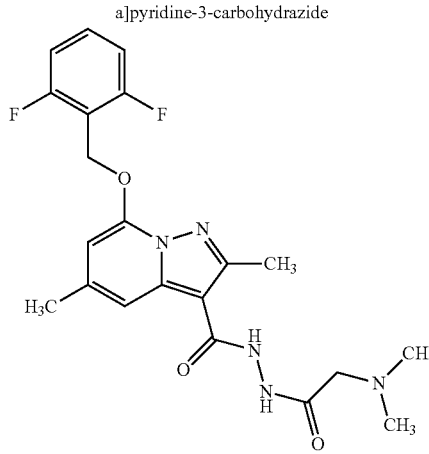<br>(49% of theory) | LC-MS (Method 2):<br>$R_t$ = 0.62 min<br>MS (ESIpos):<br>m/z = 432 (M + H)$^+$<br>$^1$H NMR (500 MHz, DMSO-d$_6$) δ = 2.28 (s, 6H), 2.41 (s, 3H), 2.51 (s, 3H; obscured by the solvent peak), 3.01 (s, 2H), 5.47 (s, 2H), 6.58 (s, 1H), 7.21-7.30 (m, 2H), 7.38 (s, 1H), 7.57-7.67 (m, 1H), 9.33 (s, 1H), 9.63 (s, 1H). |
| 68 | 7-[(2,6-Difluorobenzyl)oxy]-N'-(2-hydroxycyclopentyl)-2,5-dimethylpyrazolo[1,5-a]pyridine-3-carbohydrazide trifluoroacetate (mixture of stereoisomers)<br>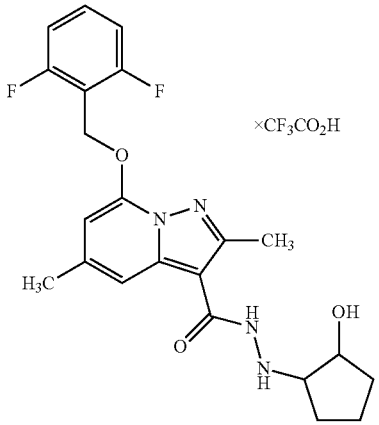 [SMILES: Cc1cc(OCc2c(F)cccc2F)n2nc(C)c(C(=O)NNC3CCCC3O)c2c1]<br>(8% of theory) | LC-MS (Method 2):<br>$R_t$ = 0.83 min<br>MS (ESpos):<br>m/z = 431 (M-TFA + H)$^+$ |
| 69 | rel-N-[(3R,4S)-4-Aminotetrahydrofuran-3-yl]-7-[(2,6-difluorobenzyl)oxy]-2,5-dimethylpyrazolo[1,5-a]pyridine-3-carboxamide (cis stereoisomer)<br>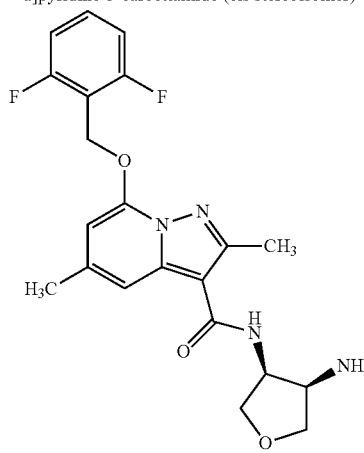<br>(40% of theory) | LC-MS (Method 2):<br>$R_t$ = 0.67 min<br>MS (ESIpos):<br>m/z = 417 (M + H)$^+$ |

TABLE 3-continued

| Example | IUPAC name/structure (yield) | Analytical data |
|---|---|---|
| 70 | N-(1-Amino-2,3-dihydro-1H-inden-2-yl)-7-[(2,6-difluorobenzyl)oxy]-2,5-dimethylpyrazolo[1,5-a]pyridine-3-carboxamide (mixture of stereoisomers)<br>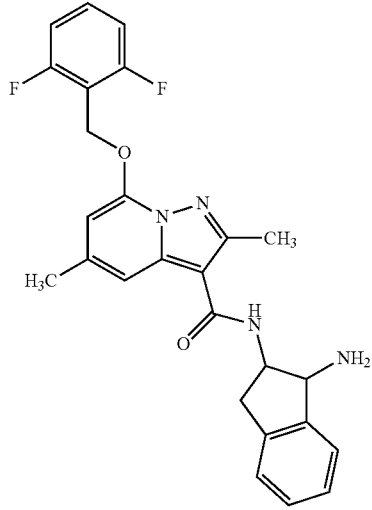 [SMILES: Cc1cc(OCc2c(F)cccc2F)n2nc(C)c(C(=O)NC3Cc4ccccc4C3N)c2c1]<br>(73% of theory) | LC-MS (Method 7):<br>$R_t$ = 2.41 and 2.45 min<br>MS (ESIpos):<br>m/z = 463 (M + H)$^+$ |
| 71 | 7-[(2,6-Difluorobenzyl)oxy]-N-[(1S,2R)-2-hydroxy-2,3-dihydro-1H-inden-1-yl]-2,5-dimethylpyrazolo[1,5-a]pyridine-3-carboxamide trifluoroacetate<br>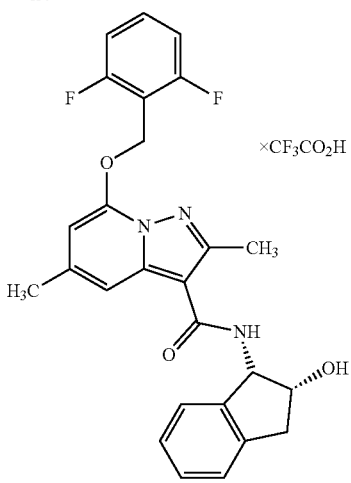<br>(41% of theory) | LC-MS(Method 2):<br>$R_t$ = 1.03 min<br>MS (ESpos):<br>m/z = 464 (M-TFA + H)$^+$ |

TABLE 3-continued

| Example | IUPAC name/structure (yield) | Analytical data |
|---|---|---|
| 72 | rac-N-{2-Amino-2-[3-(2-hydroxyethoxy)phenyl]ethyl}-7-[(2,6-difluorobenzyl)oxy]-2,5-dimethylpyrazolo[1,5-a]pyridine-3-carboxamide trifluoroacetate<br />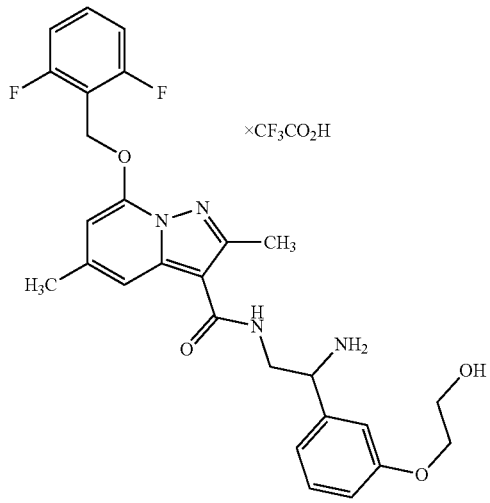 [SMILES: Cc1cc(OCc2c(F)cccc2F)n2nc(C)c(C(=O)NCC(N)c3cccc(OCCO)c3)c2c1]<br />(23% of theory; 92% purity) | LC-MS (Method 2):<br />$R_t$ = 0.71 min<br />MS (ESpos):<br />m/z = 511 (M-TFA + H)$^+$ |
| 73 | rac-N-[2-Amino-2-(2-methyl-1,3-thiazol-4-yl)ethyl]-7-[(2,6-difluorobenzyl)oxy]-2,5-dimethylpyrazolo[1,5-a]pyridine-3-carboxamide trifluoroacetate<br />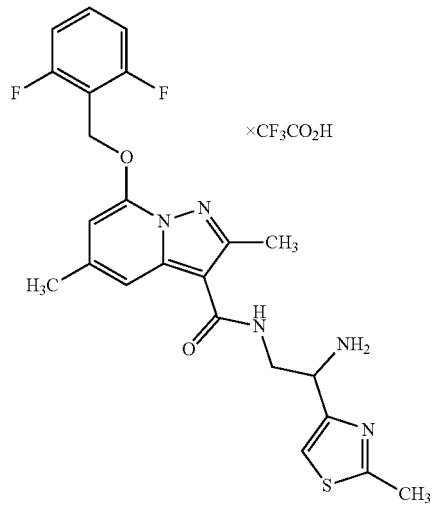 [SMILES: Cc1cc(OCc2c(F)cccc2F)n2nc(C)c(C(=O)NCC(N)c3csc(C)n3)c2c1]<br />(24% of theory) | LC-MS (Method 2):<br />$R_t$ = 0.72 min<br />MS (ESpos):<br />m/z = 472 (M-TFA + H)$^+$ |

TABLE 3-continued

| Example | IUPAC name/structure (yield) | Analytical data |
|---|---|---|
| 74 | rac-7-[(2,6-Difluorobenzyl)oxy]-N-(3,4-dihydro-2H-pyrano[2,3-b]pyridin-4-yl)-2,5-dimethylpyrazolo[1,5-a]pyridine-3-carboxamide trifluoroacetate<br><br>(62% of theory) | LC-MS (Method 2):<br>$R_t$ = 0.92 min<br>MS (ESpos):<br>m/z = 465 (M-TFA + H)$^+$ |
| 75 | rac-7-[(2,6-Difluorobenzyl)oxy]-2,5-dimethyl-N-(1-methyl-1,2,3,4-tetrahydroquinolin-4-yl)pyrazolo a]pyridine-3-carboxamide trifluoroacetate<br><br>(58% of theory; 96% purity) | LC-MS (Method 2):<br>$R_t$ = 1.16 min<br>MS (ESpos):<br>m/z = 477 (M-TFA + H)$^+$ |

TABLE 3-continued

| Example | IUPAC name/structure (yield) | Analytical data |
|---|---|---|
| 76 | rac-7-[(2,6-Difluorobenzyl)oxy]-2,5-dimethyl-N-(2-oxo-1,2,3,4-tetrahydroquinolin-4-yl)pyrazolo[1,5-a]pyridine-3-carboxamide trifluoroacetate<br />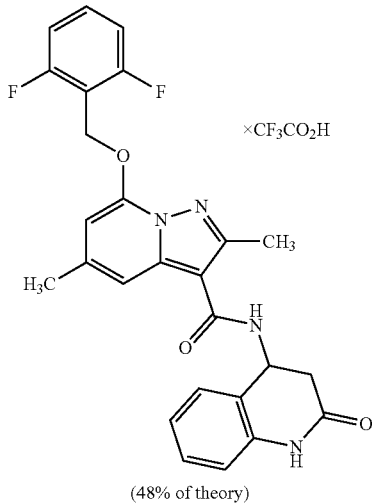<br />(48% of theory) | LC-MS(Method 2):<br />$R_t$ = 0.90 min<br />MS (ESpos):<br />m/z = 477 (M-TFA + H)$^+$ |
| 77 | rac-7-[(2,6-Difluorobenzyl)oxy]-2,5-dimethyl-N-(1-methyl-2-oxo-1,2,3,4-tetrahydroquinolin-4-yl)pyrazolo[1,5-a]pyridine-3-carboxamide trifluoroacetate<br />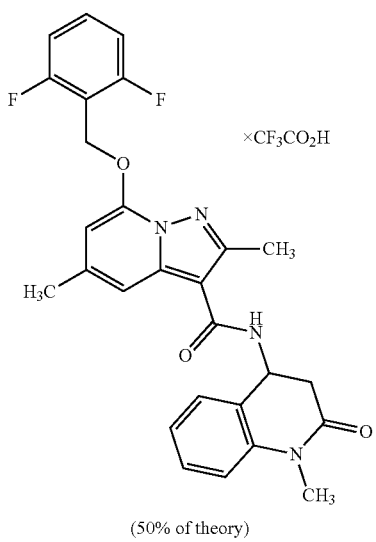<br />(50% of theory) | LC-MS (Method 2):<br />$R_t$ = 1.00 min<br />MS (ESpos):<br />m/z = 491 (M-TFA + H)$^+$ |

TABLE 3-continued

| Example | IUPAC name/structure (yield) | Analytical data |
|---|---|---|
| 78 | rac-N-[2-Amino-4-(benzyloxy)-2-methylbutyl]-7-[(2,6-difluorobenzyl)oxy]-2,5-dimethylpyrazolo[1,5-a]pyridine-3-carboxamide<br />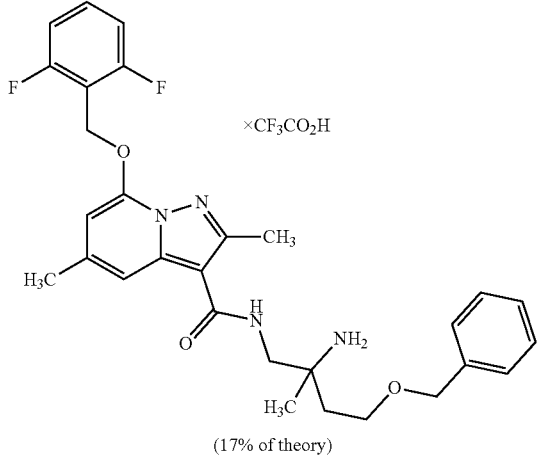<br />(17% of theory) | LC-MS (Method 2):<br />$R_t$ = 0.85 min<br />MS (ESIpos):<br />m/z = 523 (M + H)$^+$ |
| 79 | rac-N-[2-Amino-3-(3,4-difluorophenoxy)-2-methylpropyl]-7-[(2,6-difluorobenzyl)oxy]-2,5-dimethylpyrazolo[1,5-a]pyridine-3-carboxamide<br />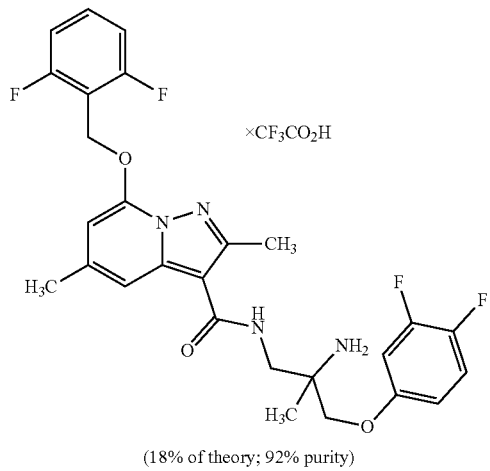<br />(18% of theory; 92% purity) | LC-MS (Method 2):<br />$R_t$ = 0.83 min<br />MS (ESIpos):<br />m/z = 531 (M + H)$^+$ |

TABLE 3-continued

| Example | IUPAC name/structure (yield) | Analytical data |
|---|---|---|
| 80 | 7-[(2,6-Difluorobenzyl)oxy]-N-(6-fluoroquinolin-4-yl)-2,5-dimethylpyrazolo[1,5-a]pyridine-3-carboxamide trifluoroacetate 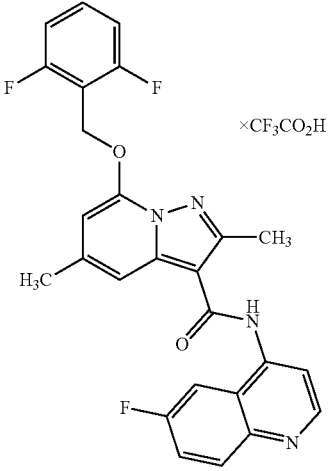 [SMILES: Cc1cc(OCc2c(F)cccc2F)n2nc(C)c(C(=O)Nc3ccnc4ccc(F)cc34)c2c1] (5% of theory; 92% purity) [2)] | LC-MS (Method 2): $R_t = 0.93$ min MS (ESpos): m/z = 477 (M-TFA + H)$^+$ |

Example 81

N-(3-Amino-2,2-difluoropropyl)-7-[(2,6-difluorobenzyl)oxy]-2,5-dimethylpyrazolo[1,5-a]pyridine-3-carboxamide

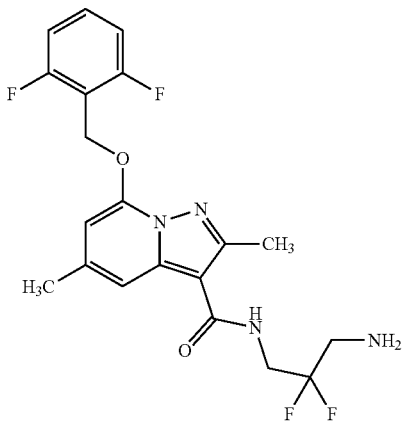 [SMILES: Cc1cc(OCc2c(F)cccc2F)n2nc(C)c(C(=O)NCC(F)(F)CN)c2c1]

77 mg (0.12 mmol) of tert-butyl {3-[({7-[(2,6-difluorobenzyl)oxy]-2,5-dimethylpyrazolo[1,5-a]pyridin-3-yl}carbonyl)amino]-2,2-difluoropropyl}carbamate trifluoroacetate from Example 112A were suspended in 0.5 ml of diethyl ether and admixed with 0.6 ml of hydrogen chloride solution (2 N in diethyl ether). The mixture was stirred at room temperature overnight. Then the mixture was diluted with acetonitrile and water, admixed with TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with a little saturated aqueous sodium hydrogencarbonate solution. The aqueous phase was extracted twice with dichloromethane. The combined organic phases were dried over sodium sulphate, filtered, concentrated and lyophilized. 47 mg of the target compound were obtained (91% of theory).

LC-MS (Method 7): $R_t=2.13$ min

MS (ESIpos): m/z=425 (M+H)$^+$

In analogy to Example 81, the example compounds shown in Table 4 were prepared by reacting the corresponding starting compounds [Boc-protected amines] with hydrogen chloride solution (2 N in diethyl ether, 5-20 equivalents), under the reaction conditions described (reaction time: 2-24 h; temperature: RT).

Illustrative Workup of the Reaction Mixture:

The reaction mixture was diluted with water, TFA or formic acid and purified by means of preparative HPLC (RP18 column, eluent:acetonitrile/water gradient with addition of 0.1% TFA or 0.05% formic acid). The crude product was additionally or alternatively purified by means of thick-layer chromatography or silica gel chromatography (eluent:dichloromethane/methanol or dichloromethane/2 M ammonia in methanol). The product-containing fractions were concentrated.

The product-containing fractions from the preparative HPLC were optionally concentrated, and the residue was taken up in dichloromethane and washed with saturated aqueous sodium hydrogencarbonate solution. The aqueous phase was extracted twice with dichloromethane, and the combined organic phases were dried over sodium sulphate, filtered, concentrated and lyophilized.

TABLE 4

| Example | IUPAC name/structure (yield) | Analytical data |
|---|---|---|
| 82 | rac-7-[(2,6-Difluorobenzyl)oxy]-2,5-dimethyl-N-(1,2,3,4-tetrahydroquinolin-2-ylmethyl)pyrazolo[1,5-a]pyridine-3-carboxamide<br>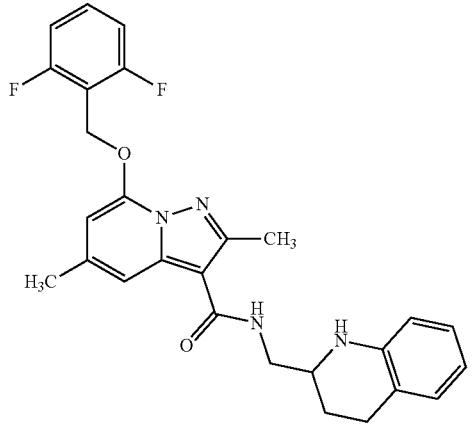 [SMILES: Cc1cc(OCc2c(F)cccc2F)n2nc(C)c(C(=O)NCC3CCc4ccccc4N3)c2c1]<br>(69% of theory) | LC-MS (Method 7):<br>$R_t$ = 2.70 min<br>MS (ESIpos):<br>m/z = 477 (M + H)$^+$ |
| 83 | rac-Ethyl 6-{2-amino-1-[({7-[(2,6-difluorobenzyl)oxy]-2,5-dimethylpyrazolo[1,5-a]pyridin-3-yl}carbonyl)amino]ethyl} pyridine-2-carboxylate trifluoroacetate<br>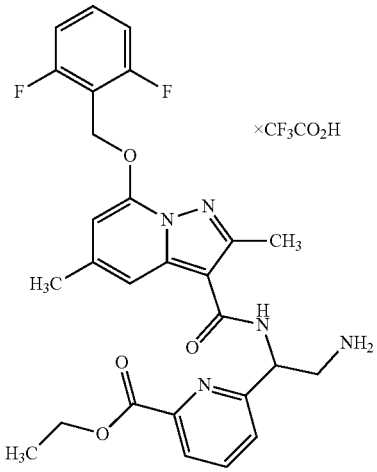<br>(80% of theory; 95% purity) | LC-MS (Method 2):<br>$R_t$ = 0.80 min<br>MS (ESpos):<br>m/z = 524 (M-TFA + H)$^+$ |

TABLE 4-continued

| Example | IUPAC name/structure (yield) | Analytical data |
|---|---|---|
| 84 | rac-N-[2-Amino-1-(4-cyanophenyl)ethyl]-7-[(2,6-difluorobenzyl)oxy]-2,5-dimethylpyrazolo[1,5-a]pyridine-3-carboxamide<br />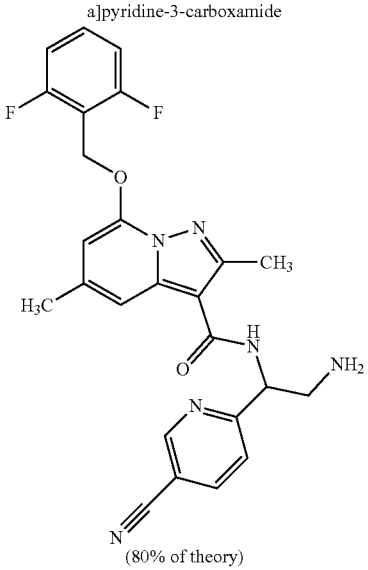<br />(80% of theory) | LC-MS (Method 2):<br />$R_t$ = 0.77 min<br />MS (ESIpos):<br />m/z = 476 (M + H)$^+$ |

Example 85 rac-N-(2-Amino-1,2-dimethylcyclopropyl)-7-[(2,6-difluorobenzyl)oxy]-2,5-dimethylpyrazolo[1,5-a]pyridine-3-carboxamide

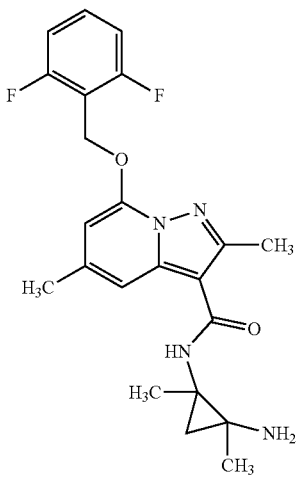 [SMILES: Cc1cc(OCc2c(F)cccc2F)n2nc(C)c(C(=O)NC3(C)CC3(C)N)c2c1]

29 mg (0.11 mmol) of rac-1,2-dimethylcyclopropane-1,2-diamine dihydrobromide (described in: W. v. d. Saal et al. Liebigs Annalen der Chemie 1994, 569-580) were initially charged in a 96-well deep-well multititre plate. A solution of 33.2 mg (0.1 mmol) of 7-[(2,6-difluorobenzyl)oxy]-2,5-dimethylpyrazolo[1,5-a]pyridine-3-carboxylic acid from Example 4A in 0.4 ml of DMF/dichloromethane (1:1, v/v) and a solution of 49.4 mg (0.13 mmol) of HATU in 0.4 ml of DMF/dichloromethane (1:1, v/v) were added successively. After adding 20.2 mg (0.20 mmol) of 4-methylmorpholine, the mixture was shaken at RT overnight. Subsequently, the mixture was heated to 60° C. and shaken at this temperature for 7 h. Then the solvent was evaporated off completely. The residue was dissolved in 0.8 ml of DMF and filtered, and the target compound was isolated by preparative LC-MS (Method 9). The product-containing fractions were concentrated under reduced pressure using a centrifugal dryer. The residue of each product fraction was dissolved in 0.6 ml of DMSO. These were combined and finally freed of the solvent in a centrifugal dryer. 2.3 mg (5% of theory) of the title compound were obtained.

LC-MS (Method 10): $R_t$=0.66 min

MS (ESIpos): m/z=415 (M+H)$^+$

In analogy to Example 85, the example compounds shown in Table 5 were prepared by reacting 7-[(2,6-difluorobenzyl)oxy]-2,5-dimethylpyrazolo[1,5-a]pyridine-3-carboxylic acid from Example 4A were reacted with the appropriate amines, which are commercially available, known from the literature or described above, under the conditions described:

TABLE 5

| Example | IUPAC name/structure (yield) | Analytical data |
|---|---|---|
| 86 | ent-7-[(2,6-Difluorobenzyl)oxy]-2,5-dimethyl-N-[2-methyl-6-(trifluoromethyl)-1,2,3,4-tetrahydro-1,5-naphthyridin-4-yl]pyrazolo[1,5-a]pyridine-3-carboxamide<br />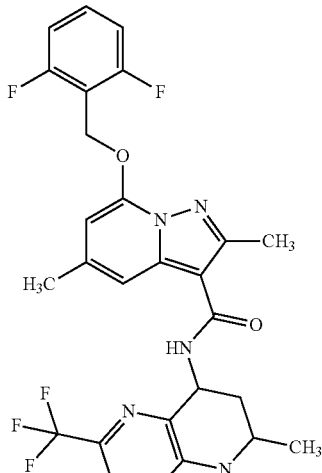<br />(2% of theory; 77% purity) | LC-MS (Method 10):<br />$R_t$ = 1.27 min<br />MS (ESIpos):<br />m/z = 546 (M + H)$^+$ |
| 87 | rac-7-[(2,6-Difluorobenzyl)oxy]-N-(3,4-dihydro-2H-chromen-4-yl)-2,5-dimethylpyrazolo[1,5-a]pyridine-3-carboxamide<br />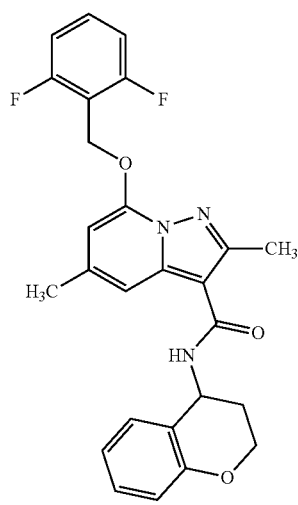 [SMILES: Cc1cc(OCc2c(F)cccc2F)n2nc(C)c(C(=O)NC3CCOc4ccccc43)c2c1]<br />(5% of theory; 84% purity) | LC-MS (Method 10):<br />$R_t$ = 1.18 min<br />MS (ESIpos):<br />m/z = 464 (M + H)$^+$ |

TABLE 5-continued

| Example | IUPAC name/structure (yield) | Analytical data |
|---|---|---|
| 88 | rac-7-[(2,6-Difluorobenzyl)oxy]-2,5-dimethyl-N-(thiomorpholin-3-ylmethyl)pyrazolo[1,5-a]pyridine-3-carboxamide<br>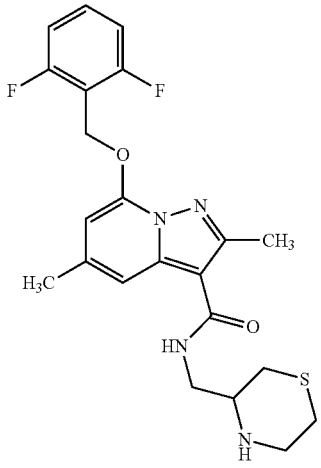 [SMILES: Cc1cc(OCc2c(F)cccc2F)n2nc(C)c(C(=O)NCC3CSCCN3)c2c1]<br>(16% of theory) | LC-MS (Method 10):<br>$R_t$ = 0.76 min<br>MS (ESIpos):<br>m/z = 447 (M + H)$^+$ |
| 89 | N-[2-(Cyclopropylamino)-2-oxoethyl]-7-[(2,6-difluorobenzyl)oxy]-2,5-dimethylpyrazolo[1,5-a]pyridine-3-carboxamide<br>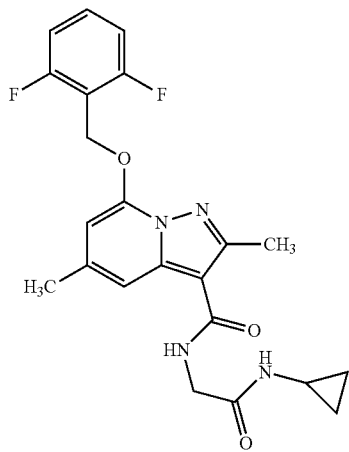 [SMILES: Cc1cc(OCc2c(F)cccc2F)n2nc(C)c(C(=O)NCC(=O)NC3CC3)c2c1]<br>(29% of theory; 79% purity) | LC-MS (Method 10):<br>$R_t$ = 0.98 min<br>MS (ESIpos):<br>m/z = 429 (M + H)$^+$ |

TABLE 5-continued

| Example | IUPAC name/structure (yield) | Analytical data |
|---|---|---|
| 90 | 7-[(2,6-Difluorobenzyl)oxy]-N[1-(3,4-difluorophenyl)cyclopropyl]-2,5-dimethylpyrazolo[1,5-a]pyridine-3-carboxamide 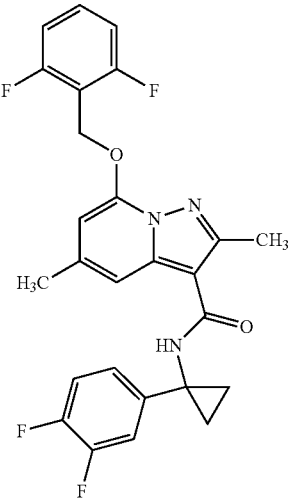 [SMILES: Cc1cc(OCc2c(F)cccc2F)n2nc(C)c(C(=O)NC3(c4ccc(F)c(F)c4)CC3)c2c1] (4% of theory; 80% purity) | LC-MS (Method 10): $R_t$ = 1.20 min MS (ESIpos): m/z = 484 (M + H)$^+$ |
| 91 | rac-N-(2-Amino-2-methylcyclobutyl)-7-[(2,6-difluorobenzyl)oxy]-2,5-dimethylpyrazolo[1,5-a]pyridine-3-carboxamide [1]) 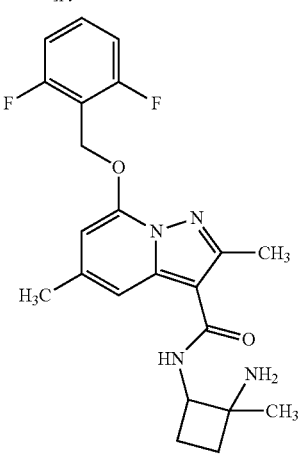 (6% of theory; 81% purity) | LC-MS (Method 10): $R_t$ = 0.75 min MS (ESIpos): m/z = 415 (M + H)$^+$ |

TABLE 5-continued

| Example | IUPAC name/structure (yield) | Analytical data |
|---|---|---|
| 92 | rac-N-(2-Amino-2,4-dimethylpentyl)-7-[(2,6-difluorobenzyl)oxy]-2,5-dimethylpyrazolo[1,5-a]pyridine-3-carboxamide 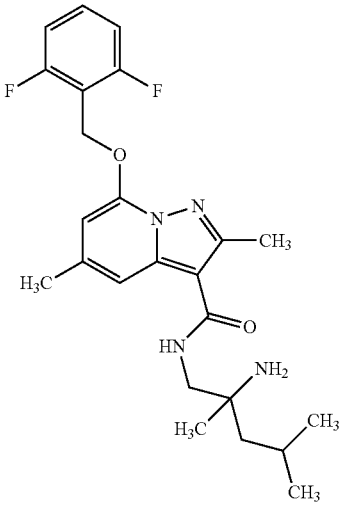 [SMILES: Cc1cc(OCc2c(F)cccc2F)n2nc(C)c(C(=O)NCC(C)(N)CC(C)C)c2c1] (22% of theory) | LC-MS (Method 10): $R_t$ = 0.83 min MS (ESIpos): m/z = 445 (M + H)$^+$ |
| 93 | 7-[(2,6-Difluorobenzyl)oxy]-2,5-dimethyl-N-[2-(4-methylpiperazin-1-yl)ethyl]pyrazolo[1,5-a]pyridine-3-carboxamide 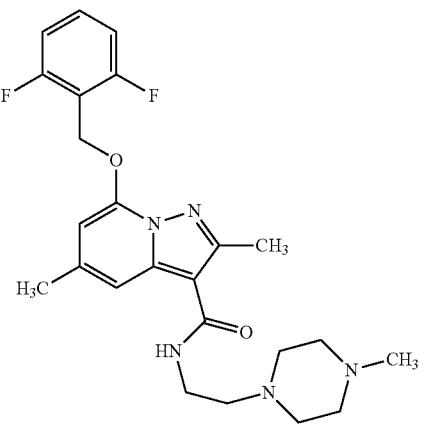 [SMILES: Cc1cc(OCc2c(F)cccc2F)n2nc(C)c(C(=O)NCCN3CCN(C)CC3)c2c1] (12% of theory) | LC-MS (Method 10): $R_t$ = 0.71 min MS (ESIpos): m/z = 458 (M + H)$^+$ |

TABLE 5-continued

| Example | IUPAC name/structure (yield) | Analytical data |
|---|---|---|
| 94 | 7-[(2,6-Difluorobenzyl)oxy]-N-[(2R)-hexan-2-yl]-2,5-dimethylpyrazolo[1,5-a]pyridine-3-carboxamide<br />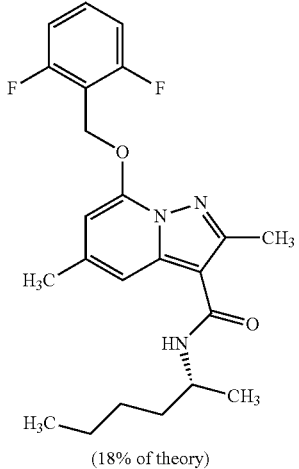<br />(18% of theory) | LC-MS (Method 10):<br />R$_t$ = 1.22 min<br />MS (ESIpos):<br />m/z = 416 (M + H)$^+$ |
| 95 | rac-7-[(2,6-Difluorobenzyl)oxy]-2,5-dimethyl-N-[(5-oxopyrrolidin-2-yl)methyl]pyrazolo[1,5-a]pyridine-3-carboxamide<br />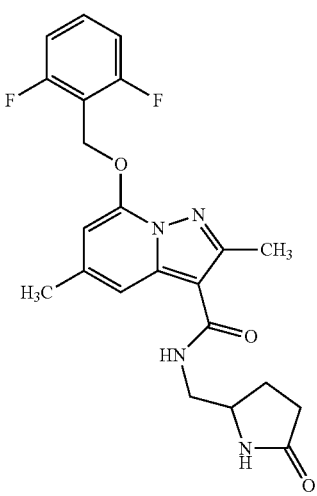 [SMILES: Cc1cc(OCc2c(F)cccc2F)n2nc(C)c(C(=O)NCC3CCC(=O)N3)c2c1]<br />(23% of theory) | LC-MS (Method 10):<br />R$_t$ = 0.94 min<br />MS (ESIpos):<br />m/z = 429 (M + H)$^+$ |

TABLE 5-continued

| Example | IUPAC name/structure (yield) | Analytical data |
|---|---|---|
| 96 | N-(2-Acetamidoethyl)-7-[(2,6-difluorobenzyl)oxy]-2,5-dimethylpyrazolo[1,5-a]pyridine-3-carboxamide 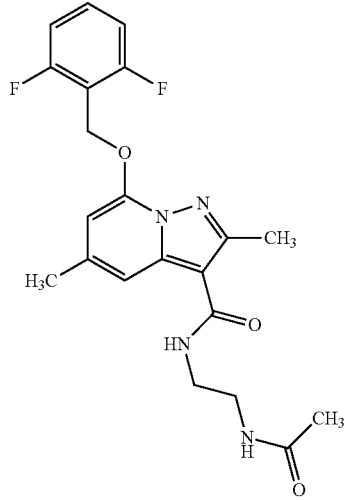 [SMILES: CC(=O)NCCNC(=O)c1c(C)nn2c(OCc3c(F)cccc3F)cc(C)cc12] (15% of theory) | LC-MS (Method 10): $R_t$ = 0.94 min MS (ESIpos): m/z = 417 (M + H)$^+$ |
| 97 | rac-N-(2-Amino-3-methoxy-2-methylpropyl)-7-[(2,6-difluorobenzyl)oxy]-2,5-dimethylpyrazolo[1,5-a]pyridine-3-carboxamide 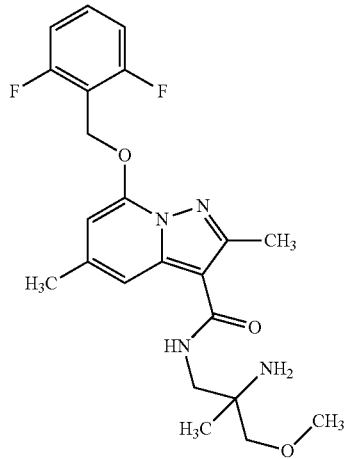 [SMILES: COCC(C)(N)CNC(=O)c1c(C)nn2c(OCc3c(F)cccc3F)cc(C)cc12] (36% of theory) | LC-MS (Method 10): $R_t$ = 0.75 min MS (ESIpos): m/z = 433 (M + H)$^+$ |

TABLE 5-continued

| Example | IUPAC name/structure (yield) | Analytical data |
|---|---|---|
| 98 | 7-[(2,6-Difluorobenzyl)oxy]-2,5-dimethyl-N-[(3R)-2-oxopyrrolidin-3-yl]pyrazolo[1,5-a]pyridine-3-carboxamide<br>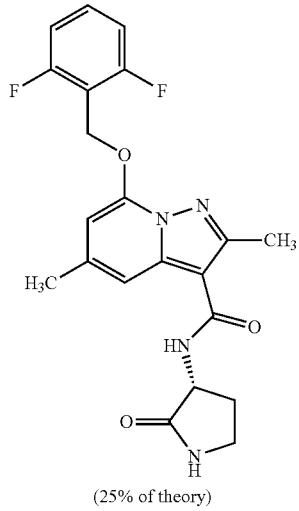<br>(25% of theory) | LC-MS (Method 10):<br>$R_t = 0.92$ min<br>MS (ESIpos):<br>m/z = 415 (M + H)$^+$ |
| 99 | rac-N-[2-Amino-3-(4-methoxyphenyl)-2-methylpropyl]-7-[(2,6-difluorobenzyl)oxy]-2,5-dimethylpyrazolo[1,5-a]pyridine-3-carboxamide<br>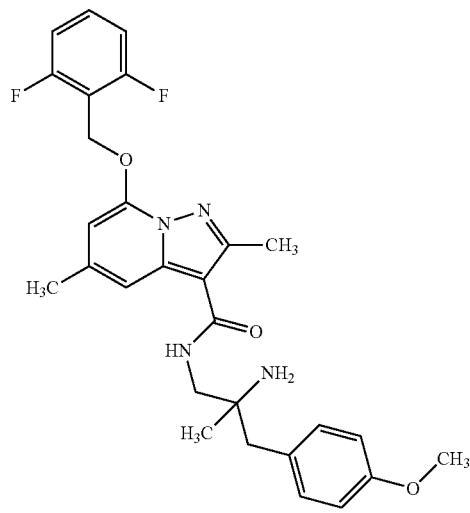 [SMILES: COc1ccc(CC(C)(N)CNC(=O)c2c(C)nn3c(OCc4c(F)cccc4F)cc(C)cc23)cc1]<br>(43% of theory) | LC-MS (Method 10):<br>$R_t = 0.85$ min<br>MS (ESIpos):<br>m/z = 509 (M + H)$^+$ |

TABLE 5-continued

| Example | IUPAC name/structure (yield) | Analytical data |
|---|---|---|
| 100 | rac-7-[(2,6-Difluorobenzyl)oxy]-2,5-dimethyl-N-[(2-oxo-1,3-oxazolidin-5-yl)methyl]pyrazolo[1,5-a]pyridine-3-carboxamide<br/>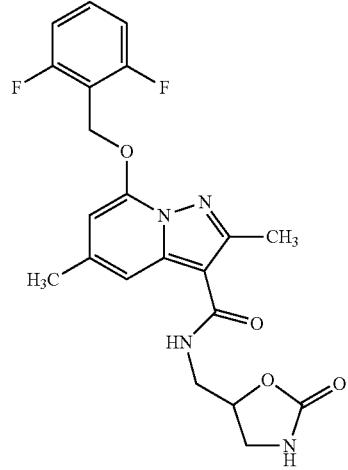 [SMILES: Cc1cc(OCc2c(F)cccc2F)n2nc(C)c(C(=O)NCC3CNC(=O)O3)c2c1]<br/>(6% of theory) | LC-MS (Method 10):<br/>$R_t$ = 0.92 min<br/>MS (ESIpos):<br/>m/z = 431 (M + H)$^+$ |
| 101 | N-(2-Amino-3,3-dimethylcyclobutyl)-7-[(2,6-difluorobenzyl)oxy]-2,5-dimethylpyrazolo[1,5-a]pyridine-3-carboxamide (isomer mixture) [2)]<br/>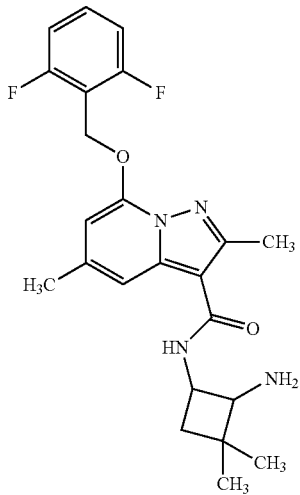 [SMILES: Cc1cc(OCc2c(F)cccc2F)n2nc(C)c(C(=O)NC3CC(C)(C)C3N)c2c1]<br/>(4% of theory; 84% purity) | LC-MS (Method 10):<br/>$R_t$ = 0.79 min<br/>MS (ESIpos):<br/>m/z = 429 (M + H)$^+$ |

TABLE 5-continued

| Example | IUPAC name/structure (yield) | Analytical data |
|---|---|---|
| 102 | rac-7-[(2,6-Difluorobenzyl)oxy]-N-(6-methoxy-1,2,3,4-tetrahydroquinolin-4-yl)-2,5-dimethylpyrazolo[1,5-a]pyridine-3-carboxamide<br>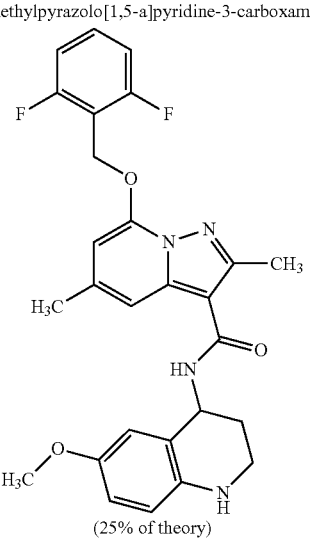<br>(25% of theory) | LC-MS (Method 10):<br>$R_t$ = 0.95 min<br>MS (ESIpos):<br>m/z = 493 (M + H)$^+$ |
| 103 | rac-N-[2-Amino-2-(quinolin-6-yl)ethyl]-7-[(2,6-difluorobenzyl)oxy]-2,5-dimethylpyrazolo[1,5-a]pyridine-3-carboxamide<br>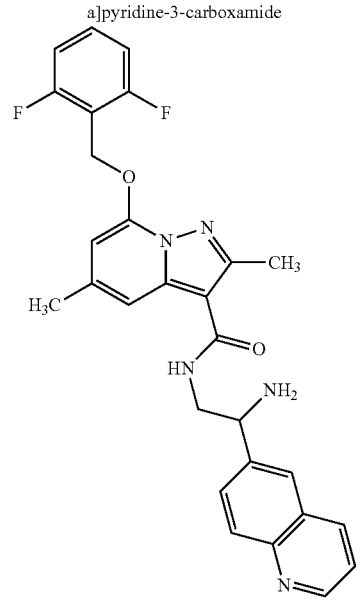<br>(9% of theory; 78% purity) | LC-MS (Method 10):<br>$R_t$ = 0.75 min<br>MS (ESIpos):<br>m/z = 502 (M + H)$^+$ |

TABLE 5-continued

| Example | IUPAC name/structure (yield) | Analytical data |
|---|---|---|
| 104 | rac-N-[2-Amino-2-(5-methyl-2-furyl)ethyl]-7-[(2,6-difluorobenzyl)oxy]-2,5-dimethylpyrazolo[1,5-a]pyridine-3-carboxamide<br>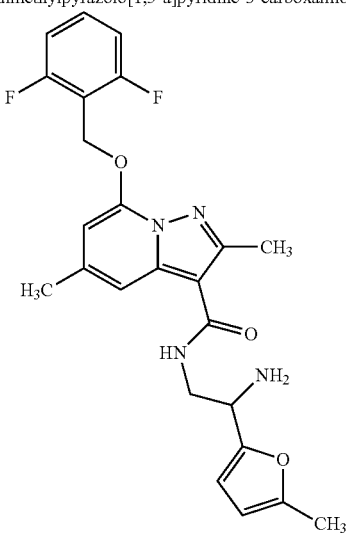<br>(9% of theory) | LC-MS (Method 10):<br>$R_t$ = 0.79 min<br>MS (ESIpos):<br>m/z = 455 (M + H)$^+$ |
| 105 | rac-N-{2-Amino-2-[3-(trifluoromethyl)phenyl]ethyl}-7-[(2,6-difluorobenzyl)oxy]-2,5-dimethylpyrazolo[1,5-a]pyridine-3-carboxamide<br>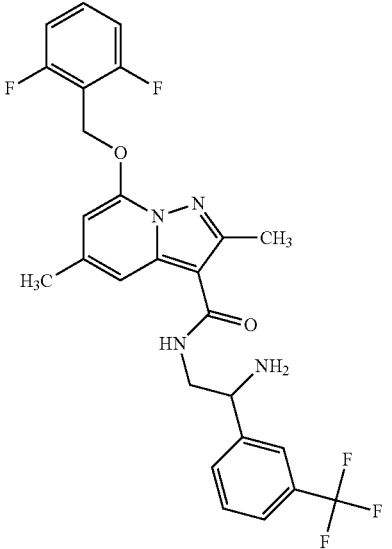 [SMILES: Cc1cc(OCc2c(F)cccc2F)n2nc(C)c(C(=O)NCC(N)c3cccc(C(F)(F)F)c3)c2c1]<br>(11% of theory) | LC-MS (Method 10):<br>$R_t$ = 0.86 min<br>MS (ESIpos):<br>m/z = 519 (M + H)$^+$ |

TABLE 5-continued

| Example | IUPAC name/structure (yield) | Analytical data |
|---|---|---|
| 106 | Ethyl {2-[({7-[(2,6-difluorobenzyl)oxy]-2,5-dimethylpyrazolo[1,5-a]pyridin-3-yl}carbonyl)amino]ethyl}carbamate<br />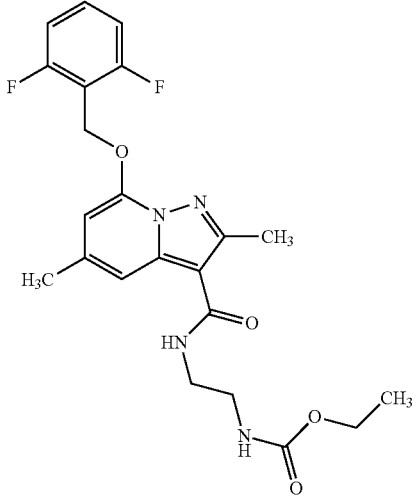 [SMILES: CCOC(=O)NCCNC(=O)c1c(C)nn2c(OCc3c(F)cccc3F)cc(C)cc12]<br />(15% of theory) | LC-MS (Method 10):<br />$R_t$ = 1.03 min<br />MS (ESIpos):<br />m/z = 447 (M + H)$^+$ |
| 107 | rac-N-(2-Amino-4,4,4-trifluorobutyl)-7-[(2,6-difluorobenzyl)oxy]-2,5-dimethylpyrazolo[1,5-a]pyridine-3-carboxamide<br />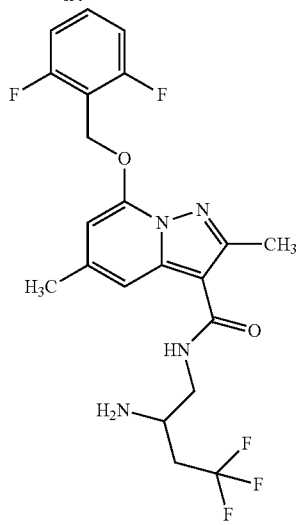<br />(2% of theory) | LC-MS (Method 10):<br />$R_t$ = 0.79 min<br />MS (ESIpos):<br />m/z = 457 (M + H)$^+$ |

TABLE 5-continued

| Example | IUPAC name/structure (yield) | Analytical data |
|---|---|---|
| 108 | rac-7-[(2,6-Difluorobenzyl)oxy]-N-(2,3-dihydro-1-benzofur-3-yl)-2,5-dimethylpyrazolo[1,5-a]pyridine-3-carboxamide<br />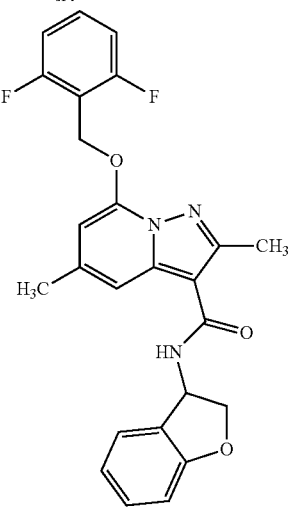<br />(3% of theory) | LC-MS (Method 10):<br />$R_t$ = 1.17 min<br />MS (ESIpos):<br />m/z = 450 (M + H)$^+$ |
| 109 | rac-N-(2-Amino-3,3,3-trifluoro-2-methylpropyl)-7-[(2,6-difluorobenzyl)oxy]-2,5-dimethylpyrazolo[1,5-a]pyridine-3-carboxamide<br />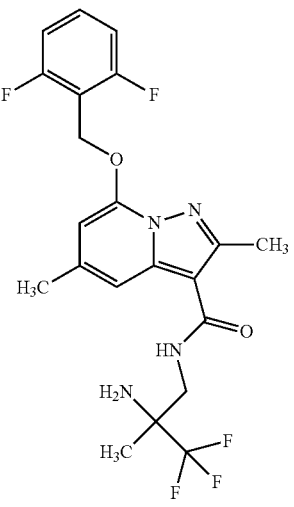 [SMILES: Cc1cc(OCc2c(F)cccc2F)n2nc(C)c(C(=O)NCC(C)(N)C(F)(F)F)c2c1]<br />(1% of theory) | LC-MS (Method 10):<br />$R_t$ = 0.92 min<br />MS (ESIpos):<br />m/z = 457 (M + H)$^+$ |

TABLE 5-continued

| Example | IUPAC name/structure (yield) | Analytical data |
|---|---|---|
| 110 | rac-N-[2-Amino-2-(2,3-dihydro-1,4-benzodioxin-6-yl)ethyl]-7-[(2,6-difluorobenzyl)oxy]-2,5-dimethylpyrazolo[1,5-a]pyridine-3-carboxamide<br>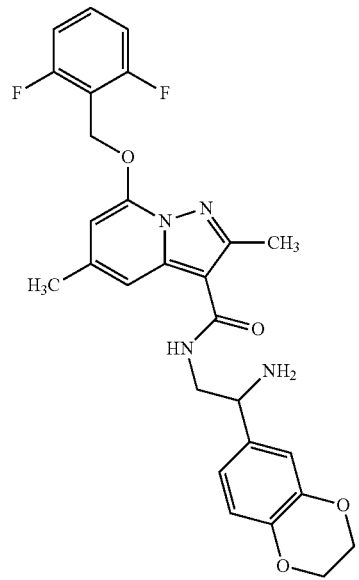 [SMILES: Cc1cc(OCc2c(F)cccc2F)n2nc(C)c(C(=O)NCC(N)c3ccc4c(c3)OCCO4)c2c1]<br>(3% of theory) | LC-MS (Method 10):<br>$R_t$ = 0.80 min<br>MS (ESIpos):<br>m/z = 509 (M + H)$^+$ |
| 111 | 7-[(2,6-Difluorobenzyl)oxy]-N-(7-fluoro-2-methyl-2,3-dihydro-1-benzofur-3-yl)-2,5-dimethylpyrazolo[1,5-a]pyridine-3-carboxamide (mixture of stereoisomers)<br>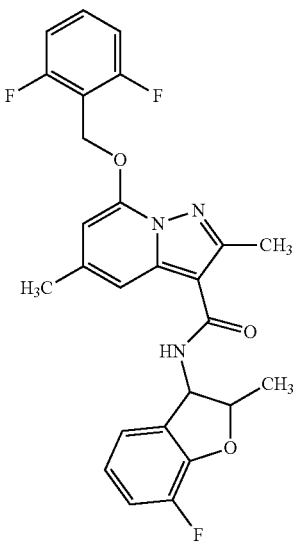 [SMILES: Cc1cc(OCc2c(F)cccc2F)n2nc(C)c(C(=O)NC3c4cccc(F)c4OC3C)c2c1]<br>(2% of theory) | LC-MS (Method 10):<br>$R_t$ = 1.22 min<br>MS (ESIpos):<br>m/z = 482 (M + H)$^+$ |

TABLE 5-continued

| Example | IUPAC name/structure (yield) | Analytical data |
|---|---|---|
| 112 | rac-N-[2-Amino-2-(1-benzothiophen-3-yl)ethyl]-7-[(2,6-difluorobenzyl)oxy]-2,5-dimethylpyrazolo[1,5-a]pyridine-3-carboxamide 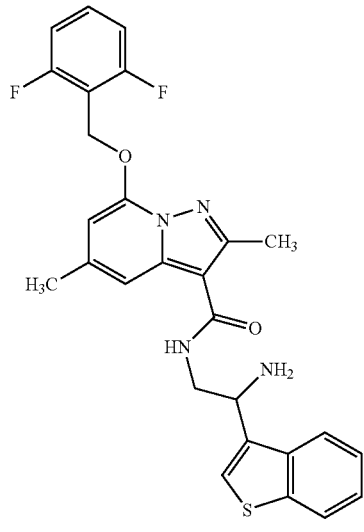 [SMILES: Cc1cc(OCc2c(F)cccc2F)n2nc(C)c(C(=O)NCC(N)c3csc4ccccc34)c2c1] (8% of theory) | LC-MS (Method 10): $R_t$ = 0.85 min MS (ESIpos): m/z = 507 (M + H)$^+$ |
| 113 | 7-[(2,6-Difluorobenzyl)oxy]-2,5-dimethyl-N-[(7S,8aS)-2-methyloctahydropyrrolo[1,2-a]pyrazin-7-yl]pyrazolo[1,5-a]pyridine-3-carboxamide 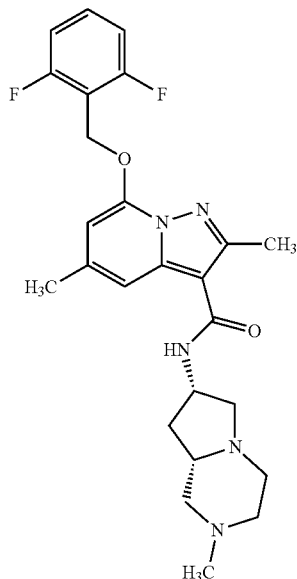 [SMILES: Cc1cc(OCc2c(F)cccc2F)n2nc(C)c(C(=O)N[C@H]3C[C@H]4CN(C)CCN4C3)c2c1] (1% of theory) | LC-MS (Method 10): $R_t$ = 0.73 min MS (ESIpos): m/z = 470 (M + H)$^+$ |

TABLE 5-continued

| Example | IUPAC name/structure (yield) | Analytical data |
|---|---|---|
| 114 | rac-Methyl 3-{1-amino-2-[({7-[(2,6-difluorobenzyl)oxy]-2,5-dimethylpyrazolo[1,5-a]pyridin-3-yl}carbonyl)amino]ethyl}benzoate<br>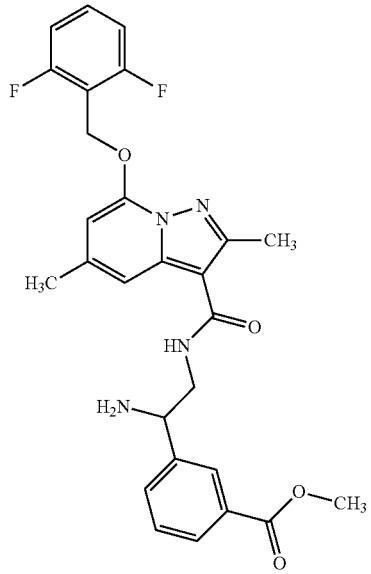 [SMILES: COC(=O)c1cccc(C(N)CNC(=O)c2c(C)nn3c(OCc4c(F)cccc4F)cc(C)cc23)c1]<br>(2% of theory) | LC-MS (Method 10):<br>$R_t$ = 0.81 min<br>MS (ESIpos):<br>m/z = 509 (M + H)$^+$ |
| 115 | rac-N-[2-Aminohex-4-en-1-yl]-7-[(2,6-difluorobenzyl)oxy]-2,5-dimethylpyrazolo[1,5-a]pyridine-3-carboxamide (E/Z mixture)<br>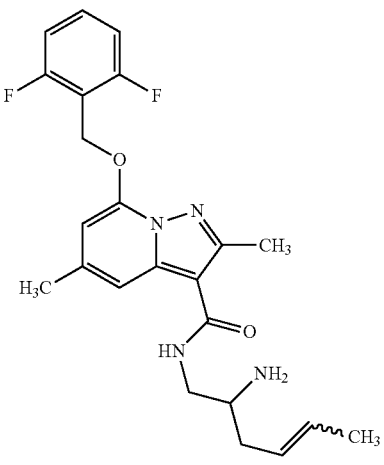<br>(3% of theory; 85% purity) | LC-MS (Method 10):<br>$R_t$ = 0.81 min<br>MS (ESIpos):<br>m/z = 429 (M + H)$^+$ |

TABLE 5-continued

| Example | IUPAC name/structure (yield) | Analytical data |
|---|---|---|
| 116 | rac-N-{2-Amino-2-[3-(difluoromethoxy)phenyl]ethyl}-7-[(2,6-difluorobenzyl)oxy]-2,5-dimethylpyrazolo[1,5-a]pyridine-3-carboxamide 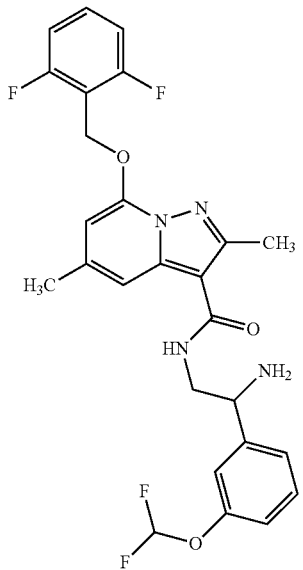 [SMILES: Cc1cc(OCc2c(F)cccc2F)n2nc(C)c(C(=O)NCC(N)c3cccc(OC(F)F)c3)c2c1] (6% of theory) | LC-MS (Method 10): R$_t$ = 0.84 min MS (ESIpos): m/z = 517 (M + H)$^+$ |
| 117 | rac-N-[2-Amino-2-(3,4,5-trifluorophenyl)ethyl]-7-[(2,6-difluorobenzyl)oxy]-2,5-dimethylpyrazolo[1,5-a]pyridine-3-carboxamide 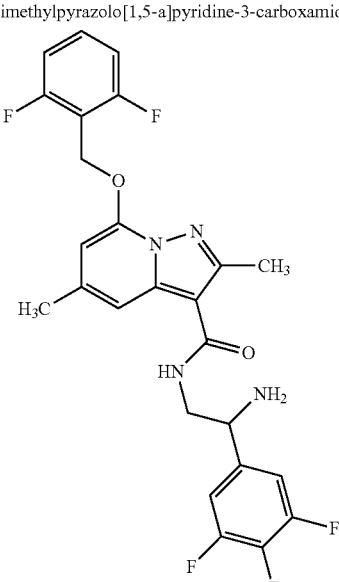 (1% of theory) | LC-MS (Method 10): R$_t$ = 0.84 min MS (ESIpos): m/z = 505(M + H)$^+$ |

Example 118

N-[(1-Aminocyclopropyl)methyl]-7-[(2,6-difluorobenzyl)oxy]-2,5-dimethylpyrazolo[1,5-a]pyridine-3-carboxamide

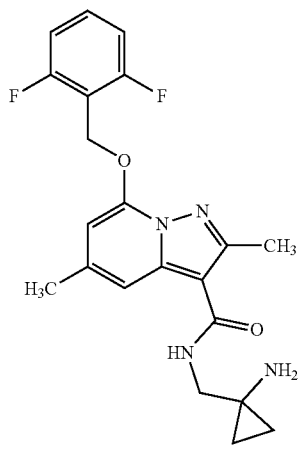 [SMILES: Cc1cc(OCc2c(F)cccc2F)n2nc(C)c(C(=O)NCC3(N)CC3)c2c1]

20.5 mg (0.11 mmol) of tert-butyl [1-(aminomethyl)cyclopropyl]carbamate were initially charged in a 96-well deep well multititre plate. A solution of 33.2 mg (0.1 mmol) of 7-[(2,6-difluorobenzyl)oxy]-2,5-dimethylpyrazolo[1,5-a]pyridine-3-carboxylic acid from Example 4A in 0.4 ml of DMF/dichloromethane (1:1, v/v) and a solution of 49.4 mg (0.13 mol) of HATU in 0.4 ml of DMF/dichloromethane (1:1, v/v) were added successively. After adding 20.2 mg (0.20 mmol) of 4-methylmorpholine, the mixture was shaken at RT overnight. Subsequently, the mixture was heated to 60° C. and shaken at this temperature for 7 h. Then the solvent was evaporated off completely. The residue was admixed with 0.6 ml of TFA and shaken at room temperature overnight. Then the mixture was concentrated fully, the residue was dissolved in 0.8 ml of DMF and filtered, and the target compound was isolated from the filtrate by preparative LC-MS (Method 9). The product-containing fractions were concentrated under reduced pressure using a centrifugal dryer. The residue of each product fraction was dissolved in 0.6 ml of DMSO. These were combined and finally freed of the solvent in a centrifugal dryer. 0.5 mg (1.3% of theory) of the title compound were obtained.

LC-MS (Method 10): $R_t$=0.74 min
MS (ESIpos): m/z=401 (M+H)$^+$

In analogy to Example 118, the example compounds shown in Table 6 were prepared by reacting 7-[(2,6-difluorobenzyl)oxy]-2,5-dimethylpyrazolo[1,5-a]pyridine-3-carboxylic acid from Example 4A with the appropriate mono-Boc-protected diamines, which are commercially available, known from the literature or described above, under the conditions described:

TABLE 6

| Example | IUPAC name/structure (yield) | Analytical data |
|---|---|---|
| 119 | rac-N-[2-Amino-1-(4-nitrophenyl)ethyl]-7-[(2,6-difluorobenzyl)oxy]-2,5-dimethylpyrazolo[1,5-a]pyridine-3-carboxamide<br><br>(2% of theory) | LC-MS (Method 10): $R_t$ = 0.75 min<br>MS (ESIpos): m/z = 496 (M + H)$^+$ |

TABLE 6-continued

| Example | IUPAC name/structure (yield) | Analytical data |
|---|---|---|
| 120 | rac-N-[2-Amino-1-(1,3-benzodioxol-5-yl)ethyl]-7-[(2,6-difluorobenzyl)oxy]-2,5-dimethylpyrazolo[1,5-a]pyridine-3-carboxamide<br />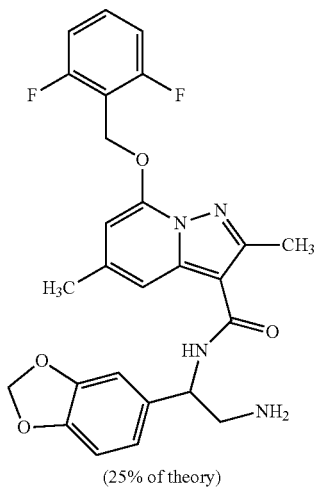<br />(25% of theory) | LC-MS (Method 10): $R_t$ = 0.81 min<br />MS (ESIpos): m/z = 495 (M + H)$^+$ |
| 121 | N-(3-Amino-3-methylbutyl)-7-[(2,6-difluorobenzyl)oxy]-2,5-dimethylpyrazolo[1,5-a]pyridine-3-carboxamide<br />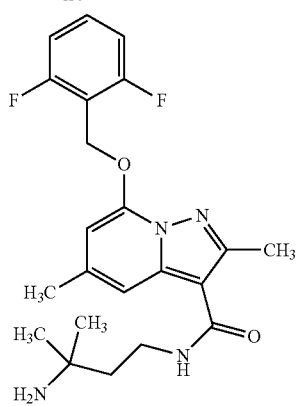 [SMILES: Cc1cc(OCc2c(F)cccc2F)n2nc(C)c(C(=O)NCCC(C)(C)N)c2c1]<br />(24% of theory) | LC-MS (Method 10): $R_t$ = 0.74 min<br />MS (ESIpos): m/z = 417 (M + H)$^+$ |

TABLE 6-continued

| Example | IUPAC name/structure (yield) | Analytical data |
|---|---|---|
| 122 | rel-7-[(2,6-Difluorobenzyl)oxy]-2,5-dimethyl-N-[(3aR,6aR)-octahydrocyclopenta[b]pyrrol-4-yl]pyrazolo[1,5-a]pyridine-3-carboxamide<br>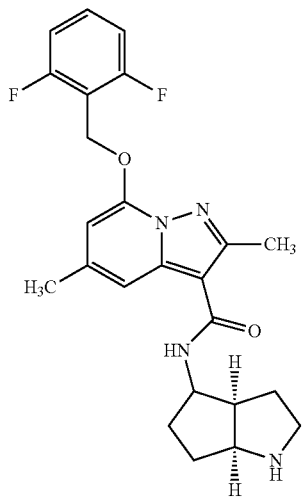 [SMILES: Cc1cc(OCc2c(F)cccc2F)n2nc(C)c(C(=O)NC3CC[C@@H]4NCC[C@H]34)c2c1]<br>(13% of theory) | LC-MS (Method 10): $R_t$ = 0.74 min<br>MS (ESIpos): m/z = 441 (M + H)$^+$ |
| 123 | rac-N-[2-Amino-1-(3-methoxyphenyl)ethyl]-7-[(2,6-difluorobenzyl)oxy]-2,5-dimethylpyrazolo[1,5-a]pyridine-3-carboxamide<br>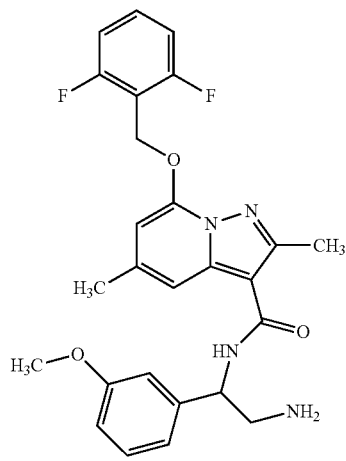<br>(17% of theory) | LC-MS (Method 10): $R_t$ = 0.82 min<br>MS (ESIpos): m/z = 481 (M + H)$^+$ |

TABLE 6-continued

| Example | IUPAC name/structure (yield) | Analytical data |
|---|---|---|
| 124 | N-[(1-Aminocyclohexyl)methyl]-7-[(2,6-difluorobenzyl)oxy]-2,5-dimethylpyrazolo[1,5-a]pyridine-3-carboxamide<br><br>(11% of theory) | LC-MS (Method 10): $R_t$ = 0.81 min<br>MS (ESIpos): m/z = 443 (M + H)$^+$ |
| 125 | 7-[(2,6-Difluorobenzyl)oxy]-2,5-dimethyl-N-[4-(piperazin-1-yl)-3-(trifluoromethyl)phenyl]pyrazolo[1,5-a]pyridine-3-carboxamide<br><br>(1% of theory; 78% purity) | LC-MS (Method 10): $R_t$ = 0.89 min<br>MS (ESIpos): m/z = 560 (M + H)$^+$ |

TABLE 6-continued

| Example | IUPAC name/structure (yield) | Analytical data |
|---|---|---|
| 126 | rac-N-[2-Amino-1-(3-bromphenyl)ethyl]-7-[(2,6-difluorobenzyl)oxy]-2,5-dimethylpyrazolo[1,5-a]pyridine-3-carboxamide<br>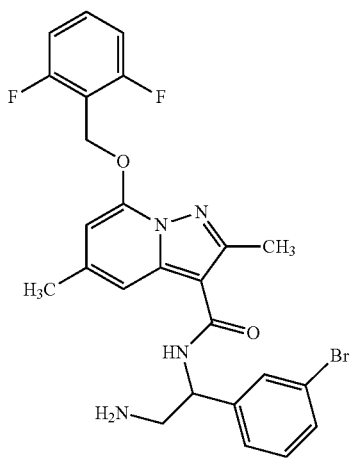 [SMILES: Cc1cc(OCc2c(F)cccc2F)n2nc(C)c(C(=O)NC(CN)c3cccc(Br)c3)c2c1]<br>(45% of theory) | LC-MS (Method 10): $R_t$ = 0 85min<br>MS (ESIpos): m/z = 529 (M + H)$^+$ |
| 127 | rac-N-(Azepan-3-yl)-7-[(2,6-difluorobenzyl)oxy]-2,5-dimethylpyrazolo[1,5-a]pyridine-3-carboxamide<br>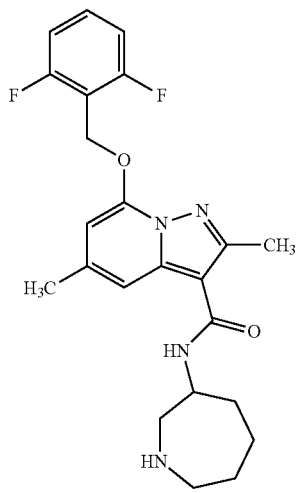 [SMILES: Cc1cc(OCc2c(F)cccc2F)n2nc(C)c(C(=O)NC3CCCCNC3)c2c1]<br>(58% of theory) | LC-MS (Method 10): $R_t$ = 0.76 min<br>MS (ESIpos): m/z = 429 (M + H)$^+$ |

TABLE 6-continued

| Example | IUPAC name/structure (yield) | Analytical data |
|---|---|---|
| 128 | rel-7-[(2,6-Difluorobenzyl)oxy]-N-[(3R,4S)-4-fluoropyrrolidin-3-yl]-2,5-dimethylpyrazolo[1,5-a]pyridine-3-carboxamide<br>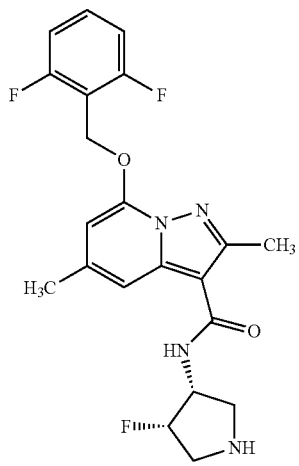 [SMILES: Cc1cc(OCc2c(F)cccc2F)n2nc(C)c(C(=O)N[C@@H]3CNC[C@@H]3F)c2c1]<br>(34% of theory) | LC-MS (Method 10): $R_t$ = 0.72 min<br>MS (ESIpos): m/z = 419 (M + H)$^+$ |
| 129 | 7-[(2,6-Difluorobenzyl)oxy]-2,5-dimethyl-N-[(2S)-piperidin-2-ylmethyl]pyrazolo[1,5-a]pyridine-3-carboxamide<br>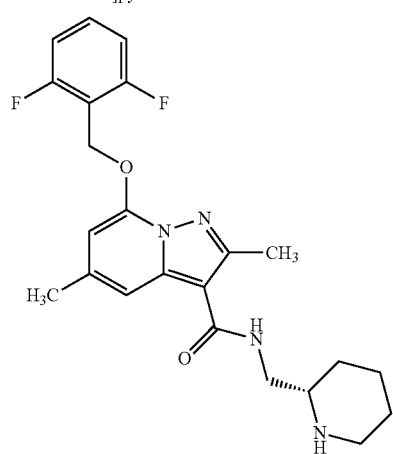<br>(31% of theory) | LC-MS (Method 10): $R_t$ = 0.76 min<br>MS (ESIpos): m/z = 429 (M + H)$^+$ |

TABLE 6-continued

| Example | IUPAC name/structure (yield) | Analytical data |
|---|---|---|
| 130 | rac-N-(3-Aminocyclopentyl)-7-[(2,6-difluorobenzyl)oxy]-2,5-dimethylpyrazolo[1,5-a]pyridine-3-carboxamide<br />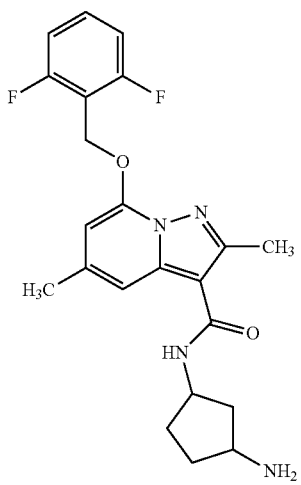 [SMILES: Cc1cc(OCc2c(F)cccc2F)n2nc(C)c(C(=O)NC3CCC(N)C3)c2c1]<br />(7% of theory) | LC-MS (Method 10): $R_t$ = 0.73 min<br />MS (ESIpos): m/z = 415 (M + H)$^+$ |
| 131 | Methyl $N^6$-({7-[(2,6-difluorobenzyl)oxy]-2,5-dimethylpyrazolo[1,5-a]pyridin-3-yl}carbonyl)-L-lysinate<br />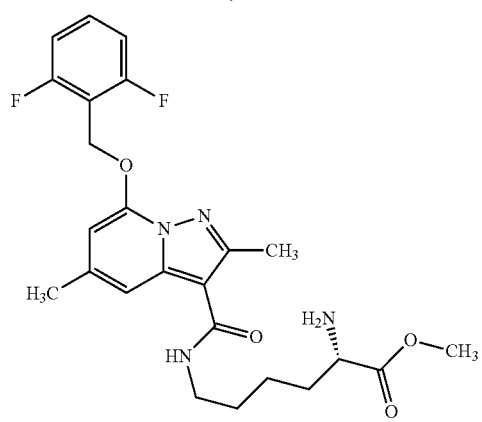<br />(2% of theory) | LC-MS (Method 10): $R_t$ = 0.78 min<br />MS (ESIpos): m/z = 475 (M + H)$^+$ |

TABLE 6-continued

| Example | IUPAC name/structure (yield) | Analytical data |
|---|---|---|
| 132 | rac-N-{2-Amino-1-[3-(trifluoromethoxy)phenyl]ethyl}-7-[(2,6-difluorobenzyl)oxy]-2,5-dimethylpyrazolo[1,5-a]pyridine-3-carboxamide<br>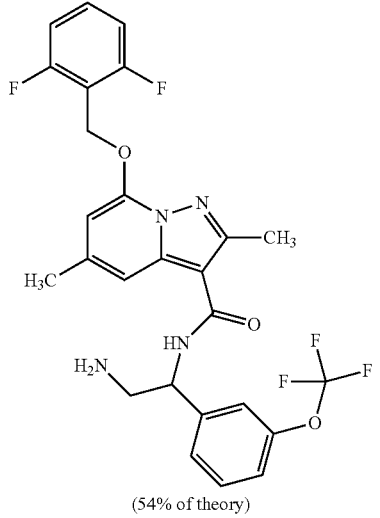<br>(54% of theory) | LC-MS (Method 10): $R_t$ = 0.88 min<br>MS (ESIpos): m/z = 535 (M + H)$^+$ |
| 133 | ent-N-[2-Amino-1-(3,4-difluorophenyl)ethyl]-7-[(2,6-difluorobenzyl)oxy]-2,5-dimethylpyrazolo[1,5-a]pyridine-3-carboxamide<br>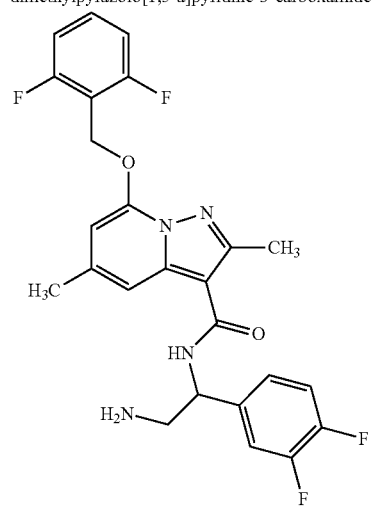<br>(21% of theory) | LC-MS (Method 10): $R_t$ = 0.84 min<br>MS (ESIpos): m/z = 487 (M + H)$^+$ |

Example 134 rac-N-[(4-Chlorophenyl)(cyano)methyl]-7-[(2,6-difluorobenzyl)oxy]-2,5-dimethylpyrazolo[1,5-a]pyridine-3-carboxamide

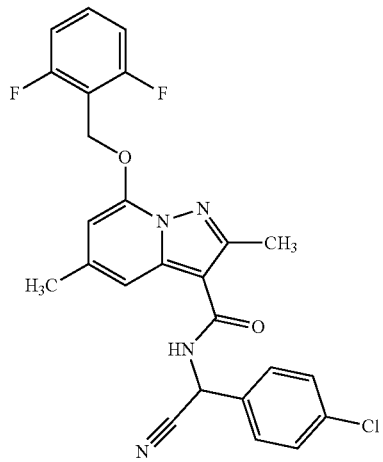 [SMILES: Cc1cc(OCc2c(F)cccc2F)n2nc(C)c(C(=O)NC(C#N)c3ccc(Cl)cc3)c2c1]

33 mg (0.10 mmol) of 7-[(2,6-difluorobenzyl)oxy]-2,5-dimethylpyrazolo[1,5-a]pyridine-3-carboxylic acid from Example 4A were initially charged in a 96-well deep well multititre plate. A solution of 17 mg (0.10 mmol) of rac-amino(4-chlorophenyl)acetonitrile in 0.4 ml of DMF and a solution of 45.6 mg (0.12 mol) of HATU in 0.4 ml of DMF were added successively. After adding 20.2 mg (0.20 mmol) of 4-methylmorpholine, the mixture was shaken at RT overnight. Then the mixture was filtered and the target compound was isolated from the filtrate by preparative LC-MS (Method 9). The product-containing fractions were concentrated under reduced pressure using a centrifugal dryer. The residue of each product fraction was dissolved in 0.6 ml of DMSO. These were combined and finally freed of the solvent in a centrifugal dryer. 0.7 mg (1.5% of theory) were obtained.

LC-MS (Method 10): $R_t$=1.22 min
MS (ESIpos): m/z=481 (M+H)$^+$

Example 135

7-[(2,6-Difluorobenzyl)oxy]-2,5-dimethyl-N-(morpholin-4-yl)pyrazolo[1,5-a]pyridine-3-carboxamide

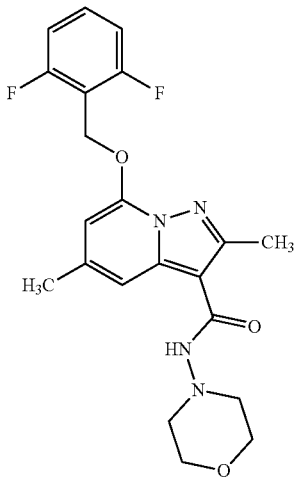 [SMILES: Cc1cc(OCc2c(F)cccc2F)n2nc(C)c(C(=O)NN3CCOCC3)c2c1]

33 mg (0.10 mmol) of 7-[(2,6-difluorobenzyl)oxy]-2,5-dimethylpyrazolo[1,5-a]pyridine-3-carboxylic acid from Example 4A were initially charged in a 96-well deep well multititre plate. A solution of 17 mg (0.10 mmol) of morpholine-4-amine in 0.4 ml of DMF and a solution of 45.6 mg (0.12 mol) of HATU in 0.4 ml of DMF were added successively. After adding 20.2 mg (0.20 mmol) of 4-methylmorpholine, the mixture was shaken at RT overnight. Then the mixture was filtered and the target compound was isolated from the filtrate by preparative LC-MS (Method 9). The product-containing fractions were concentrated under reduced pressure using a centrifugal dryer. The residue of each product fraction was dissolved in 0.6 ml of DMSO. These were combined and finally freed of the solvent in a centrifugal dryer. 0.5 mg (1% of theory) were obtained.

LC-MS (Method 10): $R_t$=0.96 min
MS (ESIpos): m/z=417 (M+H)$^+$

Example 136 rac-N-[2-Amino-2-(1-methyl-1H-pyrazol-4-yl)ethyl]-7-[(2,6-difluorobenzyl)oxy]-2,5-dimethylpyrazolo[1,5-a]pyridine-3-carboxamide

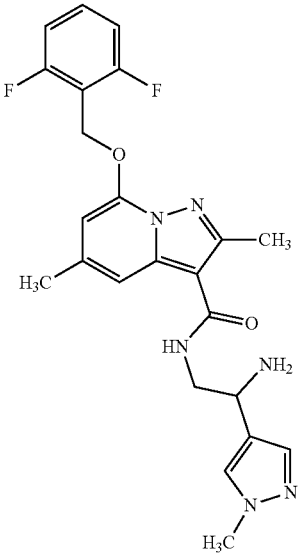 [SMILES: Cc1cc(OCc2c(F)cccc2F)n2nc(C)c(C(=O)NCC(N)c3cnn(C)c3)c2c1]

830 mg (2.50 mmol) of 7-[(2,6-difluorobenzyl)oxy]-2,5-dimethylpyrazolo[1,5-a]pyridine-3-carboxylic acid from Example 4A were admixed with 5 ml (68.5 mmol) of thionyl chloride and the mixture was stirred at RT for 2 h. Then the mixture was concentrated fully, and the residue was admixed with 10 ml of toluene and concentrated to dryness.

14.0 mg (0.10 mmol) of 1-(1-methyl-1H-pyrazol-4-yl)ethane-1,2-diamine were initially charged in a 96-well deep well multititre plate. A solution of 35.1 mg (0.10 mmol) of 7-[(2,6-difluorobenzyl)oxy]-2,5-dimethylpyrazolo[1,5-a]pyridine-3-carbonyl chloride in 0.6 ml of dichloroethane and 0.032 ml (0.40 mmol) of pyridine were added successively and the mixture was stirred at RT overnight. Then the solvent was evaporated off completely, the residue was dissolved in 0.8 ml of DMF and filtered, and the target compound was isolated from the filtrate by preparative LC-MS (Method 9). The product-containing fractions were concentrated under reduced pressure using a centrifugal dryer. The residue of each product fraction was dissolved in 0.6 ml of DMSO. These were combined and finally freed of the solvent in a centrifugal dryer. 18 mg (37% of theory; 94% purity) of the title compound were obtained.

LC-MS (Method 10): $R_t$=0.73 min
MS (ESIpos): m/z=455 (M+H)$^+$

In analogy to Example 136, the example compounds shown in Table 7 were prepared by reacting 2,5-dimethyl-7-[(2,3,6-trifluorobenzyl)oxy]pyrazolo[1,5-a]pyridine-3-carbonyl chloride with the appropriate amines, which are commercially available or have been described above, under the conditions described:

TABLE 7

| Example | IUPAC name/structure (yield) | Analytical data |
|---|---|---|
| 137 | rac-7-[(2,6-Difluorobenzyl)oxy]-2,5-dimethyl-N-(2,2,7-trimethyl-3,4-dihydro-2H-chromen-4-yl)pyrazolo[1,5-a]pyridine-3-carboxamide<br>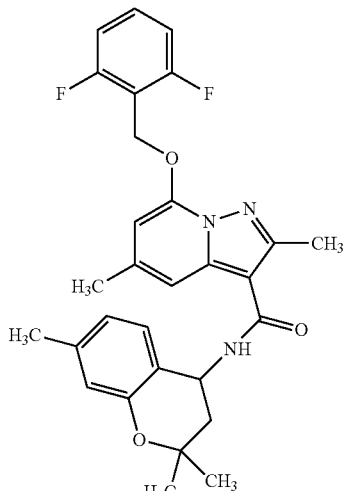<br>(13% of theory; 90% purity) | LC-MS (Method 10): $R_t$ = 1.25 min<br>MS (ESIpos): m/z = 506 (M + H)$^+$ |
| 138 | rac-7-[(2,6-Difluorobenzyl)oxy]-2,5-dimethyl-N-(1,2,3,4-tetrahydronaphthalen-1-yl)pyrazolo[1,5-a]pyridine-3-carboxamide<br>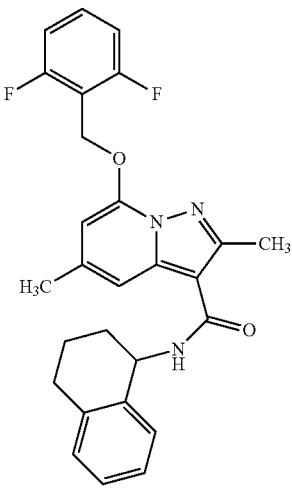 [SMILES: Cc1cc(OCc2c(F)cccc2F)n2nc(C)c(C(=O)NC3CCCc4ccccc43)c2c1]<br>(10% of theory) | LC-MS (Method 10): $R_t$ = 1.23 min<br>MS (ESIpos): m/z = 462 (M + H)$^+$ |

TABLE 7-continued

| Example | IUPAC name/structure (yield) | Analytical data |
|---|---|---|
| 139 | rac-N-(5-Amino-1,2,3,4-tetrahydronaphthalen-1-yl)-74(2,6-difluorobenzyl)oxy]-2,5-dimethylpyrazolo[1,5-a]pyridine-3-carboxamide 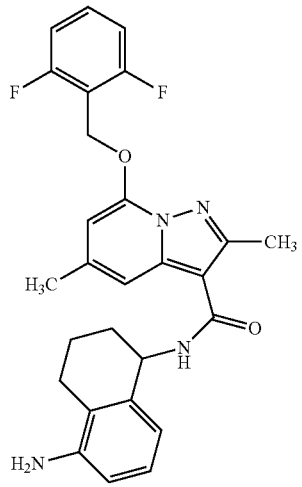 [SMILES: Cc1cc(OCc2c(F)cccc2F)n2nc(C)c(C(=O)NC3CCCc4c(N)cccc43)c2c1] (1% of theory; 80% purity) | LC-MS (Method 10): $R_t$ = 1.06 min<br>MS (ESIpos): m/z = 477 (M + H)$^+$ |
| 140 | rac-N-(8-Cyano-3,4-dihydro-2H-chromen-4-yl)-7-[(2,6-difluorobenzyl)oxy]-2,5-dimethylpyrazolo[1,5-a]pyridine-3-carboxamide 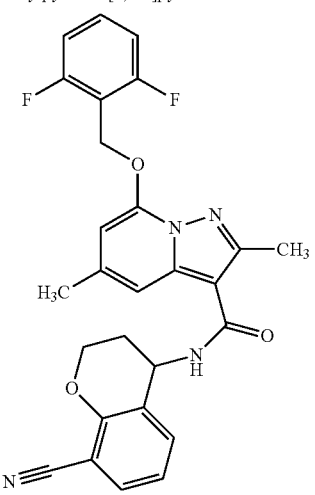 (5% of theory) | LC-MS (Method 10): $R_t$ = 1.17 min<br>MS (ESIpos): m/z = 489 (M + H)$^+$ |

TABLE 7-continued

| Example | IUPAC name/structure (yield) | Analytical data |
|---|---|---|
| 141 | rac-N-[2-Amino-2-(3-vinylphenyl)ethyl]-7-[(2,6-difluorobenzyl)oxy]-2,5-dimethylpyrazolo[1,5-a]pyridine-3-carboxamide<br>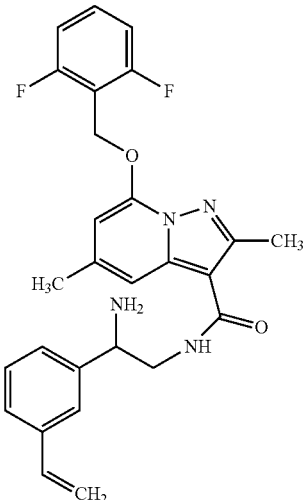 [SMILES: C=Cc1cccc(C(N)CNC(=O)c2c(C)nn3c(OCc4c(F)cccc4F)cc(C)cc23)c1]<br>(3% of theory) | LC-MS (Method 10): $R_t$ = 0.84 min<br>MS (ESIpos): m/z = 477 (M + H)$^+$ |
| 142 | rac-7-[(2,6-Difluorobenzyl)oxy]-2,5-dimethyl-N-(morpholin-2-ylmethyl)pyrazolo[1,5-a]pyridine-3-carboxamide<br>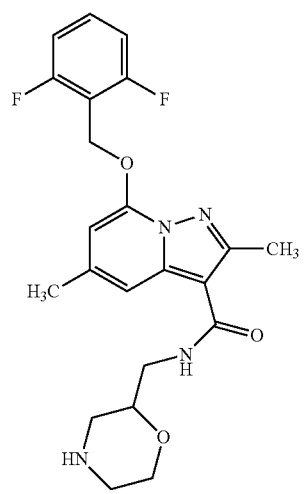 [SMILES: Cc1cc(OCc2c(F)cccc2F)n2nc(C)c(C(=O)NCC3CNCCO3)c2c1]<br>(3% of theory; 78% purity) | LC-MS (Method 10): $R_t$ = 0.72 min<br>MS (ESIpos): m/z = 431 (M + H)$^+$ |

TABLE 7-continued

| Example | IUPAC name/structure (yield) | Analytical data |
|---|---|---|
| 143 | rel-7-[(2,6-Difluorobenzyl)oxy]-N-[(1R,2R)-2-(hydroxymethyl)-2,3-dihydro-1H-inden-1-yl]-2,5-dimethylpyrazolo[1,5-a]pyridine-3-carboxamide<br>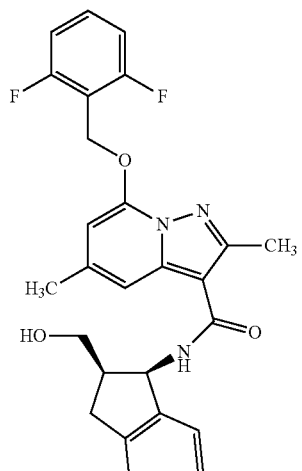<br>(14% of theory) | LC-MS (Method 10): $R_t$ = 1.14 min<br>MS (ESIpos): m/z = 478 (M + H)$^+$ |
| 144 | 7-[(2,6-Difluorobenzyl)oxy]-N-[(2R)-1-hydroxyhexan-2-yl]-2,5-dimethylpyrazolo[1,5-a]pyridine-3-carboxamide<br>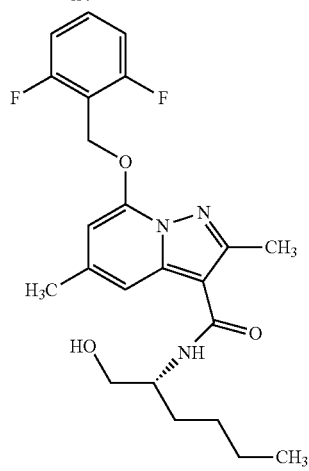<br>(25% of theory) | LC-MS (Method 10): $R_t$ = 1.08 min<br>MS (ESIpos): m/z = 432 (M + H)$^+$ |

TABLE 7-continued

| Example | IUPAC name/structure (yield) | Analytical data |
|---|---|---|
| 145 | rac-7-[(2,6-Difluorobenzyl)oxy]-N-(4,4-dimethyl-1,2,3,4-tetrahydronaphthalen-1-yl)-2,5-dimethylpyrazolo[1,5-a]pyridine-3-carboxamide 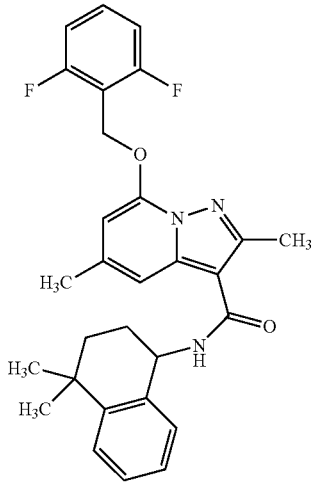 [SMILES: Cc1cc(OCc2c(F)cccc2F)n2nc(C)c(C(=O)NC3CCC(C)(C)c4ccccc43)c2c1] (8% of theory; 90% purity) | LC-MS (Method 10): $R_t$ = 1.28 min<br>MS (ESIpos): m/z = 490 (M + H)$^+$ |
| 146 | rac-7-[(2,6-Difluorobenzyl)oxy]-N-(7-methoxy-1,2,3,4-tetrahydronaphthalen-1-yl)-2,5-dimethylpyrazolo[1,5-a]pyridine-3-carboxamide 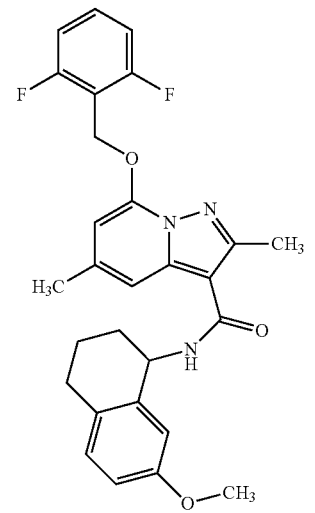 [SMILES: COc1ccc2c(c1)C(NC(=O)c1c(C)nn3c(OCc4c(F)cccc4F)cc(C)cc13)CCC2] (3% of theory; 87% purity) | LC-MS (Method 10): $R_t$ = 1.22 min<br>MS (ESIpos): m/z = 492 (M + H)$^+$ |

TABLE 7-continued

| Example | IUPAC name/structure (yield) | Analytical data |
|---|---|---|
| 147 | rac-N-(8-Chloro-3,4-dihydro-2H-chromen-4-yl)-7-[(2,6-difluorobenzyl)oxy]-2,5-dimethylpyrazolo[1,5-a]pyridine-3-carboxamide 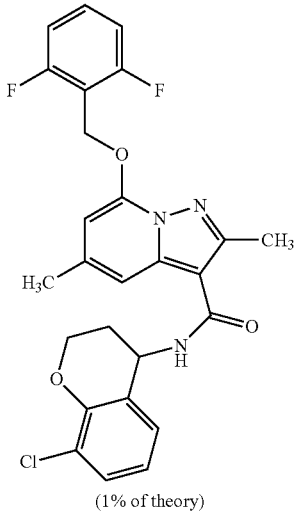 (1% of theory) | LC-MS (Method 10): $R_t$ = 1.21 min<br>MS (ESIpos): m/z = 498 (M + H)$^+$ |
| 148 | rac-7-[(2,6-Difluorobenzyl)oxy]-N-(6-fluoro-8-methyl-3,4-dihydro-2H-chromen-4-yl)-2,5-dimethylpyrazolo[1,5-a]pyridine-3-carboxamide 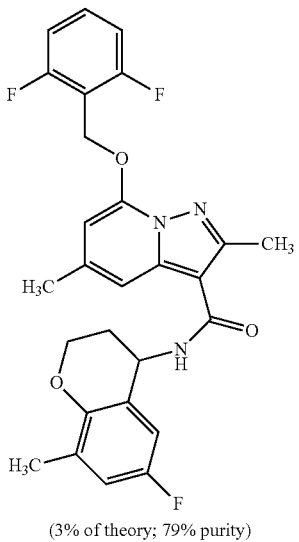 (3% of theory; 79% purity) | LC-MS (Method 10): $R_t$ = 1.23 min<br>MS (ESIpos): m/z = 496 (M + H)$^+$ |

TABLE 7-continued

| Example | IUPAC name/structure (yield) | Analytical data |
|---|---|---|
| 149 | 7-[(2,6-Difluorobenzyl)oxy]-2,5-dimethyl-N-[(3S)-2-oxopyrrolidin-3-yl]pyrazolo[1,5-a]pyridine-3-carboxamide 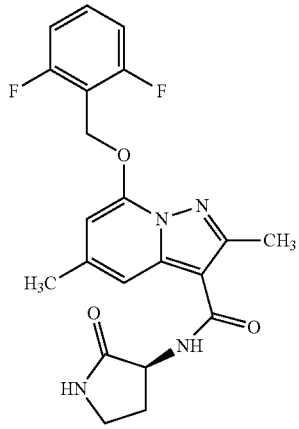 [SMILES: Cc1cc(OCc2c(F)cccc2F)n2nc(C)c(C(=O)N[C@H]3CCNC3=O)c2c1] (2% of theory; 90% purity) | LC-MS (Method 10): $R_t$ = 0.92 min<br>MS (ESIpos): m/z = 415 (M + H)$^+$ |
| 150 | rac-7-[(2,6-Difluorobenzyl)oxy]-N-(6-fluoro-1,2,3,4-tetrahydronaphthalen-1-yl)-2,5-dimethylpyrazolo[1,5-a]pyridine-3-carboxamide 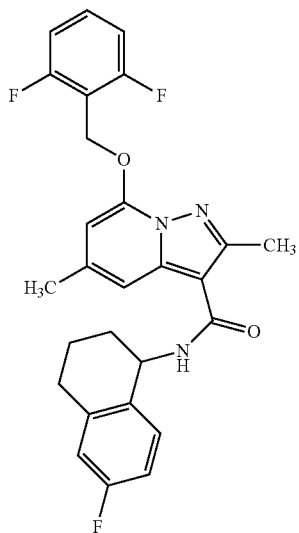 [SMILES: Cc1cc(OCc2c(F)cccc2F)n2nc(C)c(C(=O)NC3CCCc4cc(F)ccc43)c2c1] (4% of theory; 75% purity) | LC-MS (Method 10): $R_t$ = 1.23 min<br>MS (ESIpos): m/z = 480 (M + H)$^+$ |

| Example | IUPAC name/structure (yield) | Analytical data |
|---|---|---|
| 151 | N-[3-(Cyclopropylsulphamoyl)propyl]-7-[(2,6-difluorobenzyl)oxy]-2,5-dimethylpyrazolo[1,5-a]pyridine-3-carboxamide<br />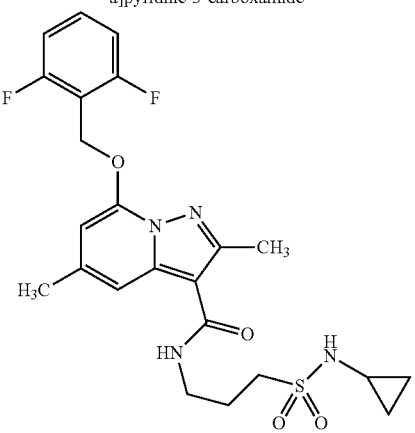<br />(17% of theory) | LC-MS (Method 10): $R_t$ = 1.02 min<br />MS (ESIpos): m/z = 493 (M + H)$^+$ |

Example 152

Methyl 4-[({7-[(2,6-difluorobenzyl)oxy]-2,5-dimethylpyrazolo[1,5-a]pyridin-3-yl}carbonyl)amino]bicyclo[2.2.2]octane-1-carboxylate

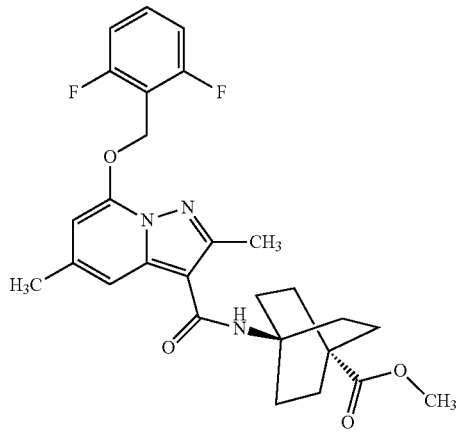

A mixture of 80 mg 7-[(2,6-difluorobenzyl)oxy]-2,5-dimethylpyrazolo[1,5-a]pyridine-3-carboxylic acid (75% purity, 0.181 mmol) from Example 4A, 76 mg of HATU (0.199 mmol) and 94 µl (0.542 mmol) of N,N-diisopropylethylamine in 0.54 ml of DMF was stirred at RT for 10 min Subsequently, 40 mg (0.217 mmol) of methyl 4-aminobicyclo[2.2.2]octane-1-carboxylate were added and the mixture was stirred at RT overnight. The reaction mixture was admixed with water and acetonitrile and purified by means of preparative HPLC (RP18 column, eluent:acetonitrile/water gradient with addition of 0.05% formic acid). 62 mg of the target compound were obtained (70% of theory).

LC-MS (Method 2): $R_t$=1.18 min

MS (ESIpos): m/z=498 (M+H)$^+$ $^1$H NMR (500 MHz, DMSO-d$_6$) δ [ppm]=7.57-7.68 (m, 1H), 7.21-7.30 (m, 3H), 6.86 (s, 1H), 6.51 (d, 1H), 5.43 (s, 2H), 3.58 (s, 3H), 2.43 (s, 3H), 2.39 (s, 3H), 1.94-2.01 (m, 6H), 1.78-1.85 (m, 6H).

Example 153

4-[({7-[(2,6-Difluorobenzyl)oxy]-2,5-dimethylpyrazolo[1,5-a]pyridin-3-yl}carbonyl)amino]bicyclo[2.2.2]octane-1-carboxylic Acid

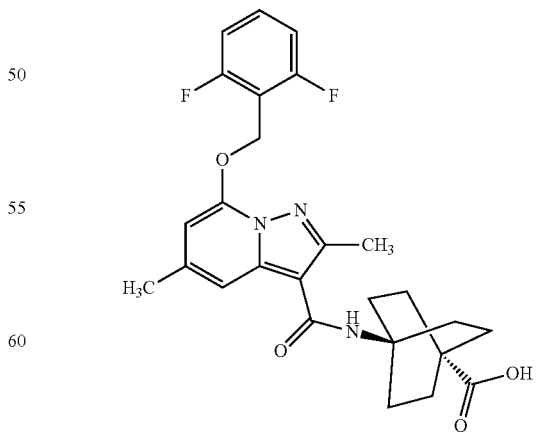

56 mg (0.113 mmol) of methyl 4-[({7-[(2,6-difluorobenzyl)oxy]-2,5-dimethylpyrazolo[1,5-a]pyridin-3- yl}carbonyl)amino]bicyclo[2.2.2]octane-1-carboxylate from Example 152 were dissolved in 1.1 ml of THF/methanol (5/1), and 8.1 mg (0.339 mmol) of lithium hydroxide were added. The mixture was stirred at 40° C. for 10 h. After cooling, the mixture was acidified with 20 μl of formic acid and purified by means of preparative HPLC (RP18 column, eluent:acetonitrile/water gradient with addition of 0.05% formic acid). 41 mg of the target compound were obtained (75% of theory).

LC-MS (Method 2): $R_t$=0.98 min

MS (ESIpos): m/z=484 (M+H)$^+$ $^1$H NMR (500 MHz, DMSO-d$_6$) δ [ppm]=12.03 (br. s, 1H), 7.56-7.66 (m, 1H), 7.20-7.39 (m, 3H), 6.83 (s, 1H), 6.50 (s, 1H), 5.43 (s, 2H), 2.43 (s, 3H), 2.39 (s, 3H), 1.93-2.00 (m, 6H), 1.76-1.83 (m, 6H).

Example 154

7-[(2,6-Difluorobenzyl)oxy]-2,5-dimethyl-N-[2-(trifluoromethyl)piperidin-4-yl]pyrazolo[1,5-a]pyridine-3-carboxamide

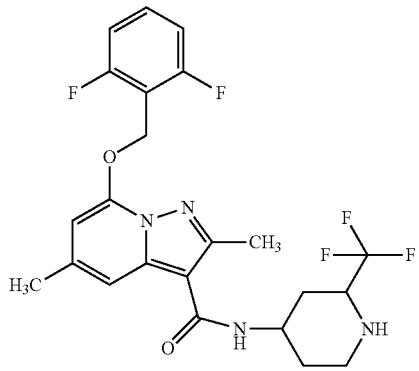 [SMILES: Cc1cc(OCc2c(F)cccc2F)n2nc(C)c(C(=O)NC3CCNC(C(F)(F)F)C3)c2c1]

A mixture of 57 mg 7-[(2,6-difluorobenzyl)oxy]-2,5-dimethylpyrazolo[1,5-a]pyridine-3-carboxylic acid (0.171 mmol) from Example 4A, 72 mg of HATU (0.188 mmol) and 0.179 ml (1.025 mmol) of N,N-diisopropylethylamine in 1.1 ml of DMF was stirred at RT for 20 min. Subsequently, 42 mg (0.205 mmol) of 2-(trifluoromethyl)piperidine-4-amine hydrochloride (Example 36A) were added and the mixture was stirred at RT overnight. The reaction mixture was admixed with water and acetonitrile and purified by means of preparative HPLC (RP18 column, eluent:acetonitrile/water gradient with addition of 0.05% formic acid). 22 mg of the target compound were obtained (27% of theory).

LC-MS (Method 2): $R_t$=0.80 min

MS (ESIpos): m/z=483 (M+H)$^+$ $^1$H NMR (500 MHz, DMSO-d$_6$) δ [ppm]=7.58-7.66 (m, 1H), 7.44 (d, 1H), 7.22-7.31 (m, 3H), 6.53 (s, 1H), 5.44 (s, 2H), 4.19-4.27 (m, 1H), 3.53-3.62 (m, 1H), 2.78-2.92 (m, 2H), 2.49 (s, 3H), 2.45-2.47 (m, 1H), 2.41 (s, 3H), 1.82-1.89 (m, 1H), 1.58-1.79 (m, 3H).

Example 155

Methyl 3-{[({7-[(2,6-difluorobenzyl)oxy]-2,5-dimethylpyrazolo[1,5-a]pyridin-3-yl}carbonyl)amino]methyl}adamantane-1-carboxylate

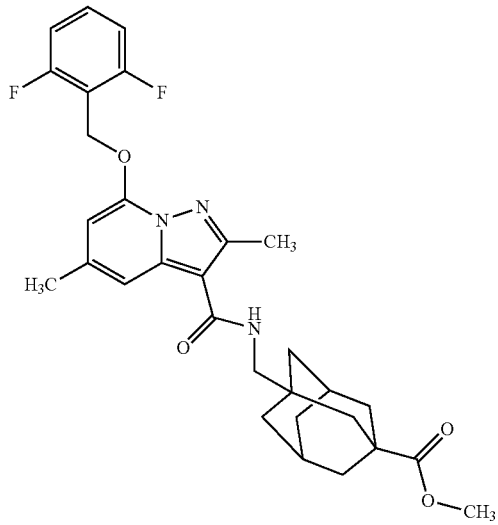 [SMILES: COC(=O)C12CC3CC(CC(CNC(=O)c4c(C)nn5c(OCc6c(F)cccc6F)cc(C)cc45)(C3)C1)C2]

A mixture of 52 mg of 7-[(2,6-difluorobenzyl)oxy]-2,5-dimethylpyrazolo[1,5-a]pyridine-3-carboxylic acid (75% purity, 0.118 mmol) from Example 4A, 72 mg of HATU (0.188 mmol) and 0.138 ml (0.792 mmol) of N,N-diisopropylethylamine in 0.7 ml of DMF was stirred at RT for 10 min. Subsequently, 53 mg (0.236 mmol) of methyl 3-(aminomethyl)adamantane-1-carboxylate from Example 37A in 0.5 ml of DMF were added and the mixture was stirred at RT overnight. The reaction mixture was admixed with water and acetonitrile and purified by means of preparative HPLC (RP18 column, eluent:acetonitrile/water gradient with addition of 0.05% formic acid). 35 mg of the target compound were obtained (53% of theory).

LC-MS (Method 2): $R_t$=1.21 min

MS (ESIpos): m/z=538 (M+H)$^+$ $^1$H NMR (500 MHz, DMSO-d$_6$) δ [ppm]=7.58-7.66 (m, 1H), 7.40-7.46 (m, 1H), 7.32 (s, 1H), 7.22-7.29 (m, 2H), 6.53 (d, 1H), 5.44 (s, 2H), 3.57 (s, 3H), 3.05 (d, 2H), 2.49 (s, 3H), 2.40 (s, 3H), 2.06 (br.s., 2H), 1.70-1.81 (m, 4H), 1.54-1.64 (m, 4H), 1.49 (s, 4H).

Example 156 rac-N-[2-Amino-4-(methylsulphanyl)butyl]-7-[(2,6-difluorobenzyl)oxy]-2,5-dimethylpyrazolo[1,5-a]pyridine-3-carboxamide

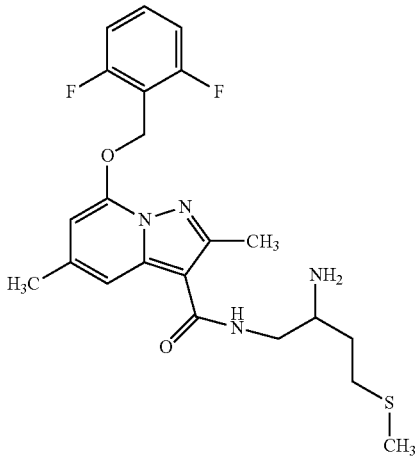

A mixture of 70 mg of 7-[(2,6-difluorobenzyl)oxy]-2,5-dimethylpyrazolo[1,5-a]pyridine-3-carboxylic acid (75% purity, 0.118 mmol) from Example 4A, 66 mg of HATU (0.174 mmol) and 0.083 ml (0.474 mmol) of N,N-diisopropylethylamine in 0.7 ml of DMF was stirred at RT for 10 min. This reaction mixture was added to a solution of 53 mg (0.236 mmol) of rac-4-(methylsulphanyl)butane-1,2-diamine dihydrochloride in 0.14 ml of DMF at 0° C. and the mixture was stirred for 60 min. The reaction mixture was admixed with water and acetonitrile and purified by means of preparative HPLC (RP18 column, eluent:acetonitrile/water gradient with addition of 0.05% formic acid). 40 mg of the target compound were obtained (54% of theory).

LC-MS (Method 2): $R_t$=0.75 min

MS (ESIpos): m/z=449 (M+H)$^+$ $^1$H NMR (500 MHz, DMSO-d$_6$) δ [ppm]=7.56-7.67 (m, 2H), 7.42 (br.s, 1H), 7.23-7.29 (m, 2H), 6.59 (d, 1H), 5.45 (s, 2H), 3.35-3.54 (m, 3H), 2.59-2.66 (2H), 2.52 (s, 3H), 2.43 (s, 3H), 2.06 (s, 3H), 1.83-1.93 (m, 1H), 1.73-1.83 (m, 1H), 1.19 (br.s, 2H).

Example 157 rac-N-[2-Amino-4-(methylsulphonyl)butyl]-7-[(2,6-difluorobenzyl)oxy]-2,5-dimethylpyrazolo[1,5-a]pyridine-3-carboxamide

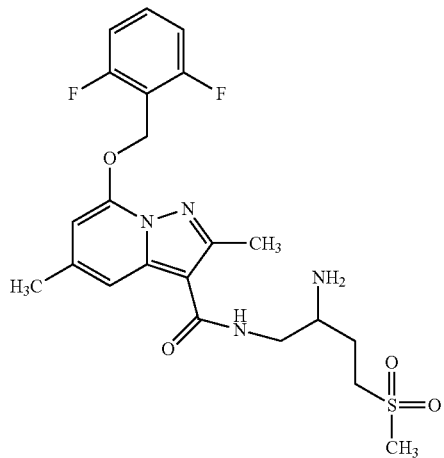 [SMILES: Cc1cc(OCc2c(F)cccc2F)n2nc(C)c(C(=O)NCC(N)CCS(C)(=O)=O)c2c1]

38 mg (0.085 mmol) of rac-N-[2-amino-4-(methylsulphanyl)butyl]-7-[(2,6-difluorobenzyl)oxy]-2,5-dimethylpyrazolo[1,5-a]pyridine-3-carboxamide from Example 156 were dissolved in 0.85 ml of dichloromethane and cooled to 0° C. Subsequently, 51 mg (0.213 mmol, 72% purity) of 3-chlorobenzenecarboperoxo acid were added and the mixture was stirred at 0° C. for 1 h. The reaction mixture was diluted with dichloromethane, washed twice with 1 N aqueous sodium hydroxide solution and twice with water, and concentrated by rotary evaporation. The crude product was purified by means of preparative HPLC (RP18 column, eluent:acetonitrile/water gradient with addition of 0.05% formic acid). 11 mg of the target compound were obtained (26% of theory).

LC-MS (Method 2): $R_t$=0.68 min

MS (ESIpos): m/z=481 (M+H)$^+$ $^1$H NMR (500 MHz, DMSO-d$_6$) δ [ppm]=8.22 (s, 1H), 7.57-7.68 (m, 1H), 7.48-7.55 (m, 1H), 7.39 (s, 1H), 7.22-7.30 (m, 2H), 6.55 (d, 1H), 5.44 (s, 2H), 3.15-3.36 (m, partly concealed by the water peak), 2.98-3.06 (m, 1H), 2.96 (s, 3H), 2.41 (s, 3H), 1.86-1.96 (m, 1H), 1.62-1.74 (m, 1H).

Example 158 rac-N-(2-Amino-2-methylpentyl)-7-[(2,3-difluorobenzyl)oxy]-2,5-dimethylpyrazolo[1,5-a]pyridine-3-carboxamide

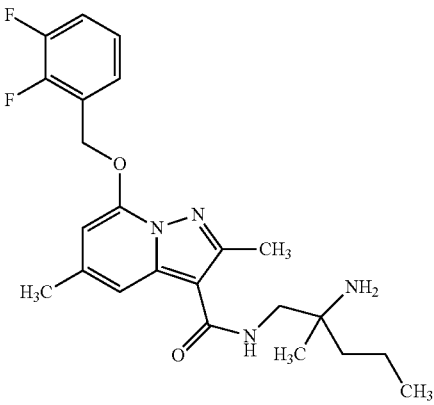 [SMILES: CCCC(C)(N)CNC(=O)c1c(C)nn2c(OCc3cccc(F)c3F)cc(C)cc12]

A solution of 35 mg (0.066 mmol) of rac-{1-[({7-[(2,3-difluorobenzyl)oxy]-2,5-dimethylpyrazolo[1,5-a]pyridin-3-yl}carbonyl)amino]-2-methylpentan-2-yl}carbamic acid tert-butyl ester (Example 118A) in 2 ml of dichloromethane was admixed with 0.079 ml (1.03 mmol) of trifluoroacetic acid. The resulting solution was stirred at room temperature overnight. The solvent was drawn off under reduced pressure and the residue was purified by preparative HPLC chromatography (Method 21), which gave 6 mg (27% of theory) of the target compound.

LC-MS (Method 18): $R_t$=8.91 min

MS (ESpos): m/z=431.24 (M+H)$^+$ $^1$H NMR (600 MHz, DMSO-d$_6$): δ [ppm]=0.86 (t, 3H), 0.97 (s, 3H), 1.25-1.39 (m, 2H), 1.27-1.33 (m, 2H), 2.38 (s, 3H), 2.52 (s, 3H), 3.13 (dd, 1H), 3.15-3.20 (m, 1H), 5.50 (s, 2H), 6.52 (d, 1H), 7.22 (t, 1H), 7.28-7.34 (m, 1H), 7.37 (s, 1H), 7.48 (t, 1H), 7.50-7.56 (m, 1H).

$^{13}$C NMR (151 MHz, DMSO-d$_6$): δ [ppm]=14.0, 14.8, 16.5, 21.4, 25.8, 43.3, 48.8, 52.1, 64.8, 93.9, 103.8, 108.7, 118.2, 125.2, 125.2, 126.2, 138.2, 141.8, 148.2, 148.4, 149.8, 150.7, 163.5.

Example 159 rac-N-(2-Amino-2-methylpentyl)-7-(cyclohexylmethoxy)-2,5-dimethylpyrazolo[1,5-a]pyridine-3-carboxamide

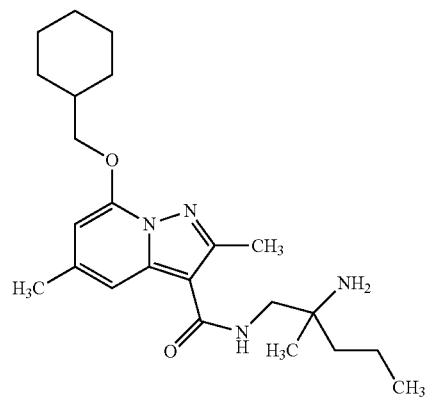 [SMILES: CCCC(C)(N)CNC(=O)c1c(C)nn2c(OCC3CCCCC3)cc(C)cc12]

A solution of 40 mg (0.047 mmol, 59% pure) of rac-[1-({[7-(cyclohexylmethoxy)-2,5-dimethylpyrazolo[1,5-a]pyridin-3-yl]carbonyl}amino)-2-methylpentan-2-yl]carbamic acid tert-butyl ester (Example 121A) in 2 ml of dichloromethane was admixed with 0.072 ml (0.94 mmol) of trifluoroacetic acid. The resulting solution was stirred at room temperature overnight. After the reaction had ended, the solvent was drawn off under reduced pressure and the residue was purified by preparative HPLC chromatography (Method 21), which gave 8 mg (43% of theory) of the target compound.

LC-MS (Method 18): $R_t$=10.32 min

MS (ESpos): m/z=401.26 (M+H)$^+$ $^1$H NMR (500 MHz, DMSO-d$_6$): δ [ppm]=0.87 (t, 3H), 0.98 (s, 3H), 1.03-1.14 (m, 2H), 1.15-1.39 (m, 7H), 1.67 (d, 1H), 1.73 (d, 2H), 1.84-1.95 (m, 3H), 2.36 (s, 3H), 2.54 (s, 3H), 3.11-3.21 (m, 2H), 4.10 (t, 2H), 6.32 (s, 1H), 7.20 (t, 1H), 7.31 (s, 1H).

Example 160 rac-N-(2-Amino-2-methylpentyl)-2,5-dimethyl-7-(3-methylbutoxy)pyrazolo[1,5-a]pyridine-3-carboxamide

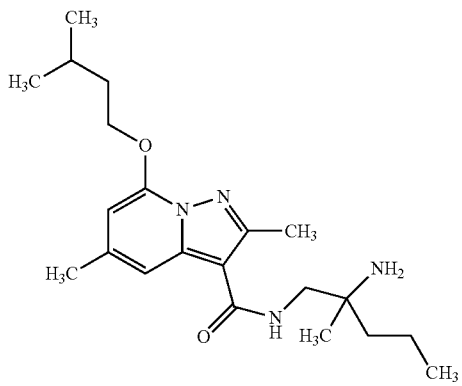 [SMILES: CCCC(C)(N)CNC(=O)c1c(C)nn2c(OCCC(C)C)cc(C)cc12]

A solution of 80 mg (0.091 mmol, 54% pure) of rac-[1-({[2,5-dimethyl-7-(3-methylbutoxy)pyrazolo[1,5-a]pyridin-3-yl]carbonyl}amino)-2-methylpentan-2-yl]carbamic acid tert-butyl ester (Example 124A) in 4 ml of dichloromethane was admixed with 0.140 ml (1.82 mmol) of trifluoroacetic acid. The resulting solution was stirred at room temperature overnight. After the reaction had ended, the solvent was drawn off under reduced pressure and the residue was purified by preparative HPLC chromatography (Method 21), which gave 17 mg (50% of theory) of the target compound.

LC-MS (Method 18): $R_t$=8.88 min

MS (ESpos): m/z=375.25 (M+H)$^+$ $^1$H NMR (500 MHz, DMSO-d$_6$): δ [ppm]=0.87 (t, 3H), 0.96 (d, 6H), 0.98 (s, 3H), 1.21-1.38 (m, 4H), 1.74 (q, 2H), 1.79-1.90 (m, 1H), 2.37 (s, 3H), 2.54 (s, 3H), 3.09-3.22 (m, 2H), 4.31 (t, 2H), 6.35 (s, 1H), 7.19 (t, 1H), 7.31 (s, 1H).

$^{13}$C NMR (126 MHz, DMSO-d$_6$): δ [ppm]=14.0, 14.8, 16.6, 21.5, 22.3, 24.4, 25.8, 36.9, 43.4, 48.8, 52.0, 68.1, 93.1, 104.3, 108.4, 138.4, 141.8, 149.1, 150.5, 163.6.

Example 161 rac-N-(2-Amino-2-methylpentyl)-7-[(2,6-difluoro-3-methoxybenzyl)oxy]-2,5-dimethylpyrazolo[1,5-a]pyridine-3-carboxamide

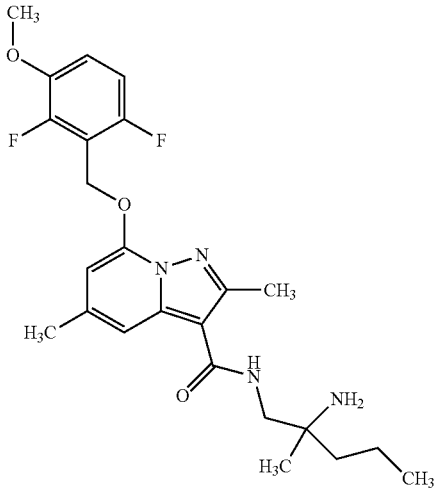 [SMILES: CCCC(C)(N)CNC(=O)c1c(C)nn2c(OCc3c(F)ccc(OC)c3F)cc(C)cc12]

rac-{1-[({7-[(2,6-Difluoro-3-methoxybenzyl)oxy]-2,5-dimethylpyrazolo[1,5-a]-pyridin-3-yl}carbonyl)amino]-2-methylpentan-2-yl}carbamic acid tert-butyl ester (Example 125A) in 4 ml of dichloromethane was admixed with 3 ml of trifluoroacetic acid. The resulting solution was stirred at room temperature for 3 h. After the reaction had ended, the solvent was drawn off under reduced pressure and the residue was purified by preparative HPLC chromatography (Method 21), which gave 10 mg (11% of theory, over 2 stages) of the target compound.

LC-MS (Method 18): $R_t$=8.94 min

MS (ESpos): m/z=461.31 (M+H)$^+$ $^1$H NMR (500 MHz, DMSO-d$_6$): δ [ppm]=0.86 (t, 3H), 0.97 (s, 3H), 1.25-1.39 (m, 4H), 2.40 (s, 3H), 3.10-3.20 (m, 2H), 3.86 (s, 3H), 5.43 (s, 2H), 6.64 (d, 1H), 7.16-7.24 (m, 2H), 7.35 (q, 1H), 7.38 (s, 1H).

Example 162 rac-N-(2-Amino-2-methylpentyl)-7-[(3-cyano-2,6-difluorobenzyl)oxy]-2,5-dimethylpyrazolo[1,5-a]pyridine-3-carboxamide

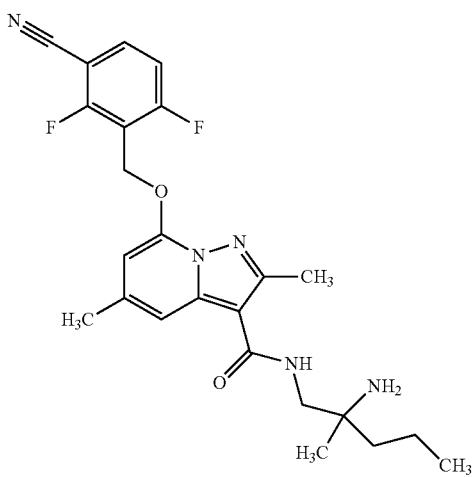 [SMILES: CCCC(C)(N)CNC(=O)c1c(C)nn2c(OCc3c(F)ccc(C#N)c3F)cc(C)cc12]

Crude rac-{1-[({7-[(3-cyano-2,6-difluorobenzyl)oxy]-2,5-dimethylpyrazolo[1,5-a]pyridin-3-yl}carbonyl)amino]-2-methylpentan-2-yl}carbamic acid tert-butyl ester (Example 126A) in 4 ml of dichloromethane was admixed with 2 ml of trifluoroacetic acid. The resulting solution was stirred at room temperature for 3 h. The solvent was drawn off under reduced pressure and the residue was purified by preparative HPLC chromatography (Method 21), which gave 4.5 mg (5% of theory over 2 stages) of the target compound.

LC-MS (Method 18): $R_t$=8.41 min

MS (ESpos): m/z=456.29 (M+H)$^+$ $^1$H NMR (500 MHz, DMSO-d$_6$): δ [ppm]=0.86 (t, 3H), 0.99 (s, 3H), 1.26-1.41 (m, 4H), 2.40 (s, 3H), 3.11-3.23 (m, 2H), 5.50 (s, 2H), 6.55 (d, 1H), 7.25 (t, 1H), 7.40 (s, 1H), 7.53 (t, 1H), 8.18-8.23 (m, 1H).

Example 163 rac-N-(2-Amino-2-methylpentyl)-7-[(2,6-difluorobenzyl)oxy]-2-methylpyrazolo[1,5-a]pyridine-3-carboxamide

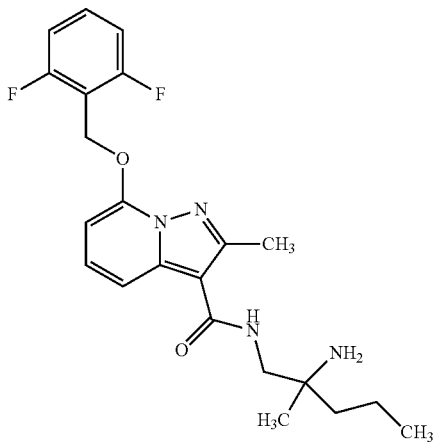 [SMILES: CCCC(C)(N)CNC(=O)c1c(C)nn2c(OCc3c(F)cccc3F)cccc12]

A solution of 45 mg (0.046 mmol, 53% pure) of rac-{1-[({7-[(2,6-difluorobenzyl)oxy]-2-methylpyrazolo[1,5-a]pyridin-3-yl}carbonyl)amino]-2-methylpentan-2-yl}carbamic acid tert-butyl ester (Example 131A) in 4 ml of dichloromethane was admixed with 0.5 ml (6.49 mmol) of trifluoroacetic acid. The resulting solution was stirred at room temperature for 2 h. The solvent was drawn off under reduced pressure and the residue was purified by preparative HPLC chromatography (Method 21), which gave 6.5 mg (34% yield) of the target compound as a white powder.

LC-MS (Method 18): $R_t$=8.53 min

MS (ESpos): m/z=417.22 (M+H)$^+$ $^1$H NMR (500 MHz, DMSO-d$_6$): δ [ppm]=0.86 (t, 3H), 0.97 (s, 3H), 1.25-1.39 (m, 4H), 2.52 (s, 3H), 3.12-3.23 (m, 2H), 5.47 (s, 2H), 6.65 (d, 1H), 7.25 (t, 2H), 7.32 (t, 1H), 7.41 (t, 1H), 7.57 (d, 1H), 7.61 (d, 1H).

Example 164 rac-N-(2-Amino-2-methylpentyl)-7-[(2-chloro-6-fluorobenzyl)oxy]-2-methylpyrazolo[1,5-a]pyridine-3-carboxamide

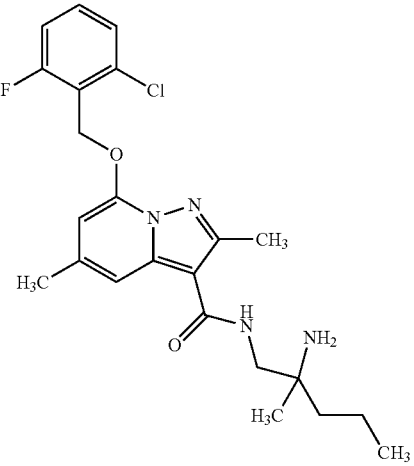 [SMILES: CCCC(C)(N)CNC(=O)c1c(C)nn2c(OCc3c(F)cccc3Cl)cc(C)cc12]

A solution of 40 mg (0.073 mmol) of rac-{1-[({7-[(2-difluorobenzyl)oxy]-2,5-dimethylpyrazolo[1,5-a]pyridin-3-yl}carbonyl)amino]-2-methylpentan-2-yl}carbamic acid tert-butyl ester (Example 138A) in 2 ml of dichloromethane was admixed with 0.113 ml of trifluoroacetic acid. The resulting mixture was stirred at room temperature for 18 hours and then heated to 40° C. Further trifluoroacetic acid (0.169 ml) was added in portions over the course of 3 hours. The reaction mixture was concentrated under reduced pressure and the remaining residue was purified by preparative HPLC chromatography (Method 21), which gave 11.0 mg (33% yield) of the target compound.

LC-MS (Method 18): $R_t$=9.08 min; m/z=447.24 (M+H)$^+$ $^1$H NMR (500 MHz, DMSO-d$_6$): δ [ppm]=0.83-0.90 (m, 3H), 1.01 (s, 3H), 1.28-1.39 (m, 4H), 2.41 (s, 3H), 2.49 (br. s, 3H), 3.20 (qd, 2H), 5.47 (s, 2H), 6.58 (s, 1H), 7.29 (t, 1H), 7.37-7.43 (m, 2H), 7.50 (d, 1H), 7.56-7.63 (m, 1H).

$^{13}$C NMR (126 MHz, DMSO-d$_6$): δ [ppm]=13.8, 14.9, 16.4, 21.4, 25.1, 42.5, 48.2, 52.9, 62.5, 93.8, 104.5, 108.7, 115.1, 120.5, 125.8, 132.6, 135.8, 138.4, 141.8, 148.6, 150.8, 161.6, 163.7.

Example 165 rac-N-(2-Amino-2-methylpentyl)-2,5-dimethyl-7-[4,4,4-trifluoro-3-(trifluoromethyl)butoxy]pyrazolo[1,5-a]pyridine-3-carboxamide

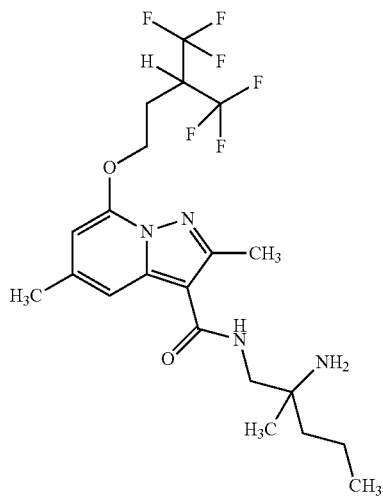 [SMILES: CCCC(C)(N)CNC(=O)c1c(C)nn2c(OCCC(C(F)(F)F)C(F)(F)F)cc(C)cc12]

A solution of 30 mg (0.051 mmol) of rac-{1-[({2,5-dimethyl-7-[4,4,4-trifluoro-3-(trifluoromethyl)butoxy]pyrazolo[1,5-a]pyridin-3-yl}carbonyl)amino]-2-methylpentan-2-yl}carbamic acid tert-butyl ester (Example 142A) in 2 ml of dichloromethane was admixed with trifluoroacetic acid (0.117 ml). The reaction mixture was stirred at room temperature for 18 hours. The solvent was evaporated off under reduced pressure and the residue was partitioned between dichloromethane and water. The organic phase was removed and concentrated under reduced pressure, and the residue was purified by preparative HPLC chromatography (Method 21), which gave 1.68 mg (7% yield) of the target compound.

LC-MS (Method 18): $R_t$=9.47 min; m/z=483.25 (M+H)$^+$ $^1$H NMR (600 MHz, DMSO-d$_6$): δ [ppm]=0.86 (t, 3H), 0.98 (s, 3H), 1.24-1.40 (m, 4H), 2.37 (s, 3H), 2.39 (q, 2H), 2.54 (s, 3H), 3.07-3.22 (m, 2H), 4.19-4.33 (m, 1H), 4.44 (t, 2H), 6.38 (d, 1H), 7.24 (t, 1H), 7.36 (s, 1H).

$^{13}$C NMR (151 MHz, DMSO-d$_6$): δ [ppm]=14.2, 14.8, 16.5, 21.4, 22.8, 25.3, 43.1, 43.4, 48.6, 52.3, 66.4, 94.0, 104.5, 108.8, 123.1, 138.3, 141.8, 148.3, 150.7, 163.6.

Example 166 rac-N-(2-Amino-2-methylpentyl)-7-[(3-fluoropyridin-2-yl)methoxy]-2,5-dimethylpyrazolo[1,5-a]pyridine-3-carboxamide

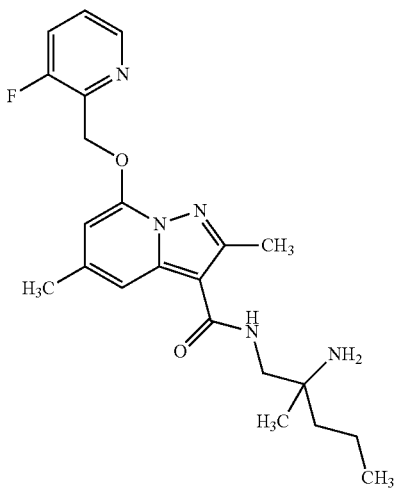 [SMILES: CCCC(C)(N)CNC(=O)c1c(C)nn2c(OCc3ncccc3F)cc(C)cc12]

20 mg (0.039 mmol) of rac-{1-[({7-[(3-fluoropyridin-2-yl)methoxy]-2,5-dimethylpyrazolo[1,5-a]pyridin-3-yl}carbonyl)amino]-2-methylpentan-2-yl}carbamic acid tert-butyl ester (Example 144A) were dissolved in 1 ml of trifluoroacetic acid. The reaction mixture was heated to 50° C. for 1 hour. Water was added, and the pH was adjusted to ~9 with 2 N sodium hydroxide solution. The aqueous phase was extracted with dichloromethane, separated off and concentrated under reduced pressure. The residue was purified by preparative HPLC chromatography (Method 21), which gave 1.59 mg (10% yield) of the target compound.

LC-MS (Method 18): $R_t$=8.17 min; m/z=414.28 (M+H)$^+$ $^1$H NMR (400 MHz, CDCl$_3$): δ [ppm]=0.87-0.95 (m, 3H), 1.12 (s, 3H), 1.28-1.52 (m, 4H), 2.36 (s, 3H), 2.68 (s, 3H), 3.14-3.33 (m, 1H), 3.33-3.45 (m, 1H), 5.56 (s, 2H), 6.24 (s, 1H), 6.43 (br. s., 1H), 7.28-7.37 (m, 1H), 7.39-7.48 (m, 1H), 7.59 (s, 1H), 8.44 (br. s., 1H).

$^{13}$C NMR (101 MHz, CDCl$_3$): δ [ppm]=15.1, 15.4, 17.4, 22.2, 26.1, 44.4, 48.8, 53.2, 67.7, 94.8, 104.0, 110.3, 124.1, 125.9, 139.5, 142.7, 144.0, 145.7, 148.9, 150.9, 158.5.

Example 167 rac-N-(2-Amino-2-methylpentyl)-5-cyclopropyl-7-[(2,6-difluorobenzyl)oxy]-2-methylpyrazolo[1,5-a]pyridine-3-carboxamide

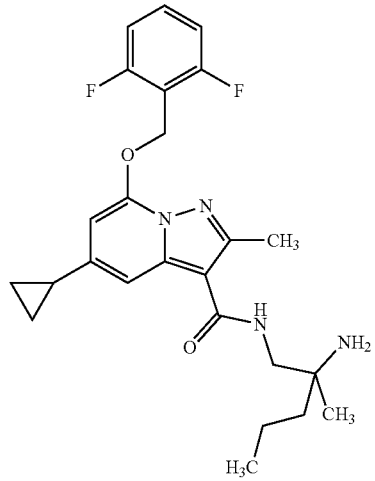 [SMILES: CCCC(C)(N)CNC(=O)c1c(C)nn2c(OCc3c(F)cccc3F)cc(C3CC3)cc12]

1 ml of trifluoroacetic acid were added to a solution of 125 mg (0.2 mmol) of rac-{1-[({5-cyclopropyl-7-[(2,6-difluorobenzyl)oxy]-2-methylpyrazolo[1,5-a]pyridin-3-yl}carbonyl)amino]-2-methylpentan-2-yl}carbamic acid tert-butyl ester (Example 150A) in 4 ml of dichloromethane. The reaction mixture was stirred at room temperature for 1 h and concentrated under reduced pressure. The residue was purified by chromatography on SCX-2 silica gel (mobile phase: methanol then 20% (2 M ammonia in methanol) in dichloromethane). This gave 40 mg of the target compound (39% of theory).

LC-MS (Method 20): $R_t$=3.39 min; m/z=457 (M+H)$^+$

1H NMR (400 MHz, DMSO-d$_6$): δ [ppm]=0.82-0.87 (m, 5H), 0.95 (s, 3H), 1.03 (ddd, 2H), 1.22-1.35 (m, 4H), 1.39 (s, 1H), 1.95-2.04 (m, 1H), 3.06-3.18 (m, 3H), 5.44 (s, 2H), 6.29 (d, 1H), 7.17-7.29 (m, 4H), 7.54-7.63 (m, 1H).

Example 168 ent-N-(2-Amino-5,5,5-trifluoro-2-methylpentyl)-2,5-dimethyl-7-[(2,3,6-trifluorobenzyl)oxy]pyrazolo[1,5-a]pyridine-3-carboxamide (Enantiomer B)

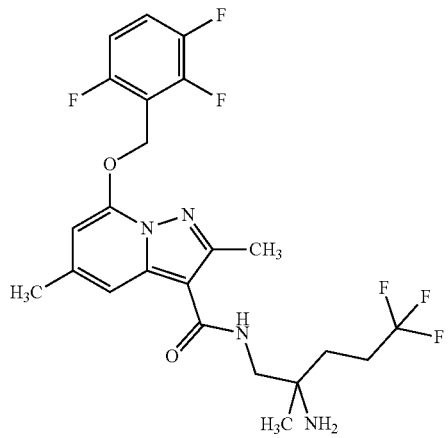 [SMILES: Cc1cc(OCc2c(F)ccc(F)c2F)n2nc(C)c(C(=O)NCC(C)(N)CCC(F)(F)F)c2c1]

61 mg (0.06 mmol) of ent-benzyl {1-[({2,5-dimethyl-7-[(2,3,6-trifluorobenzyl)oxy]pyrazolo[1,5-a]pyridin-3-yl}carbonyl)amino]-5,5,5-trifluoro-2-methylpentan-2-yl}carbamate trifluoroacetate (enantiomer B) from Example 153A were dissolved in 6.5 ml of ethanol, 14 µl (0.18 mmol) of trifluoroacetic acid and 2 mg of 10% palladium on activated carbon were added, and hydrogenation was effected at standard pressure for 1 hour. The reaction mixture was filtered by means of a Millipore filter and the filtrate was concentrated by rotary evaporation. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 23 mg of the target compound were obtained (74% of theory).

LC-MS (Method 2): $R_t$=0.79 min

MS (ESIpos): m/z=503 (M+H)$^+$ $^1$H NMR (400 MHz, DMSO-$d_6$): δ [ppm]=1.01 (s, 3H), 1.47-1.67 (m, 4H), 2.24-2.47 (m, 5H), 2.50 (s, 3H; obscured by the solvent peak), 3.14-3.25 (m, 2H), 5.49 (s, 2H), 6.55 (s, 1H), 7.27-7.37 (m, 2H), 7.41 (t, 1H), 7.64-7.75 (m, 1H).

Example 169 ent-N-(2-Amino-2-methylpentyl)-2-cyclopropyl-5-methyl-7-[(2,3,6-trifluorobenzyl)oxy]pyrazolo[1,5-a]pyridine-3-carboxamide (Enantiomer B)

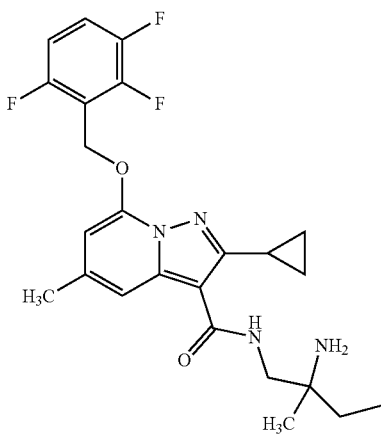

82 mg (0.11 mmol) of ent-benzyl {1-[({2-cyclopropyl-5-methyl-7-[(2,3,6-trifluorobenzyl)oxy]pyrazolo pyridin-3-yl}carbonyl)amino]-2-methylpentan-2-yl}carbamate trifluoroacetate (enantiomer B) from Example 158A were dissolved in 12 ml of ethanol, 26 µl (0.34 mmol) of trifluoroacetic acid and 3.6 mg of 10% palladium on activated carbon were added, and hydrogenation was effected at standard pressure for 1.5 hours. The reaction mixture was filtered by means of a Millipore filter and the filtrate was concentrated by rotary evaporation. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 53 mg of the target compound were obtained (98% of theory).

LC-MS (Method 2): $R_t$=0.78 min

MS (ESIpos): m/z=475 (M+H)$^+$ $^1$H NMR (400 MHz, DMSO-$d_6$): δ=0.83-0.94 (m, 5H), 0.96-1.04 (m, 5H), 1.25-1.40 (m, 4H), 1.60 (br. s, 2H), 2.31-2.42 (m, 4H), 3.12-3.25 (m, 2H), 5.49 (s, 2H), 6.53 (s, 1H), 7.25-7.34 (m, 1H), 7.38 (t, 1H), 7.46 (s, 1H), 7.62-7.73 (m, 1H).

Example 170 ent-N-(2-Amino-5,5,5-trifluoro-2-methylpentyl)-2-cyclopropyl-5-methyl-7-[(2,3,6-trifluorobenzyl)oxy]pyrazolo[1,5-a]pyridine-3-carboxamide (Enantiomer B)

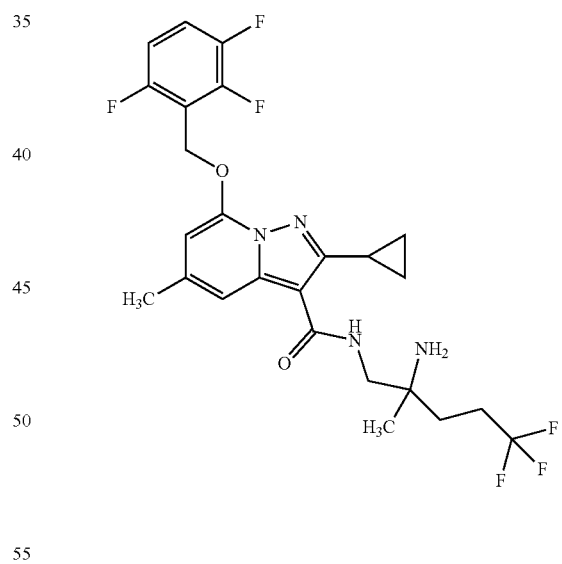

79 mg (0.10 mmol) of ent-benzyl {1-[({2-cyclopropyl-5-methyl-7-[(2,3,6-trifluorobenzyl)oxy]pyrazolo[1,5-a]pyridin-3-yl}carbonyl)amino]-5,5,5-trifluoro-2-methylpentan-2-yl}carbamate trifluoroacetate (enantiomer B) from Example 159A were dissolved in 11 ml of ethanol, 23 µl (0.30 mmol) of trifluoroacetic acid and 3.2 mg of 10% palladium on activated carbon were added, and hydrogenation was effected at standard pressure for 2 hours. Another 23 µl (0.30 mmol) of trifluoroacetic acid and 3.2 mg of 10% palladium on activated carbon were added, and the mixture was hydrogenated at standard pressure for 45 min. The reaction mixture was filtered by means of a Millipore filter and the filtrate was concentrated by rotary evaporation. The residue was dissolved again in 11 ml of ethanol, admixed with 77 μl (1 mmol) of trifluoroacetic acid and 3.2 mg of 10% palladium on activated carbon, and hydrogenated at standard pressure for 45 min. The reaction mixture was filtered by means of a Millipore filter and the filtrate was concentrated by rotary evaporation. The residue was admixed with acetonitrile, water and TFA and purified by means of preparative HPLC (RP18 column, eluent:acetonitrile/water gradient with addition of 0.1% TFA). The product fractions were combined and concentrated. Subsequently, the residue was taken up in dichloromethane and a little methanol, and washed twice with saturated aqueous sodium hydrogencarbonate solution. The aqueous phase was extracted twice with dichloromethane. The combined organic phases were dried over sodium sulphate, filtered, concentrated and lyophilized. 53 mg of the target compound were obtained (97% of theory).

LC-MS (Method 2): $R_t$=0.81 min

MS (ESIpos): m/z=529 (M+H)$^+$ $^1$H NMR (400 MHz, DMSO-d$_6$): δ=0.86-0.92 (m, 2H), 0.93-1.00 (m, 2H), 1.02 (s, 3H), 1.49-1.58 (m, 2H), 1.64 (br. s, 2H), 2.26-2.44 (m, 6H), 3.17-3.28 (m, 2H), 5.49 (s, 2H), 6.53 (s, 1H), 7.25-7.33 (m, 1H), 7.40 (s, 1H), 7.51 (t, 1H), 7.62-7.73 (m, 1H).

Example 171 rac-N-(2-Amino-2-methylpentyl)-7-[(2,6-difluorobenzyl)oxy]-5-methoxy-2-methylpyrazolo[1,5-a]pyridine-3-carboxamide

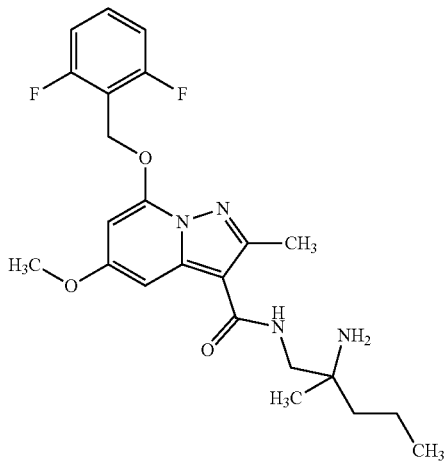

A solution of 118 mg (0.157 mmol, 73% purity) of rac-{1-[({7-[(2,6-difluorobenzyl)oxy]-5-methoxy-2-methylpyrazolo[1,5-a]pyridin-3-yl}carbonyl)amino]-2-methylpentan-2-yl}carbamic acid tert-butyl ester (Example 164A) in 12 ml of dichloromethane was admixed with 1.5 ml of trifluoroacetic acid. The resulting mixture was stirred at room temperature for two hours. The reaction mixture was concentrated under reduced pressure and the remaining residue was purified by preparative HPLC chromatography (Method 21), which gave 37 mg (53% yield) of product.

LC-MS (Method 18): $R_t$=8.81 min; m/z=447.17 (M+H)$^+$ $^1$H NMR (600 MHz, DMSO-d$_6$): δ [ppm]=0.85 (t, J=6.7 Hz, 3H), 0.97 (s, 3H), 1.21-1.40 (m, 4H), 2.47 (s, 3H), 3.06-3.20 (m, 2H), 3.85 (s, 3H), 5.43 (s, 2H), 6.37 (d, J=2.4 Hz, 1H), 7.01 (d, J=2.4 Hz, 1H), 7.15 (t, J=5.8 Hz, 1H), 7.21-7.30 (m, 2H), 7.52-7.67 (m, 1H).

$^{13}$C NMR (151 MHz, DMSO-d$_6$): δ [ppm]=14.0, 14.8, 16.5, 25.6, 43.3, 48.6, 52.0, 55.7, 59.5, 85.4, 88.7, 104.5, 110.6, 112.0, 132.8, 142.5, 149.5, 151.1, 159.3, 161.3, 163.6.

Example 172 rac-N-(2-Amino-2-methylpentyl)-7-[(2,6-difluorobenzyl)oxy]-5-ethyl-2-methylpyrazolo[1,5-a]pyridine-3-carboxamide

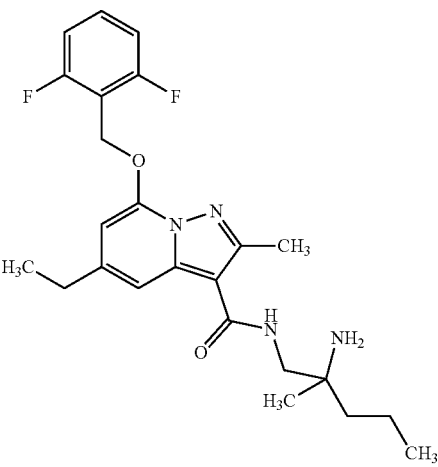 [SMILES: CCCC(C)(N)CNC(=O)c1c(C)nn2c(OCc3c(F)cccc3F)cc(OC)cc12]

A solution of 19 mg (0.033 mmol, 95% purity) of rac-{1-[({7-[(2,6-difluorobenzyl)oxy]-5-ethyl-2-methylpyrazolo[1,5-a]pyridin-3-yl}carbonyl)amino]-2-methylpentan-2-yl}carbamic acid tert-butyl ester (Example 169A) in 1 ml of dichloromethane was admixed with 0.15 ml of trifluoroacetic acid. The resulting mixture was stirred at room temperature for 2 hours. The reaction mixture was concentrated under reduced pressure and the remaining residue was purified by preparative HPLC chromatography (Method 21), which gave 4.5 mg (15% yield) of product.

LC-MS (Method 18): $R_t$=5.51 min; m/z=445.31 (M+H)$^+$ $^1$H NMR (500 MHz, DMSO-d$_6$): δ [ppm]=0.87 (t, J=6.6 Hz, 3H), 0.98 (s, 3H), 1.26 (t, J=7.5 Hz, 3H), 1.28-1.37 (m, 4H), 2.50 (s, 3H), 2.70 (q, J=7.3 Hz, 2H), 3.05-3.23 (m, 2H), 5.46 (s, 2H), 6.57 (d, J=1.2 Hz, 1H), 7.20-7.30 (m, 3H), 7.40 (s, 1H), 7.56-7.68 (m, 1H).

$^{13}$C NMR (126 MHz, DMSO-d$_6$): δ [ppm]=13.9, 14.3, 14.8, 16.5, 25.8, 28.3, 43.9, 48.7, 53.2, 59.6, 95.1, 105.0, 107.4, 110.9, 111.9, 132.9, 142.0, 145.0, 149.0, 150.8, 160.5, 163.0.

Example 173

7-[(2,6-Difluorobenzyl)oxy]-2,5-dimethyl-N-(4-methylpiperazin-1-yl)pyrazolo[1,5-a]pyridine-3-carboxamide

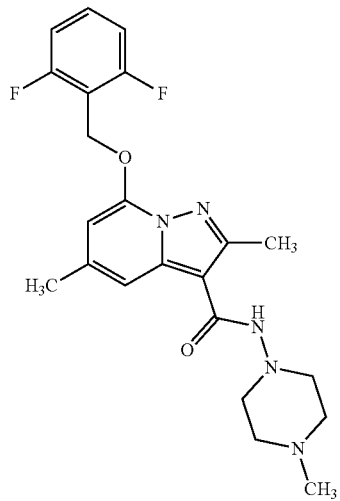 [SMILES: Cc1cc(OCc2c(F)cccc2F)n2nc(C)c(C(=O)NN3CCN(C)CC3)c2c1]

30 mg (0.09 mmol) of 7-[(2,6-difluorobenzyl)oxy]-2,5-dimethylpyrazolo[1,5-a]pyridine-3-carboxylic acid from Example 4A were initially charged together with 45 mg (0.12 mmol) of HATU and 0.08 ml (0.45 mmol) of N,N-diisopropylethylamine in 0.30 ml of DMF, and the mixture was stirred at room temperature for 10 min. Subsequently, 14 mg (0.12 mmol) of 4-methylpiperazine-1-amine were added to the reaction solution and the mixture was stirred at RT overnight. Then the mixture was diluted with acetonitrile and water, admixed with TFA and purified by means of preparative HPLC (RP18 column, eluent:acetonitrile/water gradient with addition of 0.1% TFA). The product fractions were taken up in dichloromethane and washed twice with saturated aqueous sodium hydrogencarbonate solution. The aqueous phase was extracted twice with dichloromethane, and the combined organic phases were dried over sodium sulphate, filtered, concentrated and lyophilized. 23 mg of the target compound were obtained (58% of theory).

LC-MS (Method 2): $R_t$=0.62 min
MS (ESIpos): m/z=430 (M+H)$^+$
$^1$H NMR (400 MHz, DMSO-d$_6$): δ=2.29 (s, 3H), 2.31-2.54 (m, 11H; obscured by solvent peak), 2.88 (s, 3H), 5.43 (s, 2H), 6.53 (s, 1H), 7.20-7.29 (m, 3H), 7.57-7.67 (m, 1H), 8.50 (s, 1H).

In analogy to Example 173, the example compounds shown in Table 8 were prepared by reacting 7-[(2,6-difluorobenzyl)oxy]-2,5-dimethylpyrazolo[1,5-a]pyridine-3-carboxylic acid from Example 4A with the appropriate amines [hydrazides] which are commercially available or have been described above (1.1-5 equivalents), HATU (1.1-4.5 equivalents) and N,N-diisopropylethylamine (3-12 equivalents) in DMF or in DMF/dichloromethane (1/1) under the reaction conditions described (reaction time: 1-48 h; temperature: 0° C.-RT, −20° C., RT or 60° C.).

Illustrative Workup of the Reaction Mixture:

The reaction solution was admixed with water and the solids that formed were stirred at room temperature for about 30 min. Subsequently, the solids were filtered off, washed well with water and dried under high vacuum.

Alternatively, the reaction mixture was diluted with water, TFA or formic acid and purified by means of preparative HPLC (RP18 column, eluent:acetonitrile/water gradient with addition of 0.1% TFA or 0.05% formic acid). The crude product was additionally or alternatively purified by means of thick-layer chromatography or silica gel chromatography (eluent:dichloromethane/methanol or dichloromethane/2 M ammonia in methanol). The product-containing fractions were concentrated.

The product fractions from the purifications were, if necessary, taken up in dichloromethane and washed twice with saturated aqueous sodium hydrogencarbonate solution. The aqueous phase was extracted twice with dichloromethane, and the combined organic phases were dried over sodium sulphate, filtered, concentrated and lyophilized.

TABLE 8

| Example | IUPAC name/structure (yield) | Analytical data |
|---|---|---|
| 174 | 7-[(2,6-Difluorobenzyl)oxy]-2,5-dimethyl-N'-(piperidin-1-ylacetyl)pyrazolo[1,5-a]pyridine-3-carbohydrazide<br><br>(37% of theory) | $^1$H NMR (400 MHz, DMSO-d$_6$): δ = 1.35-1.46 (m, 2H), 1.49-1.61 (m, 4H), 2.41 (s, 3H), 3.01 (br. s, 2H), 5.44 (s, 2H), 6.58 (s, 1H), 7.20-7.29 (m, 2H), 7.39 (s, 1H), 7.58-7.68 (m, 1H), 9.38 (br. s, 1H), 9.58 (br. s, 1H), [further signals hidden under solvent peaks].<br>LC-MS (Method 7): $R_t$ = 2.33 min<br>MS (ESIpos): m/z = 472 (M + H)$^+$ |

TABLE 8-continued

| Example | IUPAC name/structure (yield) | Analytical data |
|---|---|---|
| 175 | 7-[(2,6-Difluorobenzyl)oxy]-2,5-dimethyl-N'-[(2-oxopyrrolidin-1-yl)acetyl]pyrazolo[1,5-a]pyridine-3-carbohydrazide trifluoroacetate<br>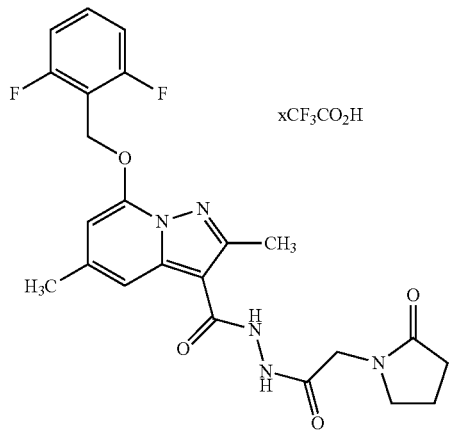 [SMILES: Cc1cc(OCc2c(F)cccc2F)n2nc(C)c(C(=O)NNC(=O)CN3CCCC3=O)c2c1]<br>(27% of theory) | LC-MS (Method 2): $R_t$ = 0.79 min<br>MS (ESpos): m/z = 472 (M-TFA + H)$^+$ |
| 176 | 7-[(2,6-Difluorobenzyl)oxy]-N-[(1S)-2-hydroxy-1-(2-thienyl)ethyl]-2,5-dimethylpyrazolo[1,5-a]pyridine-3-carboxamide<br>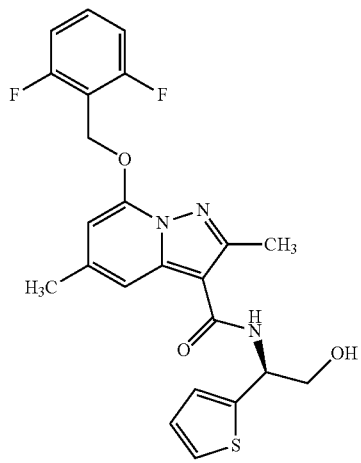 [SMILES: Cc1cc(OCc2c(F)cccc2F)n2nc(C)c(C(=O)N[C@@H](CO)c3cccs3)c2c1]<br>(46% of theory) | $^1$H NMR (400 MHz, DMSO-d$_6$): δ = 2.40 (s, 3H), 3.78 (t, 2H), 5.10 (t, 1H), 5.32 (q, 1H), 5.46 (s, 2H), 6.56 (s, 1H), 6.95-7.00 (m, 1H), 7.07 (d, 1H), 7.21-7.30 (m, 2H), 7.35-7.39 (m, 2H), 7.57-7.67 (m, 1H), 7.74 (d, 1H), [further signal hidden under solvent peak].<br>LC-MS (Method 2): $R_t$ = 0.95 min<br>MS (ESIpos): m/z = 458 (M + H)$^+$ |

TABLE 8-continued

| Example | IUPAC name/structure (yield) | Analytical data |
|---|---|---|
| 177 | 7-[(2,6-Difluorobenzyl)oxy]-N-[(1S)-2-hydroxy-1-(5-methyl-2-furyl)ethyl]-2,5-dimethylpyrazolo[1,5-a]pyridine-3-carboxamide<br>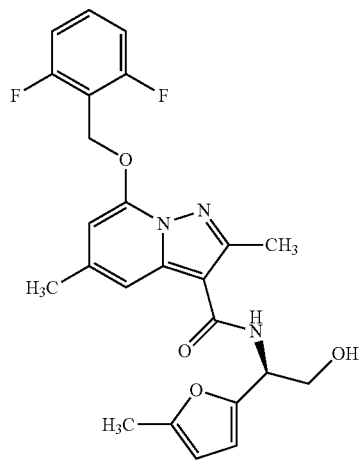 [SMILES: Cc1cc(OCc2c(F)cccc2F)n2nc(C)c(C(=O)N[C@@H](CO)c3ccc(C)o3)c2c1]<br>(17% of theory; 97% purity) | $^1$H NMR (400 MHz, DMSO-d$_6$): δ = 2.23 (s, 3H), 2.40 (s, 3H), 3.68-3.79 (m, 2H), 4.97 (br. s, 1H), 5.12 (q, 1H), 5.44 (s, 2H), 5.98 (d, 1H), 6.16 (d, 1H), 6.55 (s, 1H), 7.20-7.30 (m, 2H), 7.32 (s, 1H), 7.54 (d, 1H), 7.58-7.67 (m, 1H), [further signal hidden under solvent peak].<br>LC-MS (Method 2): R$_t$ = 0.98 min<br>MS (ESIpos): m/z = 456 (M + H)$^+$ |
| 178 | 7-[(2,6-Difluorobenzyl)oxy]-N-[(1R)-2-hydroxy-1-(5-methyl-2-furyl)ethyl]-2,5-dimethylpyrazolo[1,5-a]pyridine-3-carboxamide<br>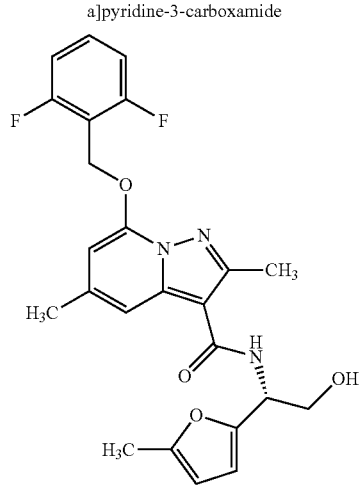<br>(16% of theory) | $^1$H NMR (400 MHz, DMSO-d$_6$): δ = 2.23 (s, 3H), 2.40 (s, 3H), 3.68-3.79 (m, 2H), 4.91-4.98 (m, 1H), 5.12 (q, 1H), 5.44 (s, 2H), 5.98 (d, 1H), 6.17 (d, 1H), 6.55 (s, 1H), 7.20-7.30 (m, 2H), 7.32 (s, 1H), 7.54 (d, 1H), 7.58-7.67 (m, 1H), [further signal hidden under solvent peak].<br>LC-MS (Method 2): R$_t$ = 0.98 min<br>MS (ESIpos): m/z = 456 (M + H)$^+$ |

Example 179

N-[(1S)-1-{5-[(1S)-1-Amino-2-methylpropyl]-1,3,4-oxadiazol-2-yl}-2-hydroxyethyl]-7-[(2,6-difluorobenzyl)oxy]-2,5-dimethylpyrazolo[1,5-a]pyridine-3-carboxamide

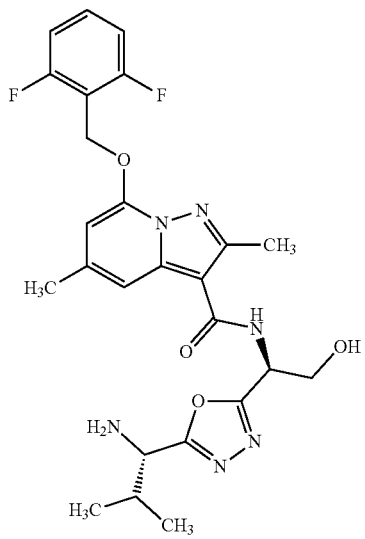 [SMILES: Cc1cc(OCc2c(F)cccc2F)n2nc(C)c(C(=O)N[C@@H](CO)c3nnc([C@@H](N)C(C)C)o3)c2c1]

211 mg (0.27 mmol; 94% purity) of tert-butyl [(1S)-1-(5-{(1S)-1-[({7-[(2,6-difluorobenzyl)oxy]-2,5-dimethylpyrazolo[1,5-a]pyridin-3-yl}carbonyl)amino]-2-hydroxyethyl}-1,3,4-oxadiazol-2-yl)-2-methylpropyl]carbamate trifluoroacetate from Example 174A were suspended in 1.5 ml of diethyl ether, and 1.36 ml (2.72 mmol) of 2 M hydrogen chloride solution in diethyl ether were added. The reaction mixture was stirred at RT for 2 h. The mixture was concentrated, diluted with acetonitrile/water, admixed with TFA and purified by means of preparative HPLC (RP18 column, eluent:acetonitrile/water gradient with addition of 0.1% TFA). The product fractions were taken up in dichloromethane and washed twice with saturated aqueous sodium hydrogencarbonate solution. The aqueous phase was extracted twice with dichloromethane, and the combined organic phases were dried over sodium sulphate, filtered, concentrated and lyophilized. 45 mg of the target compound were obtained (32% of theory).

LC-MS (Method 2): $R_t$=0.68 min

MS (ESIpos): m/z=515 (M+H)$^+$ $^1$H NMR (400 MHz, DMSO-d$_6$): δ=0.81 (d, 3H), 0.91 (d, 3H), 1.86-2.10 (m, 3H), 2.40 (s, 3H), 3.78-3.97 (m, 3H), 5.20 (t, 1H), 5.32 (q, 1H), 5.45 (s, 2H), 6.58 (s, 1H), 7.20-7.30 (m, 2H), 7.35 (s, 1H), 7.58-7.67 (m, 1H), 7.90 (d, 1H), [further signal hidden under solvent peak].

B. ASSESSMENT OF PHARMACOLOGICAL EFFICACY

The following abbreviations are used:

ATP adenosine triphosphate

Brij35 polyoxyethylene(23) lauryl ether

BSA bovine serum albumin

DTT dithiothreitol

TEA triethanolamine

The pharmacological efficacy of the inventive compounds can be shown in the following assays:

B-1. Measurement of sGC Enzyme Activity by Means of PPi Detection

Soluble guanylyl cyclase (sGC) converts GTP to cGMP and pyrophosphate (PPi) when stimulated. PPi is detected with the aid of the method described in WO 2008/061626. The signal that arises in the assay increases as the reaction progresses and serves as a measure of the sGC enzyme activity. With the aid of a PPi reference curve, the enzyme can be characterized in a known manner, for example in terms of conversion rate, stimulability or Michaelis constant.

Test Procedure

To conduct the test, 29 µl of enzyme solution (0-10 nM soluble guanylyl cyclase (prepared according to Honicka et al., Journal of Molecular Medicine 77(1999)14-23), in 50 mM TEA, 2 mM magnesium chloride, 0.1% BSA (fraction V), 0.005% Brij 35, pH 7.5) were initially charged in the microplate, and 1 µl of the stimulator solution (0-10 µM 3-morpholinosydnonimine, SIN-1, Merck in DMSO) was added. The microplate was incubated at RT for 10 min. Subsequently, 20 µl of detection mix (1.2 nM firefly luciferase (*Photinus pyralis* Luziferase, Promega), 29 µM dehydroluciferin (prepared according to Bitler & McElroy, Arch. Biochem. Biophys. 72 (1957) 358), 122 µM luciferin (Promega), 153 µM ATP (Sigma) and 0.4 mM DTT (Sigma) in 50 mM TEA, 2 mM magnesium chloride, 0.1% BSA (fraction V), 0.005% Brij 35, pH 7.5) were added. The enzyme reaction was started by adding 20 µl of substrate solution (1.25 mM guanosine 5'-triphosphate (Sigma) in 50 mM TEA, 2 mM MgCl$_2$, 0.1% BSA (fraction V), 0.005% Brij, pH 7.5) and analysed continuously in a luminometer.

B-2. Effect on a Recombinant Guanylate Cyclase Reporter Cell Line

The cellular effect of the inventive compounds is determined using a recombinant guanylate cyclase reporter cell line, as described in F. Wunder et al., *Anal. Biochem.* 339, 104-112 (2005).

Representative MEC values (MEC=minimum effective concentration) for the inventive compounds are shown in the table below (in some cases as mean values for individual determinations):

TABLE A

| Example | MEC [µM] |
|---------|----------|
| 1 | 2 |
| 2 | 0.3 |
| 3 | 0.3 |
| 4 | 0.2 |
| 5 | 0.3 |
| 6 | 1.0 |
| 7 | 1.0 |
| 8 | 0.3 |
| 9 | 1.0 |
| 10 | 1.0 |
| 11 | 1.0 |
| 12 | 3.0 |
| 13 | 1.0 |
| 14 | 0.3 |
| 15 | 3.0 |
| 16 | 0.3 |
| 17 | 0.3 |
| 18 | 3.0 |
| 19 | 0.3 |
| 20 | 0.3 |
| 21 | 0.3 |
| 22 | 0.1 |
| 23 | 0.3 |
| 24 | 0.3 |

TABLE A-continued

| Example | MEC [µM] |
|---|---|
| 25 | 0.3 |
| 26 | 0.3 |
| 27 | 0.3 |
| 28 | 1.0 |
| 29 | 0.3 |
| 30 | 0.1 |
| 31 | 1.0 |
| 32 | 0.3 |
| 33 | 3.0 |
| 34 | 1.0 |
| 35 | 1.0 |
| 36 | 3.0 |
| 37 | 10 |
| 38 | 3.0 |
| 39 | 0.3 |
| 40 | 1.0 |
| 41 | 0.3 |
| 42 | 0.3 |
| 43 | 0.1 |
| 44 | 0.3 |
| 45 | 0.3 |
| 46 | 2.0 |
| 47 | 1.0 |
| 48 | 0.3 |
| 49 | 0.3 |
| 50 | 0.3 |
| 51 | 1.0 |
| 52 | 0.3 |
| 53 | 3.0 |
| 54 | 0.3 |
| 55 | 0.1 |
| 56 | 0.3 |
| 57 | 0.3 |
| 58 | 0.03 |
| 59 | 3.0 |
| 60 | 3.0 |
| 61 | 10 |
| 62 | 3.0 |
| 63 | 1.0 |
| 64 | 3.0 |
| 65 | 3.0 |
| 66 | 0.3 |
| 67 | 3.0 |
| 68 | 10 |
| 69 | 10 |
| 70 | 3.0 |
| 71 | 0.3 |
| 72 | 10 |
| 73 | 3.0 |
| 74 | 0.03 |
| 75 | 0.03 |
| 76 | 0.3 |
| 77 | 0.3 |
| 78 | 1.0 |
| 79 | 3.0 |
| 80 | 0.03 |
| 81 | 1.0 |
| 82 | 1.0 |
| 83 | 3.0 |
| 84 | 1.0 |
| 86 | 3.0 |
| 87 | 0.3 |
| 88 | 1.0 |
| 89 | 3.0 |
| 90 | 0.1 |
| 91 | 3.0 |
| 92 | 0.3 |
| 93 | 10 |
| 94 | 1.0 |
| 95 | 10 |
| 96 | 10 |
| 97 | 1.0 |
| 98 | 3.0 |
| 99 | 0.1 |
| 100 | 10 |
| 101 | 3.0 |
| 102 | 1.0 |
| 103 | 10 |
| 104 | 3.0 |
| 105 | 3.0 |
| 106 | 1.0 |
| 107 | 3.0 |
| 108 | 0.3 |
| 109 | 1.0 |
| 110 | 3.0 |
| 111 | 1.0 |
| 112 | 10 |
| 113 | 3.0 |
| 114 | 10 |
| 115 | 0.3 |
| 116 | 3.0 |
| 117 | 1.0 |
| 118 | 0.3 |
| 120 | 1.0 |
| 121 | 10 |
| 122 | 10 |
| 123 | 1.0 |
| 124 | 0.3 |
| 125 | 3.0 |
| 126 | 1.0 |
| 127 | 0.3 |
| 128 | 1.0 |
| 129 | 3.0 |
| 130 | 3.0 |
| 131 | 3.0 |
| 132 | 1.0 |
| 133 | 0.3 |
| 134 | 0.3 |
| 135 | 3.0 |
| 136 | 10 |
| 137 | 1.0 |
| 138 | 0.1 |
| 139 | 1.0 |
| 140 | 0.3 |
| 141 | 3.0 |
| 142 | 10 |
| 143 | 0.3 |
| 144 | 0.1 |
| 145 | 1.0 |
| 146 | 1.0 |
| 147 | 0.3 |
| 148 | 1.0 |
| 149 | 1.0 |
| 150 | 0.3 |
| 151 | 3.0 |
| 152 | 0.3 |
| 153 | 3.0 |
| 154 | 1.0 |
| 155 | 1.0 |
| 156 | 0.3 |
| 158 | 1.0 |
| 159 | 3.0 |
| 160 | 3.0 |
| 161 | 3.0 |
| 163 | 3.0 |
| 164 | 1.0 |
| 166 | 10 |
| 167 | 3.0 |
| 168 | 0.1 |
| 169 | 0.2 |
| 170 | 0.1 |
| 171 | 1.0 |
| 172 | 0.3 |
| 173 | 1.0 |
| 174 | 1.0 |
| 175 | 10 |
| 176 | 0.3 |
| 177 | 1.0 |
| 178 | 1.0 |
| 179 | 10 |

B-3. Vasorelaxant Effect In Vitro

Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To obtain a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% ($IC_{50}$ value). The standard administration volume is 5 µl; the DMSO content in the bath solution corresponds to 0.1%.

B-4. Blood Pressure Measurement on Anaesthetized Rats

Male Wistar rats having a body weight of 300-350 g are anaesthetized with thiopental (100 mg/kg i.p.). After tracheotomy, a catheter is introduced into the femoral artery to measure the blood pressure. The substances to be tested are administered as solutions, either orally by means of a gavage or intravenously via the femoral vein (Stasch et al. Br. J. Pharmacol. 2002; 135: 344-355).

B-5. Radiotelemetry Measurement of Blood Pressure in Conscious, Spontaneously Hypertensive Rats A commercially available telemetry system from DATA SCIENCES INTERNATIONAL DSI, USA, is used for the blood pressure measurement on conscious rats described below.

The system consists of 3 main components:
implantable transmitters (Physiotel® telemetry transmitter)
receivers (Physiotel® receivers) which are connected via a multiplexer (DSI Data Exchange Matrix) to a
data acquisition computer.

The telemetry system makes it possible to continuously record blood pressure, heart rate and body motion of conscious animals in their usual habitat.

Animal Material

The studies are conducted on adult female spontaneously hypertensive rats (SHR Okamoto) with a body weight of >200 g. SHR/NCrl from the Okamoto Kyoto School of Medicine, 1963, were a cross of male Wistar Kyoto rats having greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The TA11 PA-C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as control.

Test Procedure

The telemetry measuring unit present is configured for 24 animals Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9:00 am on the day of the experiment. Following the administration, the parameters described above are measured over 24 hours.

Evaluation

After the end of the experiment, the acquired individual data are sorted using the analysis software (Dataquest™ A.R.T.™ ANALYSIS). The blank value is assumed to be the time 2 hours before administration, and so the selected data set encompasses the period from 7:00 am on the day of the experiment to 9:00 am on the following day.

The data are smoothed over a predefinable period by determination of the average (15-minute average) and transferred as a text file to a storage medium. The measured values presorted and compressed in this way are transferred into Excel templates and tabulated. For each day of the experiment, the data obtained are stored in a dedicated file bearing the experiment number. Results and test protocols are filed in paper form sorted by numbers.

LITERATURE

Klaus Witte, Kai Hu, Johanna Swiatek, Claudia Müssig, Georg Ertl and Bjorn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-6. Determination of Pharmacokinetic Parameters Following Intravenous and Oral Administration The pharmacokinetic parameters of the inventive compounds are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at −20° C. until further processing.

An internal standard (which may also be a chemically unrelated substance) is added to the samples of the inventive compounds, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by means of LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half-life), F (bioavailability), MRT (mean residence time) and CL (clearance), by means of a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}/C_{plasma}$ value.

Table B shows data of representative compounds of the present invention following intravenous administration in rats:

TABLE B

| Example | $AUC_{normal}$ [kg · h/l] | $CL_{blood}$ [l/h/kg] | $t_{1/2}$ [h] | MRT [h] |
|---|---|---|---|---|
| 39 | 0.53 | 2.46 | 6.2 | 7.8 |
| 43 | 0.49 | 2.56 | 5.9 | 7.4 |
| 55 | 0.37 | 2.76 | 2.6 | 3.5 |
| 168 | 0.45 | 2.19 | 3.2 | 4.3 |
| 169 | 0.44 | 2.21 | 4.0 | 4.9 |
| 170 | 0.32 | 2.92 | 2.6 | 3.4 |

B-7. Metabolic Study

To determine the metabolic profile of the inventive compounds, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The inventive compounds were incubated with a concentration of about 0.1-10 µM. To this end, stock solutions of the inventive compounds having a concentration of 0.01-1 mM in acetonitrile were prepared, and then pipetted with 1:100 dilution into the incubation mixture. Liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were quenched with acetonitrile (final concentration about 30%) and the protein was centrifuged off at about 15 000×g. The samples thus quenched were either analysed directly or stored at −20° C. until analysis.

The analysis is carried out by high-performance liquid chromatography with ultraviolet and mass spectrometry detection (HPLC-UV-MS/MS). To this end, the supernatants of the incubation samples are chromatographed with suitable C18 reversed-phase columns and variable eluent mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound according to the invention in the incubation mixtures.

B-8. Caco-2 Permeability Test

The permeability of a test substance was determined with the aid of the Caco-2 cell line, an established in vitro model for permeability prediction at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The Caco-2 cells (ACC No. 169, DSMZ, Deutsche Sammlung von Mikroorganismen and Zellkulturen, Brunswick, Germany) were sown in 24-well plates having an insert and cultivated for 14 to 16 days. For the permeability studies, the test substance was dissolved in DMSO and diluted to the final test concentration with transport buffer (Hanks Buffered Salt Solution, Gibco/Invitrogen, with 19.9 mM glucose and 9.8 mM HEPES). In order to determine the apical to basolateral permeability ($P_{app}$A-B) of the test substance, the solution comprising the test substance was applied to the apical side of the Caco-2 cell monolayer, and transport buffer to the basolateral side. In order to determine the basolateral to apical permeability ($P_{app}$B-A) of the test substance, the solution comprising the test substance was applied to the basolateral side of the Caco-2 cell monolayer, and transport buffer to the apical side. At the start of the experiment, samples were taken from the respective donor compartment in order to ensure the mass balance. After an incubation time of two hours at 37° C., samples were taken from the two compartments. The samples were analysed by means of LC-MS/MS and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) was also determined as quality control.

B-9. hERG Potassium Current Assay

The hERG (human ether-a-go-go related gene) potassium current makes a significant contribution to the repolarization of the human cardiac action potential (Scheel et al., 2011). Inhibition of this current by pharmaceuticals can in rare cases cause potentially lethal cardiac arrythmia, and is therefore studied at an early stage during drug development.

The functional hERG assay used here is based on a recombinant HEK293 cell line which stably expresses the KCNH2 (HERG) gene (Zhou et al., 1998). These cells are studied by means of the "whole-cell voltage-clamp" technique (Hamill et al., 1981) in an automated system (Patchliner™; Nanion, Munich, Germany), which controls the membrane voltage and measures the hERG potassium current at room temperature. The PatchControlHT™ software (Nanion) controls the Patchliner system, data capture and data analysis. The voltage is controlled by 2 EPC-10 quadro amplifiers controlled by the PatchMasterPro™ software (both: HEKA Elektronik, Lambrecht, Germany) NPC-16 chips with moderate resistance (~2 MΩ; Nanion) serve as the planar substrate for the voltage clamp experiments.

NPC-16 chips are filled with intra- and extracellular solution (cf. Himmel, 2007) and with cell suspension. After forming a gigaohm seal and establishing whole-cell mode (including several automated quality control steps), the cell membrane is clamped at the −80 mV holding potential. The subsequent voltage clamp protocol changes the command voltage to +20 mV (for 1000 ms), −120 mV (for 500 ms), and back to the −80 mV holding potential; this is repeated every 12 s. After an initial stabilization phase (about 5-6 minutes), test substance solution is introduced by pipette in rising concentrations (e.g. 0.1, 1, and 10 µmol/l) (exposure about 5-6 minutes per concentration), followed by several washing steps.

The amplitude of the upward "tail" current which is generated by a change in potential from +20 mV to −120 mV serves to quantify the hERG potassium current, and is described as a function of time (IgorPro™ Software). The current amplitude at the end of various time intervals (for example stabilization phase before first substance, first/second/third concentration of test substance) serves to establish a concentration/effect curve, from which the half-maximum inhibiting concentration $IC_{50}$ of the test substance is calculated.

Hamill O P, Marty A, Neher E, Sakmann B, Sigworth F J Improved patch-clamp techniques for high-resolution current recording from cells and cell-free membrane patches. Pfluegers Arch 1981; 391:85-100.

Himmel H M. Suitability of commonly used excipients for electrophysiological in-vitro safety pharmacology assessment of effects on hERG potassium current and on rabbit Purkinje fiber action potential. J Pharmacol Toxicol Methods 2007; 56:145-158.

Scheel O, Himmel H, Rascher-Eggstein G, Knott T. Introduction of a modular automated voltage-clamp platform and its correlation with manual human ether-a-go-go related gene voltage-clamp data. Assay Drug Dev Technol 2011; 9:600-607.

Zhou Z F, Gong Q, Ye B, Fan Z, Makielski J C, Robertson G A, January C T. Properties of hERG channels stably expressed in HEK293 cells studied at physiological temperature. Biophys J 1998; 74:230-241.

C. WORKING EXAMPLES OF PHARMACEUTICAL COMPOSITIONS

The inventive compounds can be converted to pharmaceutical formulations as follows:

Tablet:
Composition:
100 mg of the inventive compound, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:
The mixture of inventive compound, lactose and starch is granulated with a 5% solution (w/w) of the PVP in water. The granules are dried and mixed with the magnesium stearate for 5 minutes. This mixture is compressed in a conventional tablet press (see above for format of the tablet). The guide value used for the pressing is a pressing force of 15 kN.

Suspension for Oral Administration:
Composition:
1000 mg of the inventive compound, 1000 mg of ethanol (96%), 400 mg of Rhodigel® (xanthan gum from FMC, Pennsylvania, USA) and 99 g of water.

A single dose of 100 mg of the inventive compound corresponds to 10 ml of oral suspension.

Production:
The Rhodigel is suspended in ethanol; the inventive compound is added to the suspension. The water is added while stirring. The mixture is stirred for about 6 h before swelling of the Rhodigel is complete.

Solution for Oral Administration:
Composition:
500 mg of the inventive compound, 2.5 g of polysorbate and 97 g of polyethylene glycol 400. A single dose of 100 mg of the inventive compound corresponds to 20 g of oral solution.

Production:
The compound according to the invention is suspended in the mixture of polyethylene glycol and polysorbate while stirring. The stirring operation is continued until dissolution of the compound according to the invention is complete.

i.v. Solution:
The inventive compound is dissolved in a concentration below the saturation solubility in a physiologically acceptable solvent (e.g. isotonic aqueous sodium chloride solution, glucose solution 5% and/or PEG 400 solution 30%). The solution obtained is subjected to sterile filtration and dispensed into sterile and pyrogen-free injection vessels.

The invention claimed is:
1. A compound of the formula (I)

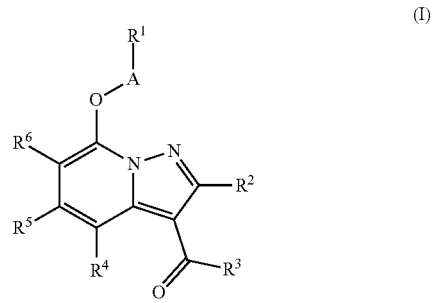

in which

A is $CH_2$, $CD_2$ or $CH(CH_3)$, $R^1$ is $(C_4\text{-}C_6)$-alkyl, $(C_3\text{-}C_7)$-cycloalkyl, pyridyl or phenyl,
where $(C_4\text{-}C_6)$-alkyl may be substituted up to six times by fluorine,
where $(C_3\text{-}C_7)$-cycloalkyl may be substituted by 1 to 4 substituents each independently selected from fluorine, trifluoromethyl and $(C_1\text{-}C_4)$-alkyl,
where pyridyl is substituted by 1 or 2 substituents each selected independently from the group of halogen, cyano and $(C_1\text{-}C_4)$-alkyl,
and
where phenyl may be substituted by 1 to 4 substituents each independently selected from the group of halogen, cyano, monofluoromethyl, difluoromethyl, trifluoromethyl, $(C_1\text{-}C_4)$-alkyl, $(C_2\text{-}C_3)$-alkynyl, $(C_1\text{-}C_4)$-alkoxy, $(C_3\text{-}C_5)$-cycloalkyl, difluoromethoxy and trifluoromethoxy, or may be substituted on two adjacent carbon atoms in the phenyl by a difluoromethylenedioxy bridge, $R^2$ is hydrogen, $(C_1\text{-}C_4)$-alkyl, $(C_1\text{-}C_4)$-alkoxymethyl, cyclopropyl, cyclobutyl, monofluoromethyl, difluoromethyl or trifluoromethyl, $R^3$ is a group of the formula

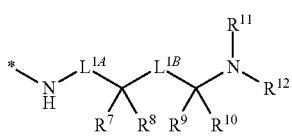

or

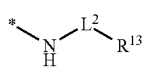

or

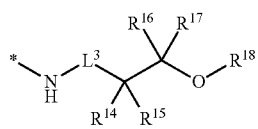

or

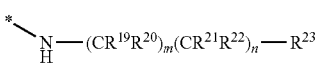

where
* is the attachment site to the carbonyl group,
$L^{1A}$ is a bond, methanediyl, 1,2-ethanediyl or 1,3-propanediyl,
in which methanediyl, 1,2-ethanediyl or 1,3-propanediyl may be substituted by 1 or 2 substituents each independently selected from the group of fluorine, trifluoromethyl, $(C_1\text{-}C_4)$-alkyl, $(C_3\text{-}C_5)$-cycloalkyl, hydroxyl and $(C_1\text{-}C_4)$-alkoxy,
$L^{1B}$ is a bond, methanediyl or 1,2-ethanediyl,
$L^2$ is a bond or $(C_1\text{-}C_4)$-alkanediyl,
in which $(C_1\text{-}C_4)$-alkanediyl may be substituted by 1 to 3 substituents each independently selected from the group of fluorine, trifluoromethyl, $(C_1\text{-}C_4)$-alkyl, $(C_3\text{-}C_5)$-cycloalkyl, hydroxyl and $(C_1\text{-}C_4)$-alkoxy,
$L^3$ is a bond, methanediyl or 1,2-ethanediyl,
in which methanediyl or 1,2-ethanediyl may be substituted by 1 or 2 substituents each independently selected from the group of fluorine, trifluoromethyl, $(C_1\text{-}C_4)$-alkyl, $(C_3\text{-}C_7)$-cycloalkyl, hydroxyl and $(C_1\text{-}C_4)$-alkoxy, $R^7$ is hydrogen, $(C_1\text{-}C_6)$-alkyl, $(C_3\text{-}C_7)$-cycloalkyl, $(C_2\text{-}C_6)$-alkenyl, $(C_2\text{-}C_6)$-alkynyl, cyano, 5- to 10-membered heteroaryl or phenyl,
in which $(C_1\text{-}C_6)$-alkyl may be substituted by 1 or 2 substituents each independently selected from the group of difluoromethoxy, trifluoromethoxy, hydroxyl, $(C_1\text{-}C_4)$-alkoxy, $(C_1\text{-}C_4)$-alkoxycarbonyl, $(C_1\text{-}C_4)$-alkylsulphonyl, $(C_1\text{-}C_4)$-alkylthio, benzyloxy, phenoxy, 5- or 6-membered heteroaryl and phenyl, and may be substituted up to six times by fluorine,
in which benzyloxy, phenoxy, 5- or 6-membered heteroaryl and phenyl may be substituted by 1 to 3 substituents each independently selected from the group of halogen and $(C_1\text{-}C_4)$-alkoxy,
in which $(C_3\text{-}C_7)$-cycloalkyl may be substituted by 1 or 2 fluorine, trifluoromethyl, $(C_1\text{-}C_4)$-alkyl or $(C_1\text{-}C_4)$-alkoxy substituents,
in which phenyl and 5- to 10-membered heteroaryl may be substituted by 1 to 4 substituents each independently selected from the group of halogen, cyano, nitro, trifluoromethyl, difluoromethyl, $(C_1\text{-}C_4)$-alkyl, $(C_2\text{-}C_4)$-alkenyl, $(C_1\text{-}C_4)$-alkoxy, difluoromethoxy, trifluoromethoxy, $(C_1\text{-}C_4)$-alkoxycarbonyl and $(C_1\text{-}C_4)$-alkylsulphonyl,
in which $(C_1\text{-}C_4)$-alkoxy may be substituted by hydroxyl,
in which $(C_1\text{-}C_4)$-alkyl may be substituted by amino or hydroxyl,
and
in which phenyl may be substituted on two adjacent carbon atoms in the phenyl by a methylenedioxy bridge or ethylenedioxy bridge,
or
may be fluorine when $L^{1A}$ is not a bond, $R^8$ is hydrogen or $(C_1\text{-}C_6)$-alkyl,
or
may be fluorine when $L^{1A}$ is not a bond,
or
$R^7$ and $R^8$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1\text{-}C_4)$-alkyl, $R^9$ is hydrogen, $(C_1\text{-}C_6)$-alkyl, $(C_3\text{-}C_7)$-cycloalkyl, $(C_2\text{-}C_6)$-alkenyl, $(C_2\text{-}C_6)$-alkynyl, cyano, 5- to 10-membered heteroaryl or phenyl,
in which $(C_1\text{-}C_6)$-alkyl may be substituted by 1 or 2 substituents each independently selected from the group of difluoromethoxy, trifluoromethoxy, hydroxyl, $(C_1\text{-}C_4)$-alkoxy, $(C_1\text{-}C_4)$-alkoxycarbonyl, $(C_1\text{-}C_4)$-alkylsulphonyl, $(C_1\text{-}C_4)$-alkylthio, benzyloxy, phenoxy, 5- or 6-membered heteroaryl and phenyl, and may be substituted up to six times by fluorine,
in which benzyloxy, phenoxy, 5- or 6-membered heteroaryl and phenyl may be substituted by 1 to 3 substituents each independently selected from the group of halogen and $(C_1-C_4)$-alkoxy,
in which $(C_3-C_7)$-cycloalkyl may be substituted by 1 or 2 fluorine, trifluoromethyl, $(C_1-C_4)$-alkyl or $(C_1-C_4)$-alkoxy substituents,
in which phenyl and 5- to 10-membered heteroaryl may be substituted by 1 to 4 substituents each independently selected from the group of halogen, cyano, nitro, trifluoromethyl, $(C_1-C_4)$-alkyl, $(C_2-C_4)$-alkenyl, $(C_1-C_4)$-alkoxy, difluoromethoxy, trifluoromethoxy, $(C_1-C_4)$-alkoxycarbonyl and $(C_1-C_4)$-alkylsulphonyl,
in which $(C_1-C_4)$-alkoxy may be substituted by hydroxyl,
and
in which phenyl may be substituted on two adjacent carbon atoms in the phenyl by a methylenedioxy bridge or ethylenedioxy bridge,
$R^{10}$ is hydrogen or $(C_1-C_6)$-alkyl,
or
$R^9$ and $R^{10}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^7$ and $R^9$ together with the carbon atoms to which they are bonded form a 3- to 7-membered carbocycle or a 4- to 7-membered heterocycle,
in which the 3- to 7-membered carbocycle and the 4- to 7-membered heterocycle may be substituted by 1 or 2 $(C_1-C_4)$-alkyl substituents,
and
in which the 3- to 7-membered carbocycle and the 4- to 7-membered heterocycle may be fused to a phenyl ring or a pyridyl ring, which may in turn be substituted by 1 or 2 substituents selected from halogen, $(C_1-C_4)$-alkyl and trifluoromethyl,
with the proviso that not more than one of the $R^7$ and $R^8$, $R^9$ and $R^{10}$, and $R^7$ and $R^9$ radical pairs at the same time forms a carbo- or heterocycle,
with the proviso that the $R^7$ and $R^9$ radicals are not at the same time both phenyl or 5- or 6-membered heteroaryl,
$R^{11}$ is hydrogen or $(C_1-C_4)$-alkyl,
in which $(C_1-C_4)$-alkyl may be substituted by 1 or 2 substituents each independently selected from the group of hydroxyl and $(C_1-C_4)$-alkoxy, and may be substituted up to six times by fluorine,
$R^{12}$ is hydrogen, $(C_1-C_6)$-alkyl, $(C_1-C_4)$-alkylcarbonyl, $(C_1-C_4)$-alkoxycarbonyl, $(C_3-C_7)$-cycloalkyl, phenyl or benzyl,
in which $(C_1-C_6)$-alkyl may be substituted by 1 to 3 substituents each independently selected from the group of fluorine, trifluoromethyl, hydroxyl, $(C_1-C_4)$-alkoxy and phenoxy,
and in which phenyl and benzyl may be substituted by 1 to 3 substituents each independently selected from the group of halogen and trifluoromethyl,
or
$R^{11}$ and $R^{12}$ together with the nitrogen atom to which they are bonded form a 4- to 7-membered azaheterocycle,
in which the 4- to 7-membered azaheterocycle may be substituted by $(C_1-C_4)$-alkyl,
$R^{13}$ is 5- to 10-membered azaheterocyclyl bonded via a ring carbon atom or 5- or 6-membered heterocyclyl bonded via a ring nitrogen atom,
in which 5- to 10-membered azaheterocyclyl bonded via a ring carbon atom may be substituted by 1 to 2 trifluoromethyl, $(C_3-C_7)$-cycloalkyl, oxo and benzyl substituents, and up to four times by $(C_1-C_4)$-alkyl and up to twice by fluorine,
in which 5- to 10-membered azaheterocyclyl may be fused to a phenyl ring or a pyridyl ring, which may in turn be substituted by 1 or 2 substituents selected from halogen, $(C_1-C_4)$-alkyl, $(C_1-C_4)$-alkoxy and trifluoromethyl,
in which 5- or 6-membered heterocyclyl bonded via a ring nitrogen atom may be substituted by $(C_1-C_4)$-alkyl or $(C_1-C_4)$-cycloalkyl,
in which $(C_1-C_4)$-alkyl may be substituted by difluoromethyl or trifluoromethyl,
or
may be amino when $L^2$ is a bond,
in which amino may be substituted by $(C_1-C_{10})$-alkyl, $(C_1-C_4)$-alkylcarbonyl, $(C_3-C_6)$-carbocyclyl, 4- to 7-membered heterocyclyl, phenyl or 5- or 6-membered heteroaryl,
in which $(C_1-C_4)$-alkylcarbonyl may be substituted by monoalkylamino, dialkylamino or 5- or 6-membered heterocyclyl bonded via a ring nitrogen atom,
in which 5- or 6-membered heterocyclyl bonded via a ring nitrogen atom may be substituted by oxo,
in which $(C_3-C_6)$-carbocyclyl and 4- to 7-membered heterocyclyl may be substituted by hydroxyl,
and
in which phenyl and 5- or 6-membered heteroaryl may be substituted by 1 to 3 substituents each independently selected from the group of halogen, $(C_1-C_4)$-alkyl and trifluoromethyl,
$R^{14}$ is hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, —(C=O)NR$^{24}$R$^{25}$, 5- or 6-membered heteroaryl or phenyl,
in which $(C_1-C_6)$-alkyl may be substituted by 1 or 2 substituents each independently selected from the group of difluoromethoxy, trifluoromethoxy, hydroxyl, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy, and may be substituted up to six times by fluorine,
in which phenyl, phenoxy and benzyloxy may in turn be substituted by 1 to 3 halogen substituents,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy, in which $R^{24}$ is hydrogen, $(C_1-C_4)$-alkyl, $(C_3-C_7)$-cycloalkyl, aryl or naphthyl,
in which $R^{25}$ is hydrogen or methyl,
and
in which phenyl and 5- or 6-membered heteroaryl may be substituted by 1 to 3 substituents each independently selected from the group of halogen, cyano, trifluoromethyl, difluoromethyl, $(C_1-C_4)$-alkyl, $(C_1-C_4)$-alkoxy and $(C_1-C_4)$-alkylsulphonyl,
in which $(C_1-C_4)$-alkyl may be substituted by amino or hydroxyl,
$R^{15}$ is hydrogen or $(C_1-C_6)$-alkyl,
in which $(C_1-C_4)$-alkyl may be substituted by hydroxyl,
or
$R^{14}$ and $R^{15}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
$R^{16}$ is hydrogen, $(C_1-C_6)$-alkyl, $(C_2-C_6)$-alkenyl, $(C_2-C_6)$-alkynyl, $(C_3-C_7)$-cycloalkyl, $(C_1-C_4)$-alkoxycarbonyl, 5- or 6-membered heteroaryl or phenyl,
in which $(C_1-C_6)$-alkyl may be substituted by 1 or 2 substituents each independently selected from the group of fluorine, trifluoromethyl, difluoromethoxy, trifluoromethoxy, hydroxyl, $(C_1-C_4)$-alkoxy, $(C_1-C_4)$-alkoxycarbonyl, $(C_1-C_4)$-alkylthio, $(C_1-C_4)$-alkylsulphonyl, phenyl, phenoxy and benzyloxy, and may be substituted up to six times by fluorine,
in which phenyl, phenoxy and benzyloxy may in turn be substituted by 1 to 3 halogen substituents,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy,
and
in which phenyl and 5- or 6-membered heteroaryl may be substituted by 1 to 3 substituents each independently selected from the group of halogen, cyano, trifluoromethyl, $(C_1-C_4)$-alkyl, $(C_1-C_4)$-alkoxy and $(C_1-C_4)$-alkylsulphonyl,
$R^{17}$ is hydrogen or $(C_1-C_6)$-alkyl,
in which $(C_1-C_4)$-alkyl may be substituted by hydroxyl,
or
$R^{16}$ and $R^{17}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
with the proviso that the $R^{14}$ and $R^{16}$ radicals are not at the same time both phenyl or 5- or 6-membered heteroaryl,
or
$R^{14}$ and $R^{16}$ together with the carbon atoms to which they are bonded form a 3- to 7-membered carbocycle or a 4- to 7-membered heterocycle, with the proviso that not more than one of the $R^{14}$ and $R^{15}$, $R^{16}$ and $R^{17}$, and $R^{14}$ and $R^{16}$ radical pairs at the same time forms a carbo- or heterocycle,
$R^{18}$ is hydrogen or $(C_1-C_4)$-alkyl,
in which $(C_1-C_4)$-alkyl may be substituted by 1 to 5 fluorine substituents,
m is 0, 1 or 2,
n is 0 or 1,
$R^{19}$ is hydrogen, cyano or $(C_1-C_6)$-alkyl,
in which $(C_1-C_6)$-alkyl may be substituted by 1 to 5 fluorine substituents,
$R^{20}$ is hydrogen or $(C_1-C_4)$-alkyl,
in which $(C_1-C_4)$-alkyl may be substituted by 1 to 5 fluorine substituents,
$R^{21}$ is hydrogen or $(C_1-C_6)$-alkyl,
in which $(C_1-C_6)$-alkyl may be substituted by 1 to 5 fluorine substituents,
$R^{22}$ is hydrogen or $(C_1-C_4)$-alkyl,
in which $(C_1-C_4)$-alkyl may be substituted by 1 to 5 fluorine substituents,
or
$R^{19}$ and $R^{20}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^{21}$ and $R^{22}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^{19}$ and $R^{21}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
with the proviso that not more than one of the $R^{19}$ and $R^{20}$, $R^{21}$ and $R^{22}$, and $R^{19}$ and $R^{21}$ radical pairs at the same time forms a carbo- or heterocycle,
$R^{23}$ is $(C_1-C_6)$-alkyl, $(C_1-C_6)$-alkoxy, $(C_1-C_4)$-alkoxycarbonyl, hydroxycarbonyl, aminocarbonyl, aminosulphonyl, 5- to 10-membered heterocyclyl bonded via a ring carbon atom, 5- to 10-membered carbocyclyl, phenyl or 5- to 10-membered heteroaryl,
in which $(C_1-C_6)$-alkyl may be substituted by cyano, and up to six times by fluorine,
in which $(C_1-C_6)$-alkoxy may be substituted by hydroxyl, amino, monoalkylamino, dialkylamino, cyclopropyl, phenyl or $(C_2-C_4)$-alkenyl,
in which aminocarbonyl may be substituted by $(C_1-C_6)$-alkyl or $(C_3-C_6)$-cycloalkyl,
in which aminosulphonyl may be substituted by $(C_1-C_6)$-alkyl or $(C_3-C_6)$-cycloalkyl,
in which phenyl may be substituted by 1 to 3 substituents each independently selected from the group of halogen, cyano, trifluoromethyl, difluoromethyl, ($C_1$-$C_6$)-alkyl, ($C_1$-$C_4$)-alkylcarbonyl, ($C_1$-$C_4$)-alkoxycarbonyl, hydroxycarbonyl, —(C=O)$NR^{26}R^{27}$, ($C_1$-$C_4$)-alkylsulphonyl, ($C_3$-$C_6$)-cycloalkylsulphonyl, ($C_1$-$C_4$)-alkylthio, ($C_1$-$C_4$)-alkoxy, trifluoromethoxy, difluoromethoxy, phenoxy, hydroxyl, 5- to 10-membered heteroaryl, 4- to 7-membered heterocyclyl and ($C_3$-$C_7$)-cycloalkyl, in which ($C_1$-$C_6$)-alkyl may be substituted by 1 or 2 substituents each independently selected from the group of fluorine, trifluoromethoxy, ($C_1$-$C_4$)-alkylcarbonyl, —(C=O)$NR^{26}R^{27}$, ($C_1$-$C_4$)-alkoxy, ($C_3$-$C_6$)-cycloalkyl, morpholinyl, piperidinyl, pyrrolidinyl, piperazinyl, phenyl, hydroxyl and amino, in which phenyl may be substituted by 1 to 3 halogen substituents, in which amino may be substituted by 1 or 2 substituents each independently selected from ($C_1$-$C_6$)-alkyl, ($C_1$-$C_4$)-alkylcarbonyl, ($C_3$-$C_6$)-cycloalkylsulphonyl, ($C_1$-$C_4$)-alkylsulphonyl and methoxy-($C_1$-$C_4$)-alkyl, in which ($C_3$-$C_6$)-cycloalkyl may be substituted by amino or hydroxyl, and in which $R^{26}$ and $R^{27}$ are each independently hydrogen, ($C_1$-$C_4$)-alkyl or ($C_3$-$C_7$)-cycloalkyl, in which 5- to 10-membered heteroaryl may be substituted by 1 to 3 substituents each independently selected from the group of fluorine, chlorine, cyano, ($C_1$-$C_6$)-alkyl, trifluoromethyl, ($C_1$-$C_4$)-alkoxy, amino, ($C_1$-$C_4$)-alkoxycarbonyl, hydroxycarbonyl, —(C=O)$NR^{25}R^{26}$, phenyl, pyridyl, pyrimidyl, 1,3-thiazol-5-yl and ($C_3$-$C_7$)-cycloalkyl, in which ($C_1$-$C_6$)-alkyl may be substituted by 1 to 3 substituents each independently selected from the group of halogen, cyano, hydroxyl, amino, trifluoromethyl, difluoromethyl, ($C_1$-$C_4$)-alkylsulphonyl, ($C_1$-$C_4$)-alkylcarbonyl, ($C_1$-$C_4$)-alkoxycarbonyl, hydroxycarbonyl, ($C_1$-$C_4$)-alkylthio, ($C_1$-$C_4$)-alkoxy, trifluoromethoxy, difluoromethoxy, phenoxy, phenyl, pyridyl, pyrimidyl, 5-membered heteroaryl, tetrahydrothiophenyl-1,1-dioxide, ($C_3$-$C_7$)-cycloalkyl, morpholinyl, piperidinyl, pyrrolidinyl, 2-oxopyrrolidin-1-yl, piperazinyl, tetrahydrothiophenyl-1,1-dioxide, thiomorpholinyl-1,1-dioxide and azetidine, in which 5-membered heteroaryl may be substituted by 1 to 3 substituents each independently selected from the group of halogen, ($C_1$-$C_4$)-alkyl and ($C_1$-$C_4$)-alkoxy, in which piperidinyl may be substituted by 1 to 4 fluorine substituents, in which phenyl may be substituted by 1 to 3 substituents each independently selected from the group of halogen, ($C_1$-$C_4$)-alkyl and ($C_1$-$C_4$)-alkoxy, in which azetidine may be substituted by hydroxyl, in which piperazinyl may be substituted by 1 to 3 substituents each independently selected from the group of ($C_1$-$C_4$)-alkyl, ($C_3$-$C_7$)-cycloalkyl and trifluoromethyl, and in which $R^{26}$ and $R^{27}$ are each independently hydrogen, ($C_1$-$C_4$)-alkyl or ($C_3$-$C_7$)-cycloalkyl, in which 5- to 10-membered heterocyclyl bonded via a ring carbon atom may be substituted by 1 to 3 substituents each independently selected from the group of oxo, fluorine, trifluoromethyl, hydroxyl and ($C_1$-$C_4$)-alkyl, in which 5- to 10-membered heterocyclyl bonded via a ring carbon atom may be fused to a phenyl ring or a pyridyl ring, which may in turn be substituted by 1 to 3 substituents selected from the group of halogen, ($C_1$-$C_4$)-alkyl and trifluoromethyl, and in which 5- to 10-membered carbocyclyl may be substituted by 1 to 3 substituents each independently selected from the group of trifluoromethyl, fluorine, cyano, hydroxyl, hydroxycarbonyl, ($C_1$-$C_4$)-alkoxycarbonyl, amino and ($C_1$-$C_4$)-alkyl, in which ($C_1$-$C_4$)-alkyl may be substituted by hydroxyl or hydroxycarbonyl, in which 5- to 10-membered carbocyclyl may be fused to a phenyl ring or a pyridyl ring, which may in turn be substituted by 1 to 3 substituents selected from the group of halogen, ($C_1$-$C_4$)-alkyl, ($C_1$-$C_4$)-alkoxy and trifluoromethyl, $R^4$ is hydrogen, $R^5$ is hydrogen, halogen, cyano, difluoromethyl, trifluoromethyl, ($C_1$-$C_4$)-alkyl, ($C_3$-$C_7$)-cycloalkyl, ($C_2$-$C_4$)-alkynyl, ($C_1$-$C_4$)-alkylamino, difluoromethoxy, trifluoromethoxy, ($C_1$-$C_4$)-alkoxy, amino, 4- to 7-membered heterocyclyl or 5- or 6-membered heteroaryl, $R^6$ is hydrogen, cyano or halogen, and the N-oxides, salts, solvates, salts of the N-oxides and solvates of the N-oxides or salts thereof.

2. The compound of claim 1 in which

A is $CH_2$ or $CD_2$, $R^1$ is ($C_3$-$C_6$)-cycloalkyl, pyridyl or phenyl, where ($C_3$-$C_6$)-cycloalkyl may be substituted by 1 to 2 substituents each independently selected from the group of fluorine, trifluoromethyl, methyl and ethyl, where pyridyl is substituted by 1 or 2 fluorine substituents, and where phenyl may be substituted by 1 to 4 substituents each independently selected from the group of halogen, cyano, difluoromethyl, trifluoromethyl, ($C_1$-$C_4$)-alkyl, ($C_1$-$C_4$)-alkoxy and ($C_3$-$C_5$)-cycloalkyl, $R^2$ is hydrogen, ($C_1$-$C_4$)-alkyl, cyclopropyl, cyclobutyl, difluoromethyl or trifluoromethyl, $R^3$ is a group of the formula

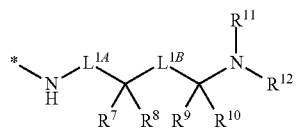

or

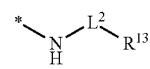

or

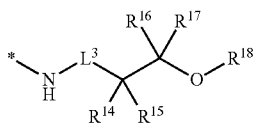

or

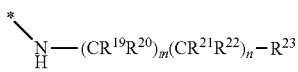

where
* is the attachment site to the carbonyl group,
$L^{1A}$ is a bond, methanediyl, 1,2-ethanediyl or 1,3-propanediyl,
$L^{1B}$ is a bond, methanediyl or 1,2-ethanediyl,
$L^2$ is a bond, methanediyl or 1,2-ethanediyl,
$L^3$ is a bond, methanediyl or 1,2-ethanediyl,
$R^7$ is hydrogen, $(C_1-C_6)$-alkyl, $(C_3-C_7)$-cycloalkyl, 5- or 6-membered heteroaryl or phenyl,
  in which $(C_1-C_6)$-alkyl may be substituted up to five times by fluorine,
  in which phenyl and 5- or 6-membered heteroaryl may be substituted by 1 to 3 substituents each independently selected from the group of fluorine, chlorine, bromine, cyano, nitro, trifluoromethyl, difluoromethyl, methyl, ethyl, methoxy, ethoxy, difluoromethoxy, trifluoromethoxy, methoxycarbonyl and ethoxycarbonyl,
  and
  in which phenyl may be substituted on two adjacent carbon atoms in the phenyl by a methylenedioxy bridge or ethylenedioxy bridge,
  or
  may be fluorine when $L^{1A}$ is not a bond,
$R^8$ is hydrogen or $(C_1-C_4)$-alkyl,
  or
  may be fluorine when $L^{1A}$ is not a bond,
or
$R^7$ and $R^8$ together with the carbon atom to which they are bonded form a 3- to 7-membered carbocycle,
$R^9$ is hydrogen, $(C_1-C_6)$-alkyl, $(C_3-C_5)$-cycloalkyl, cyano, 5- to 10-membered heteroaryl or phenyl,
  in which $(C_1-C_6)$-alkyl may be substituted by $(C_1-C_4)$-alkoxy, $(C_1-C_4)$-alkoxycarbonyl, $(C_1-C_4)$-alkylsulphonyl, $(C_1-C_4)$-alkylthio, benzyloxy, phenoxy, 5- or 6-membered heteroaryl and phenyl, and may be substituted up to five times by fluorine,
    in which benzyloxy, phenoxy, 5- or 6-membered heteroaryl and phenyl may be substituted by 1 to 3 substituents each independently selected from the group of fluorine, chlorine, bromine, methoxy and ethoxy,
  in which $(C_3-C_5)$-cycloalkyl may be substituted by 1 or 2 fluorine, trifluoromethyl, methyl, ethyl, methoxy or ethoxy substituents,
  in which phenyl and 5- to 10-membered heteroaryl may be substituted by 1 to 3 substituents each independently selected from the group of fluorine, chlorine, bromine, cyano, nitro, trifluoromethyl, methyl, ethyl, ethenyl, propenyl, methoxy, ethoxy, difluoromethoxy, trifluoromethoxy, methoxycarbonyl and ethoxycarbonyl,
    in which methoxy and ethoxy may be substituted by hydroxyl,
    and
    in which phenyl may be substituted on two adjacent carbon atoms in the phenyl by a methylenedioxy bridge or ethylenedioxy bridge,
$R^{10}$ is hydrogen or $(C_1-C_4)$-alkyl,
or
$R^9$ and $R^{10}$ together with the carbon atom to which they are bonded form a 3- to 7-membered carbocycle or a 4- to 7-membered heterocycle,
or
$R^7$ and $R^9$ together with the carbon atoms to which they are bonded form a 3- to 7-membered carbocycle or a 4- to 7-membered heterocycle,
  in which the 3- to 7-membered carbocycle and the 4- to 7-membered heterocycle may be substituted by 1 or 2 $(C_1-C_4)$-alkyl substituents,
  and
  in which the 3- to 7-membered carbocycle and the 4- to 7-membered heterocycle may be fused to a phenyl ring or a pyridyl ring, which may in turn be substituted by 1 or 2 substituents selected from fluorine, chlorine, bromine, methyl, ethyl and trifluoromethyl,
with the proviso that not more than one of the $R^7$ and $R^8$, $R^9$ and $R^{10}$, and $R^7$ and $R^9$ radical pairs at the same time forms a carbo- or heterocycle,
with the proviso that the $R^7$ and $R^9$ radicals are not at the same time both phenyl or 5- or 6-membered heteroaryl,
$R^{11}$ is hydrogen or $(C_1-C_4)$-alkyl,
  in which $(C_1-C_4)$-alkyl may be substituted up to five times by fluorine,
$R^{12}$ is hydrogen, $(C_1-C_6)$-alkyl, $(C_3-C_5)$-cycloalkyl or $(C_1-C_4)$-alkylcarbonyl,
  in which $(C_1-C_6)$-alkyl may be substituted up to five times by fluorine,
or
$R^{11}$ and $R^{12}$ together with the nitrogen atom to which they are bonded form a 4- to 7-membered azaheterocycle,
  in which the 4- to 7-membered azaheterocycle may be substituted by methyl or ethyl,
$R^{13}$ is 5- to 10-membered azaheterocyclyl bonded via a ring carbon atom or 5- or 6-membered heterocyclyl bonded via a ring nitrogen atom,
  in which 5- to 10-membered azaheterocyclyl bonded via a ring carbon atom may be substituted by 1 or 2 trifluoromethyl, $(C_3-C_7)$-cycloalkyl, oxo and benzyl substituents, and up to four times by $(C_1-C_4)$-alkyl and up to twice by fluorine,
  in which 5- to 10-membered azaheterocyclyl may be fused to a phenyl ring or a pyridyl ring, which may in turn be substituted by 1 or 2 substituents selected from fluorine, chlorine, methyl, $(C_1-C_4)$-alkyl and trifluoromethyl,
  in which 5- or 6-membered heterocyclyl bonded via a ring nitrogen atom may be substituted by $(C_1-C_4)$-alkyl or $(C_1-C_4)$-cycloalkyl,
  or
  may be amino when $L^2$ is a bond,
  in which amino may be substituted by $(C_1-C_4)$-alkyl, $(C_1-C_4)$-alkylcarbonyl, $(C_3-C_6)$-carbocyclyl, 4- to 7-membered heterocyclyl, phenyl or 5- or 6-membered heteroaryl, in which $(C_1-C_4)$-alkylcarbonyl may be substituted by monoalkylamino, dialkylamino or 5- or 6-membered heterocyclyl bonded via a ring nitrogen atom,
in which 5- or 6-membered heterocyclyl bonded via a ring nitrogen atom may be substituted by oxo,
in which $(C_3-C_6)$-carbocyclyl and 4- to 7-membered heterocyclyl may be substituted by hydroxyl,
and
in which phenyl and 5- or 6-membered heteroaryl may be substituted by 1 to 3 substituents each independently selected from the group of fluorine, chlorine, methyl and trifluoromethyl, $R^{14}$ is hydrogen, $(C_1-C_6)$-alkyl, $(C_3-C_7)$-cycloalkyl, —(C=O)$NR^{24}R^{25}$, 5- or 6-membered heteroaryl or phenyl,
in which $(C_1-C_6)$-alkyl may be substituted by 1 or 2 substituents each independently selected from the group of hydroxyl and $(C_1-C_4)$-alkoxy, and may be substituted up to six times by fluorine,
in which $R^{24}$ is hydrogen, $(C_1-C_4)$-alkyl, aryl or naphthyl,
in which $R^{25}$ is hydrogen,
and
in which phenyl and 5- or 6-membered heteroaryl may be substituted by 1 to 3 substituents each independently selected from the group of fluorine, chlorine, bromine, trifluoromethyl, difluoromethyl, methyl, ethyl and 1-amino-2-methylpropyl, $R^{15}$ is hydrogen or $(C_1-C_6)$-alkyl,
in which $(C_1-C_4)$-alkyl may be substituted by hydroxyl,
or
$R^{14}$ and $R^{15}$ together with the carbon atom to which they are bonded form a 3- to 7-membered carbocycle, $R^{16}$ is hydrogen, $(C_1-C_6)$-alkyl or $(C_3-C_7)$-cycloalkyl,
in which $(C_1-C_6)$-alkyl may be substituted by 1 or 2 substituents each independently selected from the group of hydroxyl and $(C_1-C_4)$-alkoxy, and may be substituted up to six times by fluorine,
in which $(C_3-C_7)$-cycloalkyl may be substituted by 1 or 2 substituents each independently selected from the group of fluorine, trifluoromethyl, $(C_1-C_4)$-alkyl and $(C_1-C_4)$-alkoxy, $R^{17}$ is hydrogen or $(C_1-C_6)$-alkyl,
or
$R^{16}$ and $R^{17}$ together with the carbon atom to which they are bonded form a 3- to 6-membered carbocycle,
in which the 3- to 6-membered carbocycle may be substituted by 1 or 2 substituents each independently selected from the group of fluorine, methyl and ethyl,
or
$R^{14}$ and $R^{16}$ together with the carbon atoms to which they are bonded form a 3- to 7-membered carbocycle or a 4- to 7-membered heterocycle,
with the proviso that not more than one of the $R^{14}$ and $R^{15}$, $R^{16}$ and $R^{17}$, and $R^{14}$ and $R^{16}$ radical pairs at the same time forms a carbo- or heterocycle, $R^{18}$ is hydrogen or $(C_1-C_4)$-alkyl,
in which $(C_1-C_4)$-alkyl may be substituted by 1 to 5 fluorine substituents,
m is 0 or 1,
n is 0 or 1,
$R^{19}$ is hydrogen, cyano or $(C_1-C_4)$-alkyl,
in which $(C_1-C_4)$-alkyl may be substituted by 1 to 5 fluorine substituents, $R^{20}$ is hydrogen or $(C_1-C_4)$-alkyl,
in which $(C_1-C_4)$-alkyl may be substituted by 1 to 5 fluorine substituents, $R^{21}$ is hydrogen or $(C_1-C_4)$-alkyl,
in which $(C_1-C_4)$-alkyl may be substituted by 1 to 5 fluorine substituents, $R^{22}$ is hydrogen or $(C_1-C_4)$-alkyl,
in which $(C_1-C_4)$-alkyl may be substituted by 1 to 5 fluorine substituents,
or
$R^{19}$ and $R^{20}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^{21}$ and $R^{22}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
or
$R^{19}$ and $R^{21}$ together with the carbon atom to which they are bonded form a 3- to 7-membered carbocycle or a 4- to 7-membered heterocycle,
in which the 3- to 7-membered carbocycle and the 4- to 7-membered heterocycle may in turn be substituted by 1 or 2 substituents each independently selected from the group of fluorine and $(C_1-C_4)$-alkyl,
with the proviso that not more than one of the $R^{19}$ and $R^{20}$, $R^{21}$ and $R^{22}$, and $R^{19}$ and $R^{21}$ radical pairs at the same time forms a carbo- or heterocycle, $R^{23}$ is $(C_1-C_6)$-alkyl, $(C_1-C_6)$-alkoxy, $(C_1-C_4)$-alkoxycarbonyl, hydroxycarbonyl, aminocarbonyl, aminosulphonyl, 5- to 10-membered heterocyclyl bonded via a ring carbon atom, 5- to 10-membered carbocyclyl, phenyl or 5- to 10-membered heteroaryl,
in which $(C_1-C_6)$-alkyl may be substituted by cyano and up to six times by fluorine,
in which $(C_1-C_6)$-alkoxy may be substituted by hydroxyl or $(C_2-C_4)$-alkenyl,
in which aminocarbonyl may be substituted by $(C_1-C_6)$-alkyl or $(C_3-C_6)$-cycloalkyl,
in which aminosulphonyl may be substituted by $(C_1-C_6)$-alkyl or $(C_3-C_6)$-cycloalkyl,
in which phenyl may be substituted by 1 to 3 substituents each independently selected from the group of halogen, cyano, trifluoromethyl, difluoromethyl, $(C_1-C_4)$-alkyl, $(C_1-C_4)$-alkoxy, 5- to 10-membered heteroaryl and 4- to 7-membered heterocyclyl,
in which $(C_1-C_6)$-alkyl may be substituted by 1 or 2 substituents each independently selected from the group of fluorine, trifluoromethoxy, $(C_1-C_4)$-alkoxy, $(C_3-C_6)$-cycloalkyl, hydroxyl and amino,
in which 5- to 10-membered heteroaryl may be substituted by 1 to 3 substituents each independently selected from the group of fluorine, chlorine, cyano, $(C_1-C_4)$-alkyl, trifluoromethyl, $(C_1-C_4)$-alkoxy and amino,
in which $(C_1-C_4)$-alkyl may be substituted by 1 to 3 substituents each independently selected from the group of halogen, cyano, hydroxyl, amino, trifluoromethyl, difluoromethyl, $(C_1-C_4)$-alkoxy, trifluoromethoxy, difluoromethoxy and phenyl,
in which phenyl may be substituted by 1 to 3 halogen substituents,
in which 5- to 10-membered heterocyclyl bonded via a ring carbon atom may be substituted by 1 or 2 substituents each independently selected from the group of oxo, fluorine, trifluoromethyl, hydroxyl and $(C_1-C_4)$-alkyl,
in which 5- to 10-membered heterocyclyl bonded via a ring carbon atom may be fused to a phenyl ring or a pyridyl ring, which may in turn be substituted by 1 to 3 substituents selected from the group of halogen, $(C_1-C_4)$-alkyl, $(C_1-C_4)$-alkoxy and trifluoromethyl,
and
in which 5- to 10-membered carbocyclyl may be substituted by 1 or 2 substituents each independently selected from the group of trifluoromethyl, fluorine, cyano, hydroxyl, hydroxycarbonyl, $(C_1-C_4)$-alkoxycarbonyl, amino and $(C_1-C_4)$-alkyl,
in which 5- to 10-membered carbocyclyl may be fused to a phenyl ring or a pyridyl ring, which may in turn be substituted by 1 to 3 substituents selected from the group of halogen, $(C_1-C_4)$-alkyl, $(C_1-C_4)$-alkoxy and trifluoromethyl,
$R^4$ is hydrogen,
$R^5$ is hydrogen, fluorine, chlorine, bromine, cyano, difluoromethyl, trifluoromethyl, $(C_1-C_4)$-alkyl, methoxy, $(C_3-C_5)$-cycloalkyl or $(C_2-C_4)$-alkynyl,
$R^6$ is hydrogen or fluorine,
and the N-oxides, salts, solvates, salts of the N-oxides and solvates of the N-oxides or salts thereof.

3. The compound of claim 1 in which
A is $CH_2$,
$R^1$ is cyclohexyl, pyridyl or phenyl,
where pyridyl is substituted by 1 or 2 F substituents, and
where phenyl may be substituted by 1 to 4 substituents each independently selected from the group of fluorine, chlorine, cyano, methyl, ethyl, methoxy, ethoxy and cyclopropyl,
$R^2$ is methyl, cyclopropyl, difluoromethyl or trifluoromethyl,
$R^3$ is a group of the formula

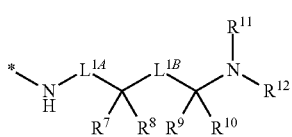

or

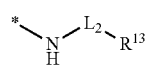

or

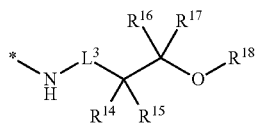

or

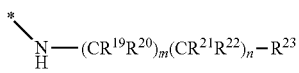

where
* is the attachment site to the carbonyl group,
$L^{1A}$ is a bond or methanediyl,
$L^{1B}$ is a bond,
$L^2$ is a bond,
$L^3$ is a bond,
$R^7$ is hydrogen, $(C_1-C_6)$-alkyl or phenyl,
in which $(C_1-C_6)$-alkyl may be substituted up to five times by fluorine,
in which phenyl may be substituted by 1 to 3 substituents each independently selected from the group of fluorine, chlorine, bromine, trifluoromethyl, methyl, methoxy, difluoromethoxy and trifluoromethoxy,
and
in which phenyl may be substituted on two adjacent carbon atoms in the phenyl by a methylenedioxy bridge or ethylenedioxy bridge,
or
may be fluorine when $L^{1A}$ is not a bond,
$R^8$ is hydrogen, methyl or ethyl,
or
may be fluorine when $L^{1A}$ is not a bond,
$R^9$ is hydrogen, $(C_1-C_6)$-alkyl, cyclopropyl or cyclobutyl,
in which $(C_1-C_6)$-alkyl may be substituted up to five times by fluorine,
in which cyclopropyl and cyclobutyl may be substituted by trifluoromethyl,
$R^{10}$ is hydrogen or $(C_1-C_4)$-alkyl,
or
$R^9$ and $R^{10}$ together with the carbon atom to which they are bonded form a 3- to 7-membered carbocycle,
$R^{11}$ is hydrogen, methyl or ethyl,
in which ethyl may be substituted up to three times by fluorine,
$R^{12}$ is hydrogen, $(C_1-C_4)$-alkyl, cyclopropyl or cyclobutyl,
in which $(C_1-C_6)$-alkyl may be substituted up to five times by fluorine,
or
$R^{11}$ and $R^{12}$ together with the nitrogen atom to which they are bonded form a morpholinyl ring,
$R^{13}$ is 9-azabicyclo[3.3.1]nonan-3-yl, pyrrolidinyl, piperidin-4-yl, azepanyl or 1,2,3,4-tetrahydroquinolinyl,
in which piperidin-4-yl may be substituted by 1 to 5 methyl substituents and may be substituted up to twice by fluorine,
in which 1,2,3,4-tetrahydroquinolinyl may be substituted by 1 to 2 substituents each independently selected from the group of fluorine, oxo, methyl, ethyl, methoxy, ethoxy and trifluoromethyl,
in which 9-azabicyclo[3.3.1]nonan-3-yl may be substituted by methyl,
in which pyrrolidinyl may be substituted by 1 to 2 substituents independently of one another selected from the group consisting of fluorine, oxo, methyl and ethyl, $R^{14}$ is hydrogen, $(C_1-C_6)$-alkyl, —(C=O)$NR^{24}R^{25}$ or phenyl,
in which $(C_1-C_6)$-alkyl may be substituted by hydroxyl or methoxy and up to five times by fluorine,
in which $R^{24}$ is aryl or naphthyl,
in which $R^{25}$ is hydrogen,
and
in which phenyl may be substituted by 1 or 2 substituents independently of one another selected from the group consisting of fluorine, chlorine, trifluoromethyl and methyl, $R^{15}$ is hydrogen or $(C_1-C_6)$-alkyl,
$R^{16}$ is hydrogen, $(C_1-C_6)$-alkyl, cyclopropyl or cyclobutyl,
in which $(C_1-C_6)$-alkyl may be substituted up to six times by fluorine,
$R^{17}$ is hydrogen or $(C_1-C_6)$-alkyl,
or
$R^{16}$ and $R^{17}$ together with the carbon atom to which they are bonded form a 3- to 6-membered carbocycle,
in which the 3- to 6-membered carbocycle may be substituted by 1 or 2 substituents each independently selected from the group of fluorine and methyl,
$R^{18}$ is hydrogen or $(C_1-C_4)$-alkyl,
in which $(C_1-C_4)$-alkyl may be substituted by 1 to 5 fluorine substituents,
m is 0 or 1,
n is 0 or 1,
$R^{19}$ is hydrogen, cyano or methyl,
in which methyl may be substituted by 1 to 3 fluorine substituents,
$R^{20}$ is hydrogen or methyl,
in which methyl may be substituted by 1 to 3 fluorine substituents,
$R^{21}$ is hydrogen or methyl,
in which methyl may be substituted by 1 to 3 fluorine substituents,
$R^{22}$ is hydrogen or methyl,
in which methyl may be substituted by 1 to 3 fluorine substituents,
or
$R^{19}$ and $R^{20}$ together with the carbon atom to which they are bonded form a 3- to 5-membered carbocycle,
or
$R^{19}$ and $R^{21}$ together with the carbon atom to which they are bonded form a cyclopropyl ring,
with the proviso that not more than one of the $R^{19}$ and $R^{20}$, and $R^{19}$ and $R^{21}$ radical pairs at the same time forms a carbocycle,
$R^{23}$ is $(C_1-C_6)$-alkyl, 2-oxopyrrolidin-3-yl, 2-oxotetrahydrofuran-3-yl, cyclopentyl, cyclohexyl, indanyl, 1,2,4-oxadiazol-5-yl, 1H-imidazol-2-yl, 1H-pyrazol-4-yl, pyridin-3-yl, pyrimidin-5-yl, quinolin-4-yl, pyrazolo[1,5-a]pyridin-3-yl, 3,4-dihydro-2H-pyranyl, 1,2,3,4-tetrahydronaphthalenyl, bicyclo[2.2.2]octanyl, chroman-4-yl, 2,3-dihydro-1-benzofuran-3-yl, 2,3-dihydro-1H-indenyl, 3,4-dihydroquinolinyl, 3,4-dihydro-2H-pyrano[2,3-b]pyridinyl or phenyl,
in which $(C_1-C_6)$-alkyl may be substituted by cyano and up to three times by fluorine,
in which phenyl may be substituted by 1 to 3 substituents each independently selected from the group of fluorine, chlorine, cyano, trifluoromethyl, methyl, ethyl, methoxy, 1H-imidazol-1-yl and pyridyl,
in which 1,2,4-oxadiazol-5-yl, 1H-imidazol-2-yl, 1H-pyrazol-4-yl, pyridin-3-yl, pyrimidin-5-yl, quinolin-4-yl or pyrazolo[1,5-a]pyridin-3-yl may be substituted by 1 to 3 substituents each independently selected from the group of fluorine, chlorine, trifluoromethyl, $(C_1-C_3)$-alkyl, amino and hydroxyl,
in which $(C_1-C_3)$-alkyl may be substituted by fluorine, hydroxyl, amino or trifluoromethyl,
in which cyclopentyl, cyclohexyl and bicyclo[2.2.2]octanyl may be substituted by methoxycarbonyl, ethoxycarbonyl, hydroxycarbonyl and cyano,
in which chroman-4-yl, 2,3-dihydro-1-benzofuran-3-yl, 2,3-dihydro-1H-indenyl, 3,4-dihydroquinolinyl and 3,4-dihydro-2H-pyrano[2,3-b]pyridinyl may be substituted by 1 or 2 substituents selected from the group of fluorine, chlorine, methyl, ethyl, methoxy, ethoxy and trifluoromethyl,
and
in which 2,3-dihydro-1H-indenyl and indanyl may be substituted by 1 or 2 substituents selected from the group of fluorine, chlorine, methyl, ethyl, methoxy, ethoxy, hydroxyl and trifluoromethyl,
in which methyl and ethyl may be substituted by hydroxyl,
$R^4$ is hydrogen,
$R^5$ is hydrogen, fluorine, chlorine, methyl or ethyl,
$R^6$ is hydrogen,
and the N-oxides, salts, solvates, salts of the N-oxides and solvates of the N-oxides or salts thereof.

4. The compound of claim 1 in which
A is $CH_2$,
$R^1$ is a phenyl group of the formula

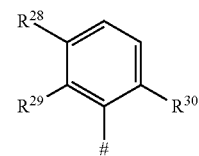

where
# is the attachment site to A,
and
$R^{28}$ is hydrogen or fluorine,
$R^{29}$ is fluorine,
$R^{30}$ is fluorine,
$R^2$ is methyl or cyclopropyl,
$R^3$ is a group of the formula

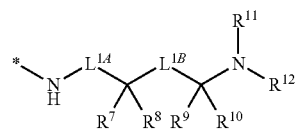

or

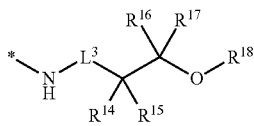

where
* is the attachment site to the carbonyl group,
$L^{1A}$ is a bond,
$L^{1B}$ is a bond,
$R^7$ is hydrogen, $(C_1-C_6)$-alkyl or phenyl,
  in which $(C_1-C_6)$-alkyl may be substituted up to five times by fluorine,
  in which phenyl may be substituted by 1 to 2 chlorine or fluorine substituents,
$R^8$ is hydrogen, methyl or ethyl,
$R^9$ is hydrogen, $(C_1-C_6)$-alkyl or cyclopropyl,
  in which $(C_1-C_6)$-alkyl may be substituted up to five times by fluorine,
$R^{10}$ is hydrogen, methyl or ethyl,
$R^{11}$ is hydrogen,
$R^{12}$ is hydrogen,
$R^{14}$ is hydrogen, $(C_1-C_6)$-alkyl or phenyl,
  in which $(C_1-C_6)$-alkyl may be substituted by hydroxyl and up to five times by fluorine, and
  in which phenyl may be substituted by 1 or 2 fluorine substituents,
$R^{15}$ is hydrogen, methyl or ethyl,
$R^{16}$ is hydrogen or $(C_1-C_6)$-alkyl,
$R^{17}$ is hydrogen, methyl or ethyl,
or
$R^{16}$ and $R^{17}$ together with the carbon atom to which they are bonded form a 3- to 6-membered carbocycle,
$R^{18}$ is hydrogen,
$R^4$ is hydrogen,
$R^5$ is hydrogen or methyl,
$R^6$ is hydrogen,
and the N-oxides, salts, solvates, salts of the N-oxides and solvates of the N-oxides or salts thereof.

5. A process for preparing the compound of claim 1 comprising
converting a compound of the formula (II)

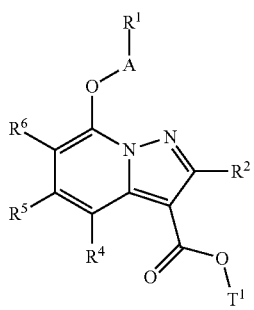

in which A, $R^1$, $R^2$, $R^4$, $R^5$ and $R^6$ are each as defined in claim 1 and
$T^1$ is $(C_1-C_4)$-alkyl or benzyl,
in an inert solvent in the presence of a suitable base or acid to a carboxylic acid of the formula (III)

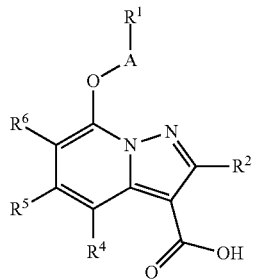

in which A, $R^1$, $R^2$, $R^4$, $R^5$ and $R^6$ are each as defined in claim 1,
subsequently reacting the carboxylic acid of the formula (III) in an inert solvent under amide coupling conditions, with an amine of the formula (IV-A), (IV-B), (IV-C) or (IV-D)

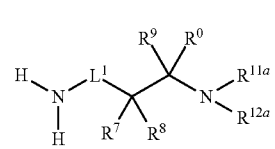

or

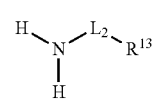

or

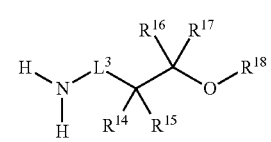

or

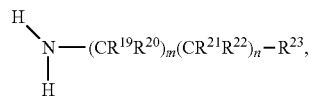

in which $L^1$, $L^2$, $L^3$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each as defined in claim 1
and
$R^{11A}$ and $R^{12A}$ are each as defined in claim 1 for $R^{11}$ and $R^{12}$ or are an amino protecting group,
then detaching any protecting groups, and optionally converting the resulting compounds of the formula (I) with the appropriate (i) solvents and/or (ii) acids or bases to the solvates, salts and/or solvates of the salts thereof.

6. A medicament comprising the compound of claim 1 in combination with an inert, non-toxic, pharmaceutically suitable excipient.

7. A medicament comprising the compound of claim 1 in combination with a further active ingredient selected from the group consisting of organic nitrates, NO donors, cGMP-PDE inhibitors, antithrombotic agents, hypotensive agents and lipid metabolism modifiers.

8. A method for treatment of heart failure, hypertension and pulmonary hypertension comprising administering an effective amount of the compound of claim 1 to a human or an animal in need thereof.

9. A method for treatment of heart failure, hypertension and pulmonary hypertension comprising administering an effective amount of the compound of claim 2 to a human or an animal in need thereof.

10. A method for treatment of heart failure, hypertension and pulmonary hypertension comprising administering an effective amount of the compound of claim 3 to a human or an animal in need thereof.

11. A method for treatment of heart failure, hypertension and pulmonary hypertension comprising administering an effective amount of the compound of claim 4 to a human or an animal in need thereof.

12. A method for treatment of heart failure, hypertension and pulmonary hypertension comprising administering an effective amount of the medicament of claim 6 to a human or an animal in need thereof.

13. A method for treatment of heart failure, hypertension and pulmonary hypertension comprising administering an effective amount of the medicament of claim 7 to a human or an animal in need thereof.

* * * * *